United States Patent
Uno

(10) Patent No.: US 11,335,860 B2
(45) Date of Patent: May 17, 2022

(54) ORGANIC ELECTROLUMINESCENCE DEVICE AND CONDENSED CYCLIC COMPOUND FOR ORGANIC ELECTROLUMINESCENCE DEVICE

(71) Applicant: Samsung Display Co., Ltd., Yongin-Si (KR)

(72) Inventor: Takuya Uno, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 402 days.

(21) Appl. No.: 16/413,536

(22) Filed: May 15, 2019

(65) Prior Publication Data
US 2019/0372019 A1 Dec. 5, 2019

(30) Foreign Application Priority Data
Jun. 1, 2018 (KR) .......... 10-2018-0063453

(51) Int. Cl.
*C07D 487/16* (2006.01)
*H01L 51/00* (2006.01)
(Continued)

(52) U.S. Cl.
CPC ........ *H01L 51/0072* (2013.01); *C07D 471/22* (2013.01); *C07D 487/16* (2013.01); *C07D 491/22* (2013.01); *C07D 495/22* (2013.01); *H01L 51/006* (2013.01); *H01L 51/0054* (2013.01); *H01L 51/0061* (2013.01);
(Continued)

(58) Field of Classification Search
None
See application file for complete search history.

(56) References Cited

U.S. PATENT DOCUMENTS

2016/0099416 A1 4/2016 Itoi
2016/0218296 A1 7/2016 Matsuoka et al.

FOREIGN PATENT DOCUMENTS

KR 10-1622828 B1 5/2016

OTHER PUBLICATIONS

Machine translation of Kim et al. (KR 101622828), translation generated Jun. 2021, 31 pages. (Year: 2021).*

* cited by examiner

*Primary Examiner* — Robert S Loewe
(74) *Attorney, Agent, or Firm* — Lewis Roca Rothgerber Christie LLP

(57) ABSTRACT

An organic electroluminescence device of an embodiment includes a first electrode and a second electrode facing each other, and at least one organic layer disposed between the first electrode and the second electrode, wherein at least one organic layer includes a condensed cyclic compound represented by Formula 1, thereby showing improved device efficiency and life.

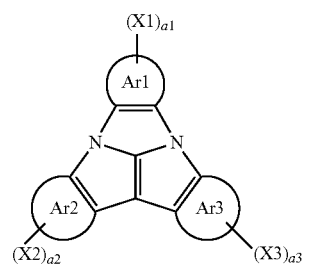

[Formula 1]

19 Claims, 2 Drawing Sheets

(51) Int. Cl.
*C07D 471/22* (2006.01)
*C07D 491/22* (2006.01)
*C07D 495/22* (2006.01)
*H01L 51/50* (2006.01)

(52) U.S. Cl.
CPC ...... *H01L 51/0073* (2013.01); *H01L 51/0074* (2013.01); *H01L 51/5012* (2013.01); *H01L 51/5092* (2013.01); *H01L 51/5096* (2013.01); H01L 51/5056 (2013.01); H01L 51/5072 (2013.01)

ORGANIC ELECTROLUMINESCENCE DEVICE AND CONDENSED CYCLIC COMPOUND FOR ORGANIC ELECTROLUMINESCENCE DEVICE

CROSS-REFERENCE TO RELATED APPLICATIONS

This U.S. non-provisional patent application claims priority under 35 U.S.C. § 119 of Korean Patent Application No. 10-2018-0063453, filed on Jun. 1, 2018, the entire content of which is hereby incorporated by reference.

BACKGROUND

The present disclosure herein relates to an organic electroluminescence device and a condensed cyclic compound used therein.

Recently, the development of an organic electroluminescence display device as an image display device is being actively conducted. The organic electroluminescence display device is so-called a self-luminescent display device in which holes and electrons injected from a first electrode and a second electrode recombine in an emission layer to produce excitons, and light is generated through the transition of the excitons thus produced to a ground state to attain display.

In the application of an organic electroluminescence device to a display device, lower driving voltage, higher emission efficiency, and longer life of the organic electroluminescence device are desired. Hence, materials for an organic electroluminescence device that stably attain the above desired qualities are being continuously developed.

Meanwhile, in order to achieve an organic electroluminescence device with high efficiency, development on a material for a hole transport layer for restraining the diffusion, etc. of the exciton energy of an emission layer is being conducted.

SUMMARY

The present disclosure provides an organic electroluminescence device having improved emission efficiency and device life.

The present disclosure also provides a condensed cyclic compound which may improve the emission efficiency and device life of an organic electroluminescence device.

An embodiment of the inventive concept provides an organic electroluminescence device including a first electrode, a second electrode disposed on the first electrode, and a plurality of organic layers disposed between the first electrode and the second electrode, wherein at least one organic layer of the plurality of organic layers includes a condensed cyclic compound represented by the following Formula 1:

[Formula 1]

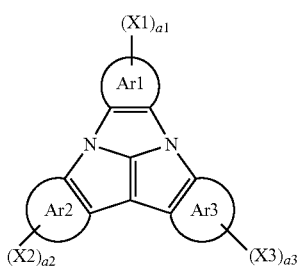

In Formula 1, each of Ar1, Ar2, and Ar3 is independently a substituted or unsubstituted aryl group having 6 to 40 carbon atoms for forming a ring, or a substituted or unsubstituted heteroaryl group having 2 to 40 carbon atoms for forming a ring, where a case where at least one of Ar2 or Ar3 is a substituted or unsubstituted carbazole group is excluded, X1 to X3 are each independently *-L-$NR_1R_2$ one of a1 to a3 is 1 and the others are 0, L is a direct linkage, a substituted or unsubstituted arylene group having 6 to 30 carbon atoms for forming a ring, or a substituted or unsubstituted heteroarylene group having 2 to 30 carbon atoms for forming a ring. $R_1$ and $R_2$ are each independently a substituted or unsubstituted alkyl group having 1 to 20 carbon atoms, a substituted or unsubstituted aryl group having 6 to 40 carbon atoms for forming a ring, or a substituted or unsubstituted heteroaryl group having 2 to 40 carbon atoms for forming a ring, or combined with each other to form a ring.

In an embodiment, the plurality of organic layers may include an emission layer, and a hole transport region disposed between the first electrode and the emission layer, and the hole transport region may include the condensed cyclic compound represented by Formula 1.

In an embodiment, the emission layer may emit blue light.

In an embodiment, the emission layer may include at least one of anthracene derivatives, pyrene derivatives, fluoranthene derivatives, chrysene derivatives, dihydro benzanthracene derivatives, or triphenylene derivatives.

In an embodiment, Formula 1 may be represented by the following Formula 1-1 or Formula 1-2:

[Formula 1-1]

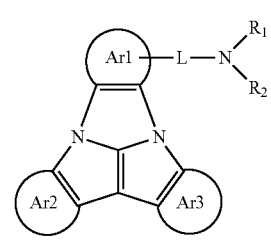

[Formula 1-2]

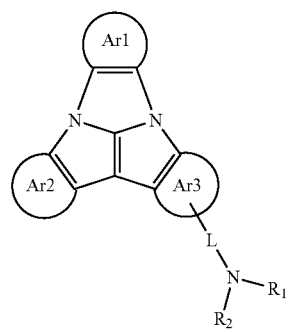

In Formula 1-1 and Formula 1-2, Ar1, Ar2, Ar3, L, $R_1$ and $R_2$ are the same as defined in Formula 1.

In an embodiment, Ar1 may be a substituted or unsubstituted benzene ring, or a substituted or unsubstituted naphthalene ring.

In an embodiment, Ar2 and Ar3 may be each independently a substituted or unsubstituted benzene ring, a substituted or unsubstituted naphthalene ring, a substituted or unsubstituted phenanthrene ring, a substituted or unsubstituted benzofuran ring, a substituted or unsubstituted dibenzofuran ring, a substituted or unsubstituted benzothiophene ring, a substituted or unsubstituted dibenzothiophene ring, a substituted or unsubstituted pyridine ring, or a substituted or unsubstituted quinoline ring.

In an embodiment, Ar2 and Ar3 may be the same.

In an embodiment, Ar2 and Ar3 may be each independently represented by any one of the following Ar-a to Ar-i:

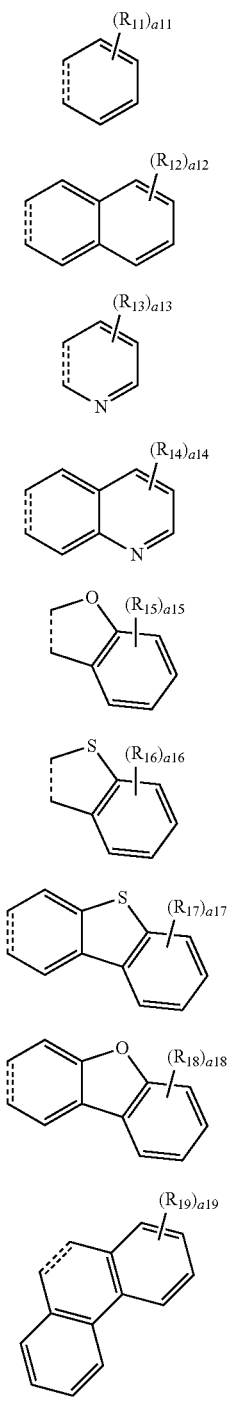

In Ar-a to Ar-i, $R_{11}$ to $R_{19}$ are each independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring, all to a19 are each independently an integer of 0 to 4, and dotted lines represent combined parts forming a condensed ring.

In an embodiment, Formula 1 may be represented by the following Formula 2-1 or Formula 2-2:

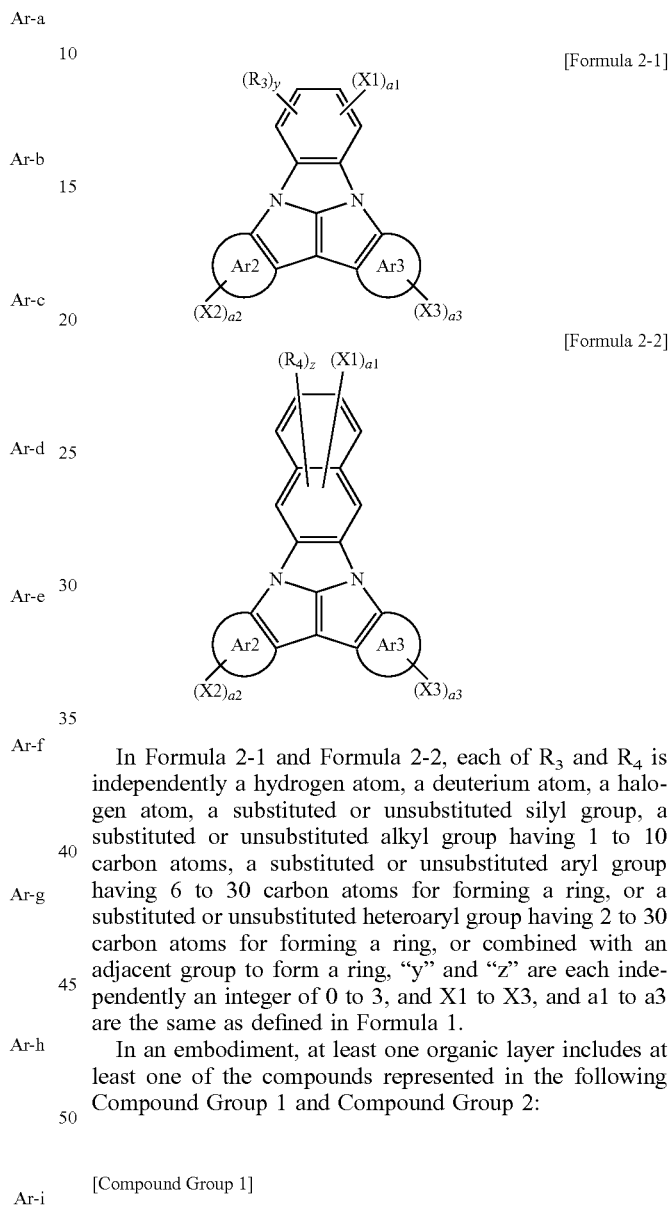

In Formula 2-1 and Formula 2-2, each of $R_3$ and $R_4$ is independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring, "y" and "z" are each independently an integer of 0 to 3, and X1 to X3, and a1 to a3 are the same as defined in Formula 1.

In an embodiment, at least one organic layer includes at least one of the compounds represented in the following Compound Group 1 and Compound Group 2:

[Compound Group 1]

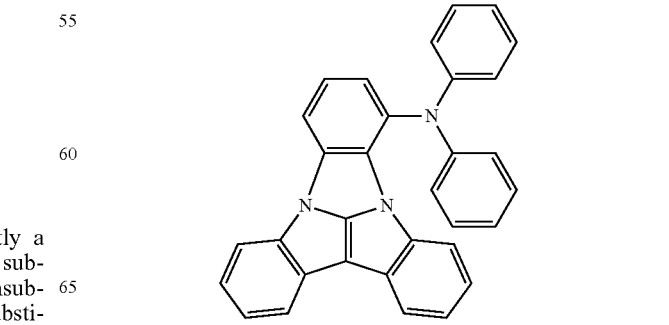

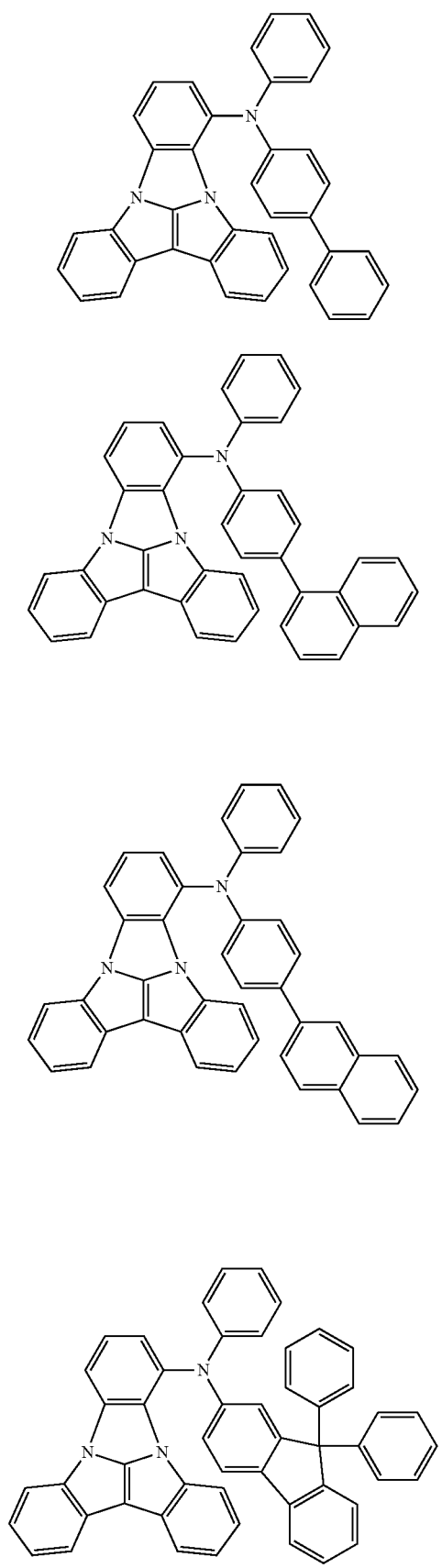
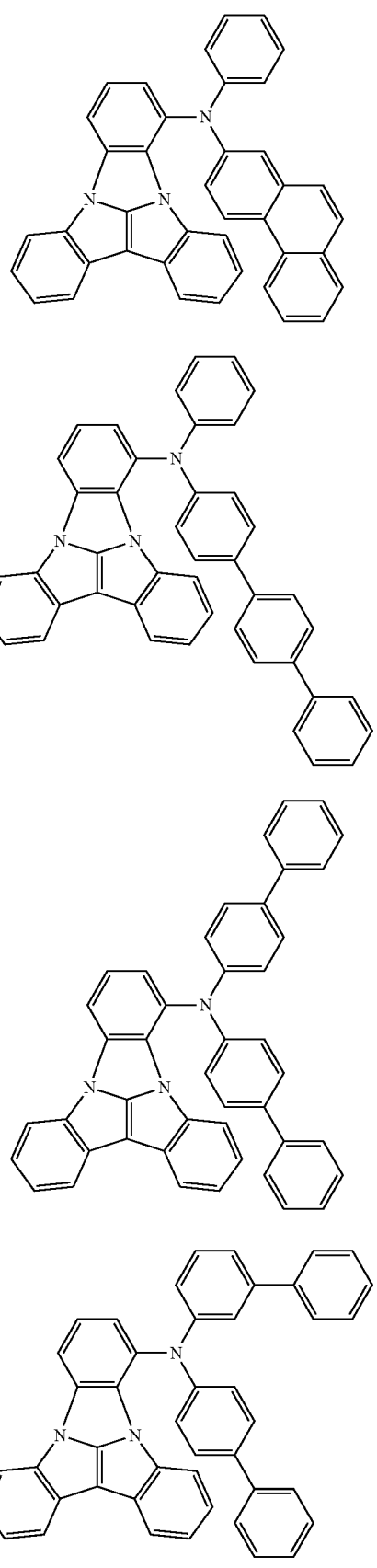

A10
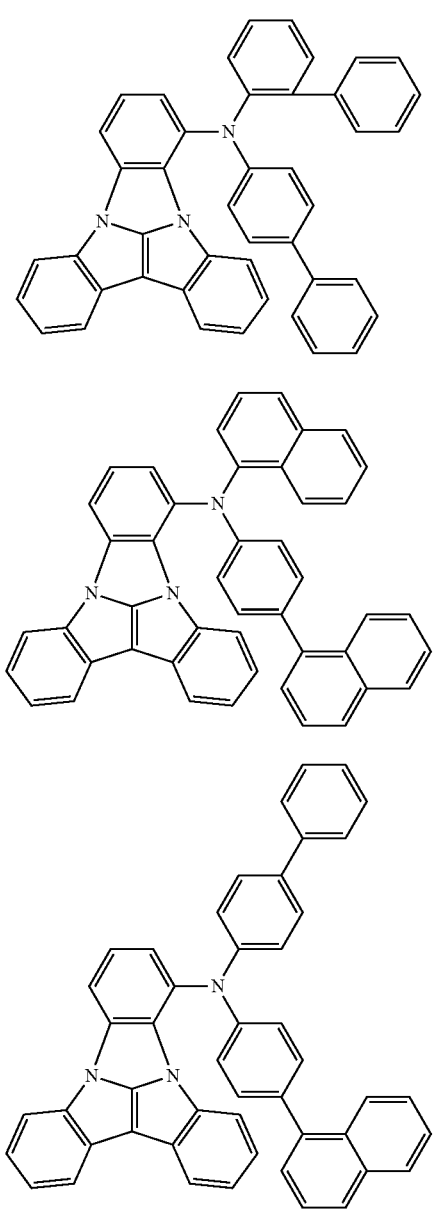
A11
A12
A13
A14
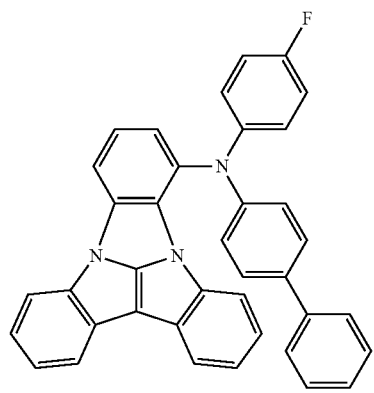
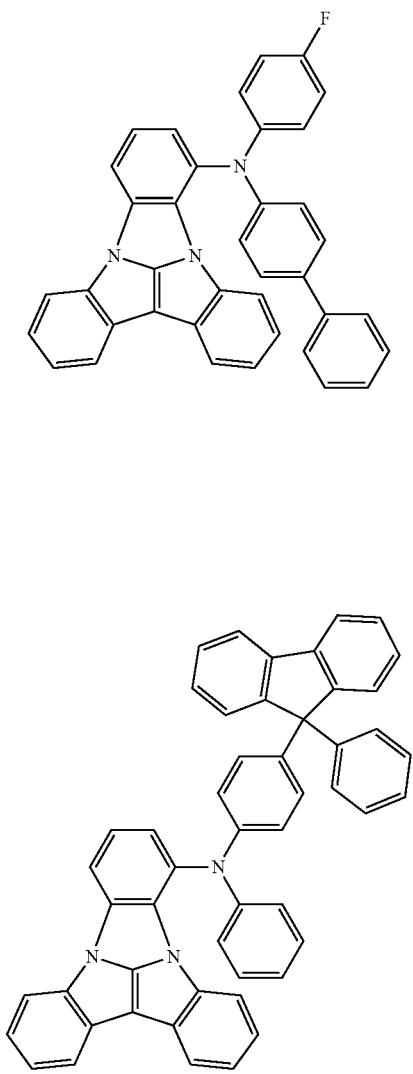
A15
A16
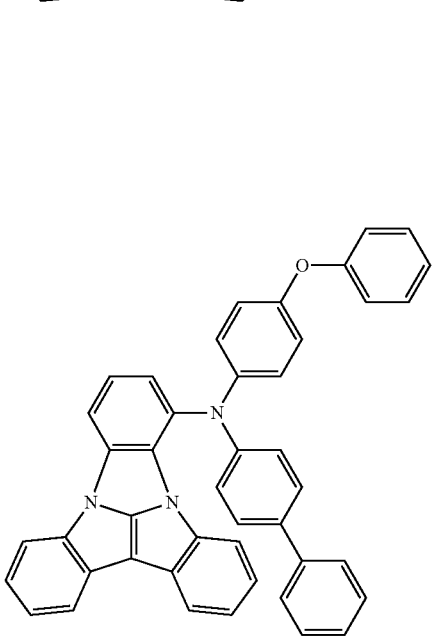

A17
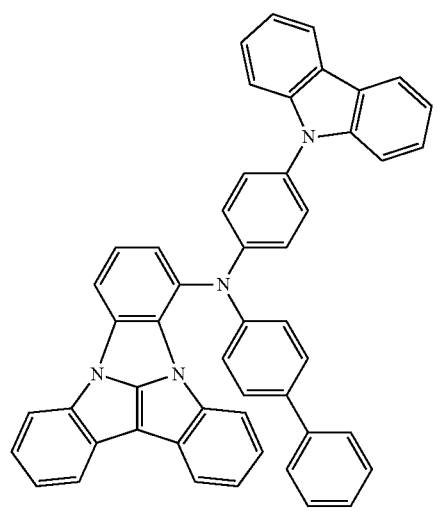
A18
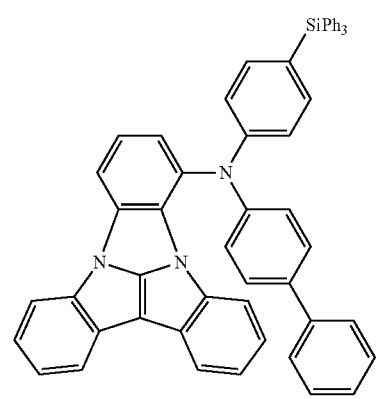
A19
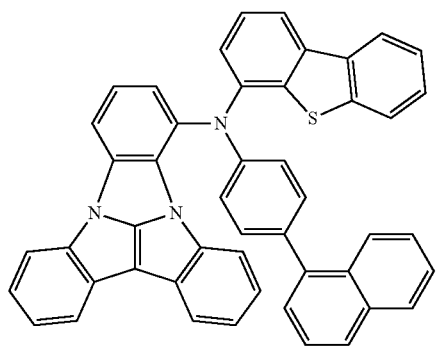
A20
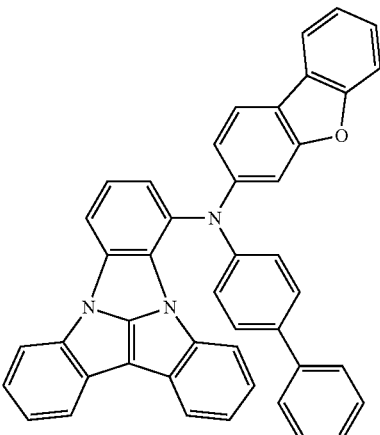
A21
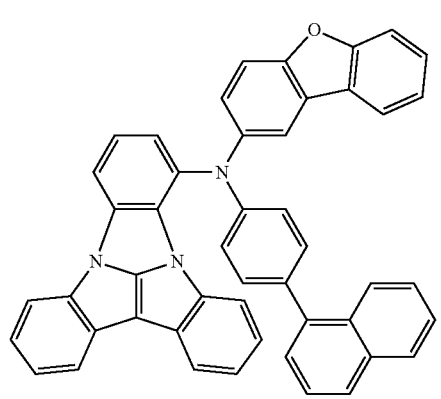
A22
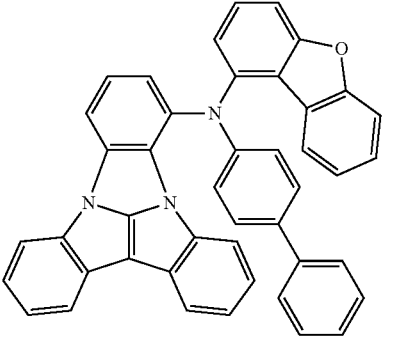
A23
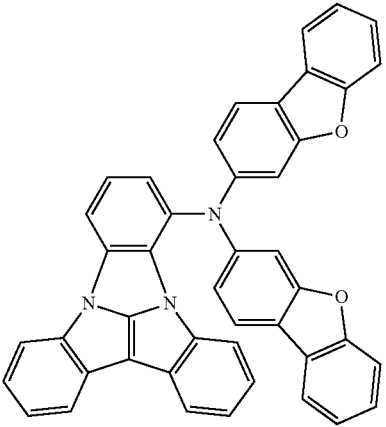

A24
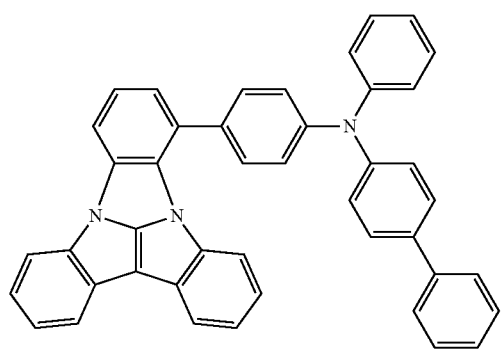
A25
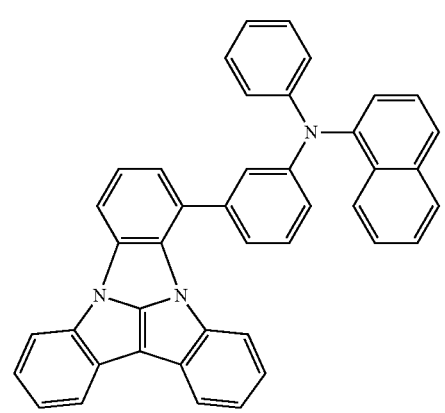
A26
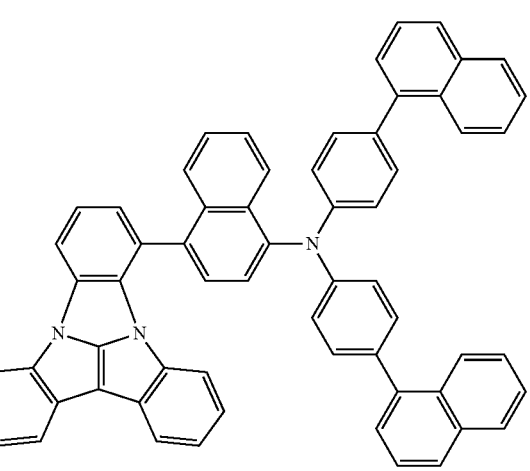
A27
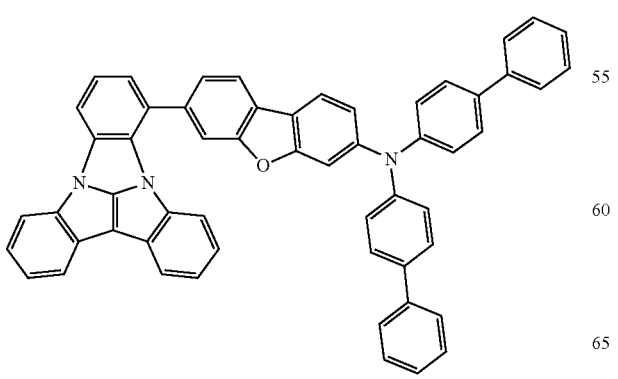
A28
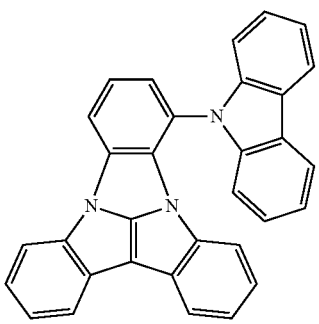
A29
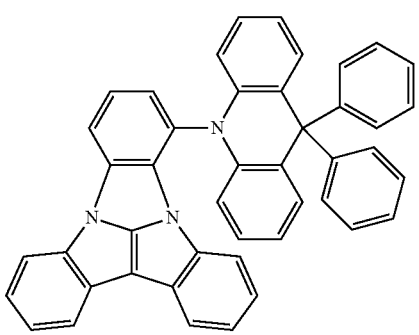
A30
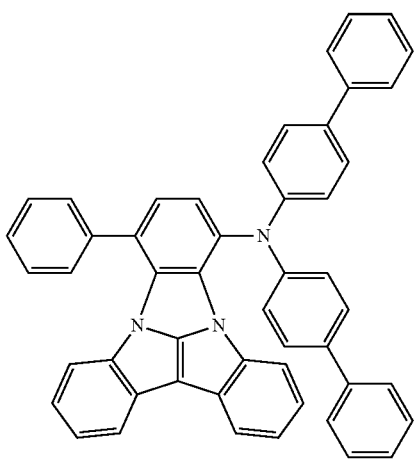
A31
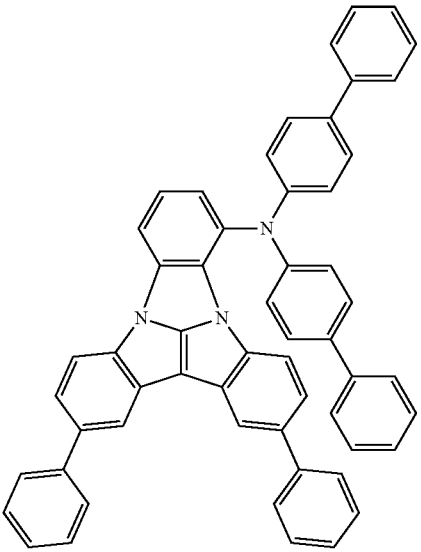

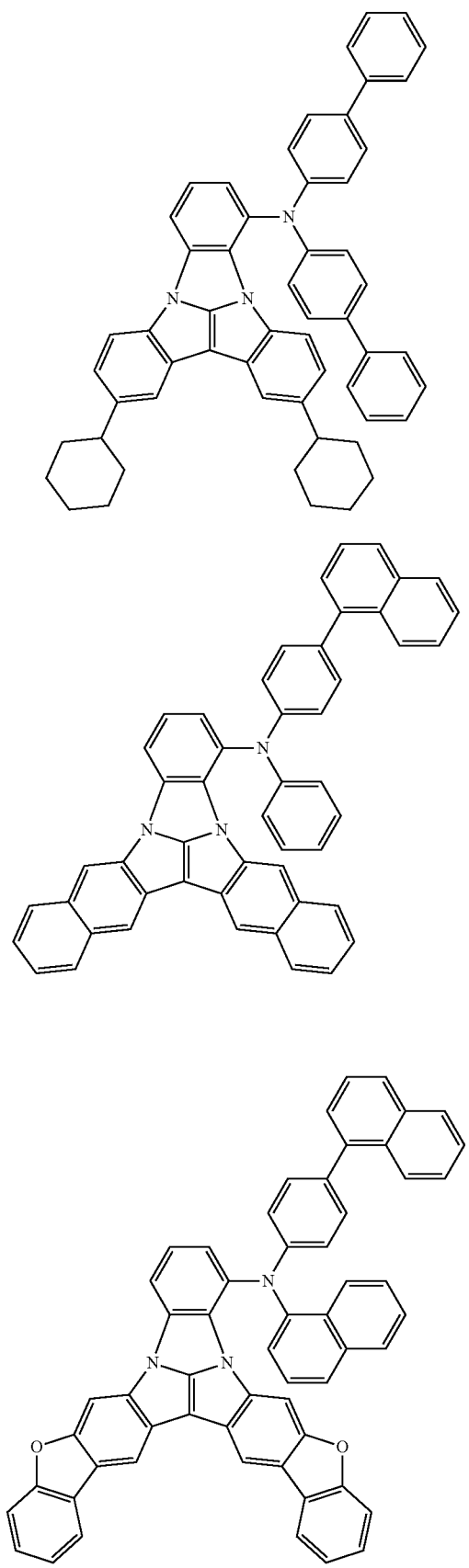
A32
A33
A34
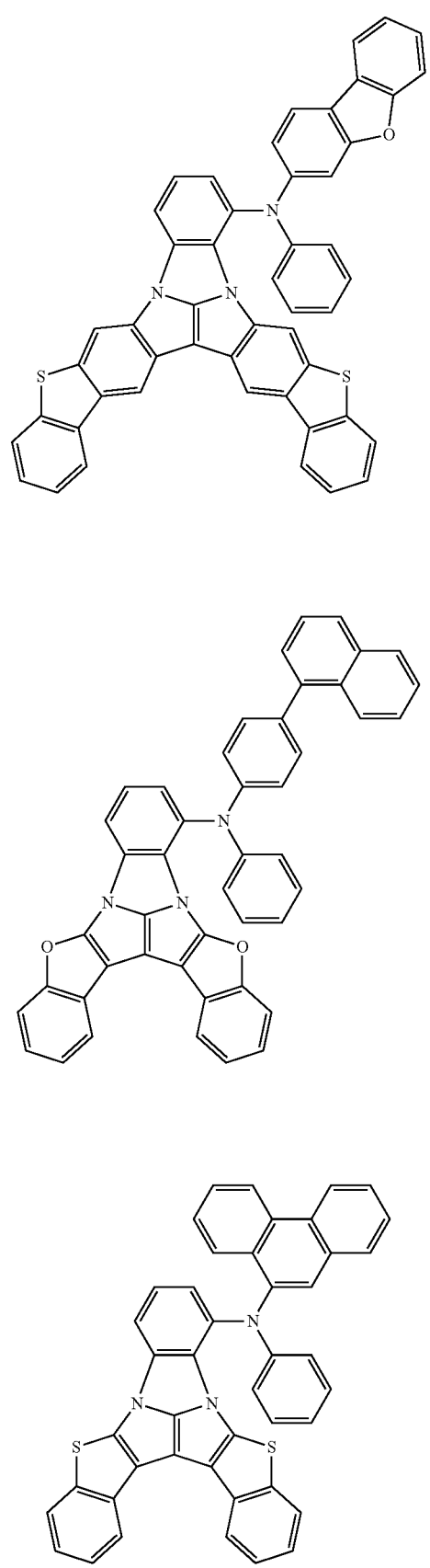
A35
A36
A37

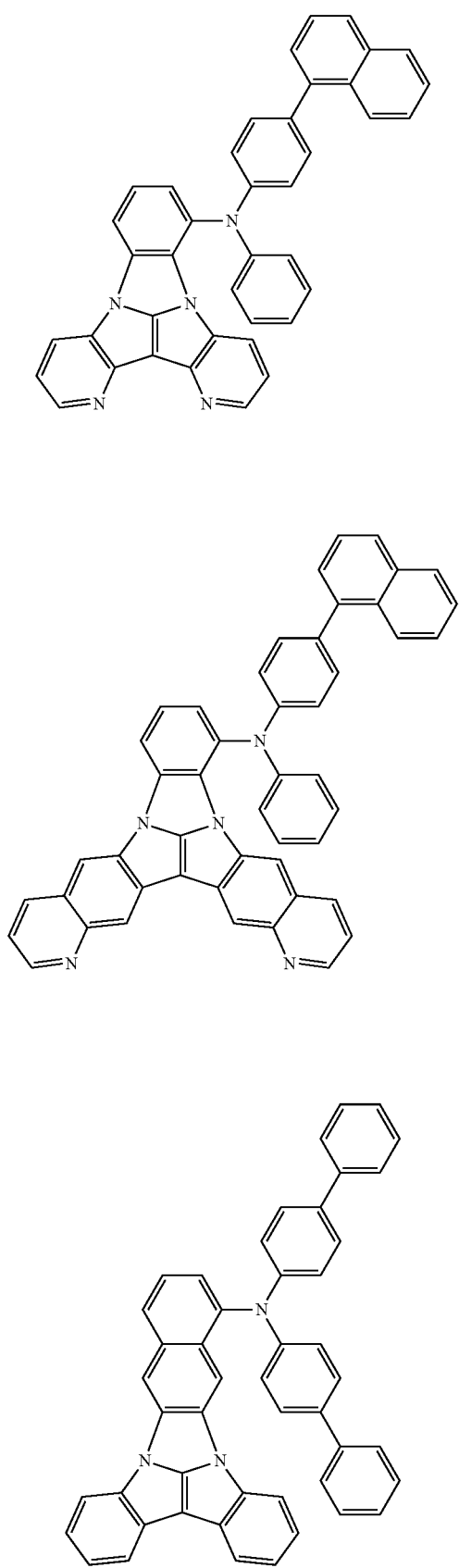
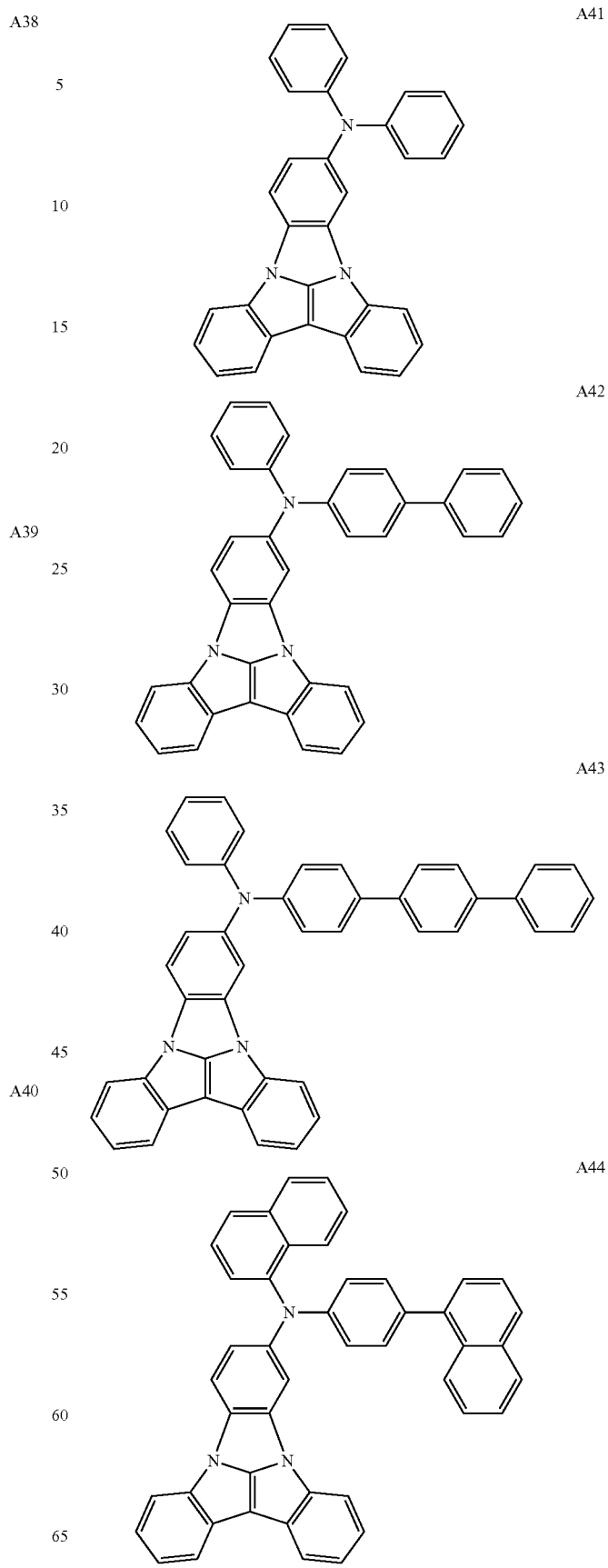

A45
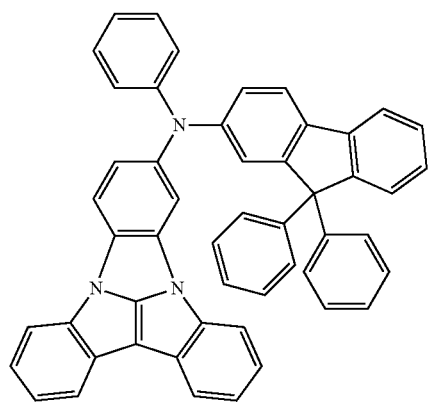
A46
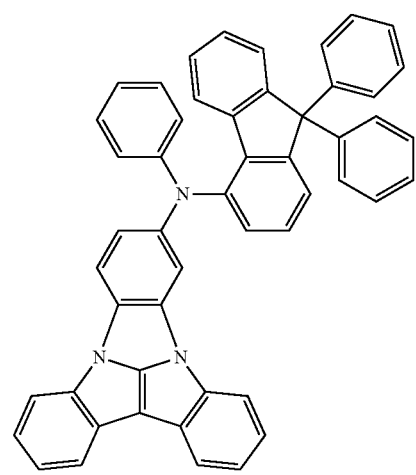
A47
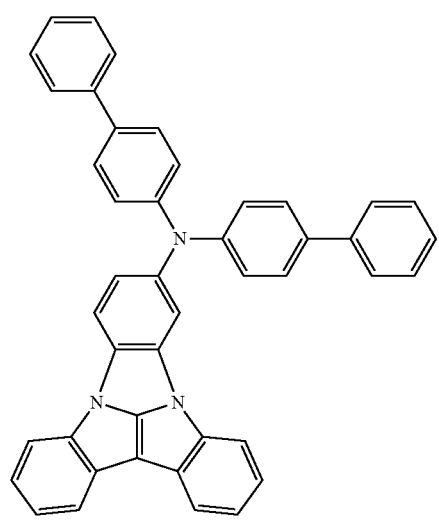
A48
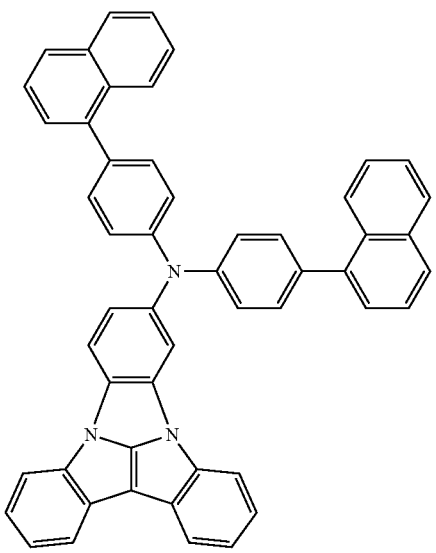
A49
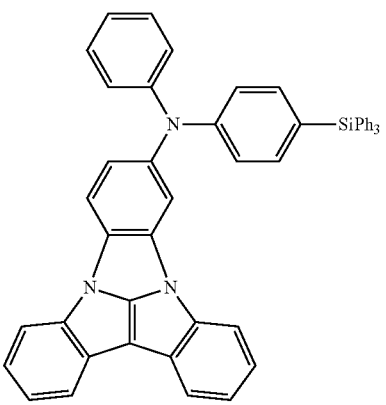
A50
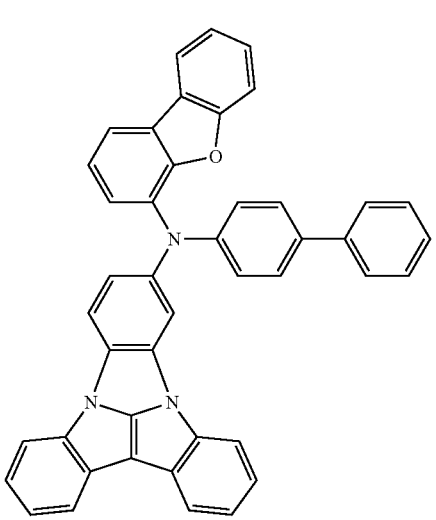

-continued
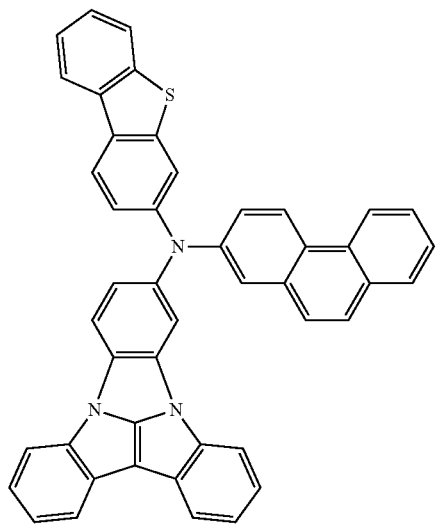
A51
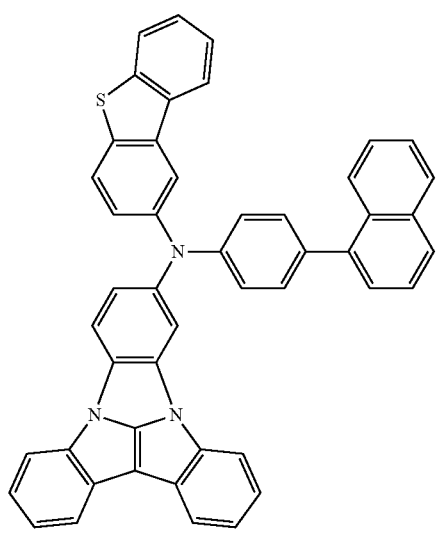
A52
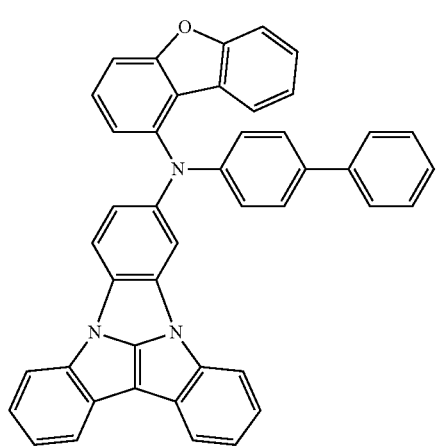
A53
-continued
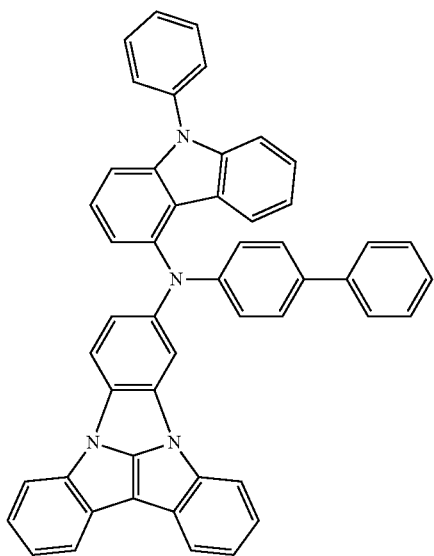
A54
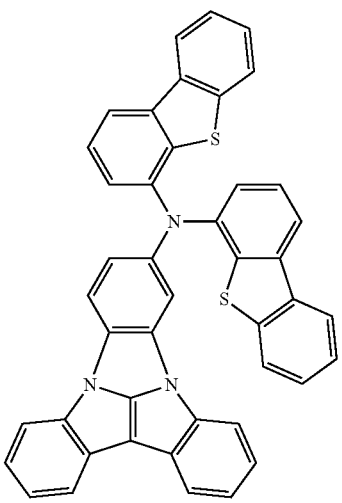
A55
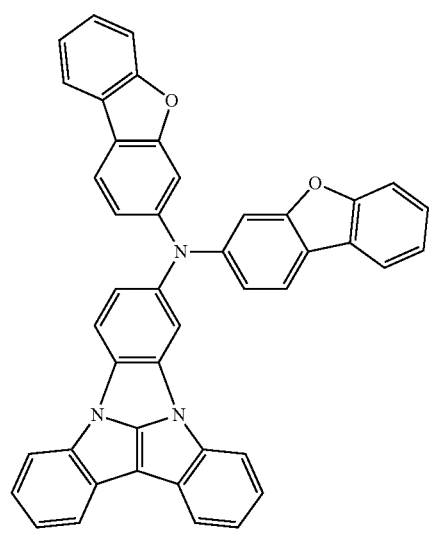
A56

A57
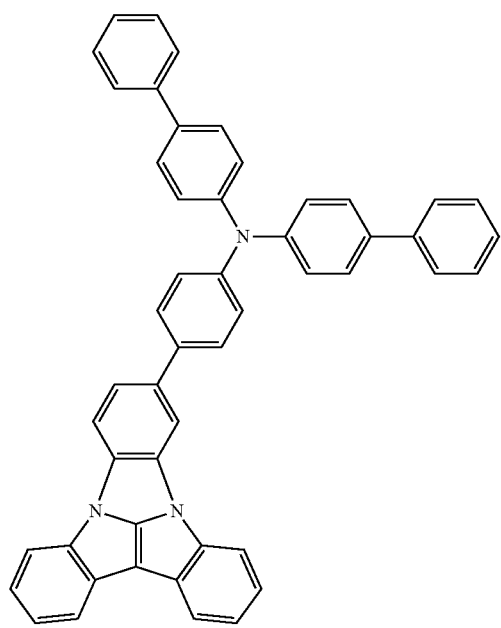
A59
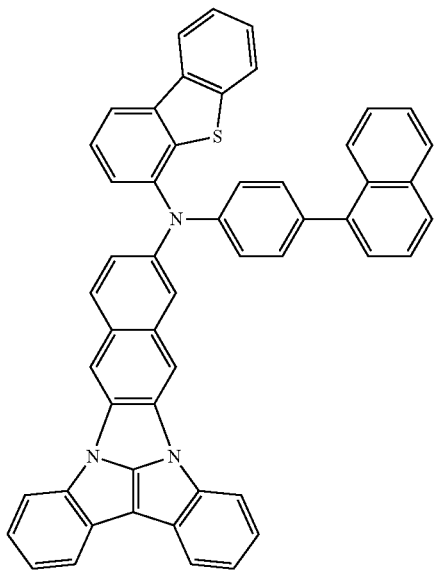
A58
A60
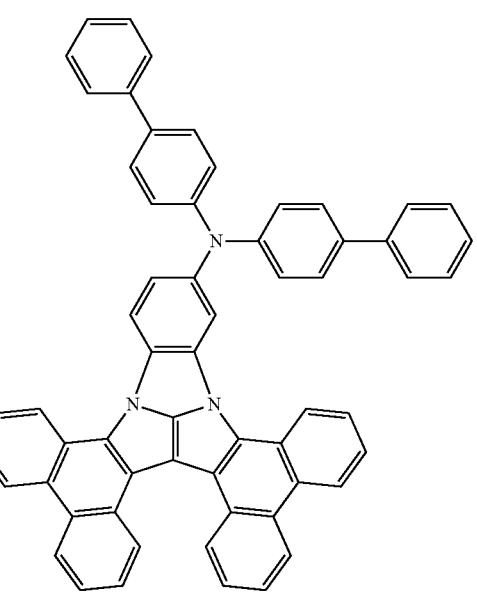

A61
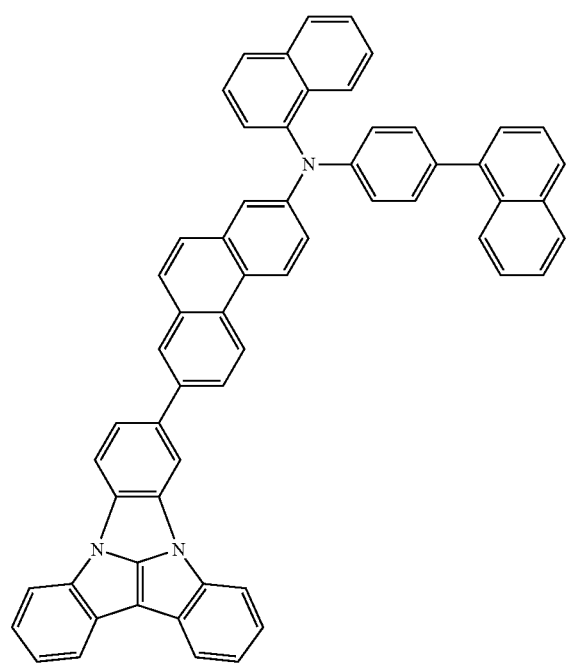
A62
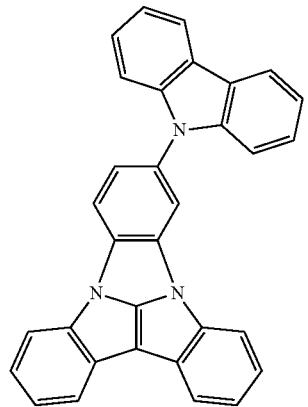
A63
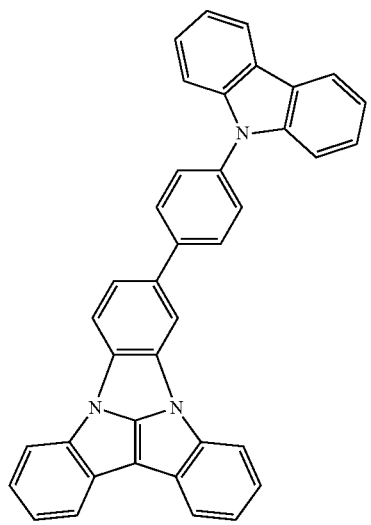
A64
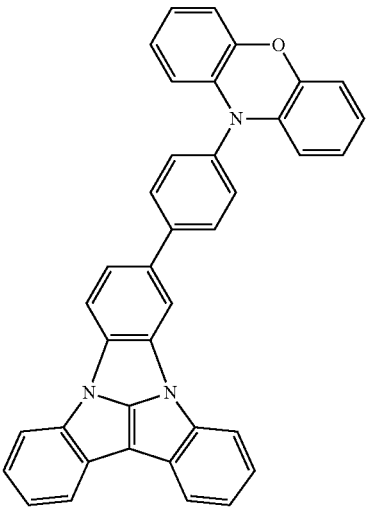
[Compound Group 2]
B1
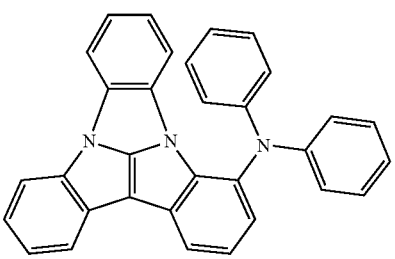
B2
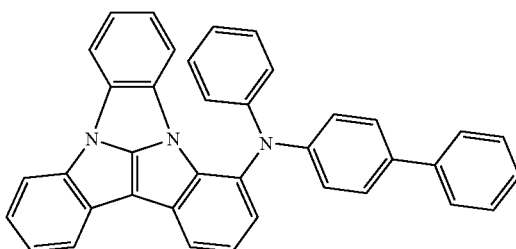
B3
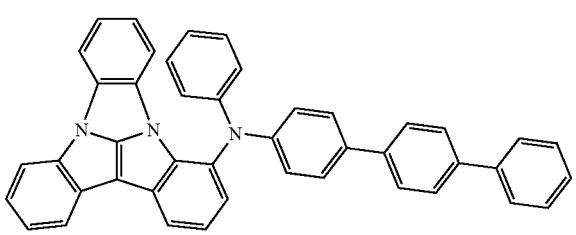
B4
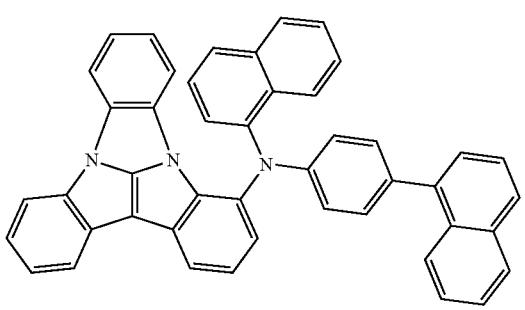

B5
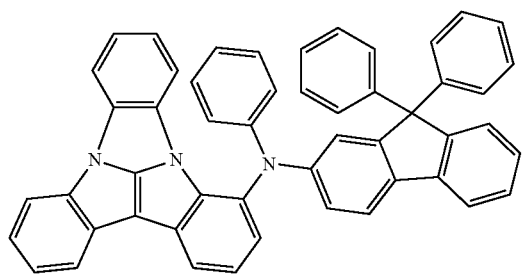
B6
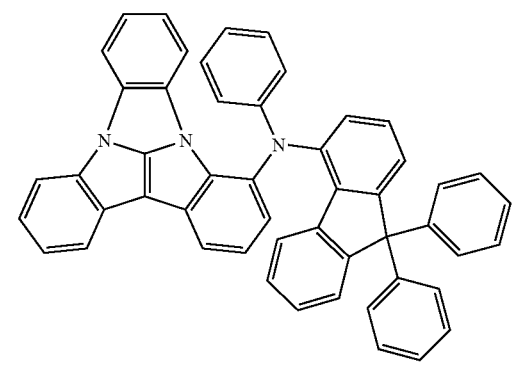
B7
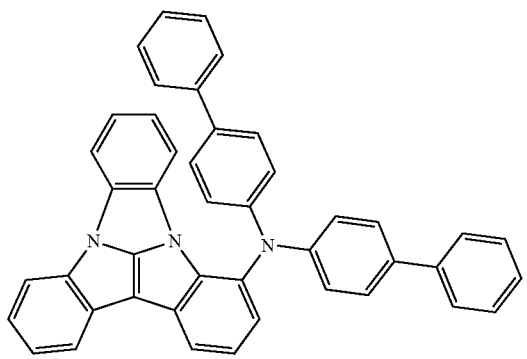
B8
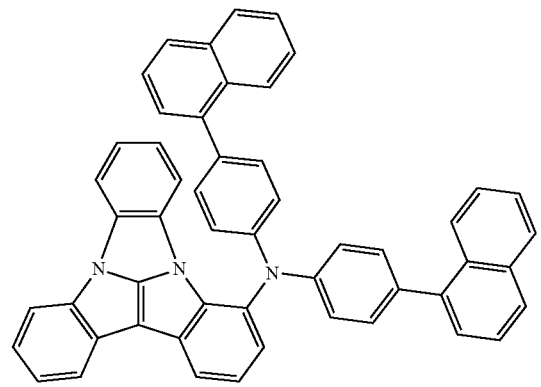
B9
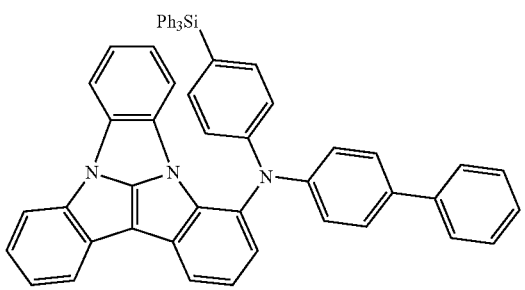
B10
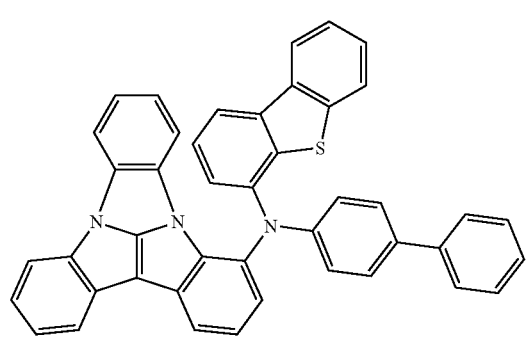
B11
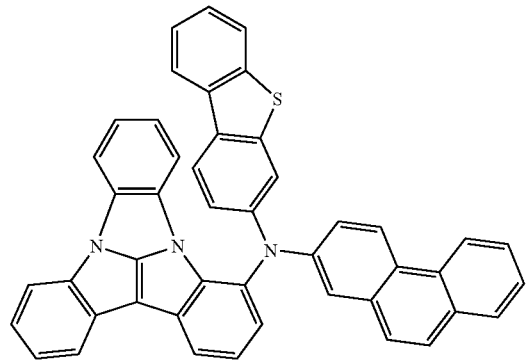
B12
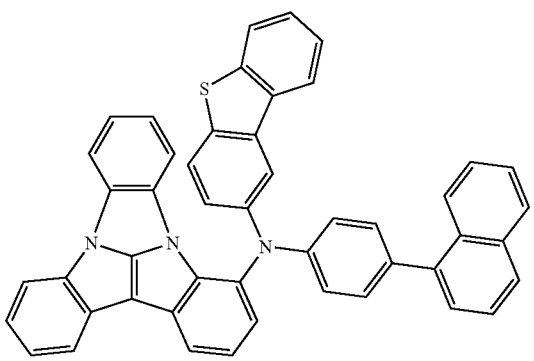

-continued
B13
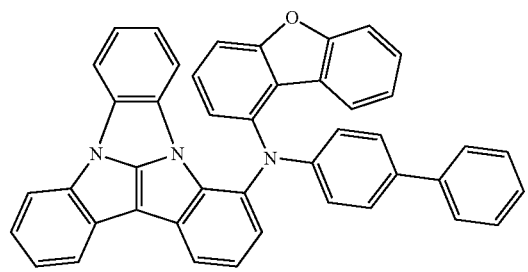
B14
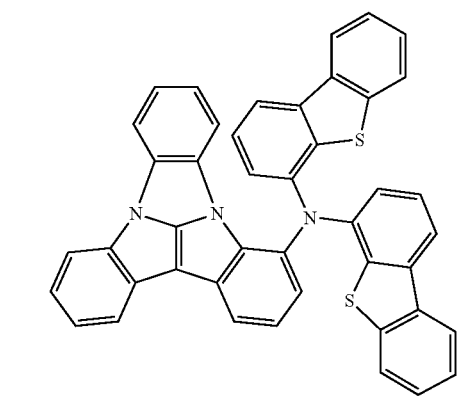
B17
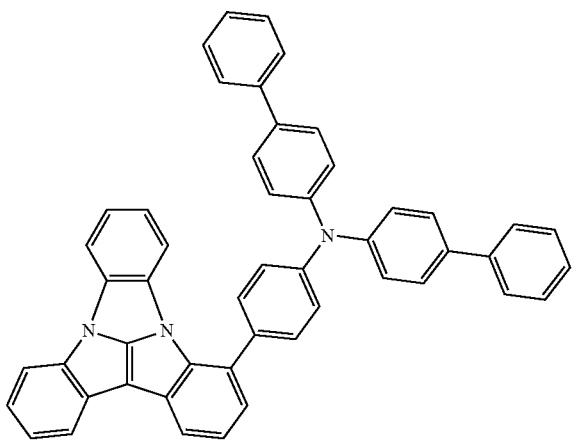
B18
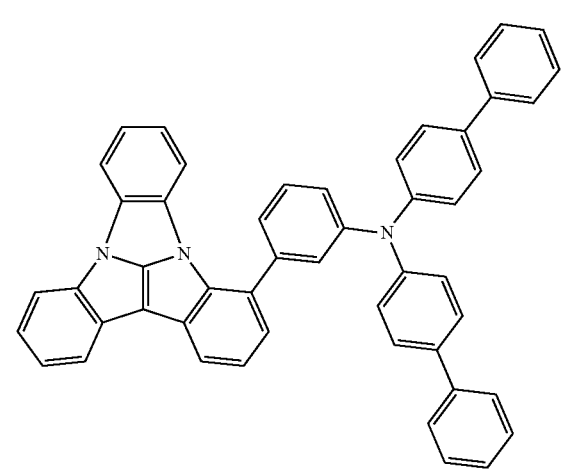
B19
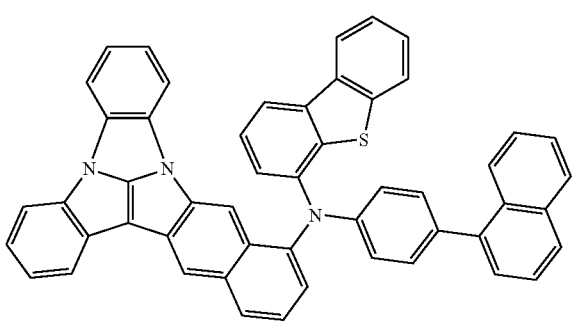
B16
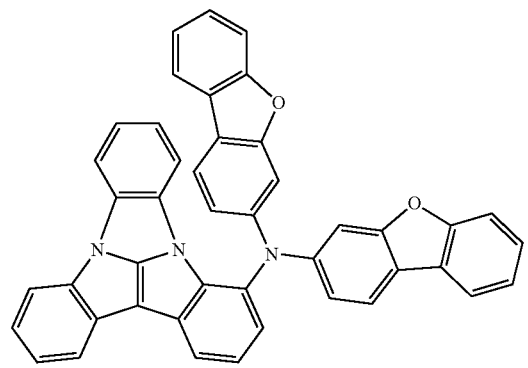
B20
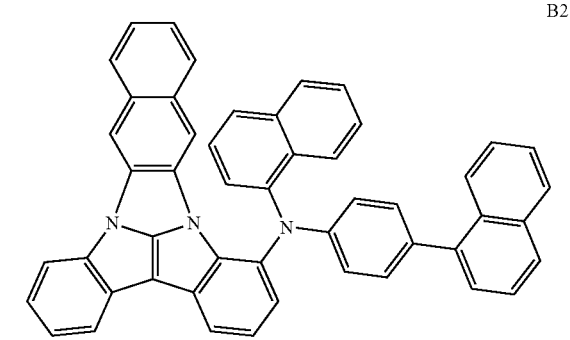

-continued
B21
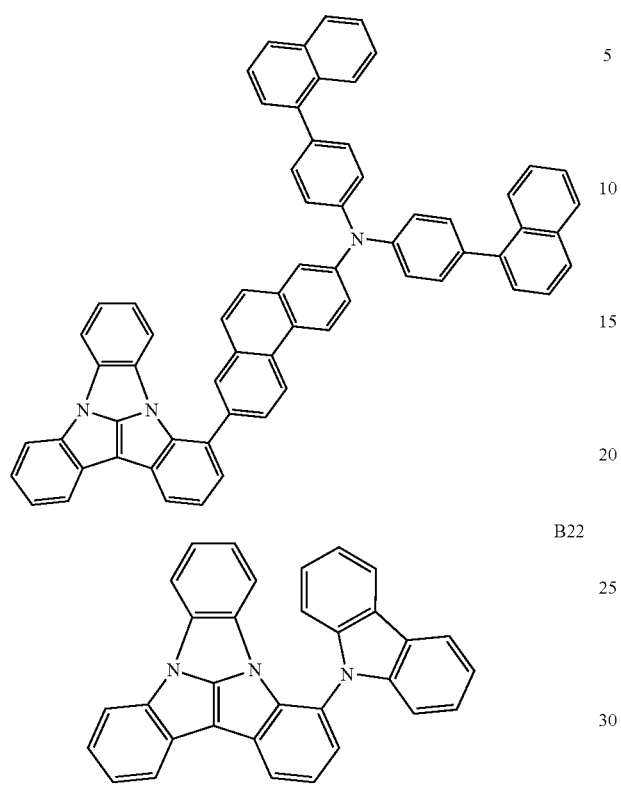
B22
B23
B24
B25
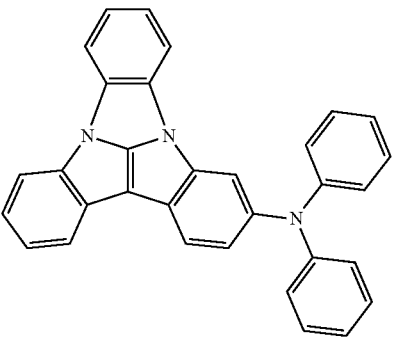
B26
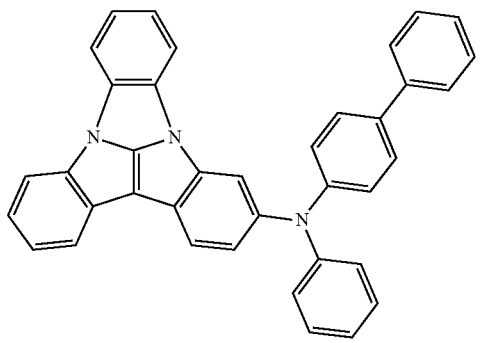
B27
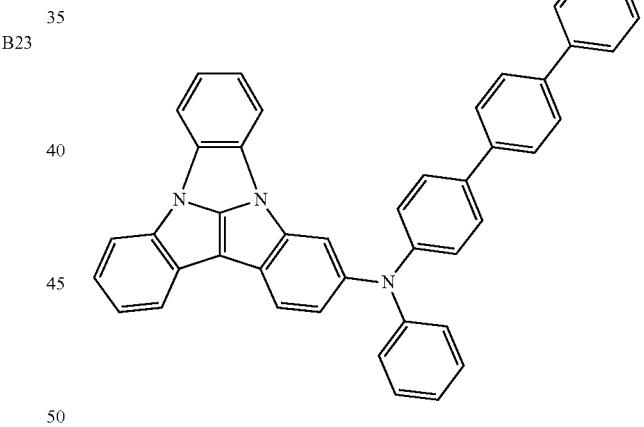
B28
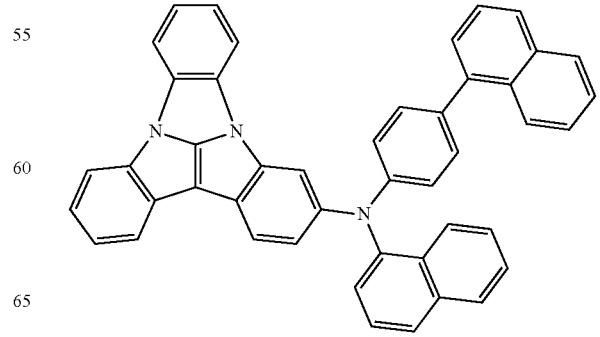

B29
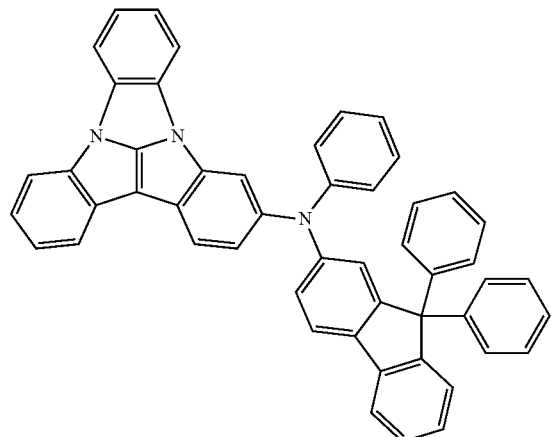
B30
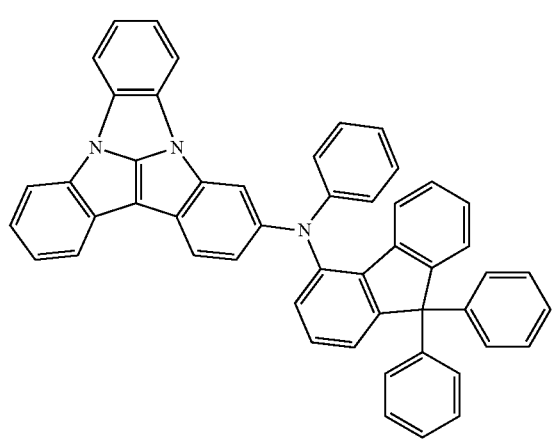
B31
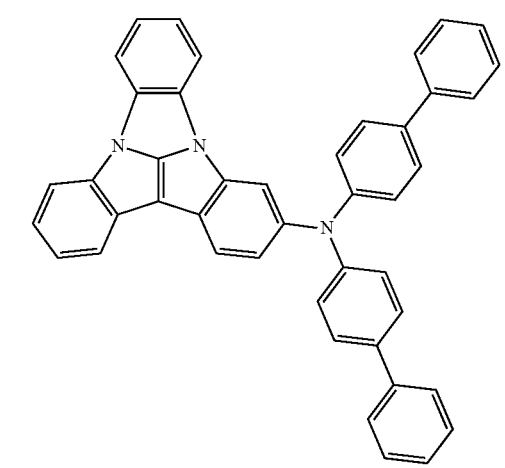
B32
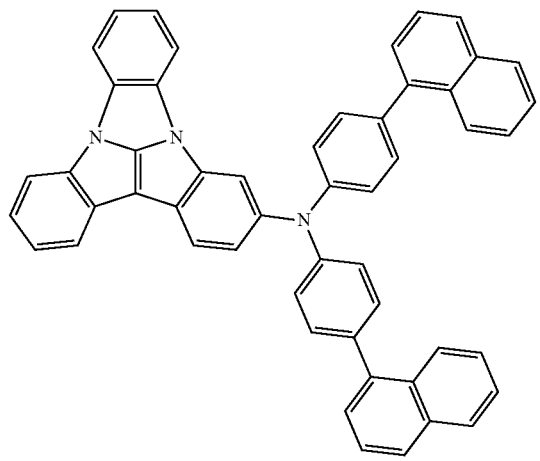
B33
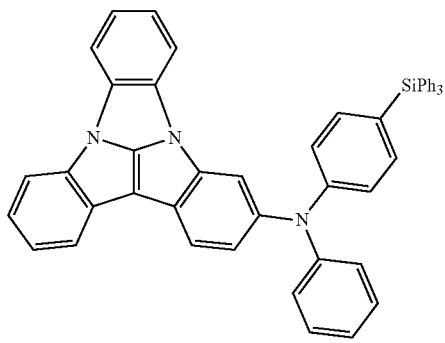
B34
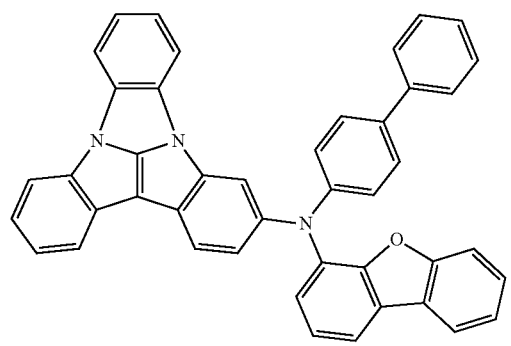
B35
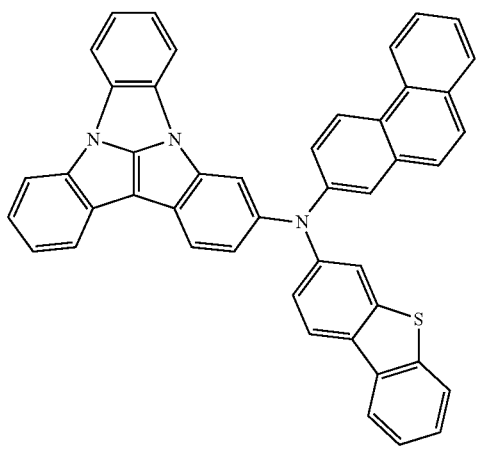

B36
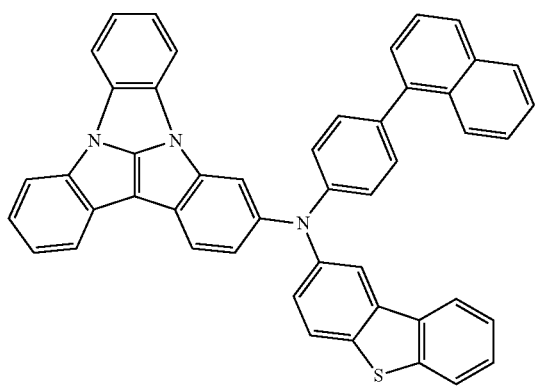
B37
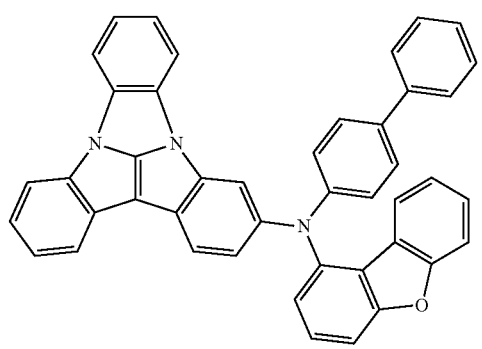
B38
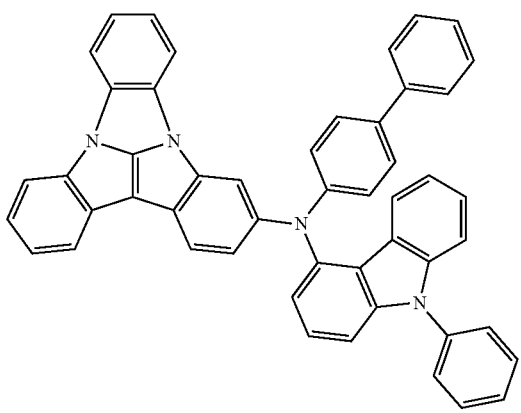
B39
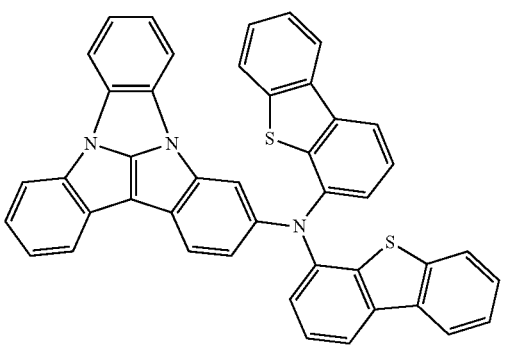
B40
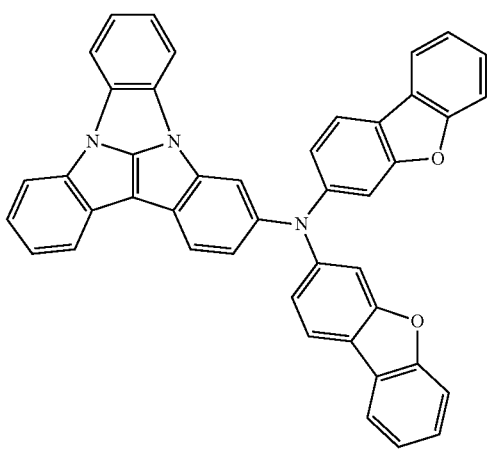
B41
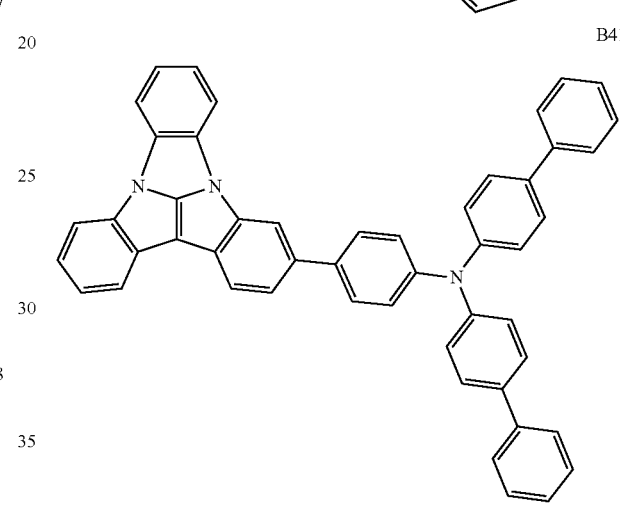
B42
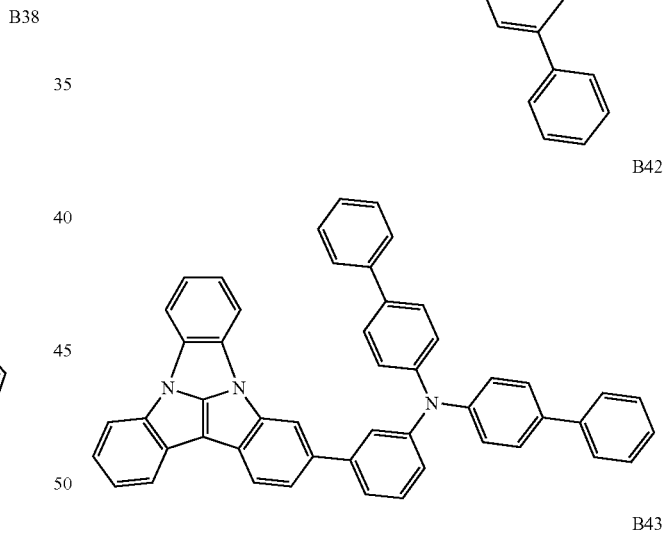
B43
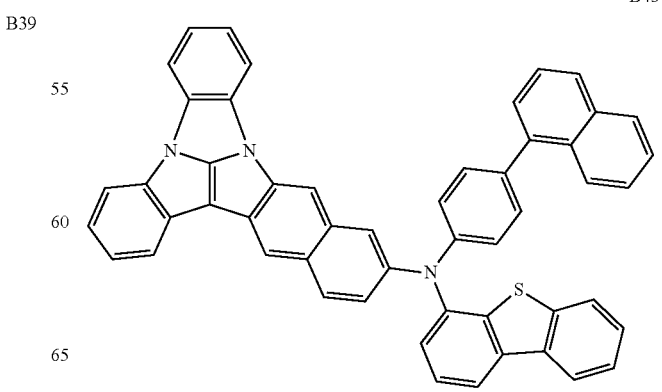

B44
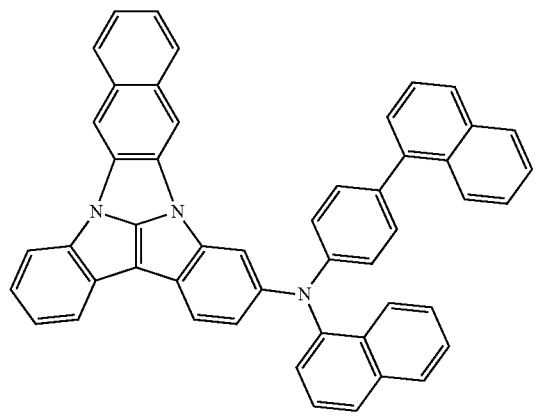
B45
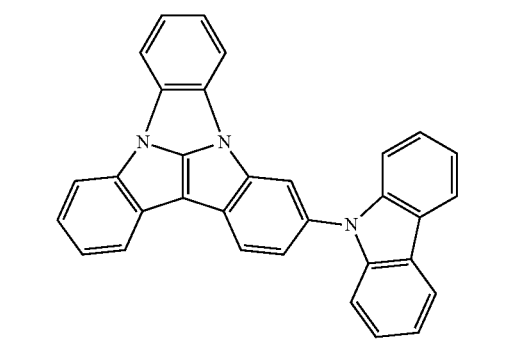
B46
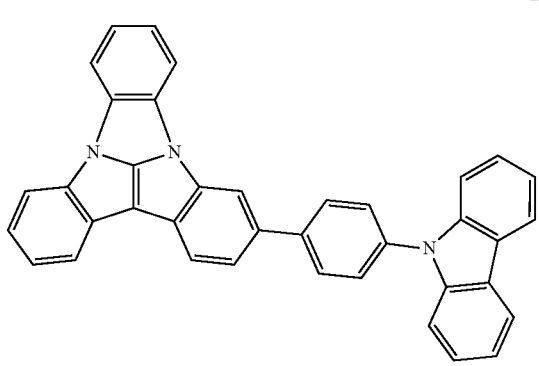
B47
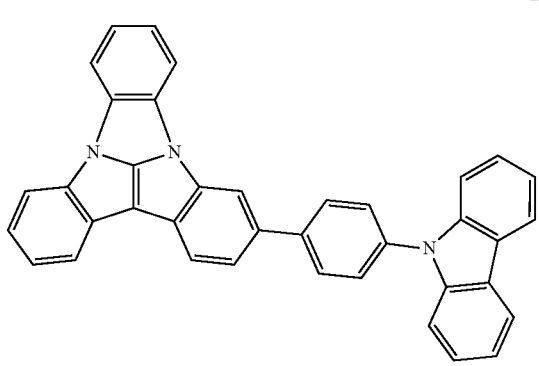
B48
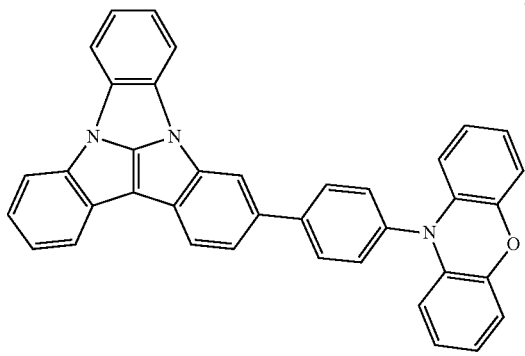
B49
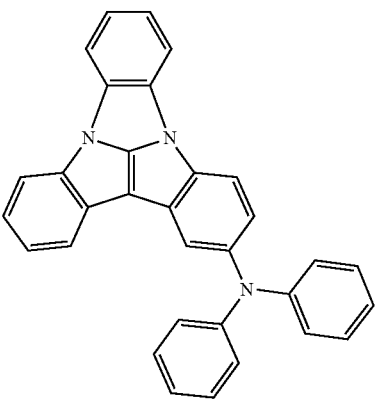
B50
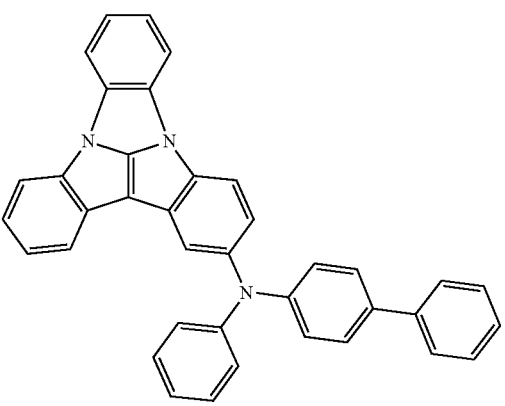
B51
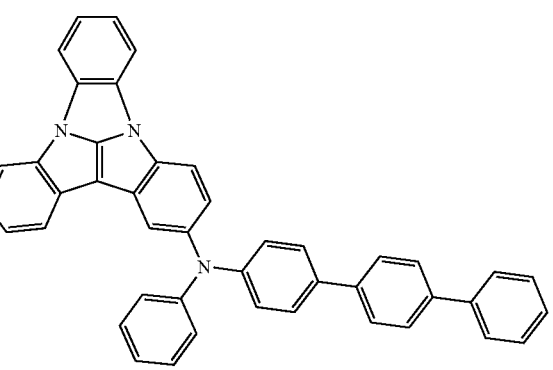

B52
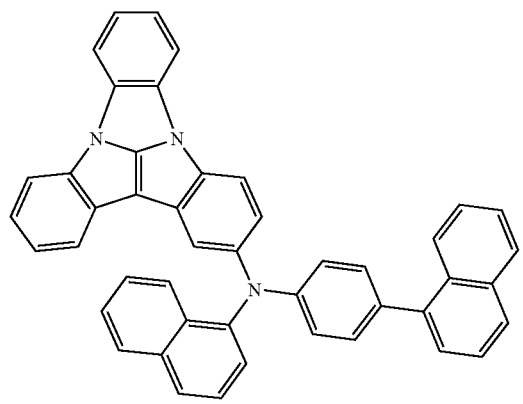
B55
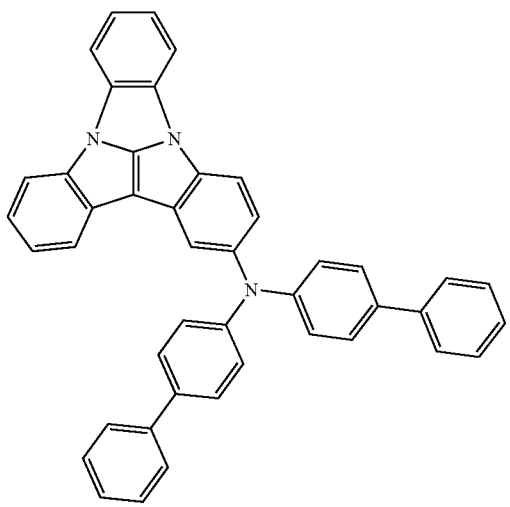
B53
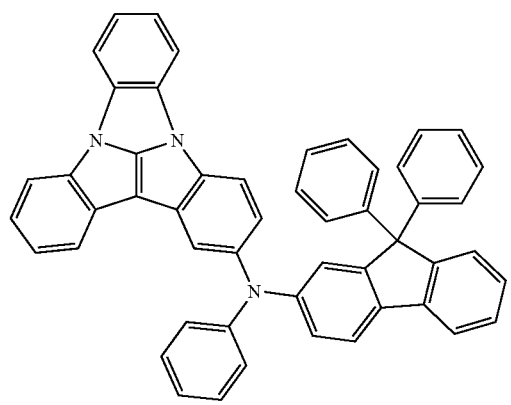
B56
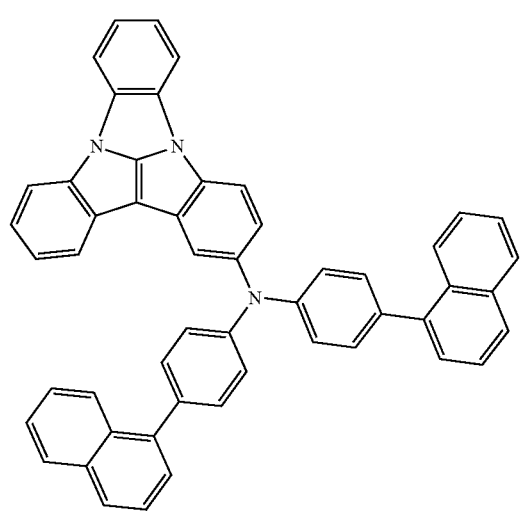
B54
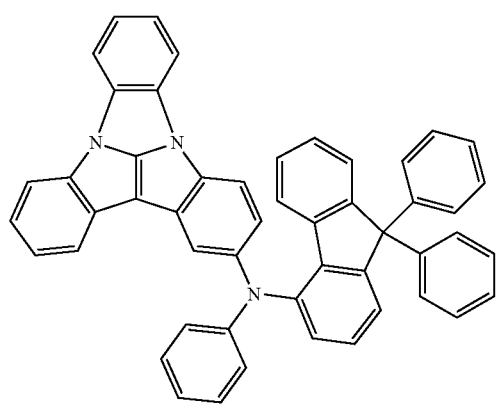
B57
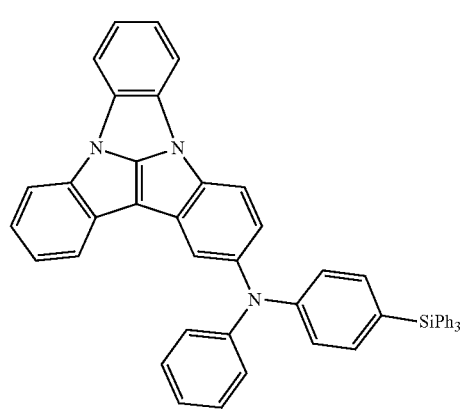

B58
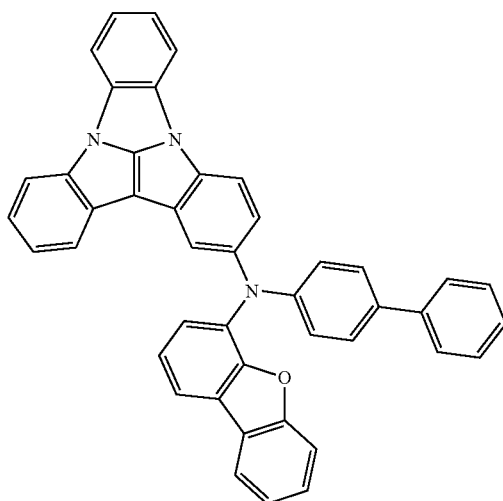
B59
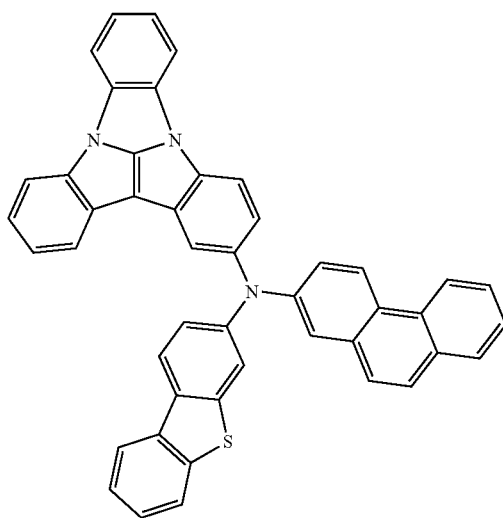
B60
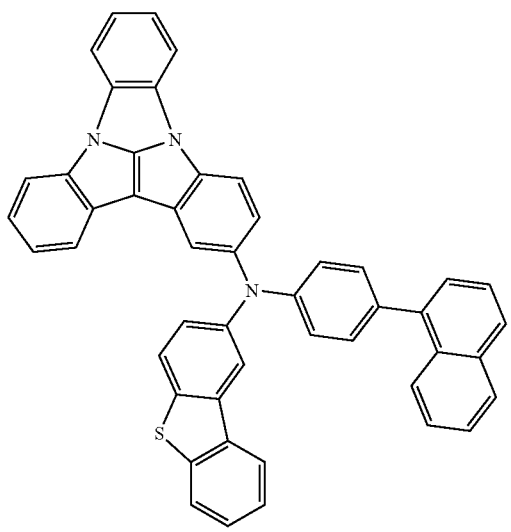
B61
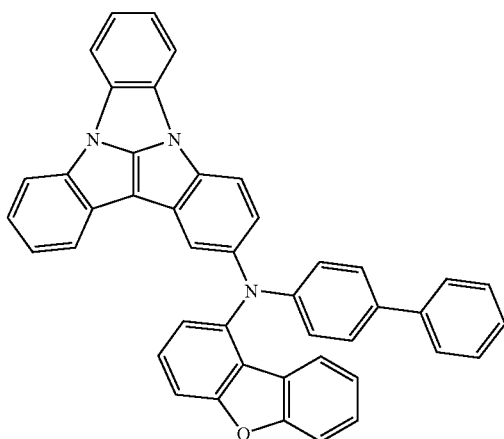
B62
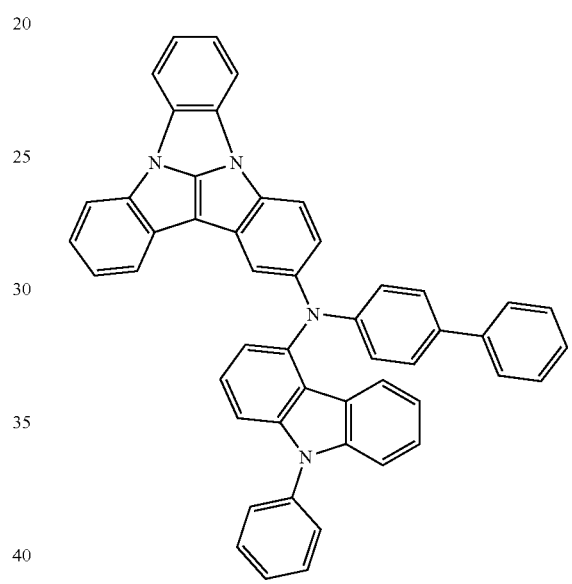
B63
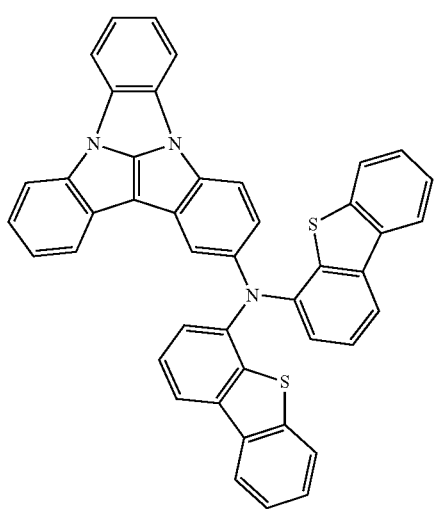

B64
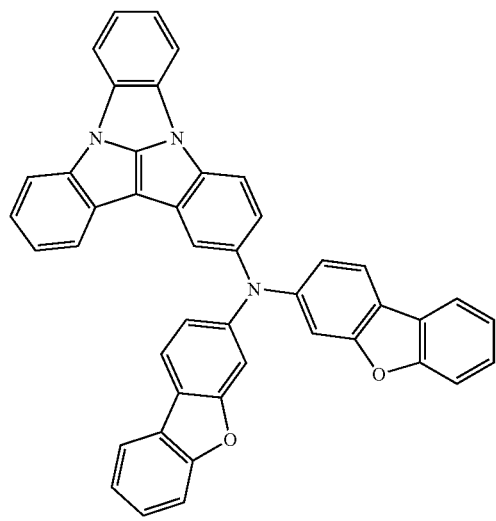
B65
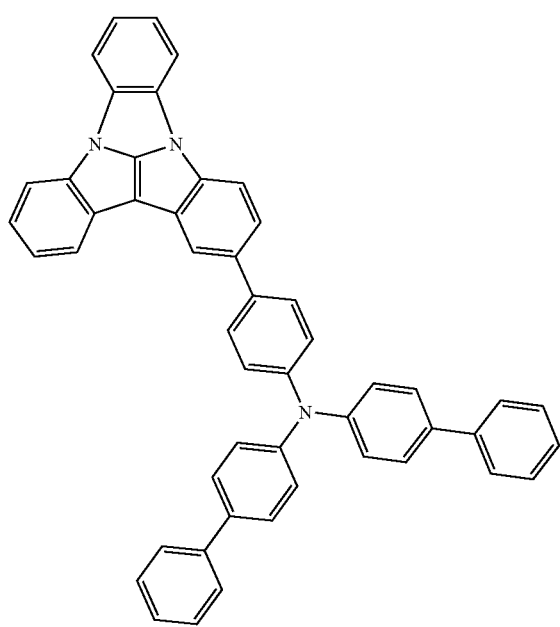
B66
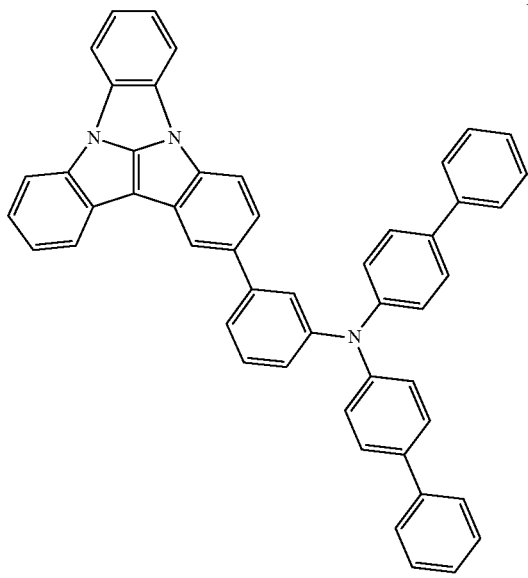
B67
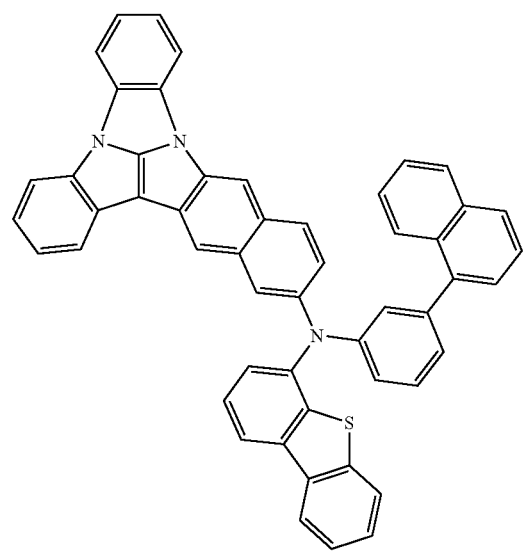
B68
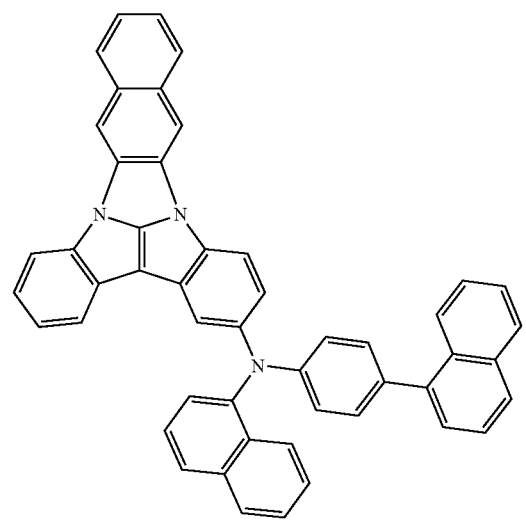

B69
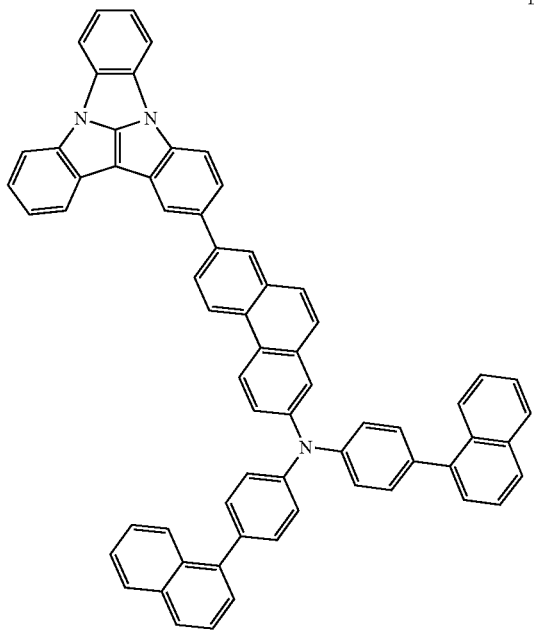
B72
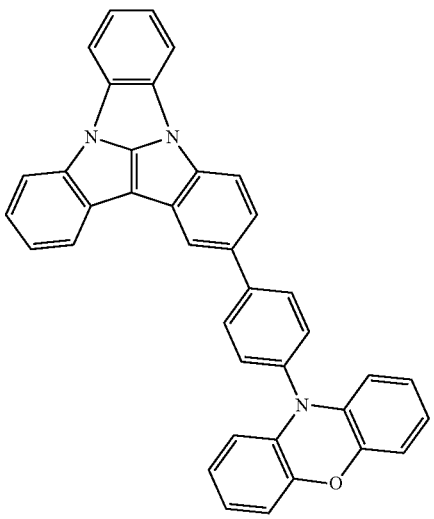
B70
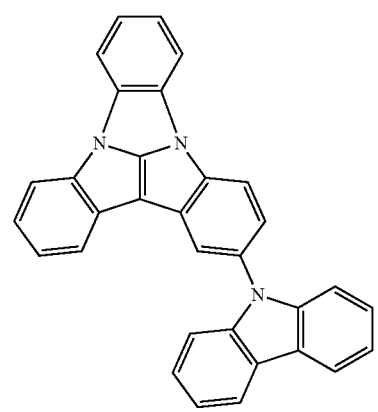
B73
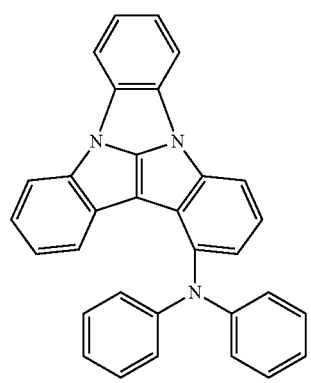
B71
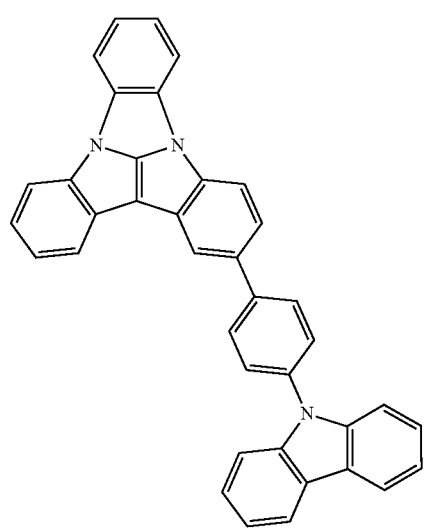
B74
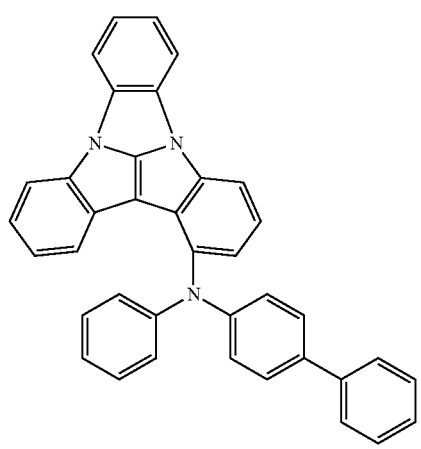

-continued
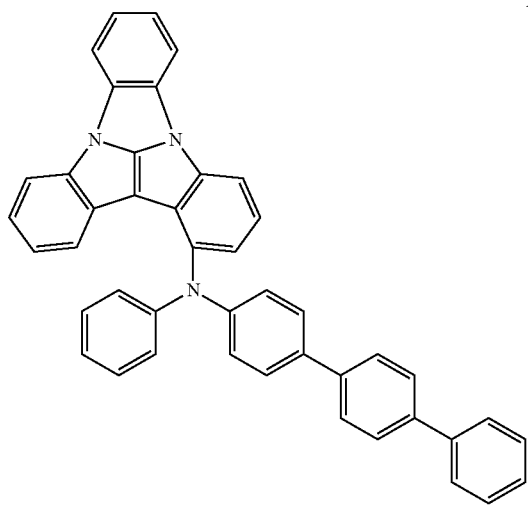
B75
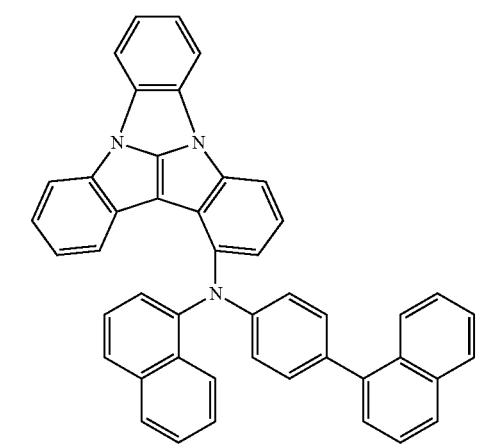
B76
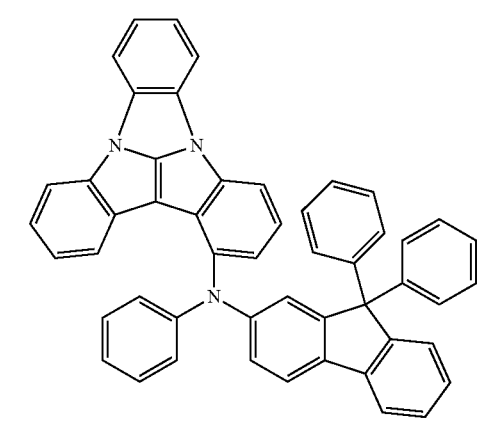
B77
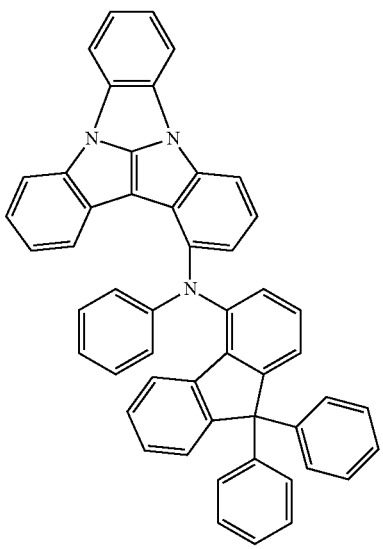
B78
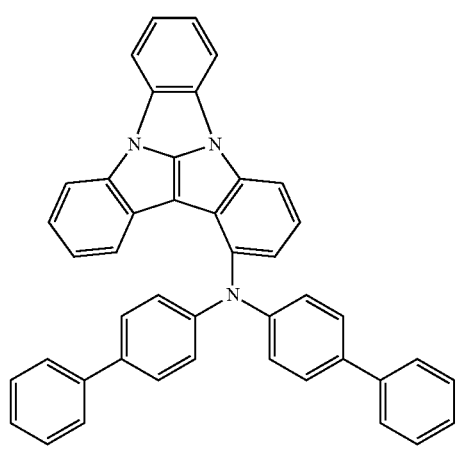
B79
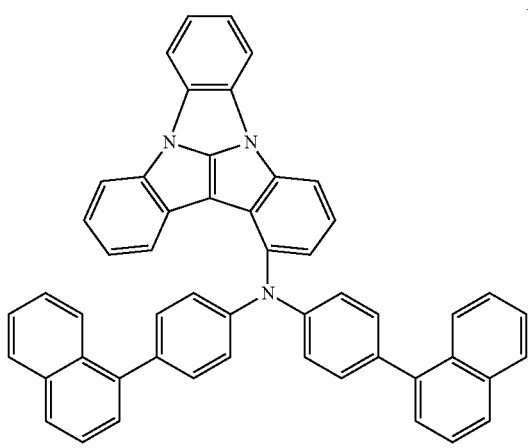
B80

B81 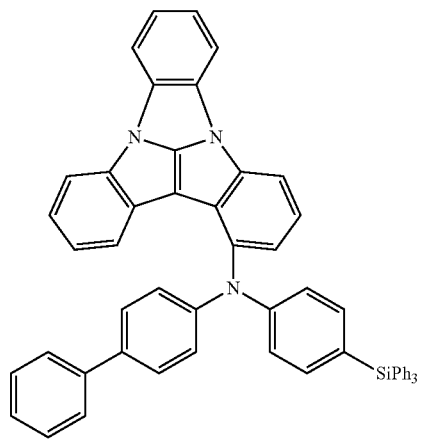
B84 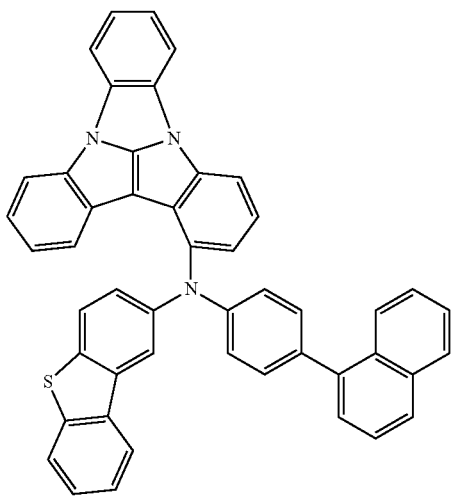
B82 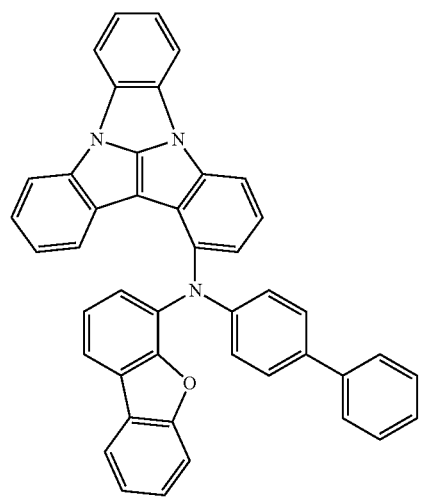
B85 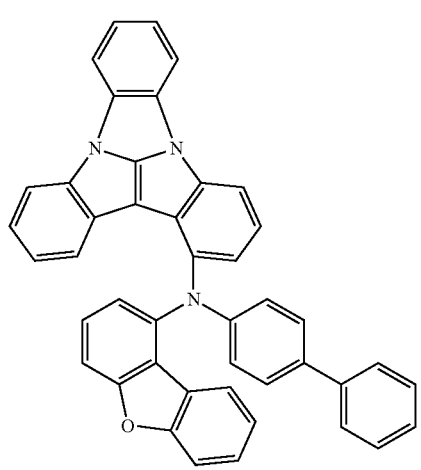
B83 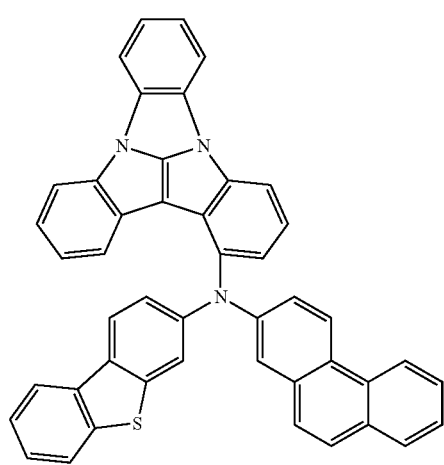
B86 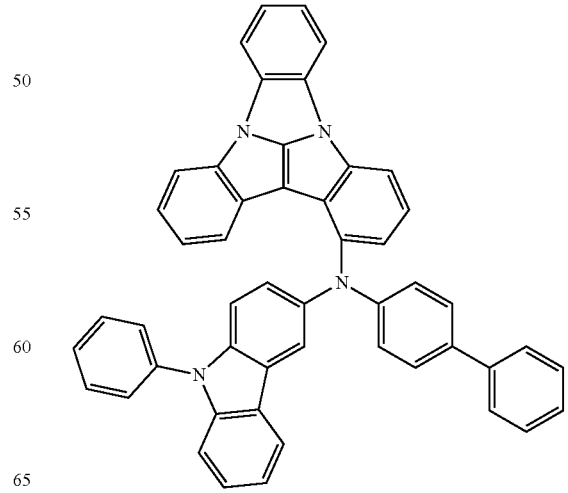

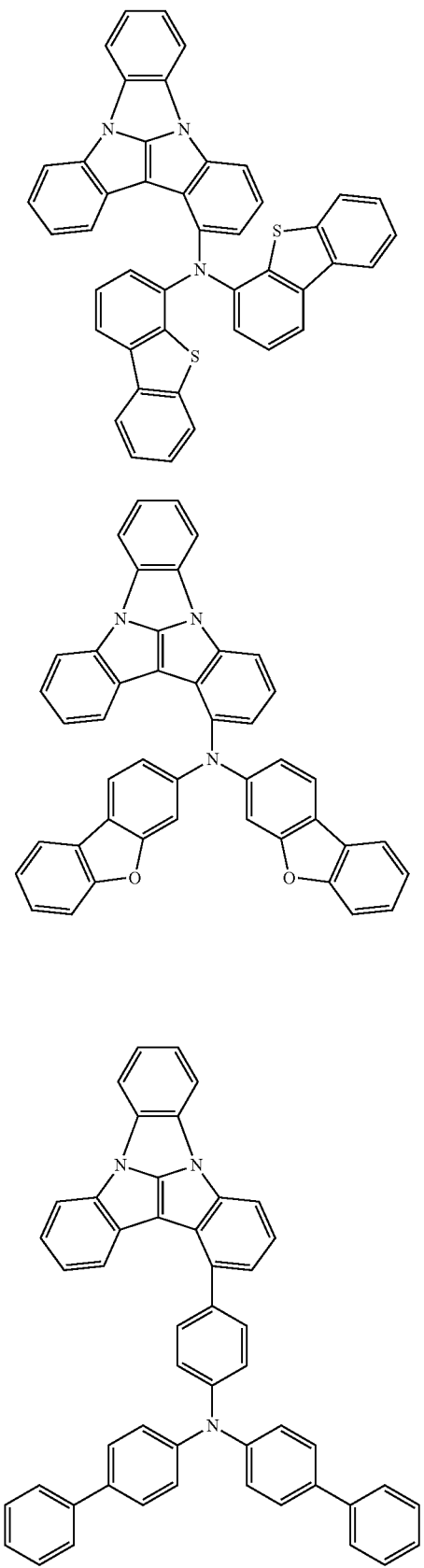
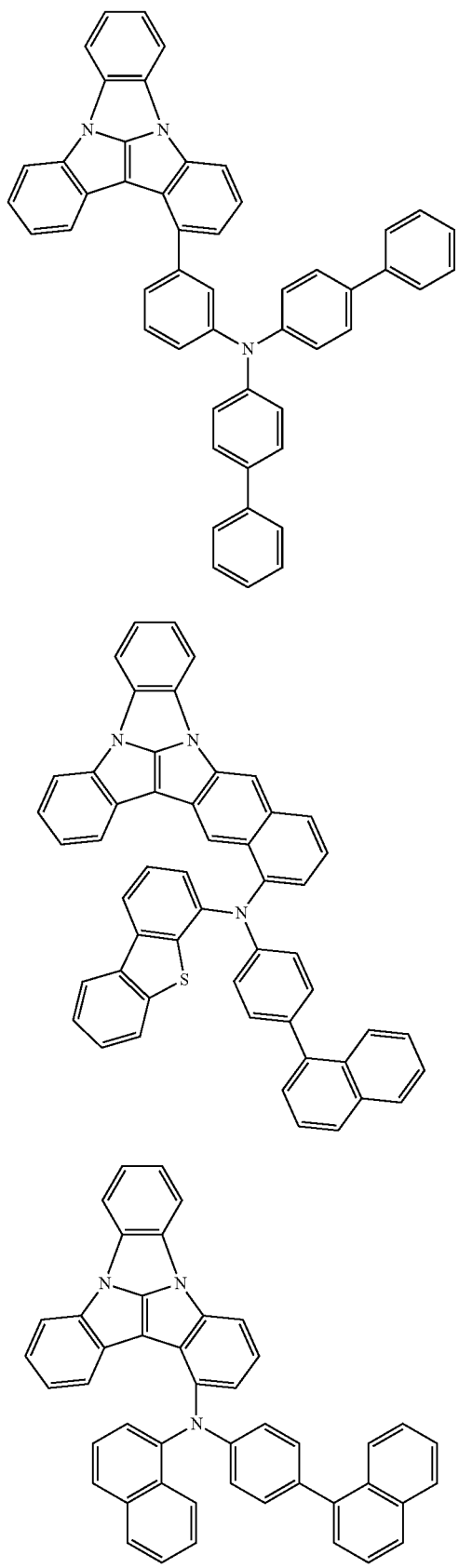

-continued

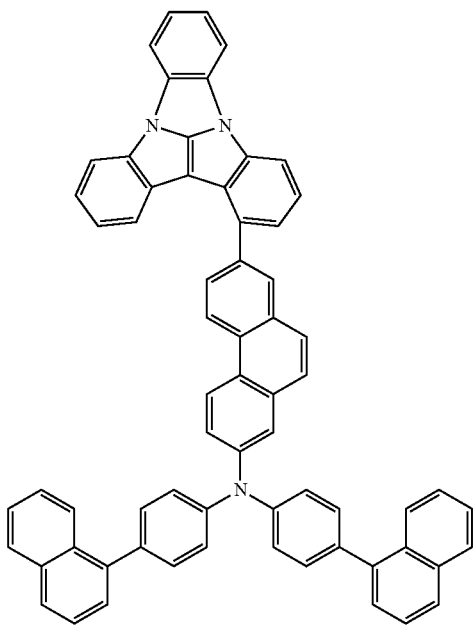
B93

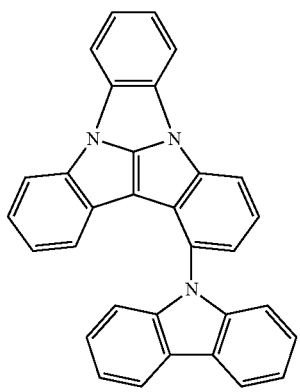
B94

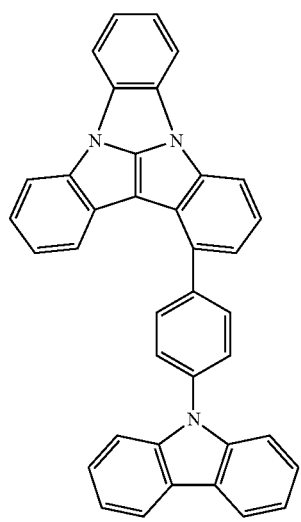
B95

-continued

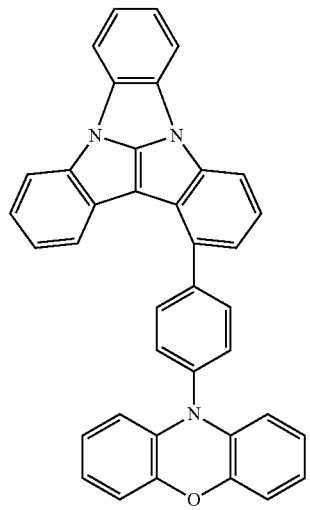
B96

In an embodiment of the inventive concept, a condensed cyclic compound represented by Formula 1 is provided.

The condensed cyclic compound of an embodiment may be used as a material for an organic electroluminescence device.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
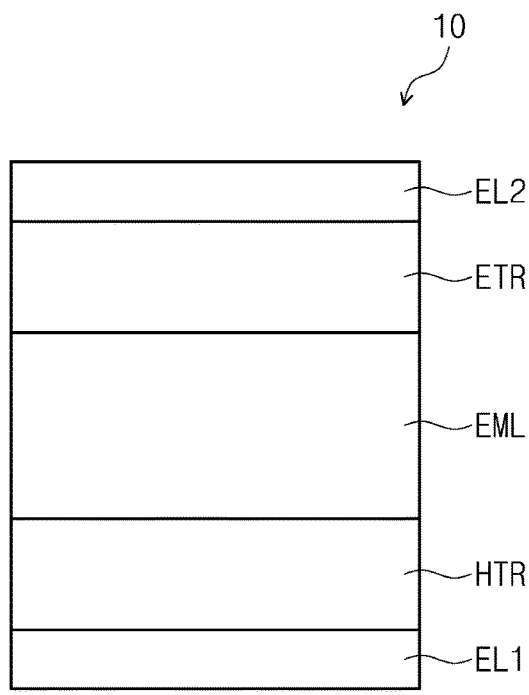
FIG. 1 is a cross-sectional view schematically illustrating an organic electroluminescence device according to an embodiment of the inventive concept.

The inventive concept may have various modifications and may be embodied in different forms, and example embodiments will be explained in detail with reference to the accompanying drawings. The inventive concept may, however, be embodied in different forms and should not be construed as limited to the embodiments set forth herein. Rather, all modifications, equivalents, and substituents which are included in the spirit and technical scope of the inventive concept should be included in the inventive concept.

Like reference numerals refer to like elements throughout. In the drawings, the dimensions of structures are exaggerated for clarity of illustration. It will be understood that, although the terms first, second, etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

In the description, it will also be understood that when a layer, a film, a region, a plate, etc. is referred to as being 'on' or "above" another part, it can be directly on the other part, or intervening layers may also be present. On the contrary, when a layer, a film, a region, a plate, etc. is referred to as being 'under' or "below" another part, it can be directly under the other part, or intervening layers may also be present. In addition, in the description, the disposition "on" may include the disposition below as well as above.

In the description, the term "substituted or unsubstituted" corresponds to substituted or unsubstituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents may be substituted or unsubstituted. For example, a biphenyl group may be interpreted as an aryl group or a phenyl group substituted with a phenyl group.

In the description, the halogen atom may include a fluorine atom, a chlorine atom, a bromine atom and an iodine atom.

In the description, the alkyl may be a linear, branched or cyclic type. The carbon number of the alkyl may be from 1 to 50, from 1 to 30, from 1 to 20, from 1 to 10, or from 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the hydrocarbon ring group means an optional functional group or substituent derived from an aliphatic hydrocarbon ring. The hydrocarbon ring group may be a saturated hydrocarbon ring group having 5 to 20 carbon atoms for forming a ring.

In the description, the aryl group means an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., without limitation.

In the description, the fluorenyl group may be substituted, and two substituents may be combined with each other to form a spiro structure. Examples of substituted fluorenyl groups are as follows. However, an embodiment of the inventive concept is not limited thereto.

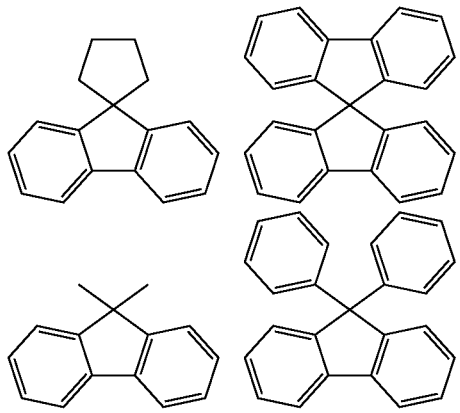

In the description, the heteroaryl may include one or more of B, O, N, P, Si and S as heteroatoms. If the heteroaryl group includes two or more heteroatoms, two or more heteroatoms may be the same or different. The heteroaryl group may be a monocyclic heterocycle or a polycyclic heterocycle. The carbon number for forming a ring of the heteroaryl may be 2 to 30, 2 to 20, or 2 to 10. Examples of the heteroaryl may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc., without limitation.

In the description, the silyl group includes an alkyl silyl group and an aryl silyl group. Examples of the silyl group may include trimethylsilyl, triethylsilyl, t-butyldimethylsilyl, vinyldimethylsilyl, prop yldimethylsilyl, triphenylsilyl, diphenylsilyl, phenylsilyl, etc. However, an embodiment of the inventive concept is not limited thereto.

In the description, the carbon number of the amino group is not specially limited, but may be 1 to 30. The amino group may include an alkyl amino group, an aryl amino group, or a heteroaryl amino group. Examples of the amino group may be a methylamino group, a dimethylamino group, a phenylamino group, a diphenylamino group, a naphthylamino group, a 9-methyl-anthracenylamino group, a triphenylamino group, etc. However, an embodiment of the inventive concept is not limited thereto.

Meanwhile, in the description, "*-" means a connecting position, and a dotted line (----) means a connecting part to form a condensed ring.

Hereinafter, an organic electroluminescence device according to an embodiment of the inventive concept and a condensed cyclic compound of an embodiment included therein will be explained with reference to attached drawings.

Figure 2:
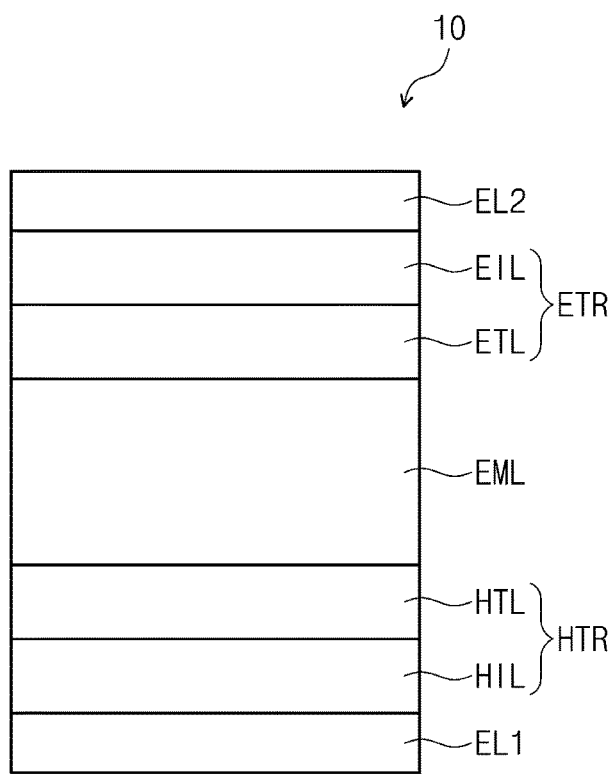
FIG. 2 is a cross-sectional view schematically illustrating an organic electroluminescence device according to an embodiment of the inventive concept.
Figure 3:
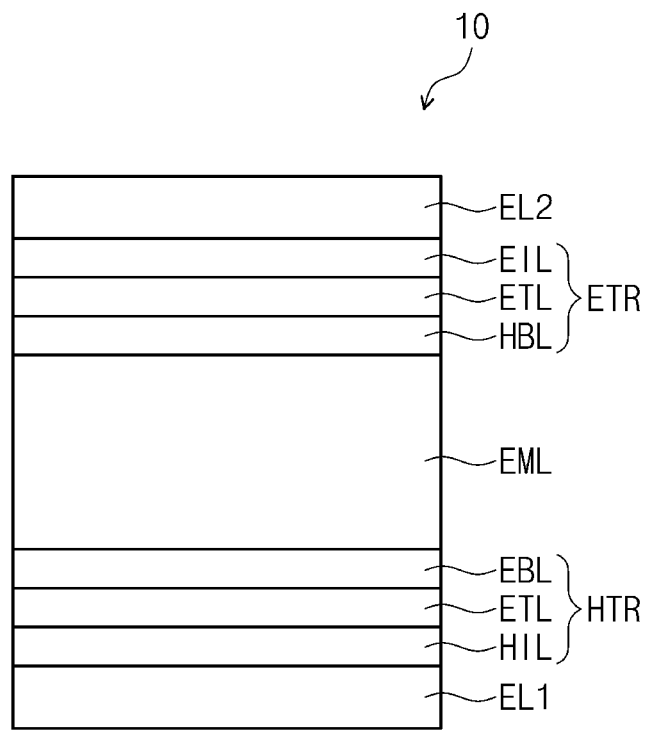
FIG. 3 is a cross-sectional view schematically illustrating an organic electroluminescence device according to an embodiment of the inventive concept.

FIG. 1, FIG. 2, and FIG. 3 are cross-sectional views schematically illustrating organic electroluminescence devices according to exemplary embodiments. Referring to FIG. 1, FIG. 2, and FIG. 3, an organic electroluminescence device 10 according to an embodiment may include a first electrode EL1, a hole transport region HTR, an emission layer EML, an electron transport region ETR, and a second electrode EL2 laminated in that order.

The first electrode EL1 and the second electrode EL2 are oppositely disposed to each other, and a plurality of organic layers may be disposed between the first electrode EL1 and the second electrode EL2. The plurality of the organic layers may include the hole transport region HTR, the emission layer EML, and the electron transport region ETR.

The organic electroluminescence device 10 of an embodiment may include the condensed cyclic compound of an embodiment, which will be explained later, in at least one organic layer of the plurality of organic layers disposed between the first electrode EL1 and the second electrode EL2. Particularly, the condensed cyclic compound of an embodiment may be included in the hole transport region HTR.

When compared with FIG. 1, FIG. 2 shows a cross-sectional view of an organic electroluminescence device 10 of an embodiment, wherein a hole transport region HTR includes a hole injection layer HIL and a hole transport layer HTL, and an electron transport region ETR includes an electron injection layer EIL and an electron transport layer ETL. In addition, when compared with FIG. 1, FIG. 3 shows a cross-sectional view of an organic electroluminescence device 10 of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. Meanwhile, in the organic electroluminescence device 10 of an embodiment, the hole transport layer HTL may include the condensed cyclic compound of an embodiment, which will be explained later.

The first electrode EL1 has conductivity. The first electrode EL1 may be formed using a metal alloy or a conductive compound. The first electrode EL1 may be an anode. In addition, the first electrode EL1 may be a pixel electrode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), and indium tin zinc oxide (ITZO). If the first electrode EL1 is the transflective electrode or the reflective electrode, the first electrode EL1 may include Ag, Mg, Cu, Al, Pt, Pd, Au, Ni, Nd, Jr, Cr, Li, Ca, LiF/Ca, LiF/Al, Mo, Ti, a compound thereof, or a mixture thereof (for example, a mixture of Ag and Mg). Also, the first electrode EL1 may have a structure of a plurality of layers including a reflective layer or a transflective layer formed using the above materials, and a transmissive conductive layer formed using ITO, IZO, ZnO, or ITZO. For example, the first electrode EL1 may include a triple layer structure of ITO/Ag/ITO. The thickness of the first electrode EL1 may be from about 1,000 Å to about 10,000 Å, for example, from about 1,000 Å to about 3,000 Å. However, an embodiment of the inventive concept is not limited thereto.

The hole transport region HTR is provided on the first electrode EL1. The hole transport region HTR may include at least one of a hole injection layer HIL, a hole transport layer HTL, a hole buffer layer (not shown), or an electron blocking layer EBL. The thickness of the hole transport region HTR may be, for example, from about 1,000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure such as a hole injection layer HIL, or a hole transport layer HTL, and may have a single layer structure formed using a hole injection material and a hole transport material. Alternatively, the hole transport region HTR may have a single layer structure formed using a plurality of different materials, or a structure laminated on the first electrode EL1 of hole injection layer HIL/hole transport layer HTL, hole injection layer HIL/hole transport layer HTL/hole buffer layer (not shown), hole injection layer HIL/hole buffer layer (not shown), hole transport layer HTL/hole buffer layer, or hole injection layer HIL/hole transport layer HTL/electron blocking layer EBL, without limitation.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include the condensed cyclic compound of an embodiment, represented by the following Formula 1:

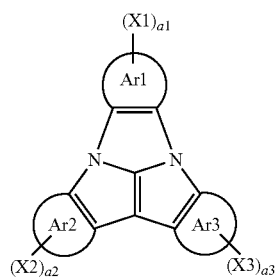

[Formula 1]

In Formula 1, Ar1 to Ar3 are each independently a substituted or unsubstituted aryl group having 6 to 40 carbon atoms for forming a ring, or a substituted or unsubstituted heteroaryl group having 2 to 40 carbon atoms for forming a ring, with the exception of a case where at least one of Ar2 and Ar3 is a carbazole group.

In Formula 1, X1, X2, and X3 may be each independently *-L-NR$_1$R$_2$. In addition, one of a1 to a3 may be 1, and the others may be 0. That is, *-L-NR$_1$R$_2$ may be combined with any one of Ar1 to Ar3.

Accordingly, the condensed ring compound represented by Formula 1 may be a monoamine compound of which core part is substituted with one amine group.

In *-L-NR$_1$R$_2$, L may be a direct linkage, a substituted or unsubstituted arylene group having 6 to 30 carbon atoms for forming a ring, or a substituted or unsubstituted heteroarylene group having 2 to 30 carbon atoms for forming a ring. In addition, in *-L-NR₁R₂, R₁ and R₂ may be each independently a substituted or unsubstituted alkyl group having 1 to 20 carbon atoms, a substituted or unsubstituted aryl group having 6 to 40 carbon atoms for forming a ring, or a substituted or unsubstituted heteroaryl group having 2 to 40 carbon atoms for forming a ring, or combined with each other to form a ring.

In the condensed ring compound represented by Formula 1, Ar1 may be a substituted or unsubstituted aryl group having 6 to 40 carbon atoms for forming a ring, or a substituted or unsubstituted heteroaryl group having 2 to 40 carbon atoms for forming a ring, which is condensed to a core part,

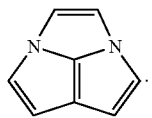

For example, Ar1 may be a substituted or unsubstituted aryl group having 6 to 18 carbon atoms for forming a ring. Particularly, Ar1 may be a substituted or unsubstituted benzene ring, or a substituted or unsubstituted naphthalene ring.

In the condensed cyclic compound represented by Formula 1, each of Ar2 and Ar3 may be a substituted or unsubstituted aryl group having 6 to 40 carbon atoms for forming a ring, or a substituted or unsubstituted heteroaryl group having 2 to 40 carbon atoms for forming a ring, which is condensed to a core part,

For example, each of Ar2 and Ar3 may be a substituted or unsubstituted aryl group having 6 to 18 carbon atoms for forming a ring, or a substituted or unsubstituted heteroaryl group having 2 to 18 carbon atoms for forming a ring. If Ar2 and Ar3 are each independently a substituted or unsubstituted heteroaryl group, at least one of N, O or S may be included as a heteroatom.

However, a case where at least one of Ar2 or Ar3 is a substituted or unsubstituted carbazole group is excluded. That is, cases where the condensed cyclic part in Formula 1 is represented by E1 to E3 are excluded.

E1

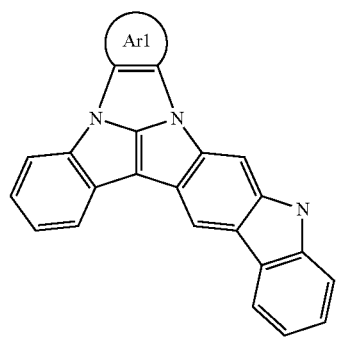

E2

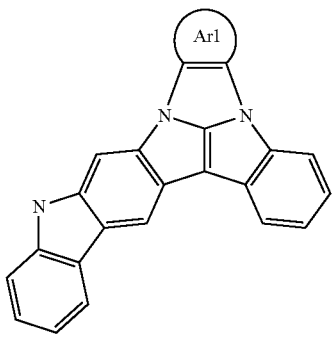

E3

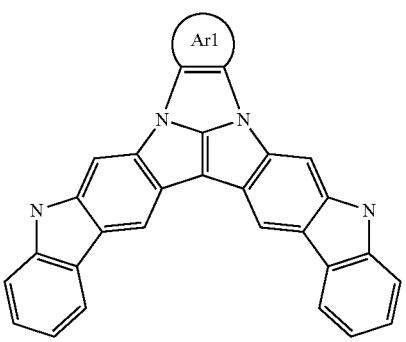

Meanwhile, each of Ar2 and Ar3 may be independently a substituted or unsubstituted benzene ring, a substituted or unsubstituted naphthalene ring, a substituted or unsubstituted phenanthrene ring, a substituted or unsubstituted benzofuran ring, a substituted or unsubstituted dibenzofuran ring, a substituted or unsubstituted benzothiophene ring, a substituted or unsubstituted dibenzothiophene ring, a substituted or unsubstituted pyridine ring, or a substituted or unsubstituted quinoline ring. Particularly, Ar2 and Ar3 may be each independently an unsubstituted benzene ring, an unsubstituted naphthalene ring, an unsubstituted phenanthrene ring, an unsubstituted benzofuran ring, an unsubstituted dibenzofuran ring, an unsubstituted benzothiophene ring, an unsubstituted dibenzothiophene ring, an unsubstituted pyridine ring, or an unsubstituted quinoline ring.

Ar2 and Ar3 may be each independently represented by any one among Ar-a to Ar-i.

Ar-a

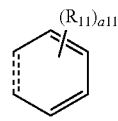

Ar-b

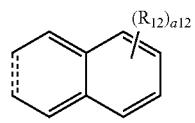

Ar-c

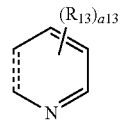

Ar-d 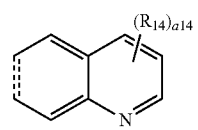

Ar-e 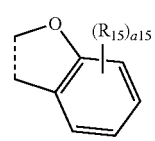

Ar-f 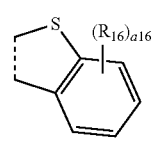

Ar-g 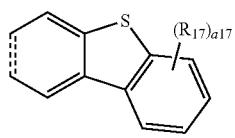

Ar-h 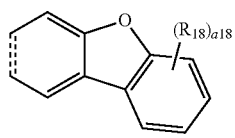

Ar-i 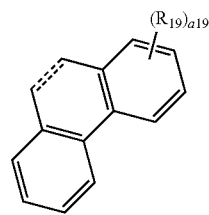

In Ar-a to Ar-i, each one of $R_{11}$ to $R_{19}$ may be independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring. In Ar-a to Ar-i, a11 to a19 may be each independently an integer of 0 to 4.

Meanwhile, Ar2 and Ar3 may be the same. In an embodiment, Ar2 and Ar3 may be the same aryl group or the same heteroaryl group.

Alternatively, Ar2 and Ar3 may be different from each other in an embodiment. For example, Ar2 and Ar3 may be different aryl groups, one among Ar2 and Ar3 may be an aryl group and the other one may be a heteroaryl group, or Ar2 and Ar3 may be different heteroaryl groups.

The condensed cyclic compound of an embodiment, represented by Formula 1, may have a condensed ring in which at least six rings are condensed by combining the cyclic groups of Ar1 to Ar3 in a core part,

The condensed ring compound of an embodiment includes a condensed ring obtained by condensing at least six rings in a core part, and may have improved thermal stability and electron tolerance.

In the condensed ring of an embodiment, represented by Formula 1, *-L-NR$_1$R$_2$ group is connected with any one among Ar1 to Ar3, and L is a linker connecting an amine group (NR$_1$R$_2$) with a core part and may be a direct linkage or any one represented by the following L1 to L4:

L1 

L2 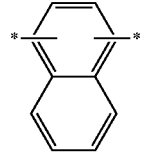

L3 

L4 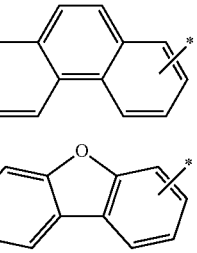

Meanwhile, $R_1$ and $R_2$ may be each independently a substituted or unsubstituted phenyl group, a substituted or unsubstituted biphenyl group, a substituted or unsubstituted naphthyl group, a substituted or unsubstituted terphenyl group, a substituted or unsubstituted dibenzothiophene group, a substituted or unsubstituted dibenzofuran group, a substituted or unsubstituted carbazole group, a substituted or unsubstituted phenanthryl group, or a substituted or unsubstituted fluorenyl group.

$R_1$ and $R_2$ may be the same or different.

In addition, $R_1$ and $R_2$ may be combined with each other to form a ring. For example, $R_1$ and $R_2$ may be combined with each other to form any one ring among S1 to S3. In S1 to S3, a "*-" part may be a part combined with a linker, L.

S1 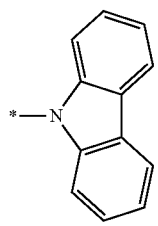

S2

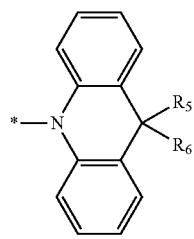

S3

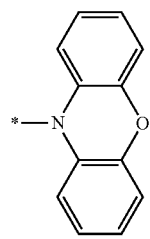

Meanwhile, each of $R_5$ and $R_6$ in S2 may be independently a hydrogen atom, a deuterium atom, a halogen atom, a substituted or unsubstituted silyl group, a substituted or unsubstituted alkyl group having 1 to 10 carbon atoms, or a substituted or unsubstituted aryl group having 6 to 30 carbon atoms for forming a ring.

The condensed cyclic compound represented by Formula 1 may be represented by the following Formula 1-1 or Formula 1-2:

[Formula 1-1]

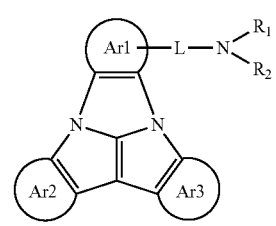

[Formula 1-2]

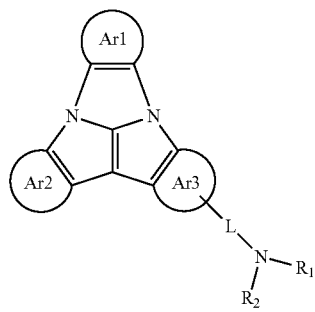

Formula 1-1 represents a case where an amine group, a *-L-NR₁R₂ part, is combined with Ar1, Formula 1-2 represents a case where an amine group, a *-L-NR₁R₂ part, is combined with Ar3. Meanwhile, although not shown, the *-L-NR₁R₂ part may be combined with Ar2.

Meanwhile, the same explanation on Formula 1 may be applied to Formula 1-1 and Formula 1-2, and the explanation on Ar1 to Ar3, L, $R_1$ and $R_2$ may be applied to Ar1 to Ar3, L, $R_1$ and $R_2$ in Formula 1-1 and Formula 1-2.

The condensed cyclic compound of an embodiment, represented by Formula 1 may be represented by the following Formula 2-1 or Formula 2-2:

[Formula 2-1]

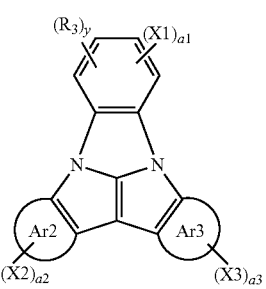

[Formula 2-2]

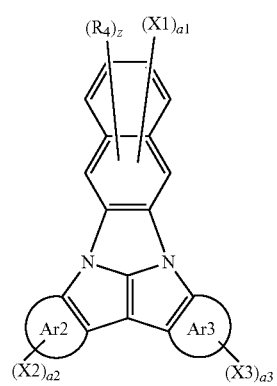

Formula 2-1 represents a case where Ar1 is a substituted or unsubstituted benzene ring in Formula 1, and Formula 2-2 represents a case where Ar1 is a substituted or unsubstituted naphthalene ring in Formula 1.

In Formula 2-1 and Formula 2-2, each of $R_3$ and $R_4$ may be independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring.

In Formula 2-1 and Formula 2-2, "y" and "z" may be each independently an integer of 0 to 3. In "y" or "z" is an integer of 2 or more, a plurality of R3 or a plurality of R4 may be the same or at least one thereof may be different.

The organic electroluminescence device 10 of an embodiment as shown in FIGS. 1 to 3 may include at least one of the condensed cyclic compounds represented in Compound Group 1 or Compound Group 2 below in at least one organic layer disposed between the first electrode EL1 and the second electrode EL2. For example, in the hole transport region HTR of the organic electroluminescence device 10 of an embodiment, at least one of the condensed cyclic compounds represented in Compound Group 1 or Compound Group 2 below may be included, particularly, a hole transport layer HTL may include at least one of the condensed cyclic compounds represented in Compound Group 1 or Compound Group 2 below.

[Compound Group 1]
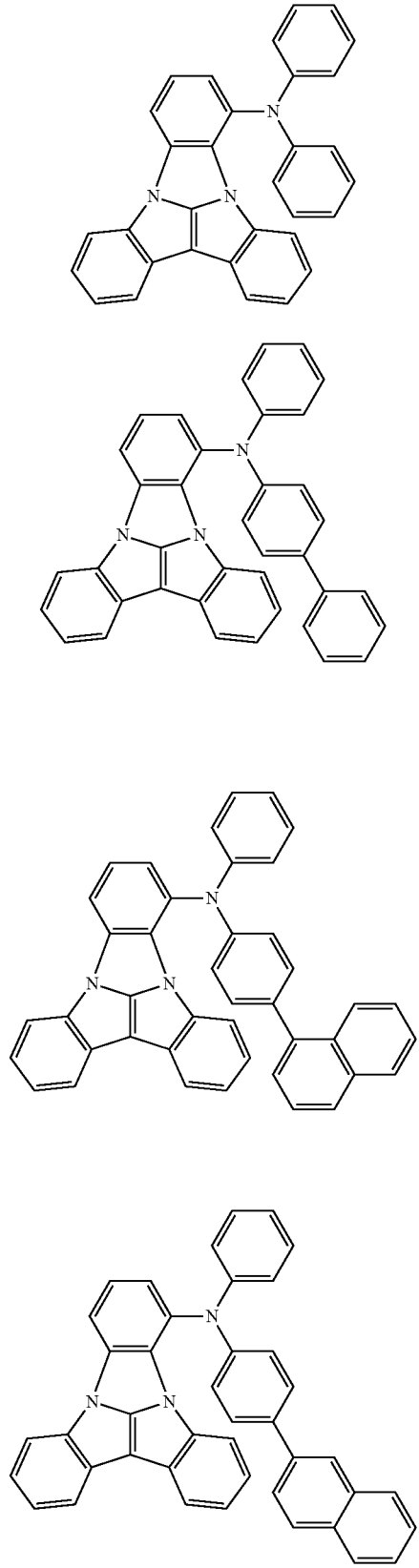
A1
A2
A3
A4
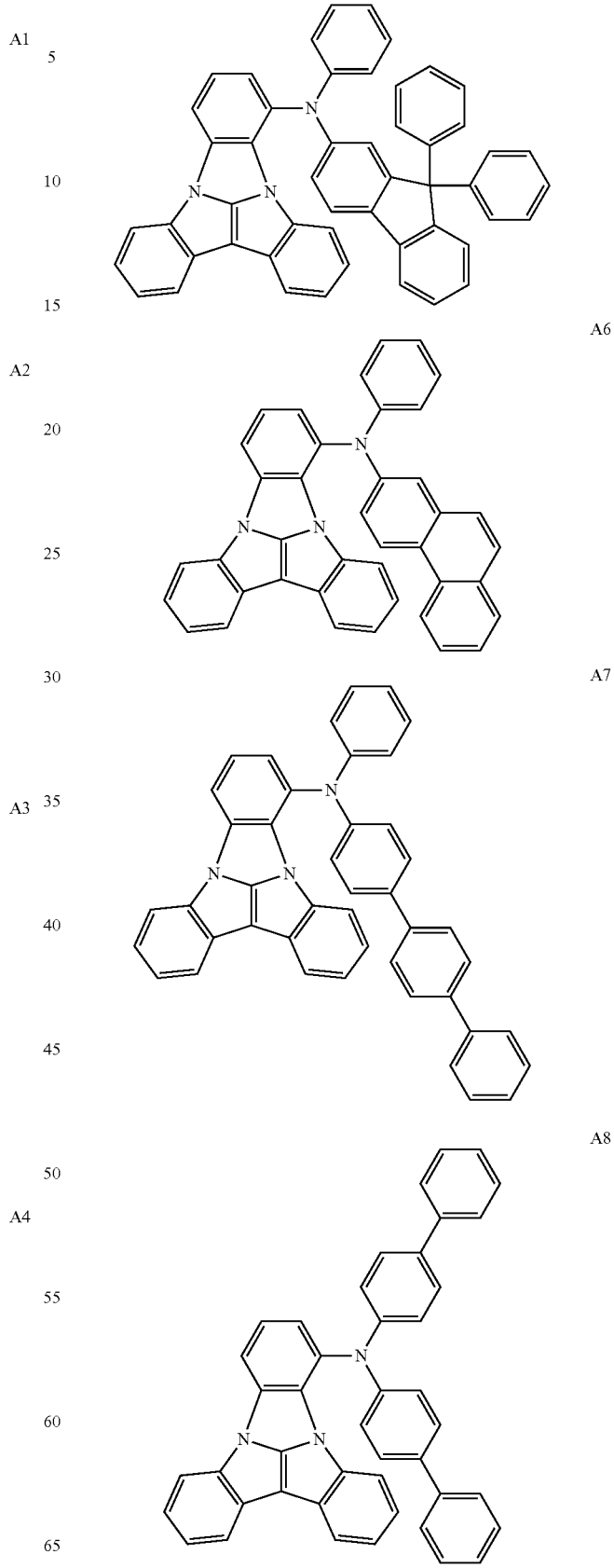
A5
A6
A7
A8

A9 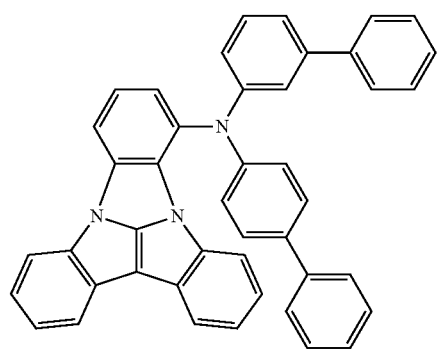
A10 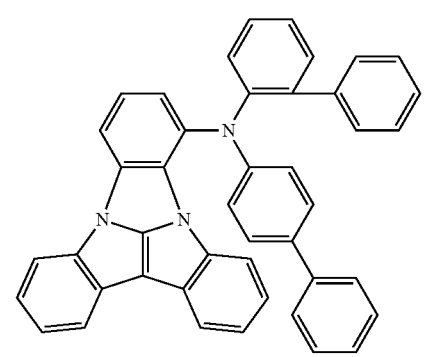
A11 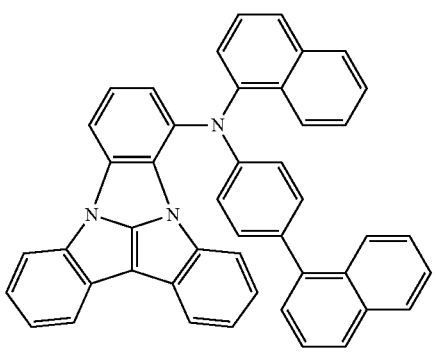
A12 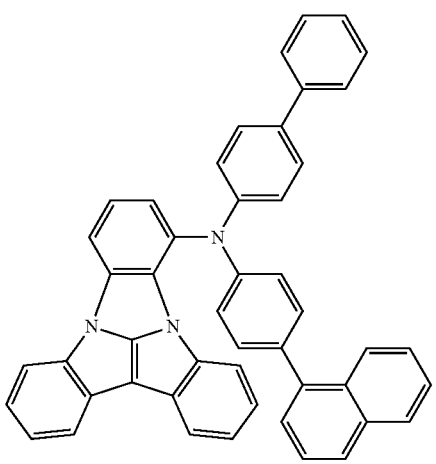
A13 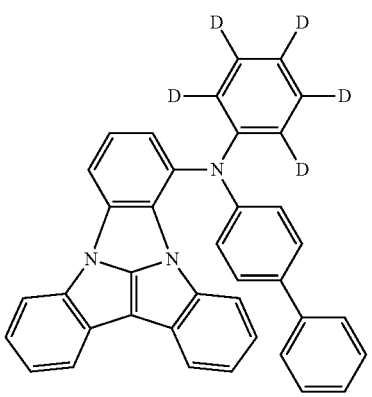
A14 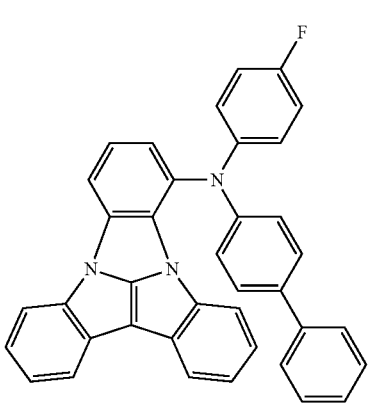
A15 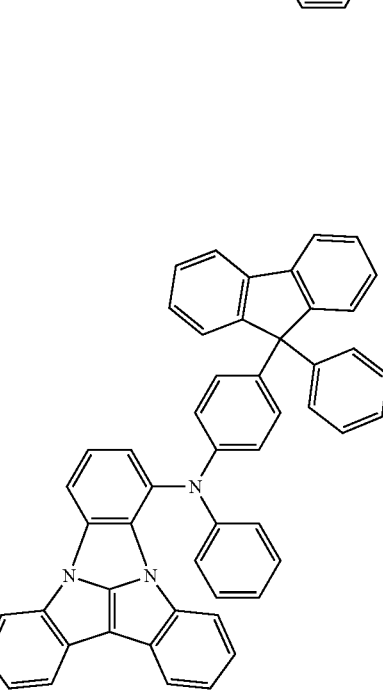

A16
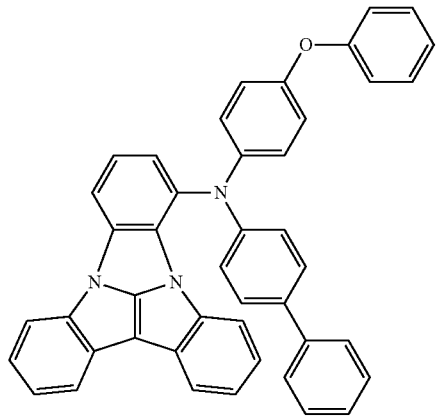
A17
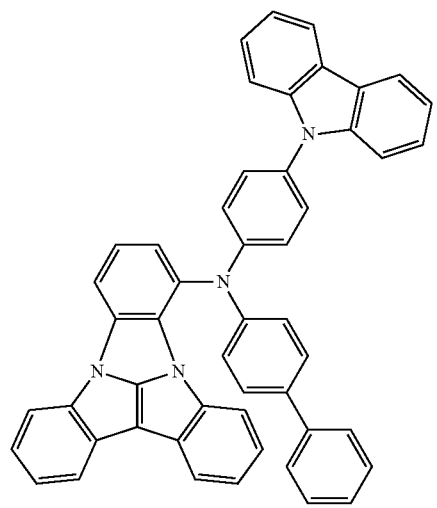
A18
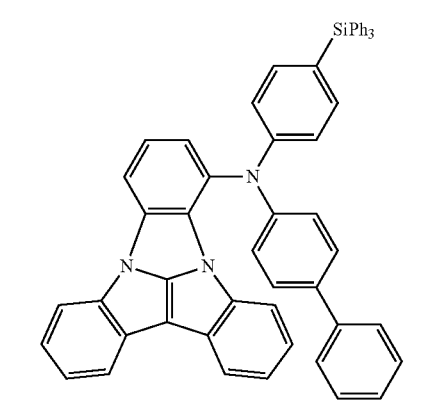
A19
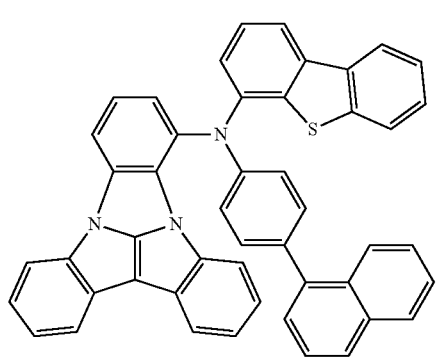
A20
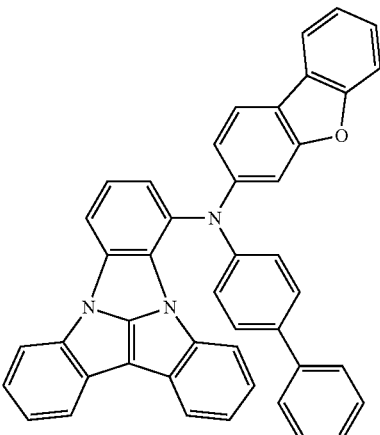
A21
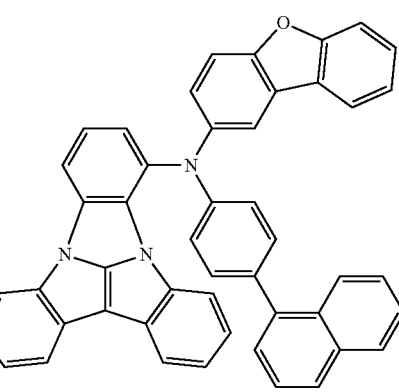
A22
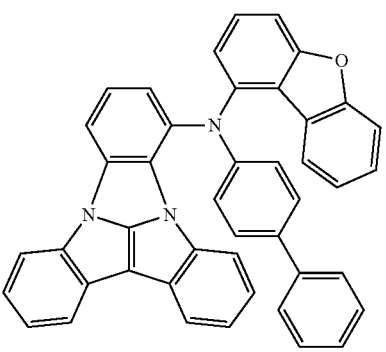
A23
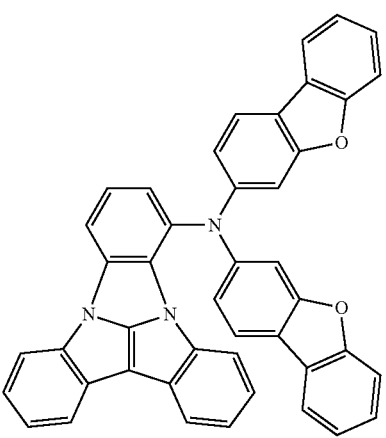

-continued
A24
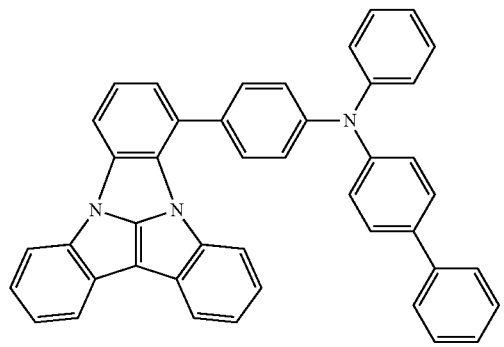
A25
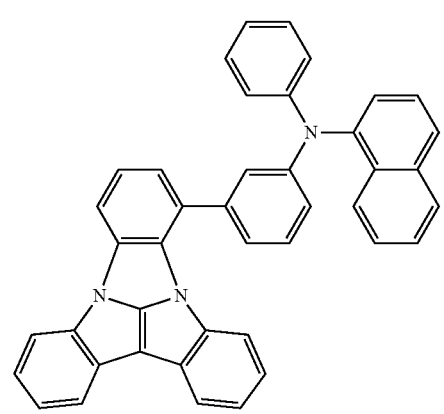
A26
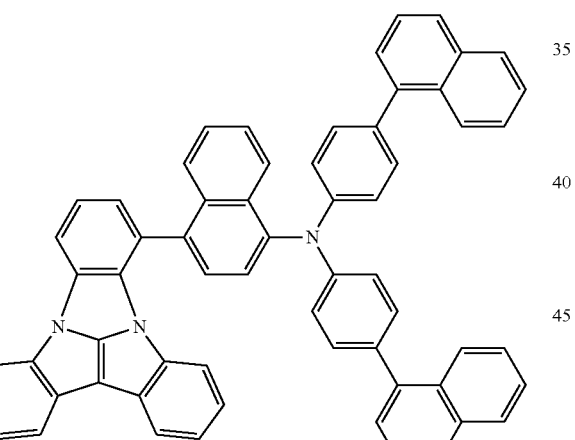
A27
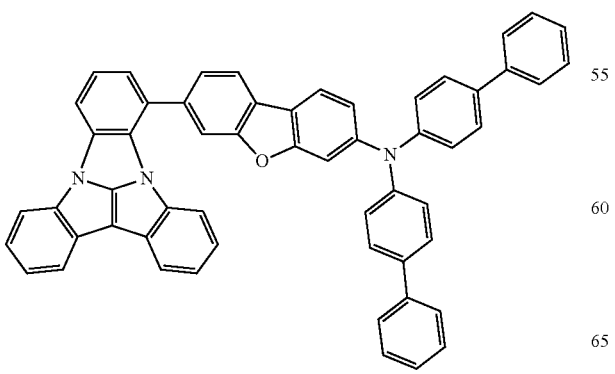
A28
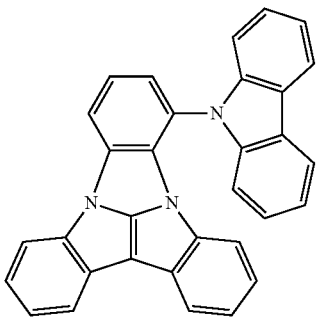
A29
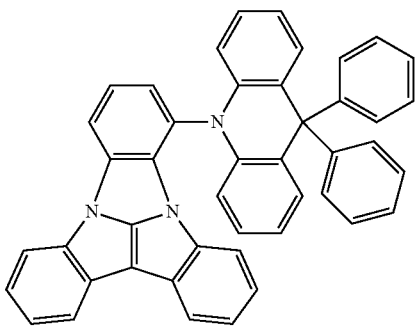
A30
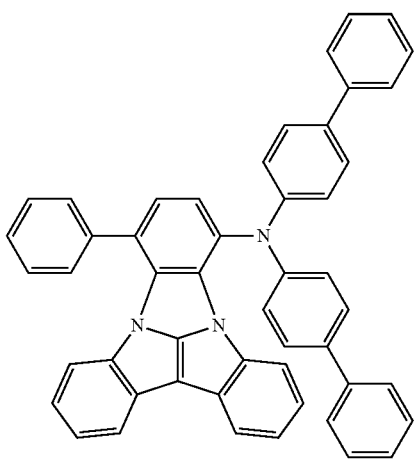
A31
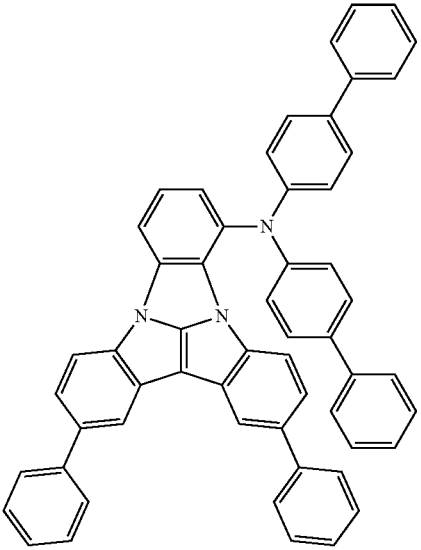

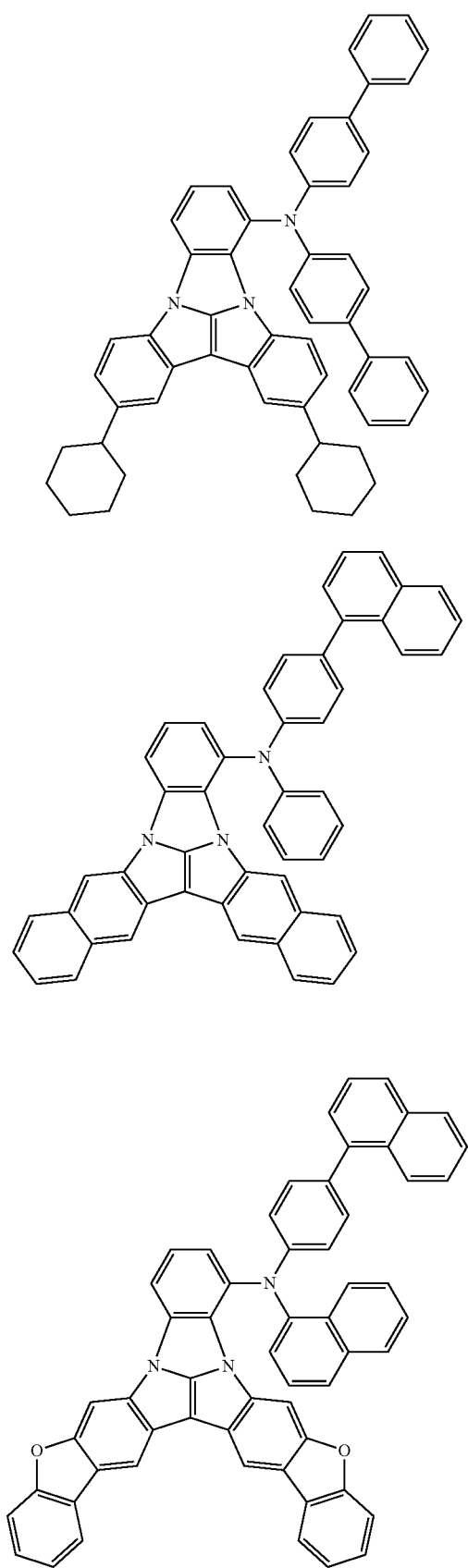

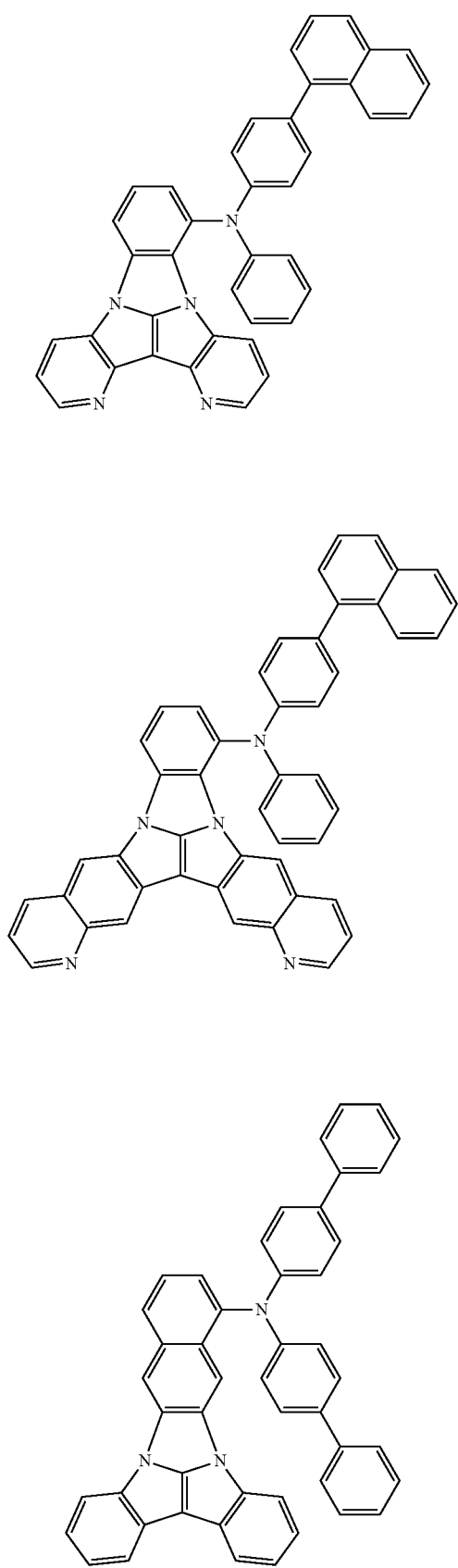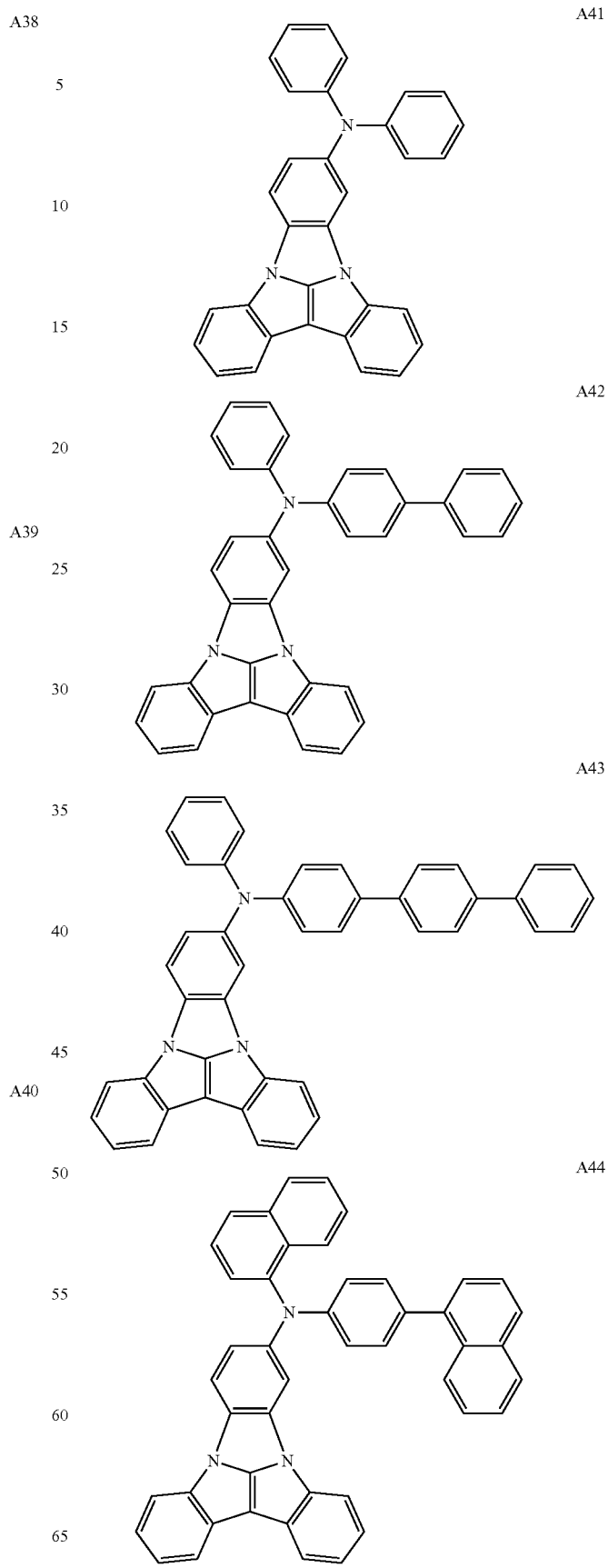

A45
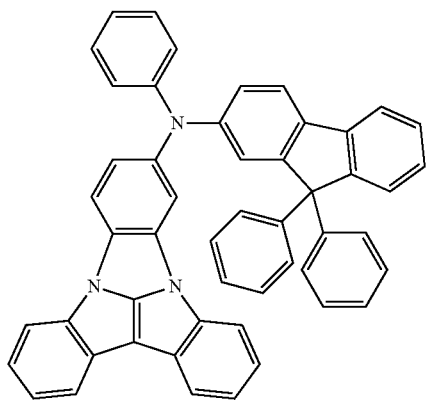
A46
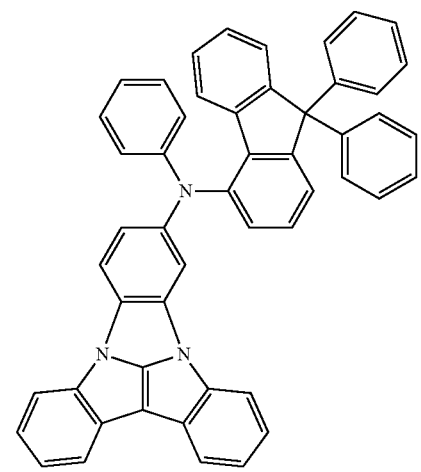
A47
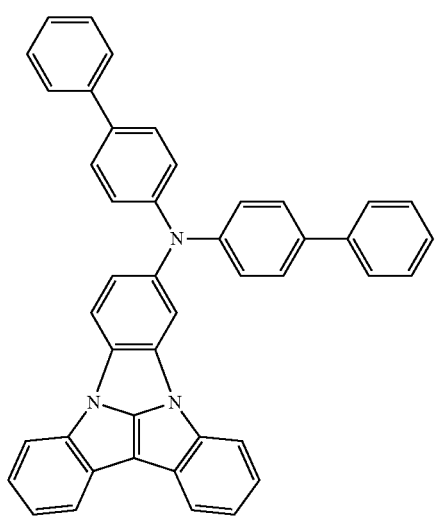
A48
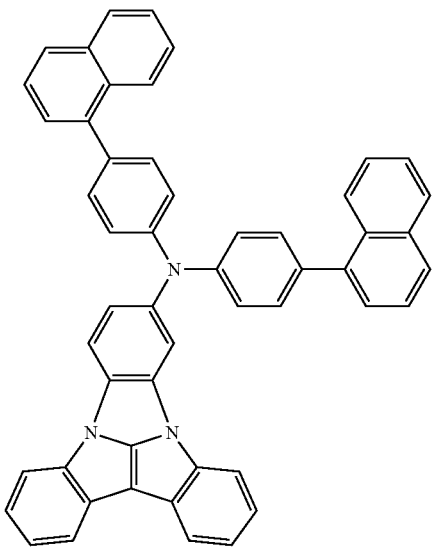
A49
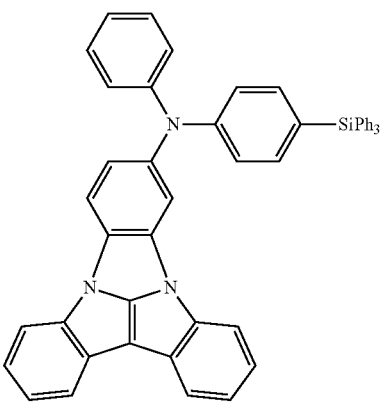
A50
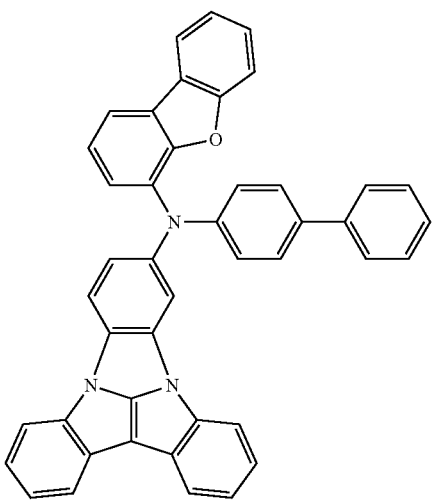

-continued
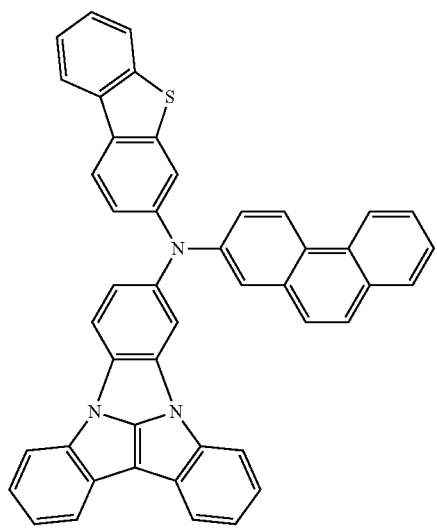
A51
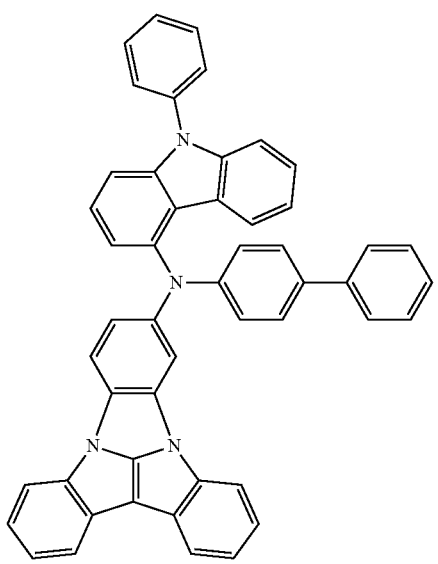
A54
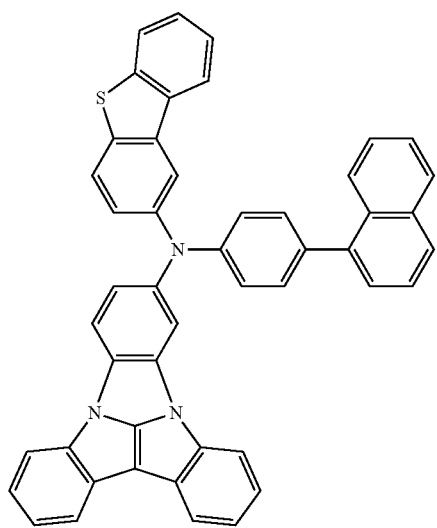
A52
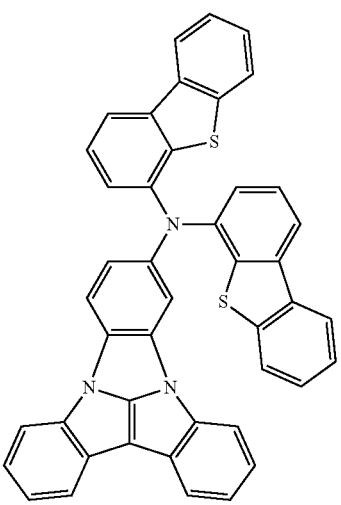
A55
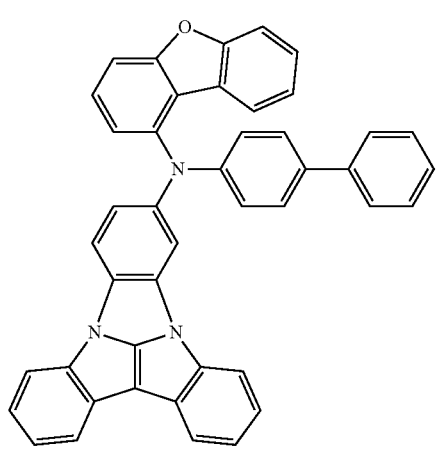
A53
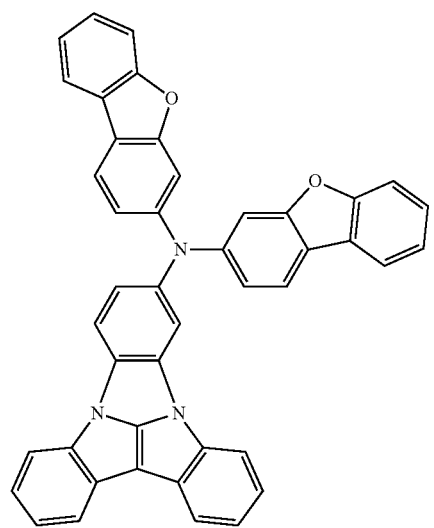
A56

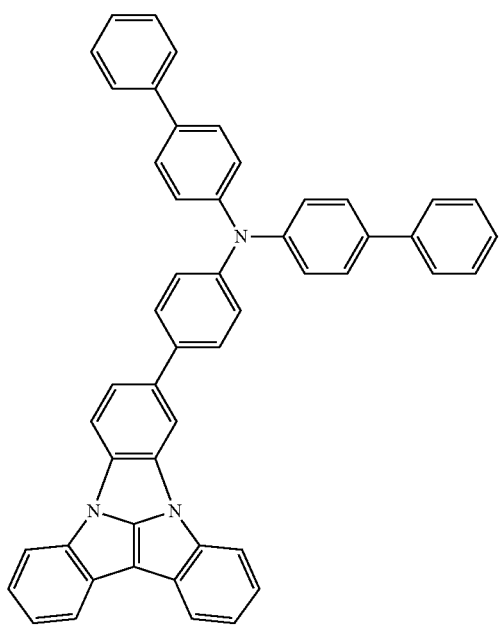
A57
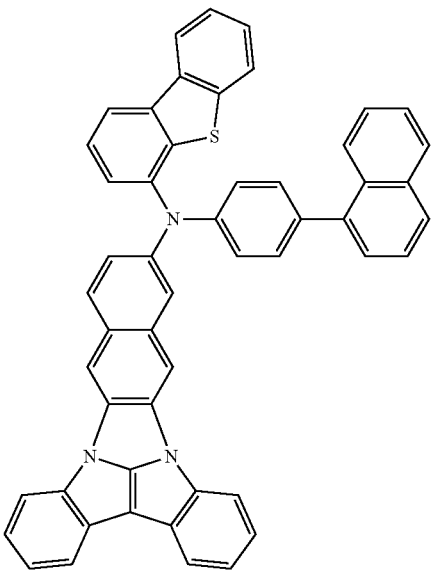
A59
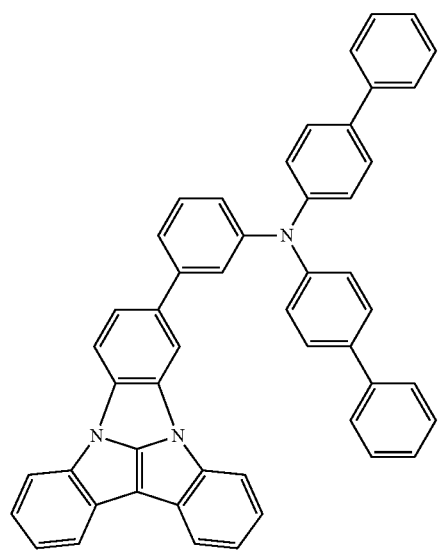
A58
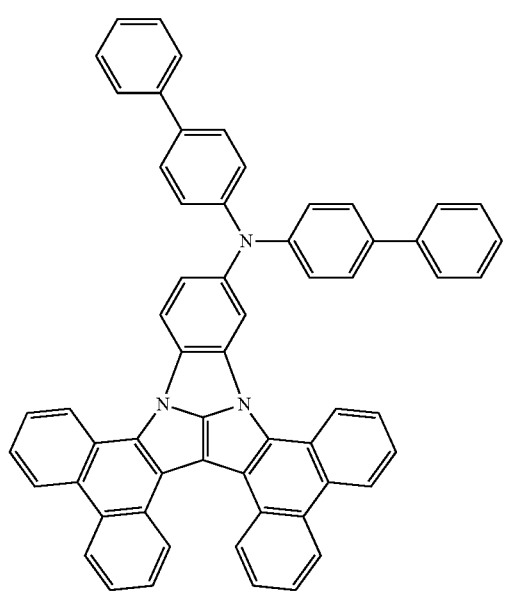
A60

-continued
A61
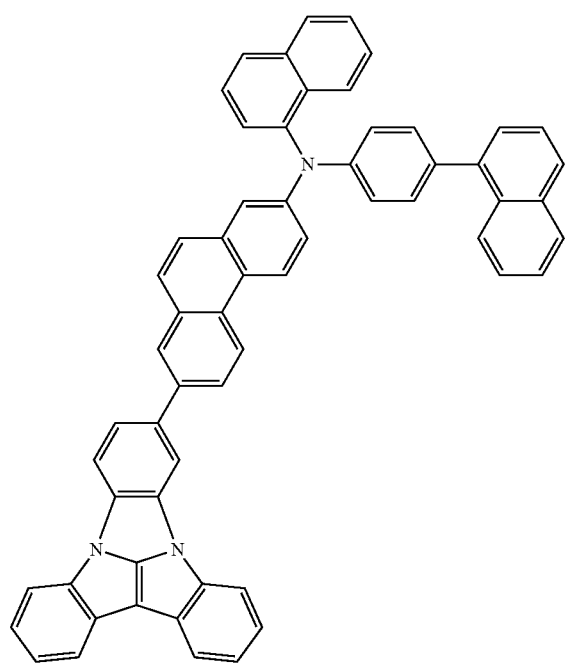
A62
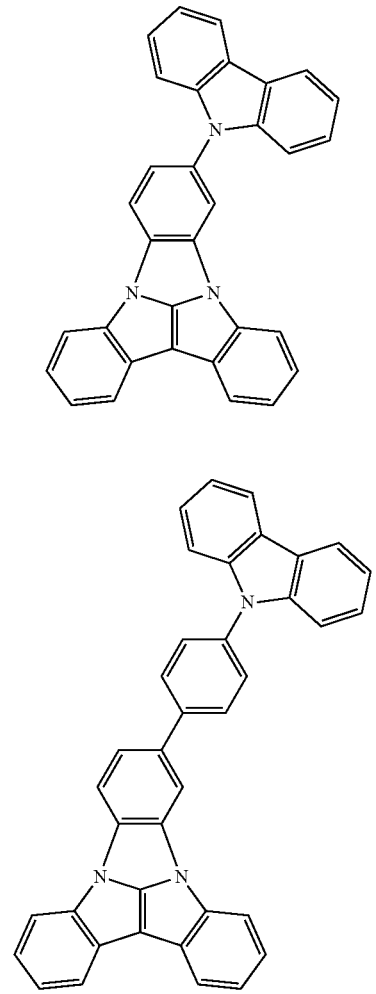
A63
A64
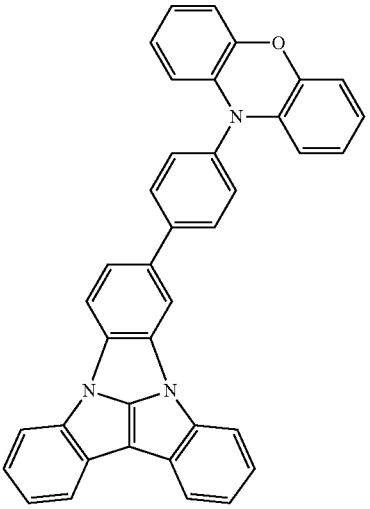
[Compound Group 2]
B1
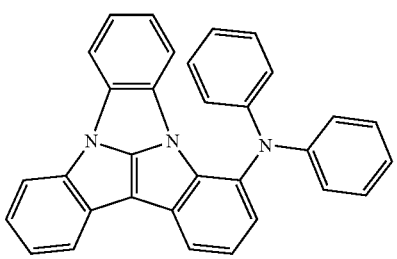
B2
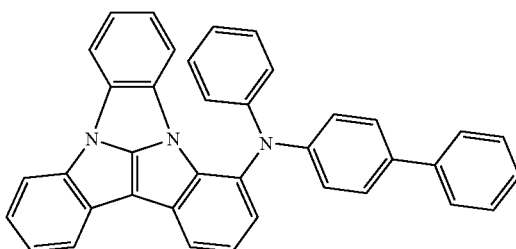
B3
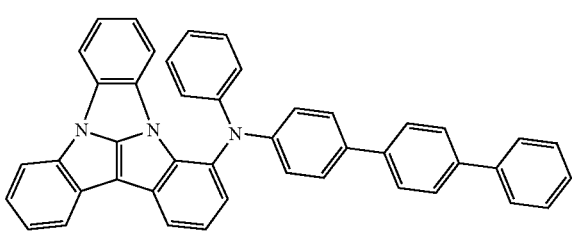
B4
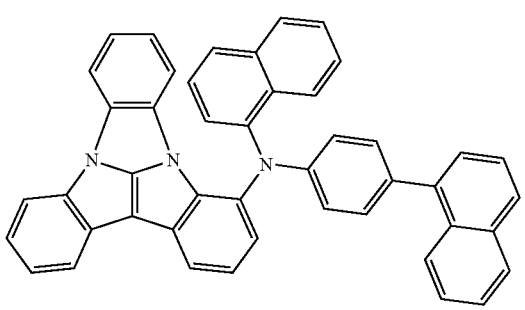

B5
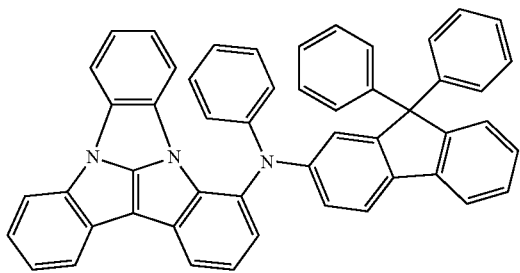
B6
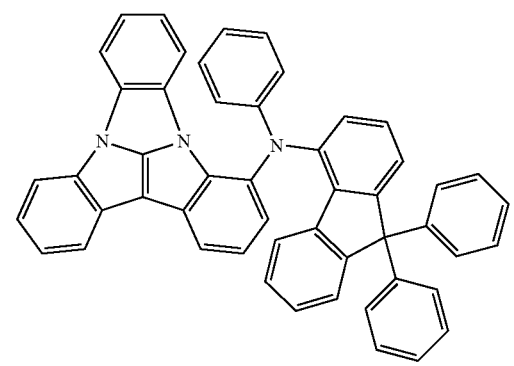
B7
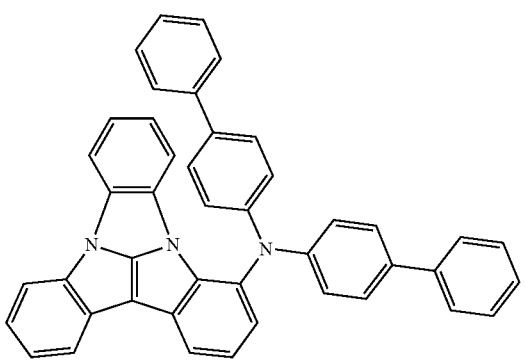
B8
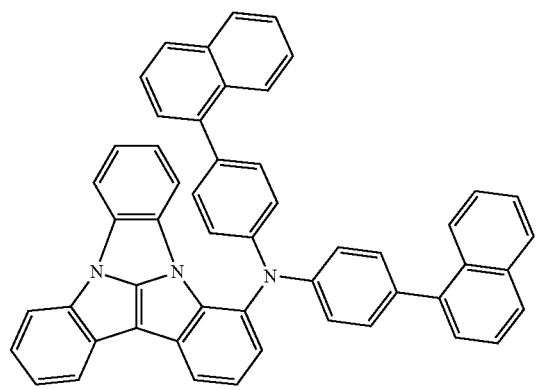
B9
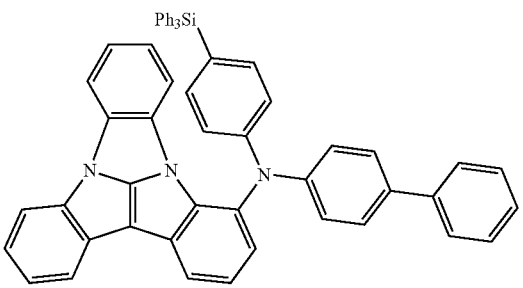
B10
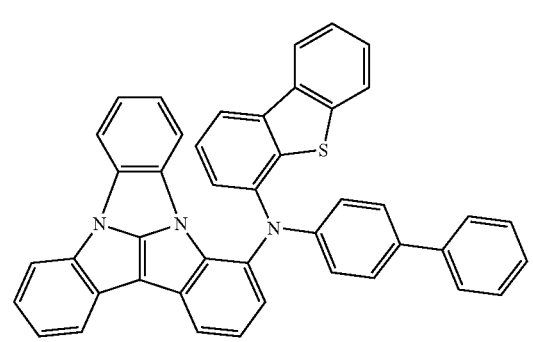
B11
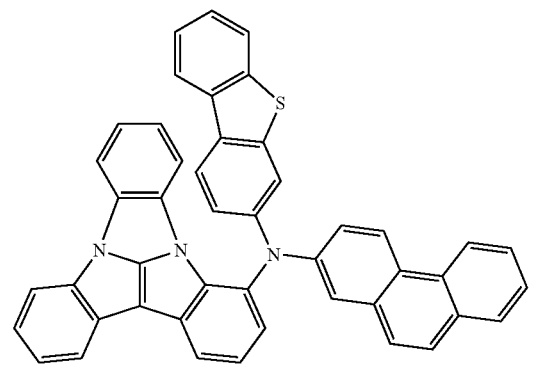
B12
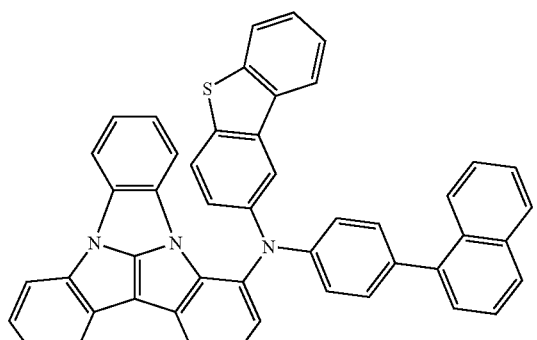

B13
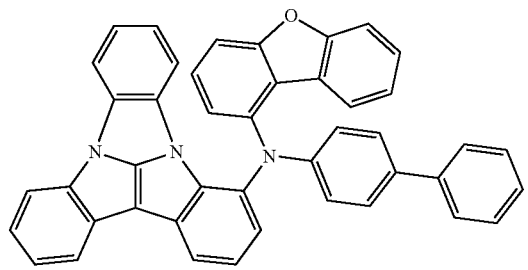
B14
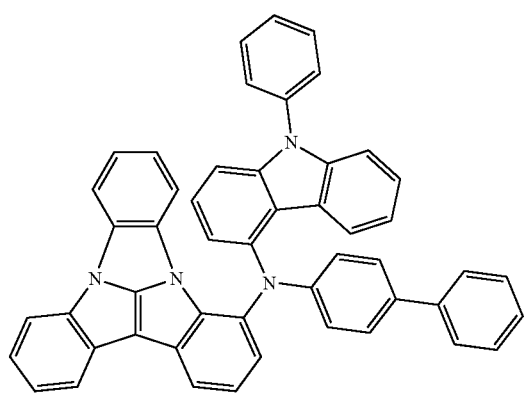
B17
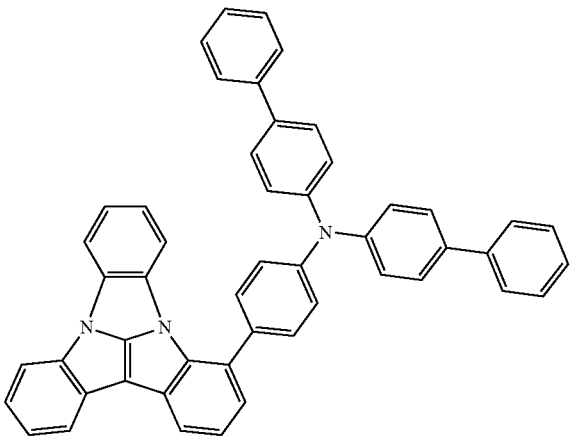
B18
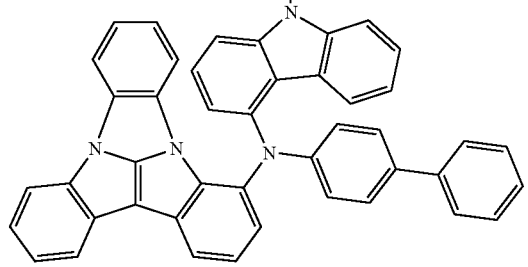
B19
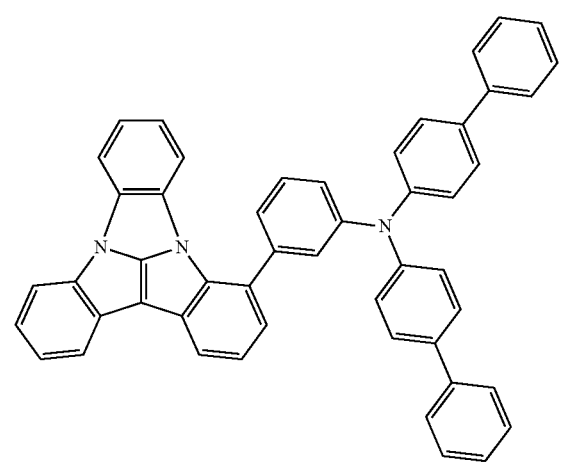
B15
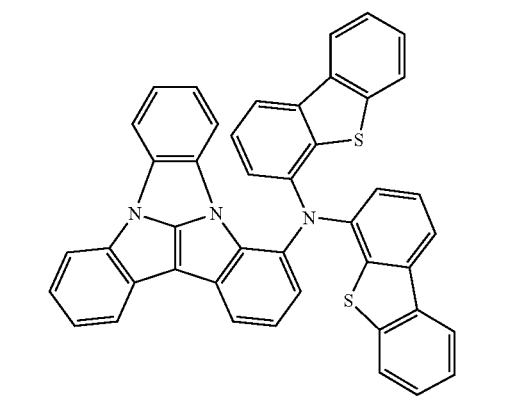
B16
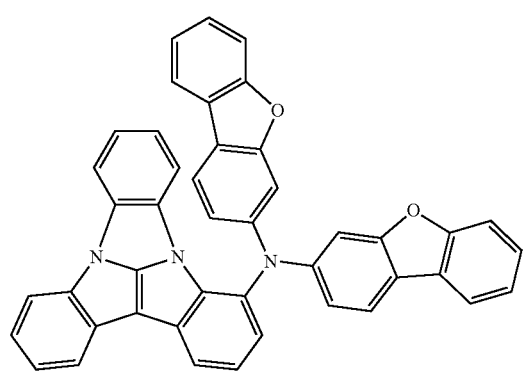
B20
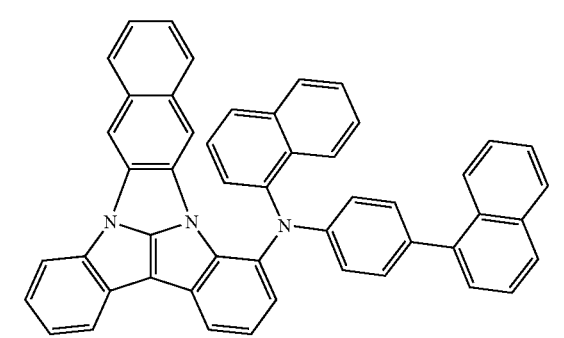

B21
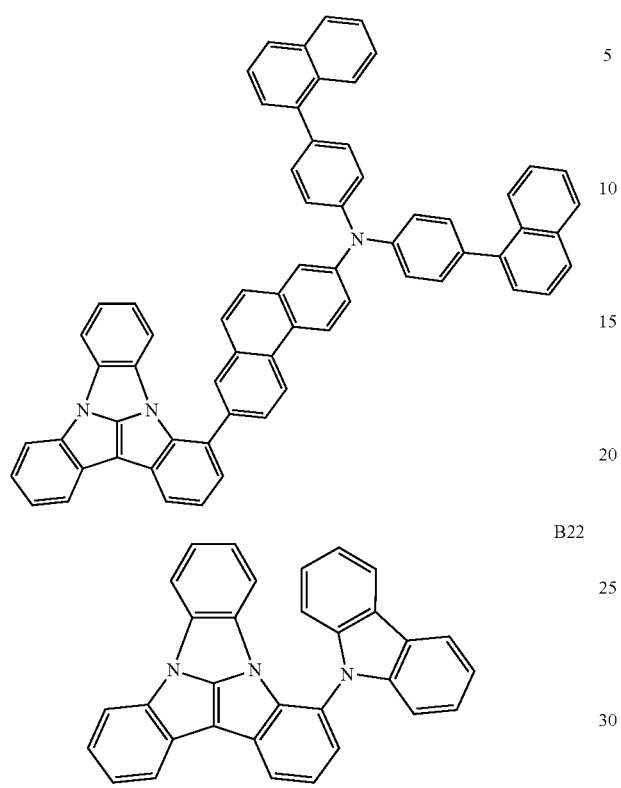
B22
B23
B24
B25
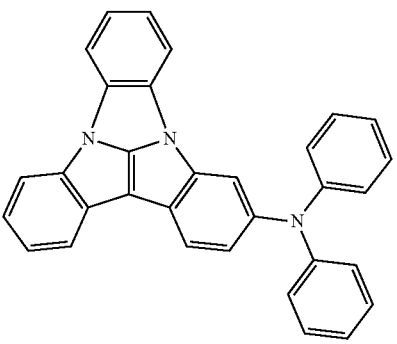
B26
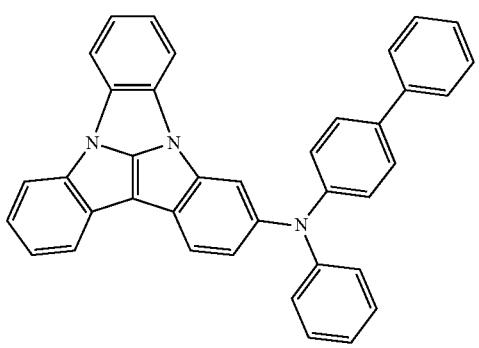
B27
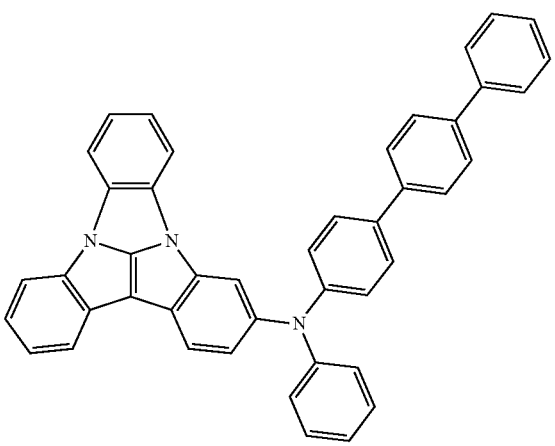
B28
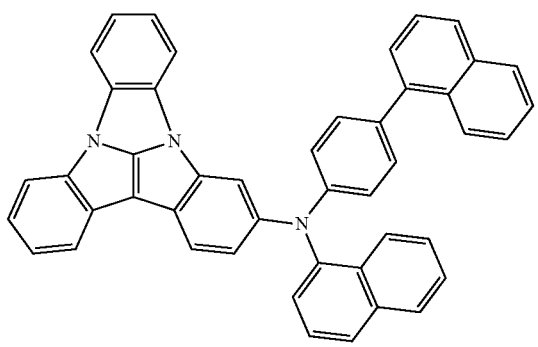

B29
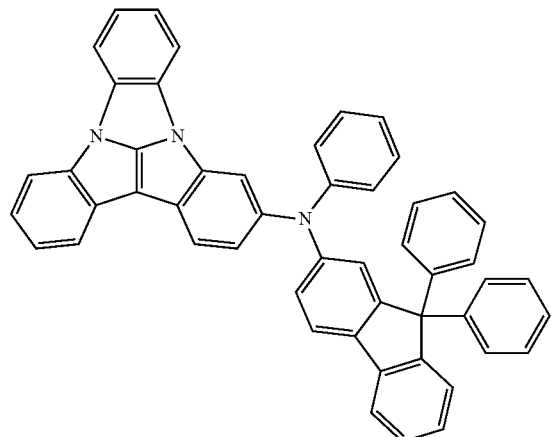
B30
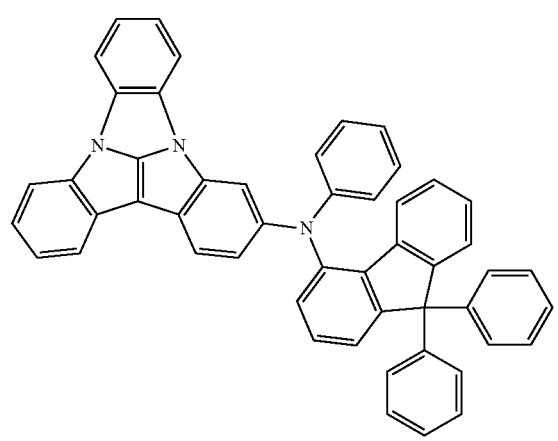
B31
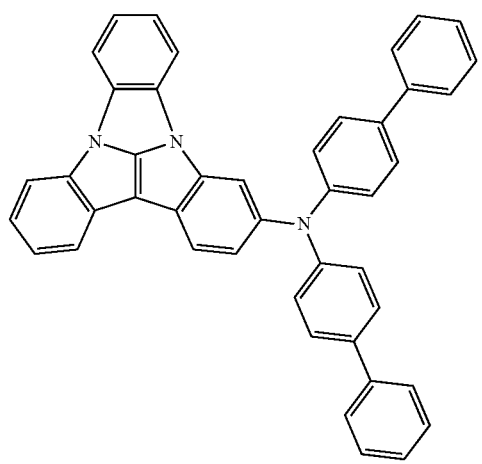
B32
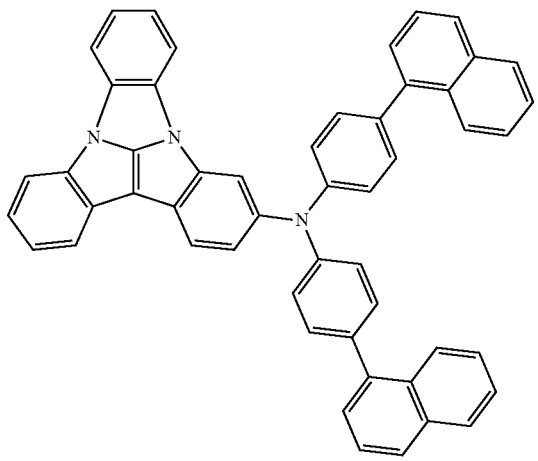
B33
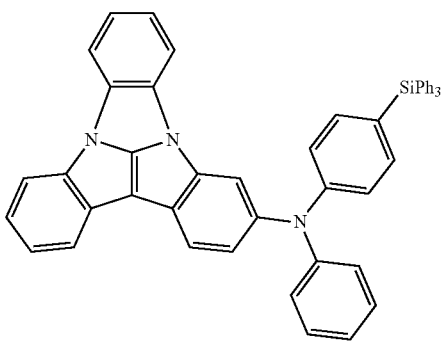
B34
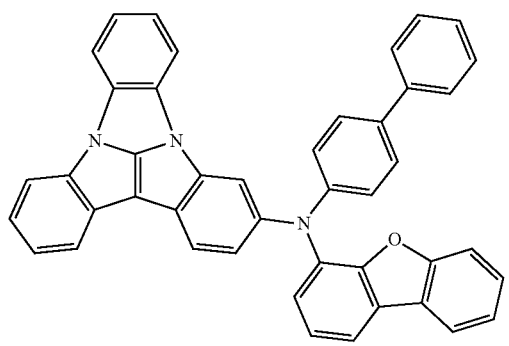
B35
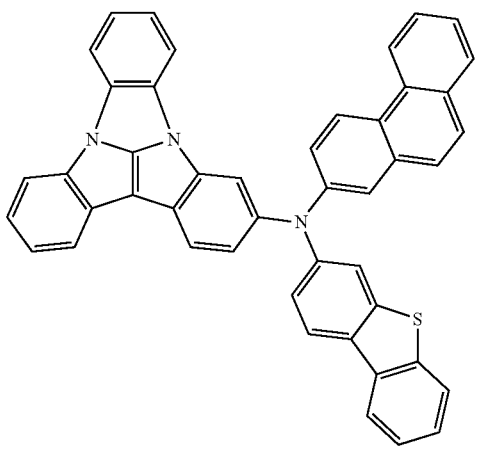

B36
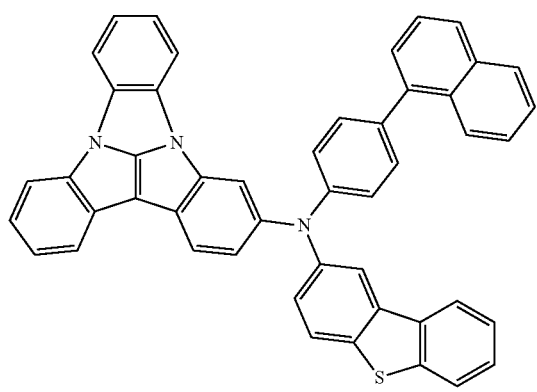
B37
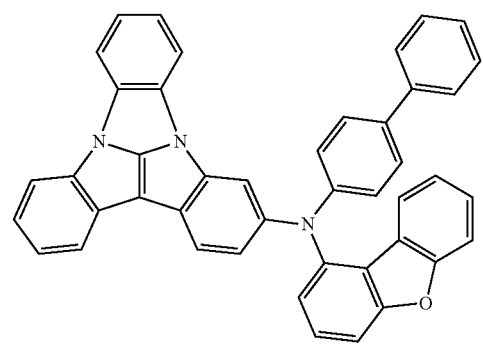
B38
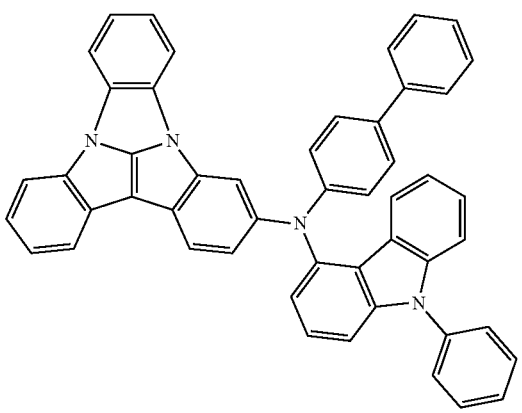
B39
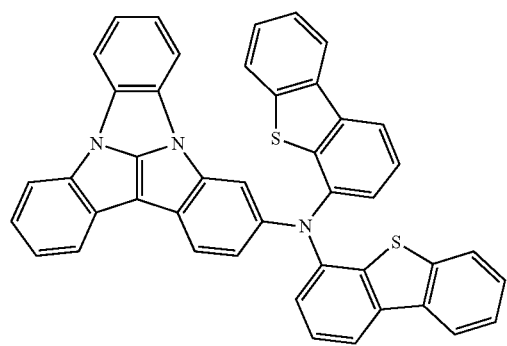
B40
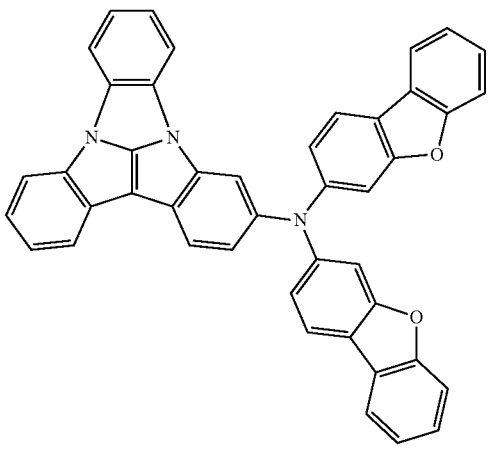
B41
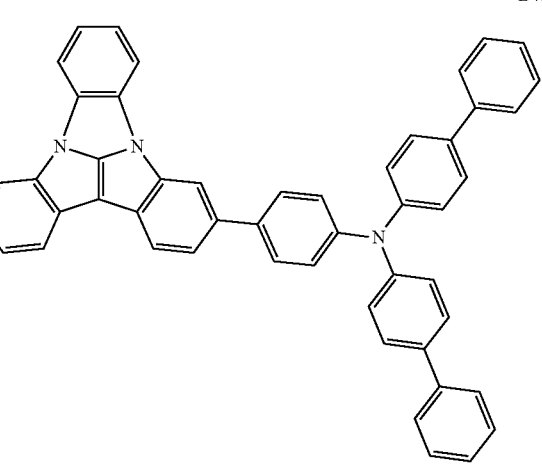
B42
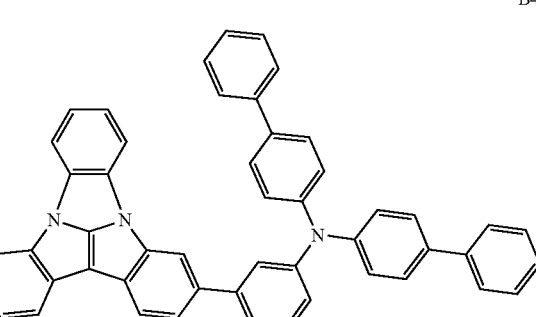
B43
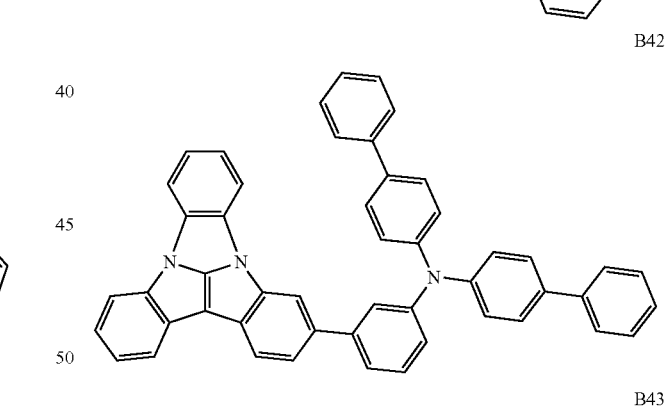

B44
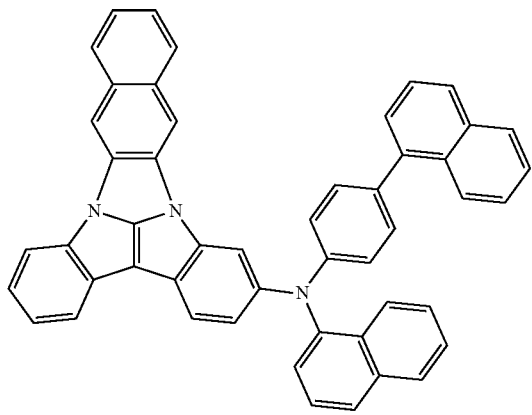
B45
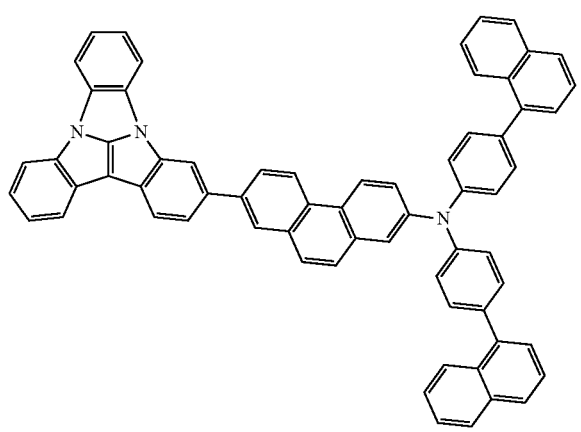
B46
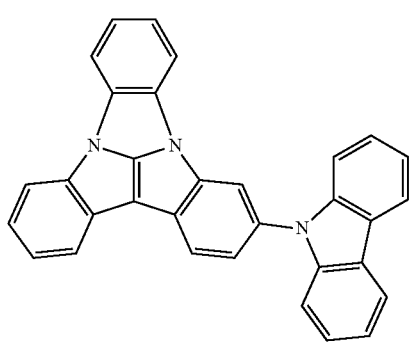
B47
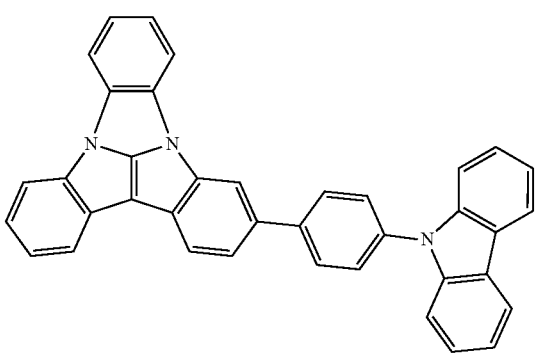
B48
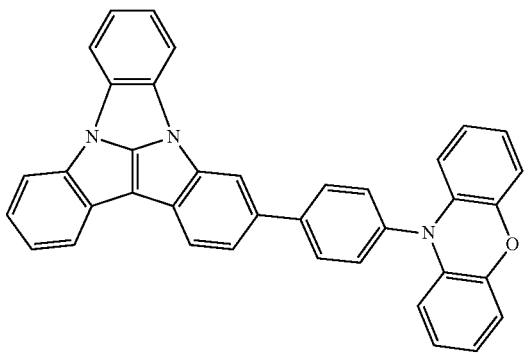
B49
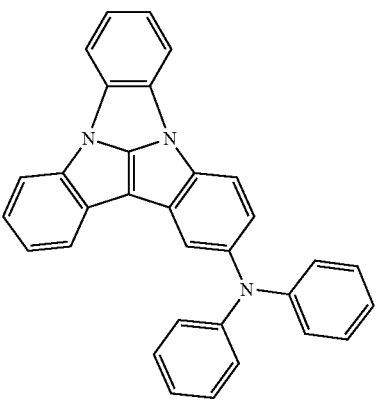
B50
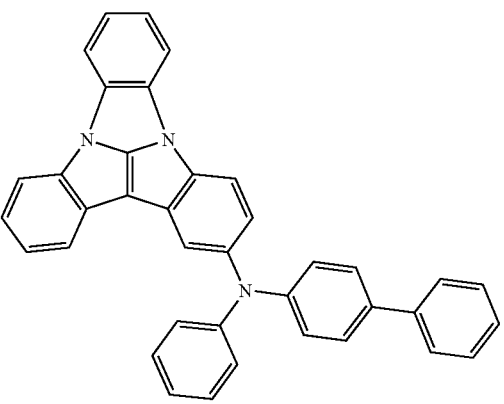
B51
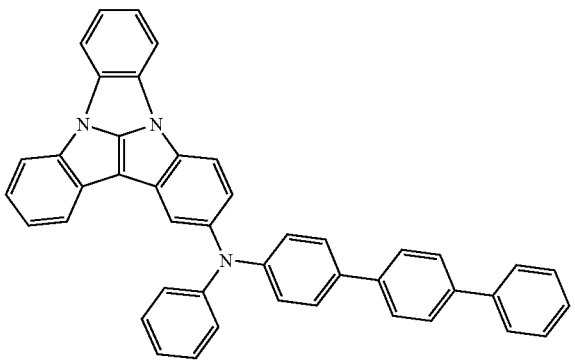

B52
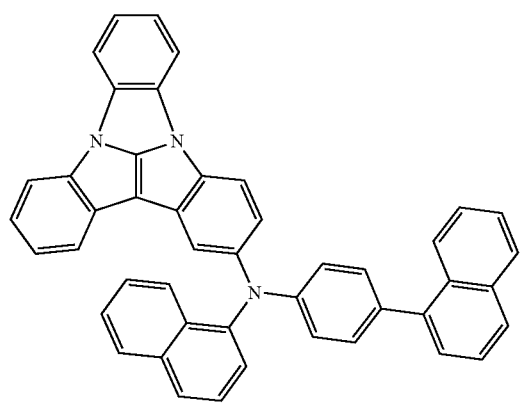
B55
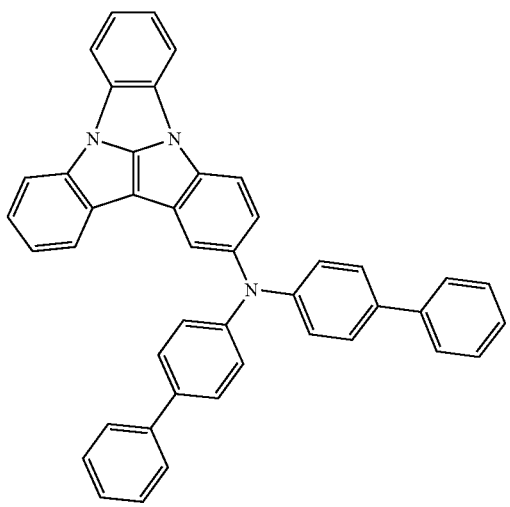
B53
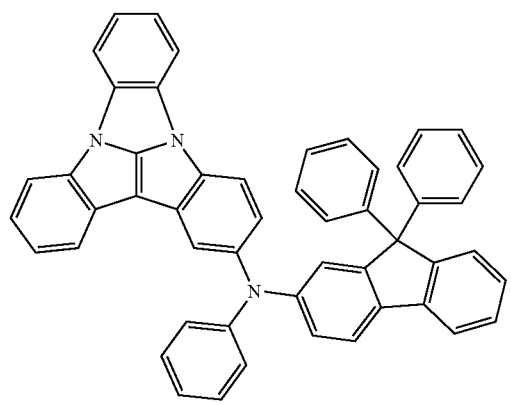
B56
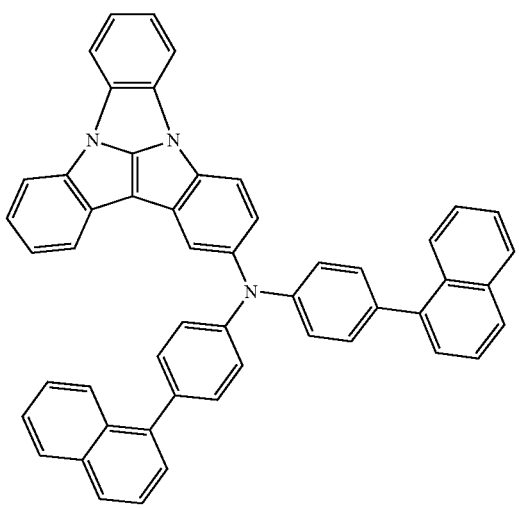
B54
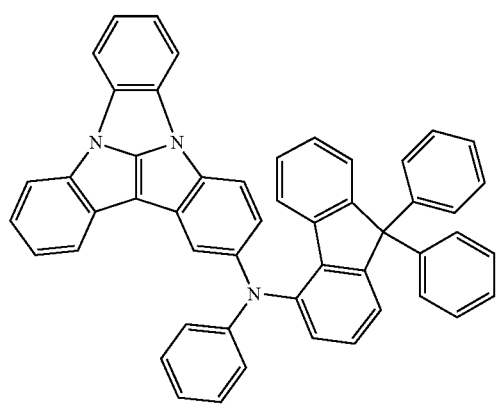
B57
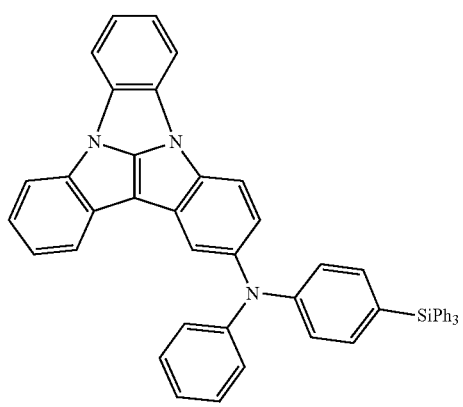

| B58 | B61 |
|---|---|
| 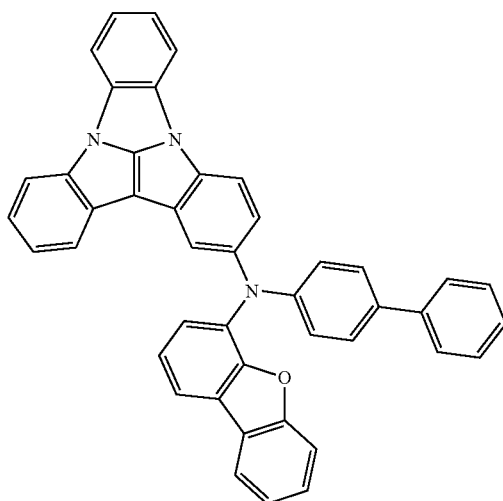 | 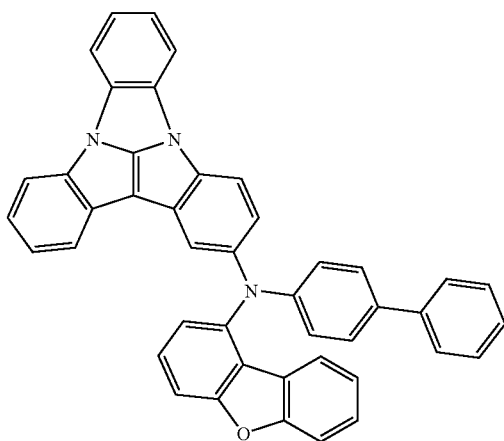 |
| B59 | B62 |
| 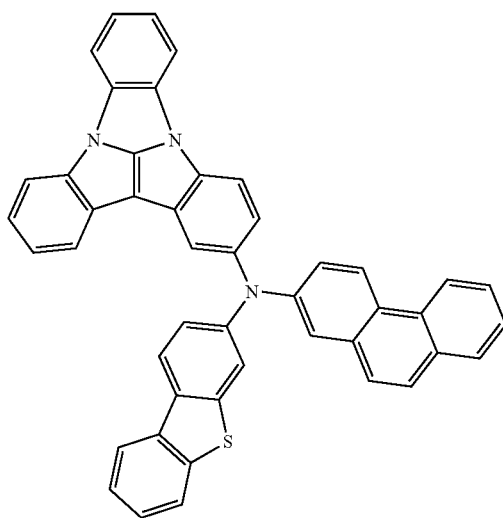 | 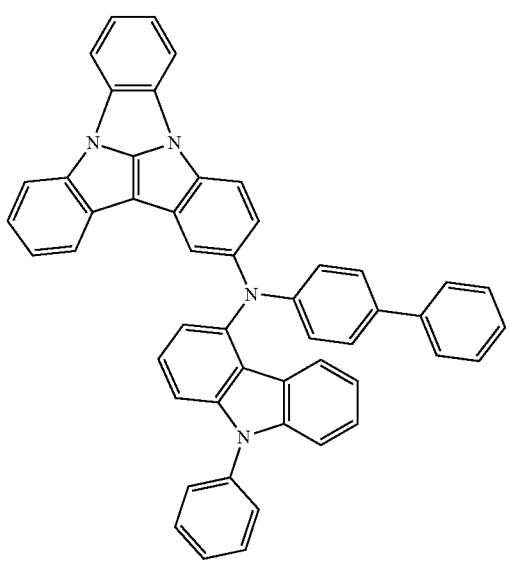 |
| B60 | B63 |
| 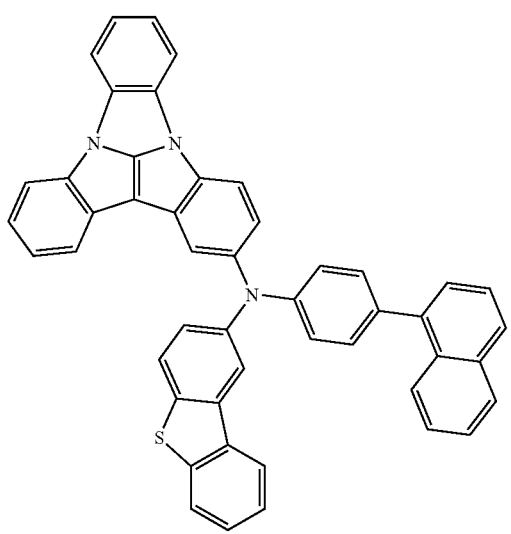 | 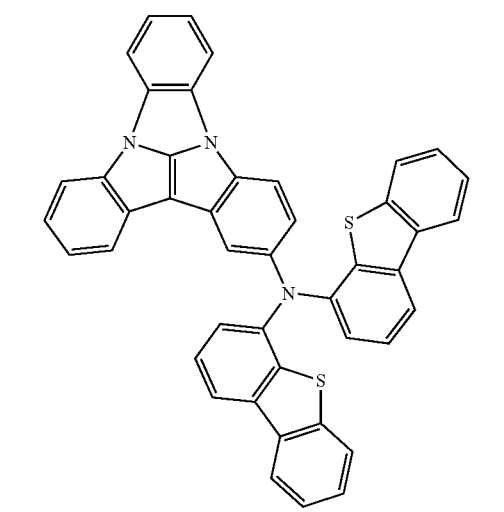 |

B64
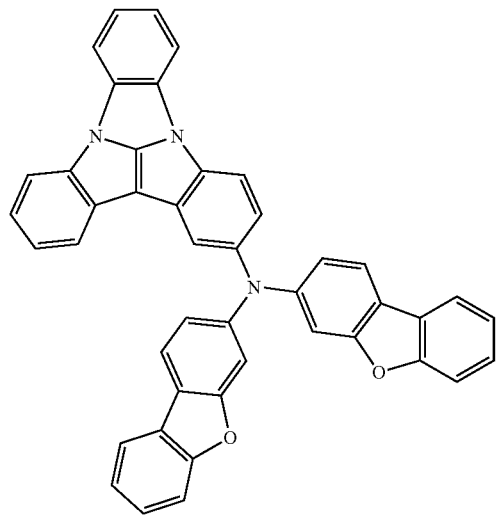
B66
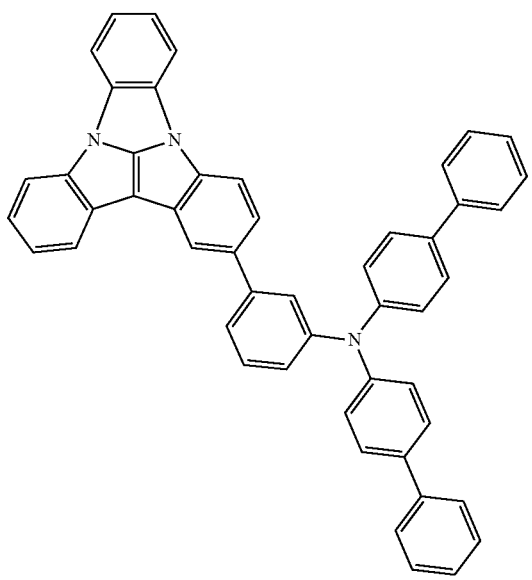
B65
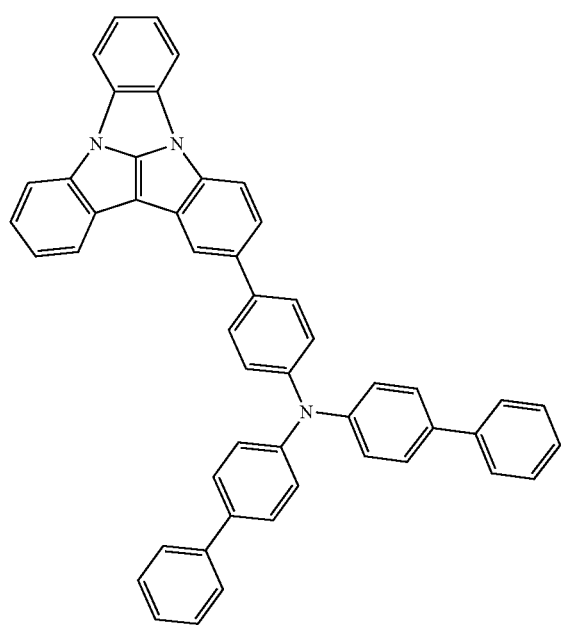
B67
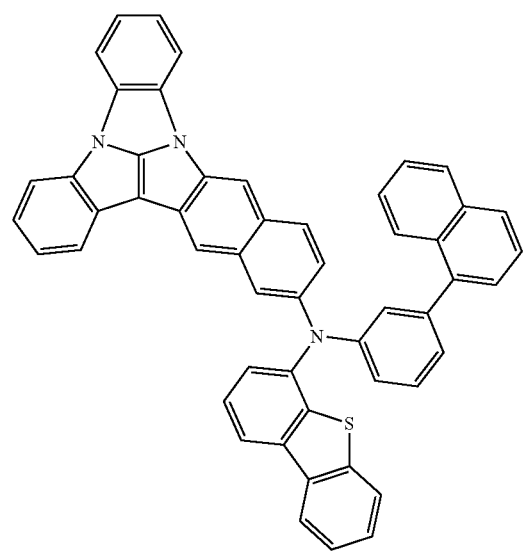

B68
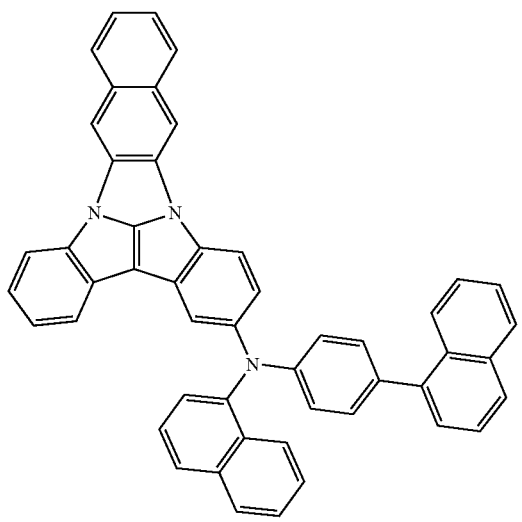
B69
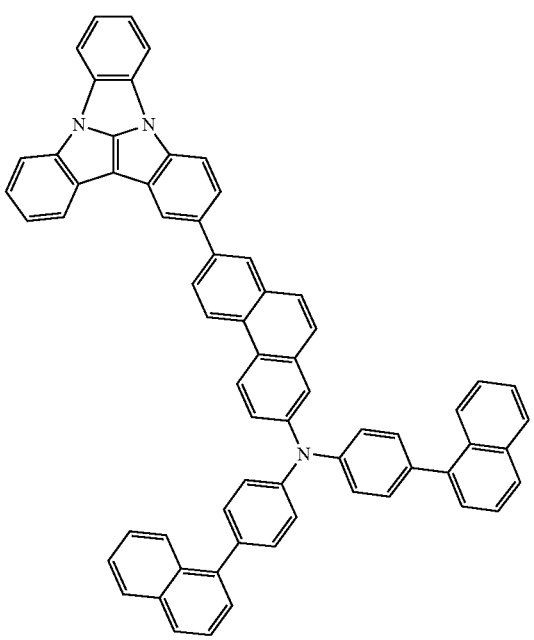
B70
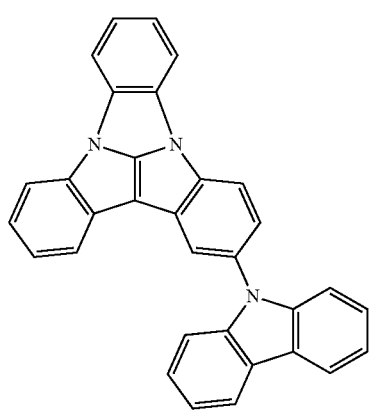
B71
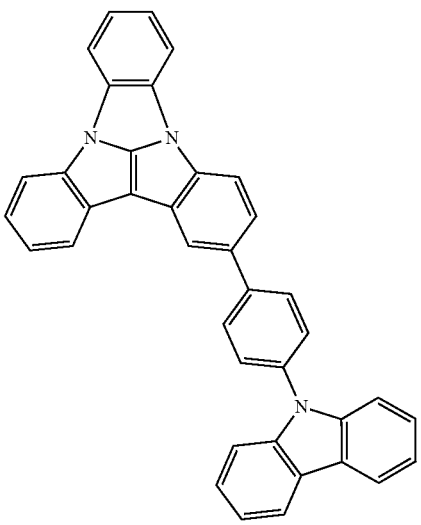
B72
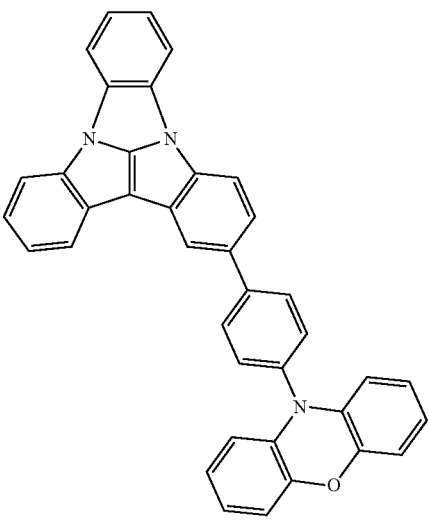
B73
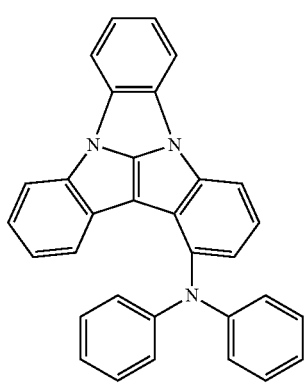

B74
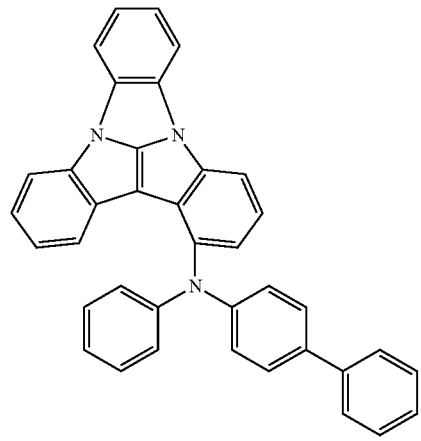
B75
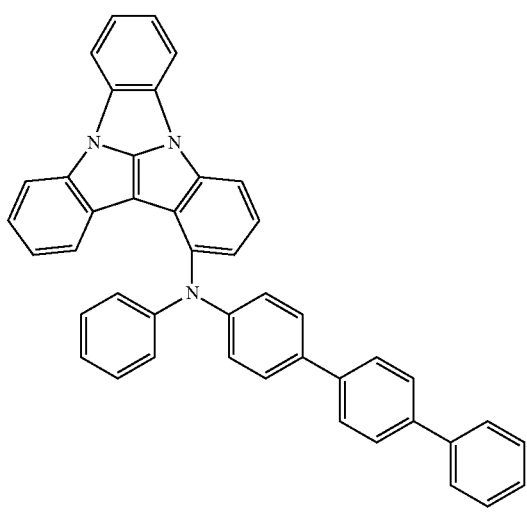
B76
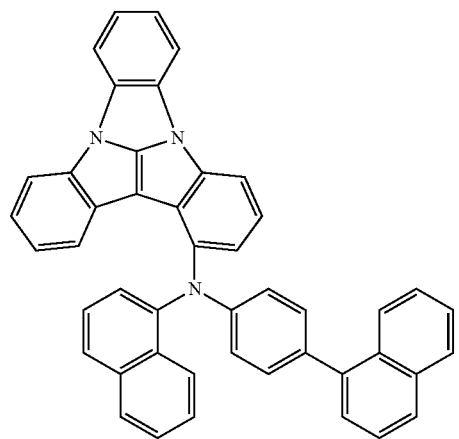
B77
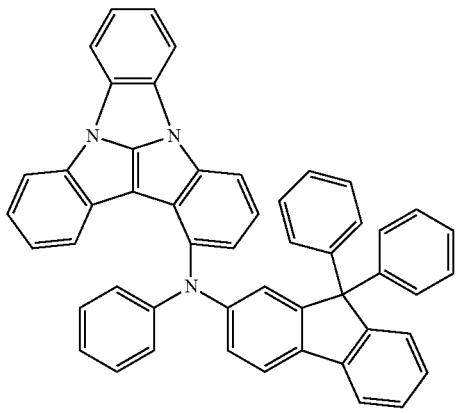
B78
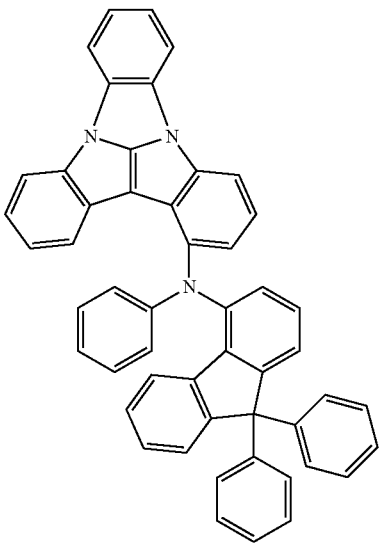
B79
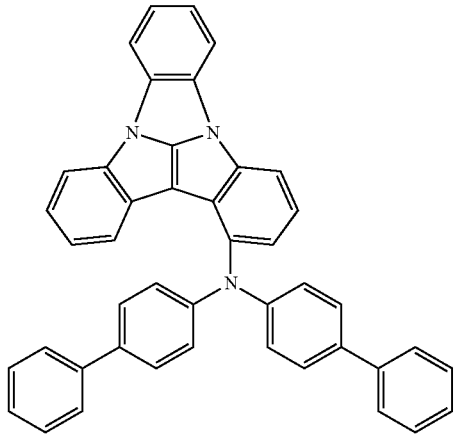

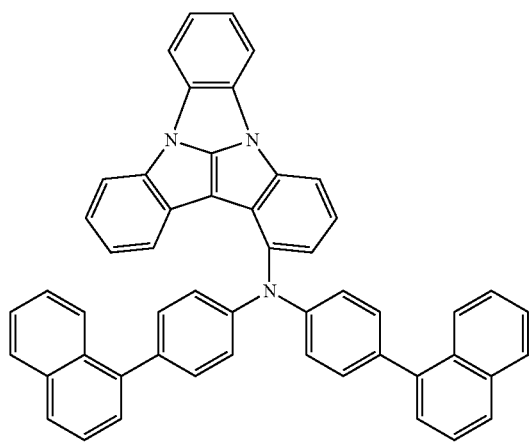
B80
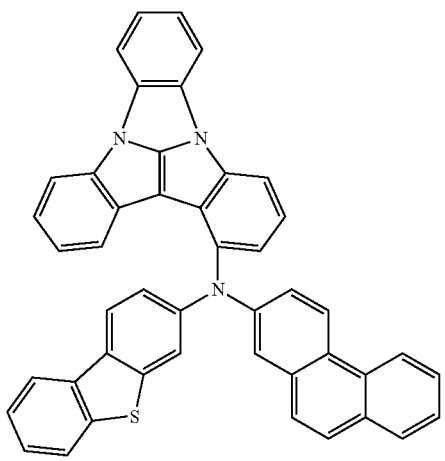
B83
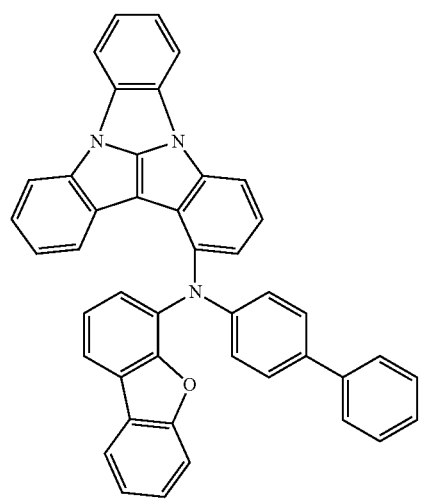
B81
B82
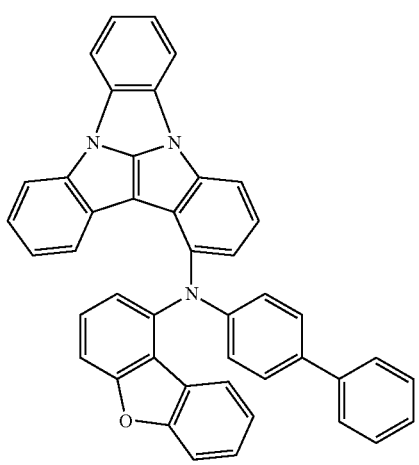
B84
B85

B86
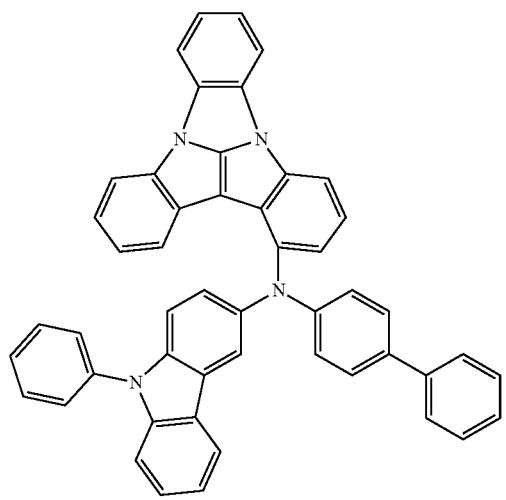
B87
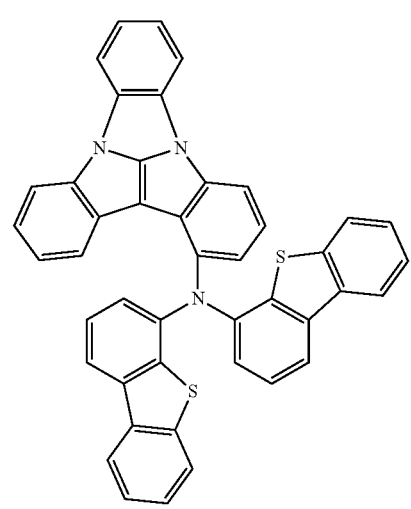
B88
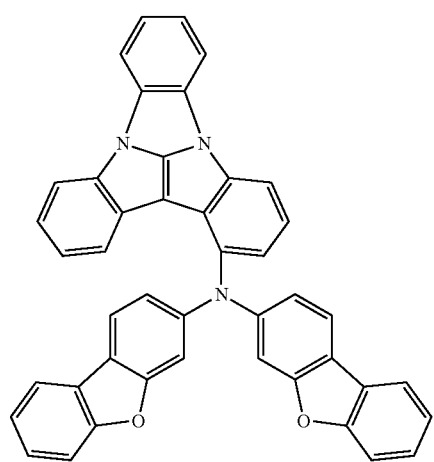
B89
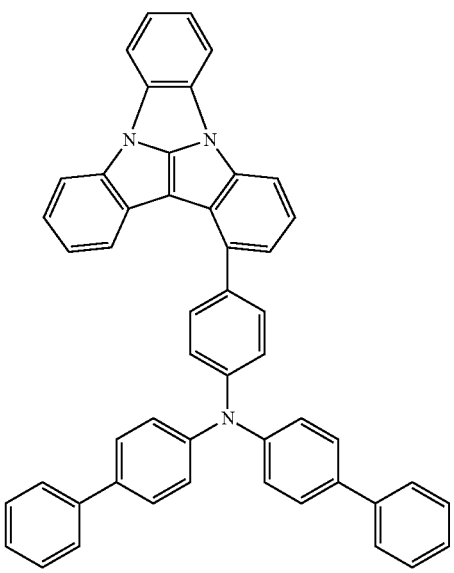
B90
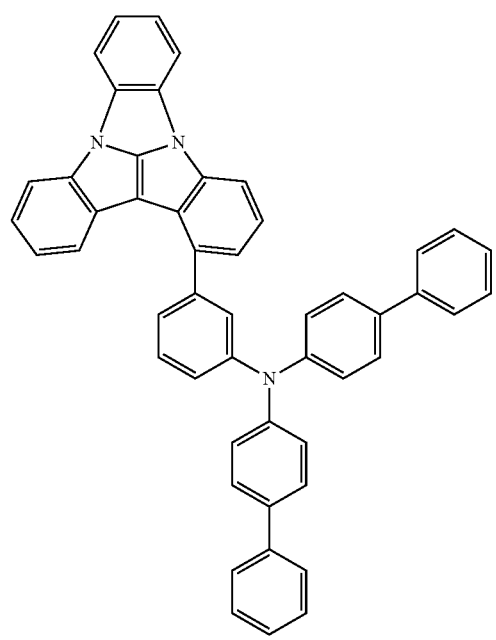

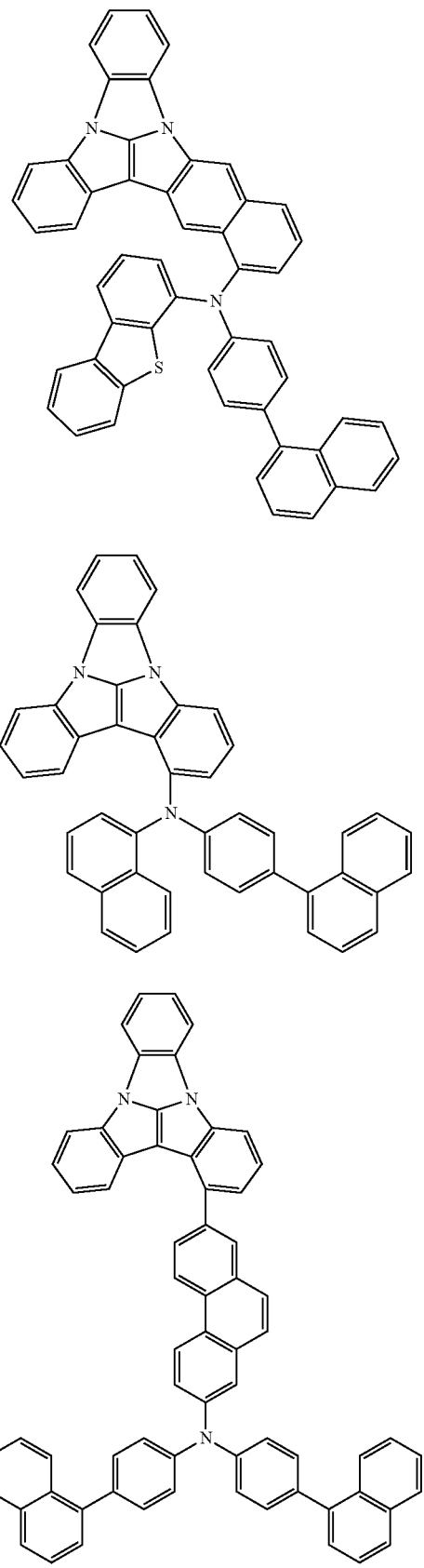
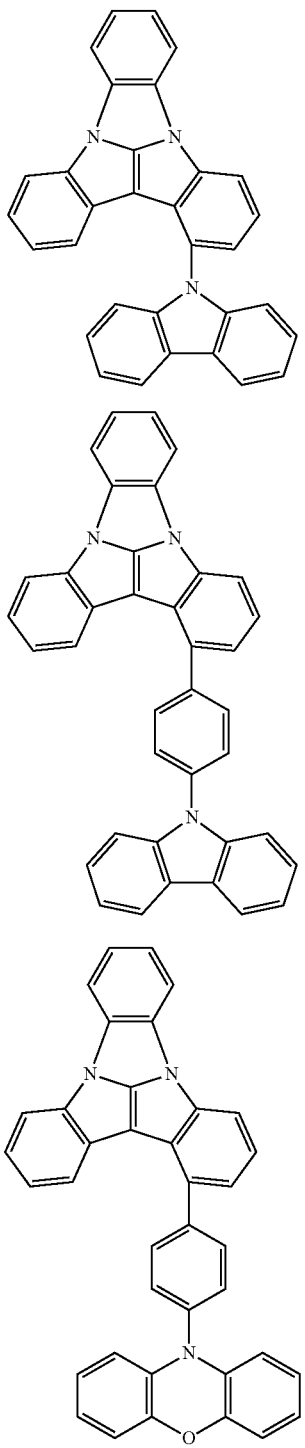

In the compounds shown in Compound Group 1 and Compound Group 2, SiPh$_3$ represents a phenyl substituted silyl group, particularly, triphenylsilyl group.

The condensed cyclic compound represented by Formula 1 includes a condensed ring obtained by condensing six or more rings in a cores part, and one amine group is substituted for the condensed ring, thereby showing excellent hole transport properties and improved thermal stability and electron tolerance.

In the organic electroluminescence device 10 of an embodiment, as shown in FIGS. 1 to 3, a hole transport region HTR may include one kind, two or more kinds of the condensed cyclic compounds in Compound Group 1 and Compound Group 2. Meanwhile, the hole transport region HTR may further include a known material in addition to the condensed compounds in Compound Group 1 or Compound Group 2.

The organic electroluminescence device 10 of an embodiment includes the condensed cyclic compound of an embodiment in a hole transport region HTR, and may further include a known hole injection material or a known hole transport material in a hole transport region HTR, or at least one of a hole injection layer HIL or a hole transport layer HTL.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino) triphenylamine (m-MTDATA), 4,4', 4''-tris(N,N-diphenylamino)triphenylamine (TDATA), 4,4', 4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl)-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h] quinoxaline-2,3,6,7,10,11-hexacarbonitrile (HAT-CN), etc.

The hole transport layer HTL may include in addition to the condensed cyclic compound of an embodiment, for example, carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4', 4''-tris(N-carbazolyl)triphenylamine (TCTA), N,N'-di (naphthalene-1-yl)-N,N'-diphenyl-benzidine (NPB), 4,4'-cyclohexylidene bis[N,N-bis(4-methylphenyl) benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material in addition to the above-described materials to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ) and 2,3,5,6,7,7,8,8-tetrafluoro-tetracyanoquinodimethane (F4-TCNQ), metal oxides such as tungsten oxide, and molybdenum oxide, without limitation.

As described above, the hole transport region HTR may further include at least one of a hole buffer layer (not shown) or an electron blocking layer EBL in addition to the hole injection layer HIL and the hole transport layer HTL. The hole buffer layer (not shown) may compensate an optical resonance distance according to the wavelength of light emitted from an emission layer EML and may increase light-emitting efficiency. Materials which may be included in the hole transport region HTR may be used as materials which may be included in the hole buffer layer (not shown). The electron blocking layer EBL is a layer which plays the role of preventing electron injection from the electron transport region ETR to the hole transport region HTR.

The emission layer EML is provided on the hole transport region HTR. The thickness of the emission layer EML may be, for example, from about 100 Å to about 1,000 Å, or from about 100 Å to about 300 Å. The emission layer EML may have a single layer formed using a single material, a single layer formed using a plurality of different materials, or a multilayer structure having a plurality of layers formed using a plurality of different materials.

The emission layer EML in the organic electroluminescence device 10 of an embodiment may include anthracene derivatives, pyrene derivatives, fluoranthene derivatives, chrysene derivatives, dihydro benzanthracene derivatives, or triphenylene derivatives. Particularly, the emission layer EML may include anthracene derivatives or pyrene derivatives.

The emission layer EML may include anthracene derivatives represented by the following Formula 3:

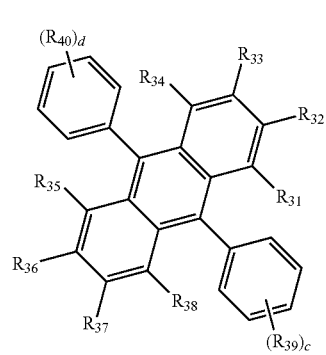

[Formula 3]

In Formula 3, $R_{31}$ to $R_{40}$ are each independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring. Meanwhile, $R_{31}$ to $R_{40}$ may be combined with an adjacent group to form a saturated hydrocarbon ring or an unsaturated hydrocarbon ring.

In Formula 3, each of "c" and "d" may be independently an integer of 0 to 5.

Formula 3 may be represented by any one of the following Formula 3-1 to Formula 3-6:

3-1
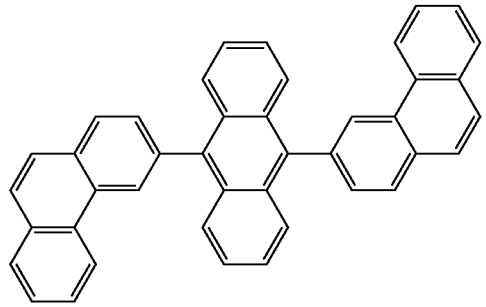

3-2
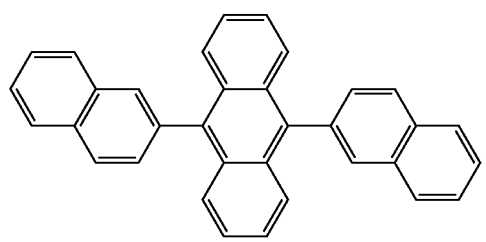

3-3
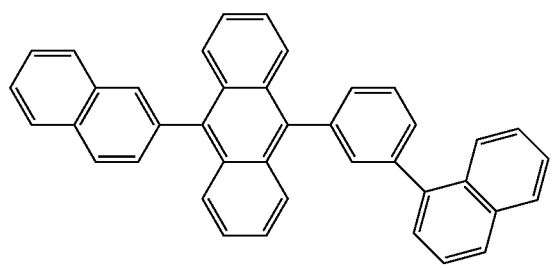

3-4
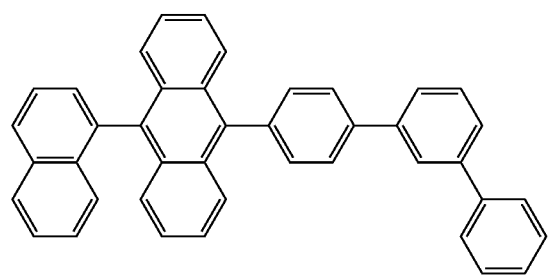

3-5
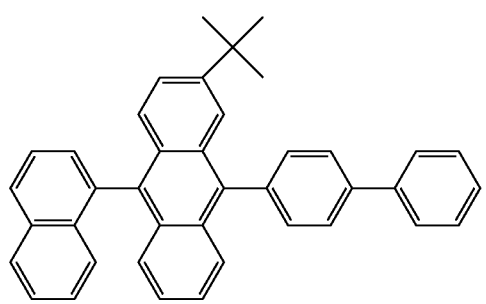

3-6
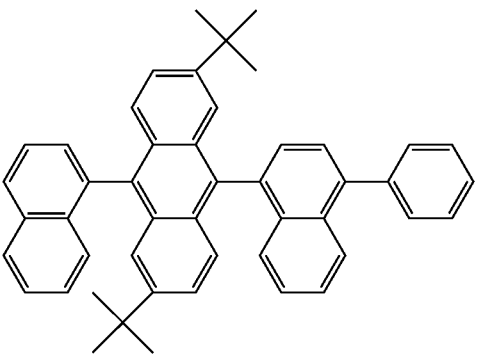

In the organic electroluminescence device 10 of an embodiment as shown in FIGS. 1 to 3, the emission layer EML may include a host and a dopant, and the emission layer EML may include the compound represented by Formula 3 as a host material.

The emission layer EML may be a blue emission layer which emits blue light having a wavelength region of less than about 470 nm. For example, the emission layer EML may be a layer emitting deep blue light which has a wavelength region of about 440 nm to about 470 nm, or about 450 nm to about 470 nm.

The emission layer EML may further include a common material known in the art as a host material. For example, the emission layer EML may include as the host material at least one of bis[2-(diphenylphosphino)phenyl] ether oxide (DPEPO), 4,4'-bis(carbazol-9-yl)biphenyl (CBP), 1,3-bis(N-carbazolyl)benzene (mCP), 2,8-bis(diphenylphosphoryl)dibenzo[b,d]furan (PPF), 4,4',4''-tris(carbazol-9-yl)-triphenylamine (TcTa) or 1,3,5-tris(N-phenylbenzimidazole-2-yl)benzene (TPBi). However, an embodiment of the inventive concept is not limited thereto. For example, tris(8-hydroxyquinolino)aluminum ($Alq_3$), 4poly(N-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethylbiphenyl (CDBP), 2-methyl-9,10-bis(naphthalen-2-yl)anthracene (MADN), bis[2-(diphenylphosphino)phenyl] ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), etc., may be used as the host material.

In an embodiment, the emission layer EML may include as a known dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

In the organic electroluminescence device 10 of an embodiment, as shown in FIGS. 1 to 3, the electron transport region ETR is provided on the emission layer EML. The electron transport region ETR may include at least one of a hole blocking layer HBL, an electron transport layer ETL or an electron injection layer EIL. However, an embodiment of the inventive concept is not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure having a plurality of different materials, or a structure laminated from the emission layer EML of electron transport layer ETL/electron injection layer EIL, or hole blocking layer HBL/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes an electron transport layer ETL, the electron transport region ETR may include an anthracene-based compound. For example, the electron transport layer may include tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq$_2$), 9,10-di(naphthalene-2-yl)anthracene (ADN), or a mixture thereof, without limitation. The thickness of the electron transport layer ETL may be from about 100 Å to about 1,000 Å and may be, for example, from about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may include, for example, LiF, lithium quinolate (LiQ), Li$_2$O, BaO, NaCl, CsF, a metal in lanthanoides such as Yb, or a metal halide such as RbCl and RbI. However, an embodiment of the inventive concept is not limited thereto. The electron injection layer EIL may also be formed using a mixture material of an electron transport material and an insulating organo metal salt. The organo metal salt may be a material having an energy band gap of about 4 eV or more. Particularly, the organo metal salt may include, for example, metal acetates, metal benzoates, metal acetoacetates, metal acetylacetonates, or metal stearates. The thickness of the electron injection layer EIL may be from about 1 Å to about 100 Å, and from about 3 Å to about 90 Å. If the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, an embodiment of the inventive concept is not limited thereto.

The second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound or a mixture including thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

Although not shown, the second electrode EL2 may be connected with an auxiliary electrode. If the second electrode EL2 is connected with the auxiliary electrode, the resistance of the second electrode EL2 may decrease.

Meanwhile, although not shown in the drawings, on the second electrode EL2 of the organic electroluminescence device 10 of an embodiment, a capping layer (not shown) may be further disposed. The capping layer (not shown) may include, for example, α-NPD, NPB, TPD, m-MTDATA, Alq3, CuPc, N4,N4,N4',N4'-tetra(biphenyl-4-yl) biphenyl-4,4'-diamine (TPD15), 4,4',4''-tris(carbazol sol-9-yl) triphenylamine (TCTA), N,N'-bis(naphthalen-1-yl), etc.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

The condensed cyclic compound may be used as a material for an organic electroluminescence device 10. The organic electroluminescence device 10 according to an embodiment of the inventive concept may include the condensed cyclic compound in at least one organic layer disposed between a first electrode EL1 and a second electrode EL2, or a capping layer (not shown) disposed on the second electrode EL2.

Particularly, the organic electroluminescence device 10 according to an embodiment of the inventive concept includes the condensed cyclic compound in at least one organic layer disposed between the first electrode EL1 and the second electrode EL2 and may show improved emission efficiency and life characteristic. Particularly, the organic electroluminescence device 10 according to an embodiment includes the condensed cyclic compound in a hole transport region HTR, thereby showing improved emission efficiency and life characteristic and low driving property.

Hereinafter, a condensed cyclic compound according to an embodiment of the inventive concept and an organic electroluminescence device of an embodiment will be explained in more detail with reference to embodiments and comparative embodiments. The following embodiments are only illustrations to assist the understanding of the inventive concept, and the scope of the inventive concept is not limited thereto

EXAMPLES

1. Synthesis of Condensed Cyclic Compounds

First, the synthetic method of the condensed cyclic compound according to an embodiment of the inventive concept will be particularly explained referring to the synthetic methods of Compound A8, Compound A48, Compound A57, Compound A59, Compound B40 and Compound B53. In addition, the synthetic methods of the condensed cyclic compounds explained below are only examples, and the synthetic method of a condensed cyclic compound according to an embodiment of the inventive concept is not limited thereto.

(1) Synthesis of Compound A8

A condensed cyclic compound according to an embodiment, Compound A8, may be synthesized, for example, by the following Reaction 1:

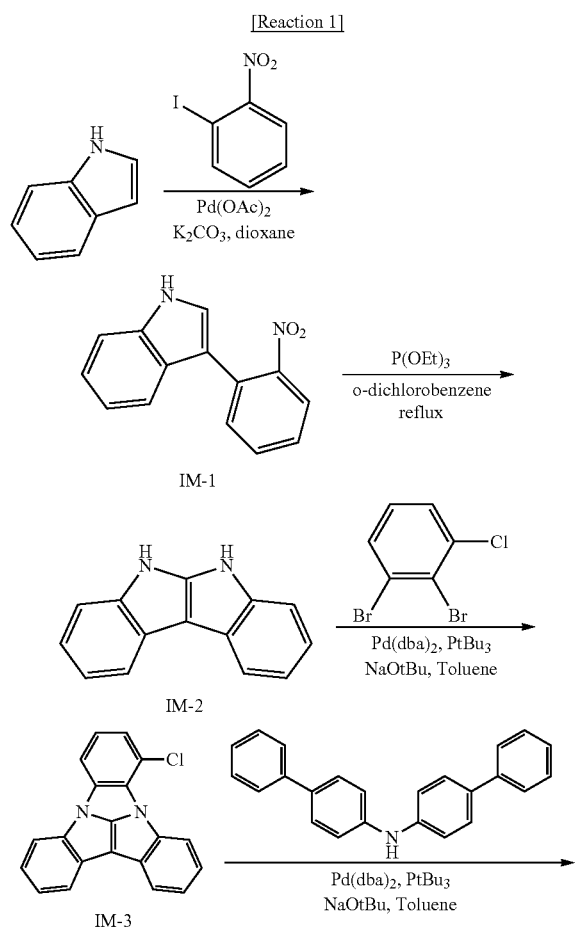

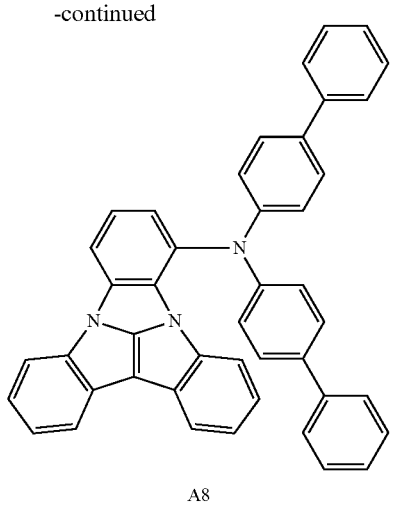

A8

<Synthesis of Intermediate IM-1>

Under an argon (Ar) atmosphere, to a 500 ml, three neck flask, 20.00 g (170.7 mmol) of indole, 12.78 g (0.1 equiv, 56.9 mmol) of Pd(OAc)$_2$, 157.30 g (2 equiv, 1.13 mol) of K$_2$CO$_3$, 51.01 g (1.2 equiv, 204.9 mmol) of 2-iodo-1-nitrobenzene and 341 ml of 1,4-dioxane were added in that order, followed by heating, stirring and refluxing for about 24 hours. After cooling to room temperature, the reaction product was filtered with celite to separate insoluble residue, water was added, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated and then, the crude product thus obtained was separated by silica gel column chromatography (using a mixture solvent of hexane and toluene as a developer) to obtain Intermediate IM-1 (17.08 g, yield 42%) as a white solid compound. A molecular ion peak of m/z=238 was observed by measuring FAB-MS, and from the result, the product was identified as Intermediate IM-1.

<Synthesis of Intermediate IM-2>

Under an argon atmosphere, to a 300 ml, three-neck flask, 15.00 g (63.0 mmol) of IM-1, 126 ml of o-dichlorobenzene and 41.85 g (4 equiv, 251.8 mmol) of P(OEt)$_3$ were added in that order, followed by heating and stirring at about 160° C. for about 24 hours. After cooling to room temperature, the reaction solvents were distilled off, and the crude product thus obtained was separated by silica gel column chromatography (using a mixture solvent of hexane and toluene as a developer) to obtain Intermediate IM-2 (10.39 g, yield 80%) as a white solid compound. A molecular ion peak of m/z=206 was observed by measuring FAB-MS, and from the result, the product was identified as Intermediate IM-2.

<Synthesis of Intermediate IM-3>

Under an argon atmosphere, to a 500 ml, three neck flask, 10.00 g (48.5 mmol) of Intermediate IM-2, 0.84 g (0.03 equiv, 1.5 mmol) of Pd(dba)$_2$, 11.65 g (2.5 equiv, 121.2 mmol) of NaOtBu, 242 ml of toluene, 13.11 g (1 equiv, 48.5 mmol) of 1,2-dibromo-3-chlorobenzene and 0.98 g (0.1 equiv, 4.8 mmol) of tBu3P were added in that order, followed by heating, stirring and refluxing for about 6 hours. After cooling to room temperature, water was added to the reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated and then, the crude product thus obtained was separated by silica gel column chromatography (using a mixture solvent of hexane and toluene as a developer) to obtain Intermediate IM-3 (11.45 g, yield 75%) as a white solid compound. A molecular ion peak of m/z=314 was observed by measuring FAB-MS, and from the result, the product was identified as Intermediate IM-3.

<Synthesis of Compound A8>

Under an argon atmosphere, to a 500 ml, three neck flask, 5.00 g (15.9 mmol) of Intermediate IM-3, 0.27 g (0.03 equiv, 0.5 mmol) of Pd(dba)$_2$, 3.05 g (2 equiv, 31.8 mmol) of NaOtBu, 80 ml of toluene, 5.62 g (1.1 equiv, 17.5 mmol) of bis(4-biphenyl)amine and 0.32 g (0.1 equiv, 1.6 mmol) of tBu3P were added in that order, followed by heating, stirring and refluxing for about 6 hours. After cooling to room temperature, water was added to the reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated and then, the crude product thus obtained was separated by silica gel column chromatography (using a mixture solvent of hexane and toluene as a developer) to obtain Compound A8 (7.62 g, yield 80%) as a white solid compound. A molecular ion peak of m/z=599 was observed by measuring FAB-MS, and from the result, the product was identified as Compound A8.

(2) Synthesis of Compound A48

A condensed cyclic compound according to an embodiment, Compound A48, may be synthesized, for example, by the following Reaction 2:

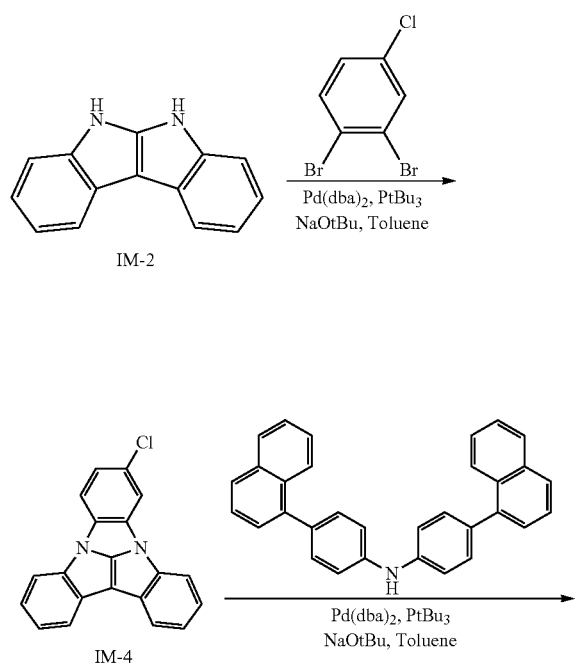

[Reaction 2]

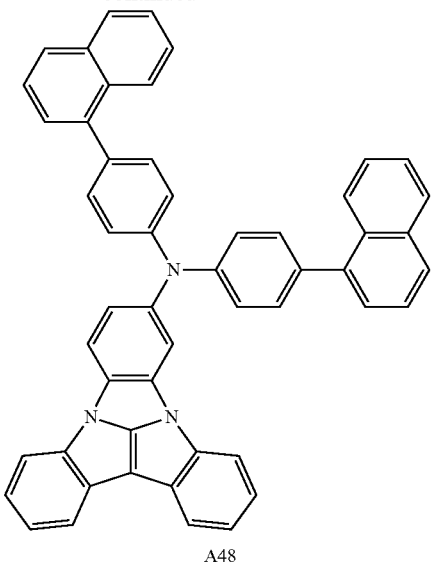

A48

<Synthesis of Intermediate IM-4>

Under an argon atmosphere, to a 500 ml, three neck flask, 10.00 g (48.5 mmol) of Intermediate IM-2, 0.84 g (0.03 equiv, 1.5 mmol) of Pd(dba)$_2$, 11.65 g (2.5 equiv, 121.2 mmol) of NaOtBu, 242 ml of toluene, 13.11 g (1 equiv, 48.5 mmol) of 1,2-dibromo-3-chlorobenzene and 0.98 g (0.1 equiv, 4.8 mmol) of tBu3P were added in that order, followed by heating, stirring and refluxing for about 6 hours. After cooling to room temperature, water was added to the reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated and then, the crude product thus obtained was separated by silica gel column chromatography (using a mixture solvent of hexane and toluene as a developer) to obtain Intermediate IM-4 (11.14 g, yield 73%) as a white solid compound. A molecular ion peak of m/z=314 was observed by measuring FAB-MS, and from the result, the product was identified as Intermediate IM-4.

<Synthesis of Compound A48>

Under an argon atmosphere, to a 500 ml, three neck flask, 5.00 g (15.9 mmol) of Intermediate IM-4, 0.27 g (0.03 equiv, 0.5 mmol) of Pd(dba)$_2$, 3.05 g (2 equiv, 31.8 mmol) of NaOtBu, 80 ml of toluene, 6.50 g (1.1 equiv, 17.5 mmol) of bis(4-(naphthalen-1-yl)phenyl)amine and 0.32 g (0.1 equiv, 1.6 mmol) of tBu3P were added in that order, followed by heating, stirring and refluxing for about 6 hours. After cooling to room temperature, water was added to the reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated and then, the crude product thus obtained was separated by silica gel column chromatography (using a mixture solvent of hexane and toluene as a developer) to obtain Compound A48 (8.77 g, yield 85%) as a white solid compound. A molecular ion peak of m/z=649 was observed by measuring FAB-MS, and from the result, the product was identified as Compound A48.

(3) Synthesis of Compound A57

A condensed cyclic compound according to an embodiment, Compound A57, may be synthesized, for example, by the following Reaction 3:

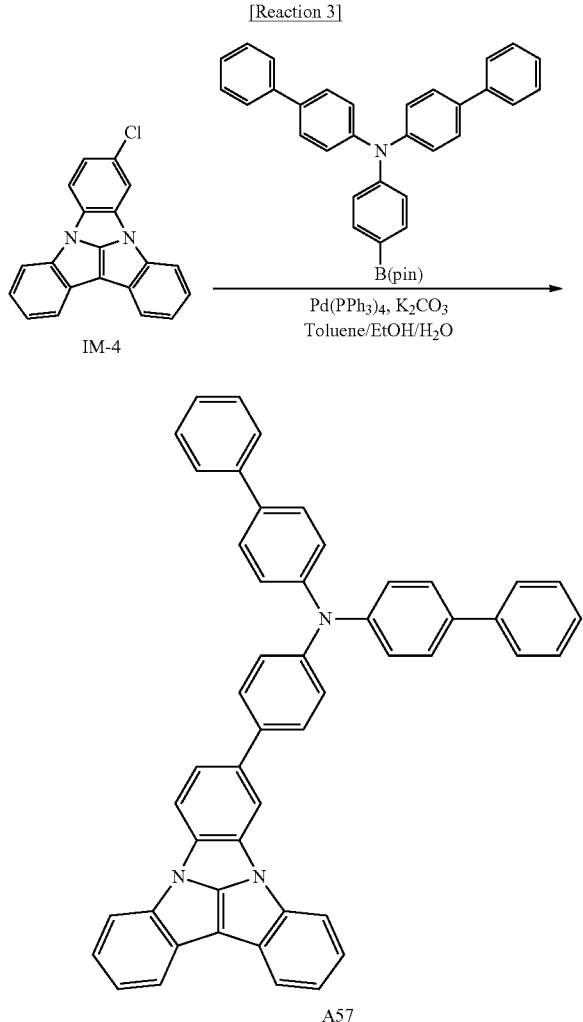

(4) Synthesis of Compound A59

A condensed cyclic compound according to an embodiment, Compound A59, may be synthesized, for example, by the following Reaction 4:

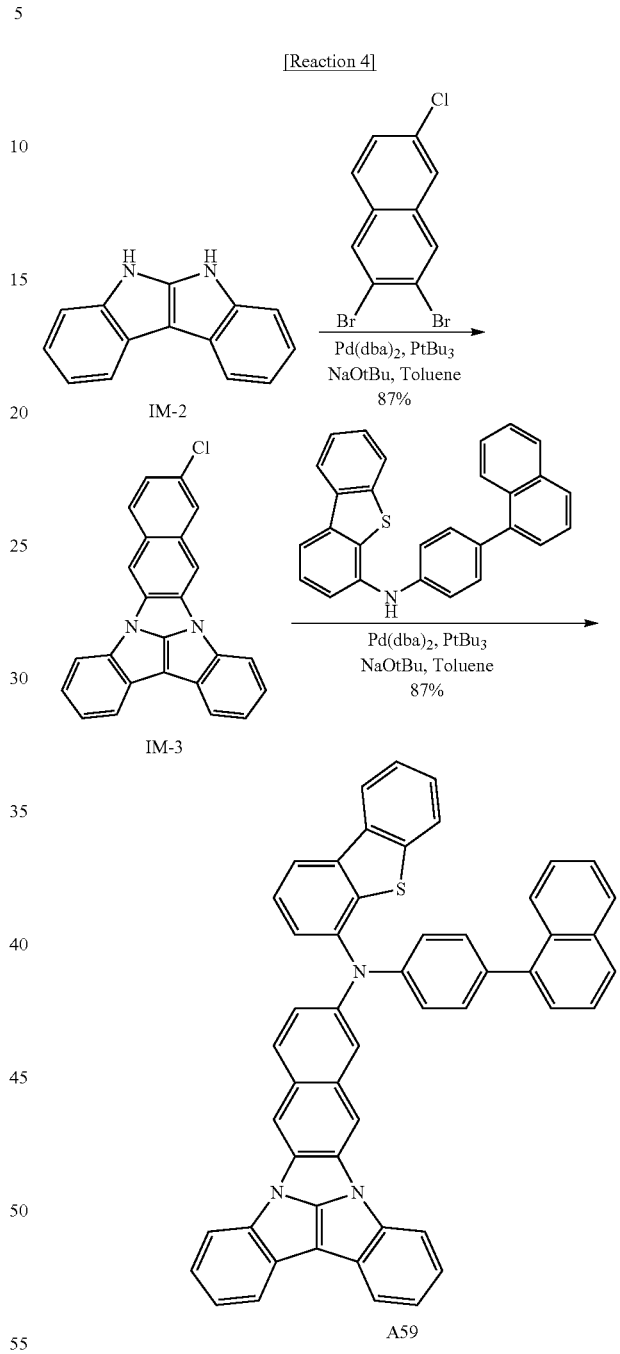

Under an argon atmosphere, to a 300 ml, three neck flask, 5.00 g (15.9 mmol) of Intermediate IM-4, 9.15 g (1.1 equiv, 17.5 mmol) of N,N-di(4-biphenylyl)-4-(4,4,5,5-tetramethyl-1,3,2-dioxaborolan-2-yl)aniline, 6.59 g (3 equiv, 47.7 mmol) of $K_2CO_3$, 0.92 g (0.05 equiv, 0.8 mmol) of $Pd(PPh_3)_4$, and 110 ml of a mixture solution of toluene/ethanol (EtOH)/water (4/2/1) were added in that order, followed by heating and stirring for about 5 hours at about 80° C. After cooling to room temperature, the reaction product was extracted with toluene. An aqueous layer was removed, and an organic layer was washed with a saline solution and dried with $MgSO_4$. $MgSO_4$ was separated, and the organic layer was concentrated. Then, the crude product thus obtained was separated by silica gel column chromatography (using a mixture solvent of hexane and toluene as a developer) to obtain Compound A57 (9.34 g, yield 87%) as a white solid compound. A molecular ion peak of m/z=675 was observed by measuring FAB-MS, and from the result, the product was identified as Compound A57.

<Synthesis of Intermediate IM-5>

Under an argon atmosphere, to a 500 ml, three neck flask, 10.00 g (48.5 mmol) of Intermediate IM-2, 0.84 g (0.03 equiv, 1.5 mmol) of $Pd(dba)_2$, 11.65 g (2.5 equiv, 121.2 mmol) of NaOtBu, 242 ml of toluene, 15.54 g (1 equiv, 48.5 mmol) of 2,3-dibromo-6-chloronaphthalene and 0.98 g (0.1 equiv, 4.8 mmol) of tBu3P were added in that order, followed by heating, stirring and refluxing for about 6 hours. After cooling to room temperature, water was added to the reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated. Then, the crude product thus obtained was separated by silica gel column chromatography (using a mixture solvent of hexane and toluene as a developer) to obtain Intermediate IM-5 (11.50 g, yield 65%) as a white solid compound. A molecular ion peak of m/z=364 was observed by measuring FAB-MS, and from the result, the product was identified as Intermediate IM-5.

<Synthesis of Compound A59>

Under an argon atmosphere, to a 500 ml, three neck flask, 5.00 g (13.7 mmol) of Intermediate IM-5, 0.24 g (0.03 equiv, 0.4 mmol) of Pd(dba)$_2$, 2.63 g (2 equiv, 27.4 mmol) of NaOtBu, 69 ml of toluene, 6.05 g (1.1 equiv, 15.1 mmol) of N-[4-(1-naphthalenyl)phenyl]-4-dibenzothiophenyl-4-amine and 0.28 g (0.1 equiv, 1.4 mmol) of tBu3P were added in that order, followed by heating, stirring and refluxing for about 6 hours. After cooling in the air to room temperature, water was added to the reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated and then, the crude product thus obtained was separated by silica gel column chromatography (using a mixture solvent of hexane and toluene as a developer) to obtain Compound A59 (7.90 g, yield 79%) as a white solid compound. A molecular ion peak of m/z=729 was observed by measuring FAB-MS, and from the result, the product was identified as Compound A59.

(5) Synthesis of Compound B40

A condensed cyclic compound according to an embodiment, Compound B40, may be synthesized, for example, by the following Reaction 5:

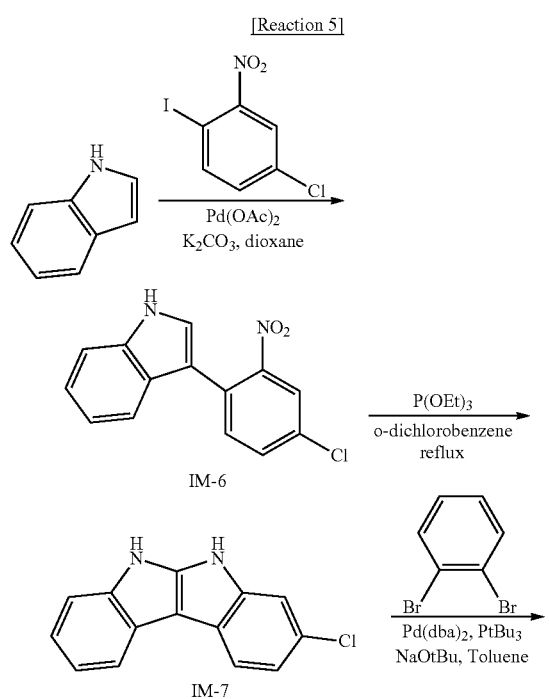

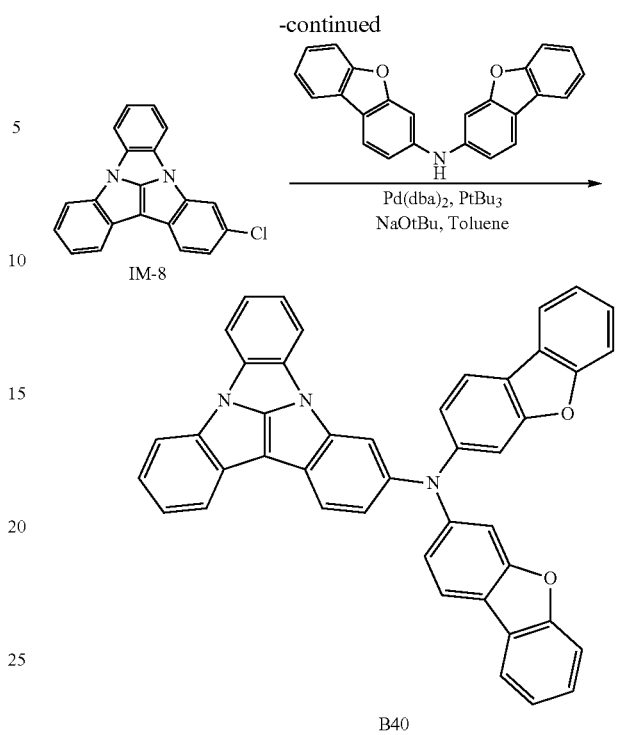

<Synthesis of Intermediate IM-6>

Under an argon atmosphere, to a 500 ml, three neck flask, 20.00 g (170.7 mmol) of indole, 7.67 g (0.1 equiv, 34.1 mmol) of Pd(OAc)$_2$, 94.38 g (2 equiv, 682.9 mmol) of K$_2$CO$_3$, 58.07 g (1.2 equiv, 204.9 mmol) of 5-chloro-2-iodo-1-nitrobenzene and 341 ml of 1,4-dioxane were added in that order, followed by heating, stirring and refluxing for about 24 hours. After cooling to room temperature, the reaction product was filtered with celite to separate insoluble residue, water was added to the remaining reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated and then, the crude product thus obtained was separated by silica gel column chromatography (using a mixture solvent of hexane and toluene as a developer) to obtain Intermediate IM-6 (18.62 g, yield 40%) as a white solid compound. A molecular ion peak of m/z=272 was observed by measuring FAB-MS, and from the result, the product was identified as Intermediate IM-6.

<Synthesis of Intermediate IM-7>

Under an argon atmosphere, to a 300 ml, three-neck flask, 15.00 g (55.0 mmol) of Intermediate IM-6, 110 ml of o-dichlorobenzene and 36.56 g (4 equiv, 220.0 mmol) of P(OEt)$_3$ were added in that order, followed by heating and stirring at about 160° C. for about 24 hours. After cooling to room temperature, the reaction solvents were distilled off, and the crude product thus obtained was separated by silica gel column chromatography (using a mixture solvent of hexane and toluene as a developer) to obtain Intermediate IM-7 (10.06 g, yield 76%) as a white solid compound. A molecular ion peak of m/z=240 was observed by measuring FAB-MS, and from the result, the product was identified as Intermediate IM-7.

Synthesis of Intermediate IM-8

Under an argon atmosphere, to a 500 ml, three neck flask, 10.00 g (41.5 mmol) of Intermediate IM-7, 0.72 g (0.03 equiv, 1.2 mmol) of Pd(dba)$_2$, 9.98 g (2.5 equiv, 103.9 mmol) of NaOtBu, 208 ml of toluene, 9.80 g (1 equiv, 41.5 mmol) of 1,2-dibromobenzene and 0.84 g (0.1 equiv, 4.2 mmol) of tBu3P were added in that order, followed by heating, stirring and refluxing for about 6 hours. After cooling to room temperature, water was added to the reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated and then, the crude product thus obtained was separated by silica gel column chromatography (using a mixture solvent of hexane and toluene as a developer) to obtain Intermediate IM-8 (10.07 g, yield 77%) as a white solid compound. A molecular ion peak of m/z=314 was observed by measuring FAB-MS, and from the result, the product was identified as Intermediate IM-8.

Synthesis of Compound B40

Under an argon atmosphere, to a 500 ml, three neck flask, 5.00 g (15.9 mmol) of Intermediate IM-8, 0.27 g (0.03 equiv, 0.5 mmol) of Pd(dba)$_2$, 3.05 g (2 equiv, 31.8 mmol) of NaOtBu, 80 ml of toluene, 6.10 g (1.1 equiv, 17.5 mmol) of N,N-bis(3-dibenzofuranyl)-amine and 0.32 g (0.1 equiv, 1.6 mmol) of tBu3P were added in that order, followed by heating, stirring and refluxing for about 6 hours. After cooling to room temperature, water was added to the reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated and then, the crude product thus obtained was separated by silica gel column chromatography (using a mixture solvent of hexane and toluene as a developer) to obtain Compound B40 (7.08 g, yield 71%) as a white solid compound. A molecular ion peak of m/z=627 was observed by measuring FAB-MS, and from the result, the product was identified as Compound B40.

(6) Synthesis of Compound B53

A condensed cyclic compound according to an embodiment, Compound B53, may be synthesized, for example, by the following Reaction 6:

[Reaction 6]

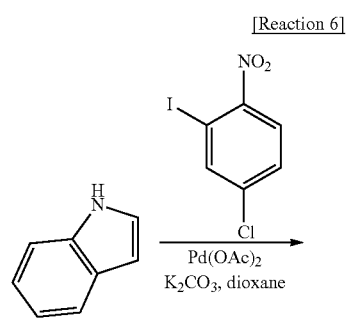

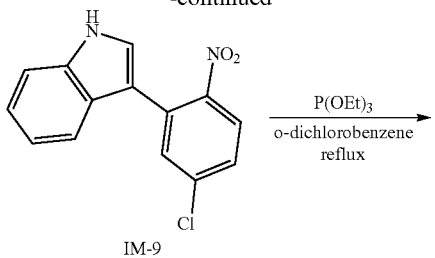

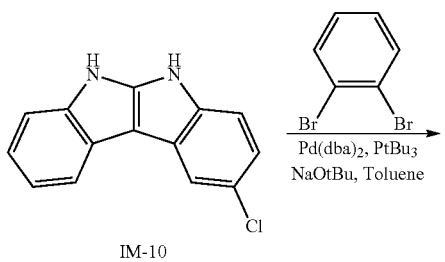

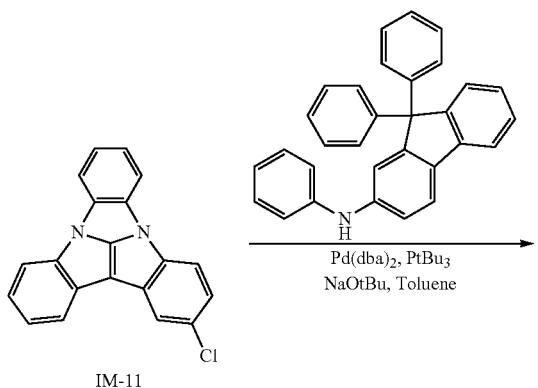

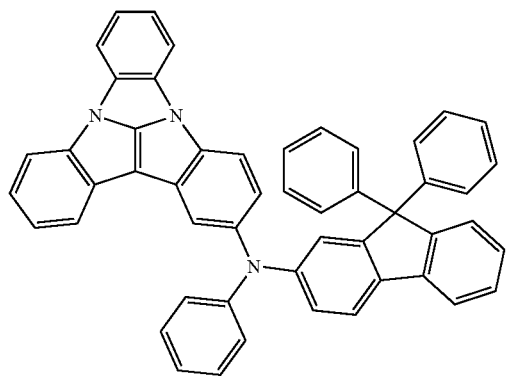

Synthesis of Intermediate IM-9

Under an argon atmosphere, to a 500 ml, three neck flask, 20.00 g (170.7 mmol) of indole, 7.67 g (0.1 equiv, 34.1 mmol) of Pd(OAc)$_2$, 94.38 g (2 equiv, 682.9 mmol) of K$_2$CO$_3$, 58.07 g (1.2 equiv, 204.9 mmol) of 4-chloro-2-iodo-1-nitrobenzene and 341 ml of 1,4-dioxane were added in that order, followed by heating, stirring and refluxing for about 24 hours. After cooling to room temperature, the reaction product was filtered with celite to separate insoluble residue, water was added to the remaining reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated, and then, the crude product thus obtained was separated by silica gel column chromatography (using a mixture solvent of hexane and toluene as a developer) to obtain Intermediate IM-9 (20.95 g, yield 45%) as a white solid compound. A molecular ion peak of m/z=272 was observed by measuring FAB-MS, and from the result, the product was identified as Intermediate IM-9.

<Synthesis of Intermediate IM-10>

Under an argon atmosphere, to a 300 ml, three-neck flask, 15.00 g (55.0 mmol) of Intermediate IM-9, 110 ml of o-dichlorobenzene and 36.56 g (4 equiv, 220.0 mmol) of P(OEt)$_3$ were added in that order, followed by heating and stirring at about 160° C. for about 24 hours. After cooling to room temperature, the reaction solvents were distilled off, and the crude product thus obtained was separated by silica gel column chromatography (using a mixture solvent of hexane and toluene as a developer) to obtain Intermediate IM-10 (10.99 g, yield 83%) as a white solid compound. A molecular ion peak of m/z=240 was observed by measuring FAB-MS, and from the result, the product was identified as Intermediate IM-10.

<Synthesis of Intermediate IM-11>

Under an argon atmosphere, to a 500 ml, three neck flask, 10.00 g (41.5 mmol) of Intermediate IM-10, 0.72 g (0.03 equiv, 1.2 mmol) of Pd(dba)$_2$, 9.98 g (2.5 equiv, 103.9 mmol) of NaOtBu, 208 ml of toluene, 9.80 g (1 equiv, 41.5 mmol) of 1,2-dibromobenzene and 0.84 g (0.1 equiv, 4.2 mmol) of tBu3P were added in that order, followed by heating, stirring and refluxing for about 6 hours. After cooling to room temperature, water was added to the reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated, and then, the crude product thus obtained was separated by silica gel column chromatography (using a mixture solvent of hexane and toluene as a developer) to obtain Intermediate IM-11 (9.81 g, yield 75%) as a white solid compound. A molecular ion peak of m/z=314 was observed by measuring FAB-MS, and from the result, the product was identified as Intermediate IM-11.

<Synthesis of Compound B53>

Under an argon atmosphere, to a 300 ml, three neck flask, 5.00 g (15.9 mmol) of Intermediate IM-11, 0.27 g (0.03 equiv, 0.5 mmol) of Pd(dba)$_2$, 3.05 g (2 equiv, 31.8 mmol) of NaOtBu, 80 ml of toluene, 7.16 g (1.1 equiv, 17.5 mmol) of N-(9,9-diphenyl-9H-fluoren-2-yl)aniline and 0.32 g (0.1 equiv, 1.6 mmol) of tBu3P were added in that order, followed by heating, stirring and refluxing for about 6 hours. After cooling to room temperature, water was added to the reaction product, and an organic layer was separately taken. To an aqueous layer, toluene was added, and an organic layer was extracted once more. The organic layer thus collected was washed with a saline solution and dried with MgSO$_4$. MgSO$_4$ was separated, and the organic layer was concentrated and then, the crude product thus obtained was separated by silica gel column chromatography (using a mixture solvent of hexane and toluene as a developer) to obtain Compound B53 (9.51 g, yield 87%) as a white solid compound. A molecular ion peak of m/z=687 was observed by measuring FAB-MS, and from the result, the product was identified as Compound B53.

2. Manufacture and Evaluation of Organic Electroluminescence Device Including Condensed Cyclic Compound (Manufacture of Organic Electroluminescence Device)

Organic electroluminescence devices of exemplary embodiments including the condensed cyclic compounds of exemplary embodiments in a hole transport layer were manufactured by the method below. Organic electroluminescence devices of Examples 1 to 6 were manufactured using the condensed cyclic compound of Compounds A8, A48, A57, A59, B40 and B53 as materials for a hole transport layer. Organic electroluminescence devices of Comparative Examples 1 to 4 were manufactured using Comparative Compounds C1 to C4 as materials for a hole transport layer.

The compounds used for forming the hole transport layer in Examples 1 to 6 and Comparative Examples 1 to 4 are listed in Table 1.

TABLE 1

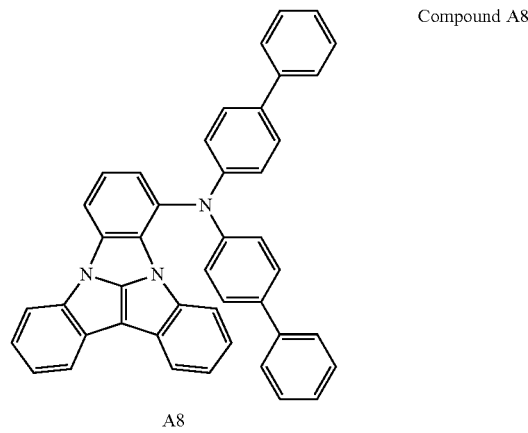

Compound A8

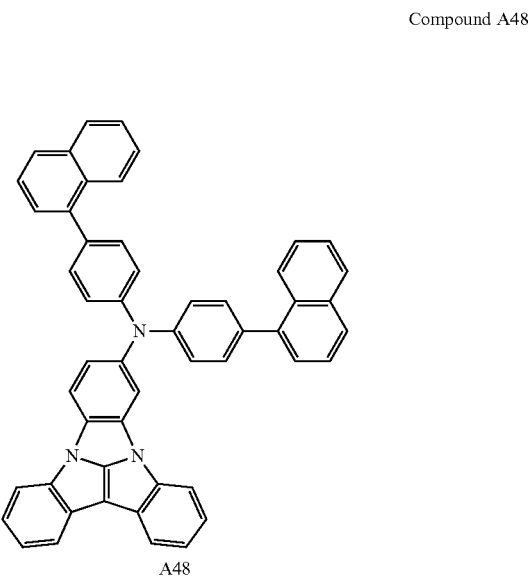

Compound A48

TABLE 1-continued
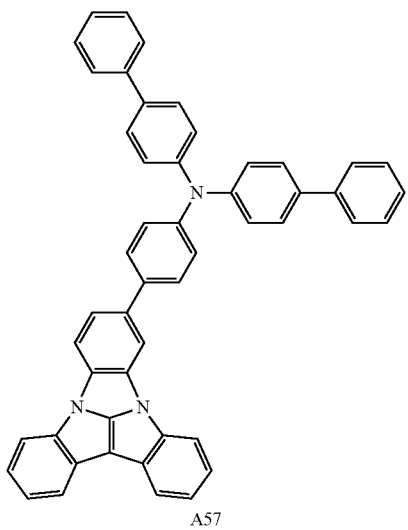
Compound A57
A57
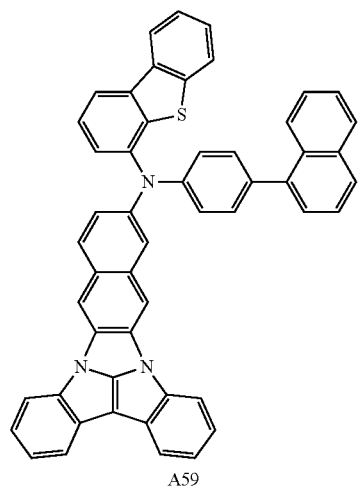
Compound A59
A59
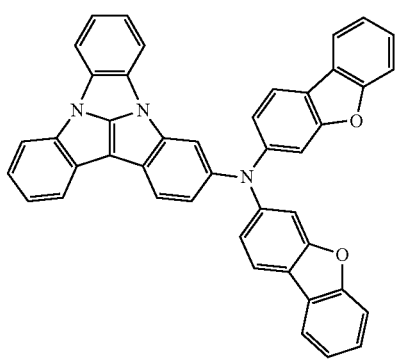
Compound B40
B40
TABLE 1-continued
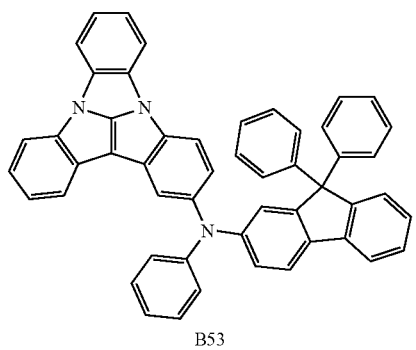 [SMILES: "B53" ; c1ccc(N(c2ccc3c(c2)C(c2ccccc2)(c2ccccc2)c2ccccc2-3)c2ccc3c(c2)c2c4ccccc4n4c5ccccc5n3c24)cc1]
Compound B53
B53
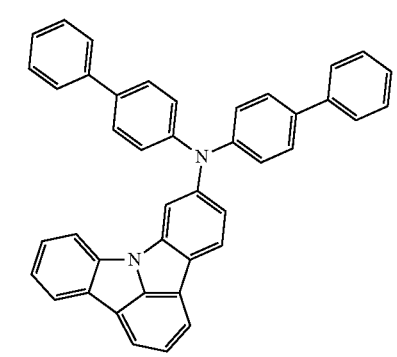
Comparative Compound C1
C1
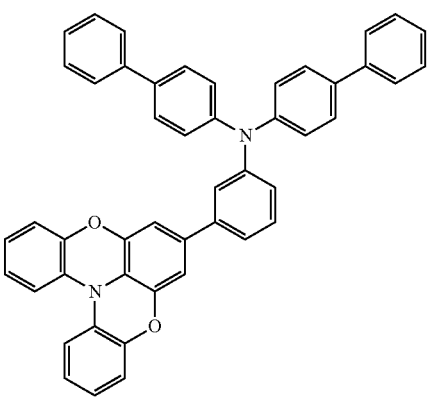
Comparative Compound C2
C2

TABLE 1-continued

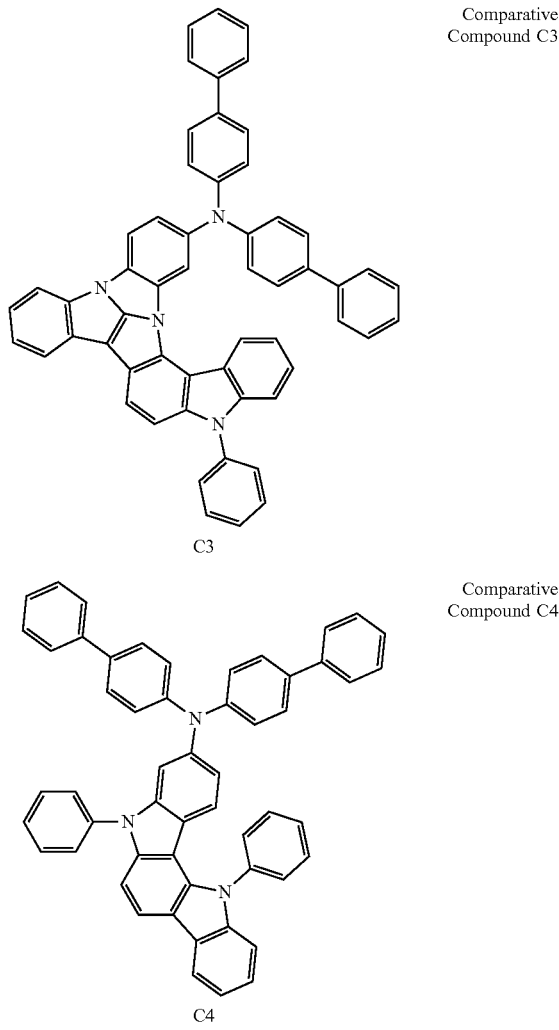

Comparative Compound C3

C3

Comparative Compound C4

C4

On a glass substrate, ITO was patterned to a thickness of about 1,500 Å and washed with ultra-pure water, and a UV ozone treatment was conducted for about 10 minutes. Then, a hole injection layer was formed using 2-TNANA to a thickness of about 600 Å. A hole transport layer was formed using the example compound or the comparative compound to a thickness of about 300 Å.

Then, an emission layer was formed using ADN doped with 3% TBP to a thickness of about 250 Å. Then, an electron transport layer was formed by depositing Alq3 to a thickness of about 250 Å and an electron injection layer was formed by depositing LiF to a thickness of about 10 Å.

Then, a second electrode was formed using Al to a thickness of about 1,000 Å.

In an embodiment, a hole injection layer, a hole transport layer, an emission layer, an electron transport layer, an electron injection layer and a second electrode were formed by using a vacuum deposition apparatus.

(Evaluation of Properties of Organic Electroluminescence Device)

The evaluation results of the organic electroluminescence devices according to Example 1 to Example 6, and Comparative Example 1 to Comparative Example 4 are shown in Table 2. In Table 2, a device driving voltage, a device efficiency and device life for the organic electroluminescence devices thus manufactured are compared and shown. In the evaluation results of the properties of the examples and the comparative examples in Table 2, the device efficiency represents a current efficiency value with respect to a current density of 10 mA/cm$^2$, and the device life represents half life showing the decreasing time of luminance from an initial luminance of 1,000 cd/m$^2$ to half.

The current density, driving voltage and emission efficiency of the organic electroluminescence devices of the examples and the comparative examples were measured using Source Meter (Keithley Instrument Co., 2400 series), Luminance Color Meter CS-200 (Konica Minolta Co.), and a program for measurement, LabVIEW 8.2 in a dark room.

TABLE 2

| Device manufacturing example | Hole transport material | Driving voltage (V) | Efficiency (cd/A) | Device life LT50 (h) |
|---|---|---|---|---|
| Example 1 | Compound A8 | 5.7 | 8.1 | 2000 |
| Example 2 | Compound A48 | 5.8 | 7.7 | 2200 |
| Example 3 | Compound A57 | 5.6 | 7.6 | 2250 |
| Example 4 | Compound A59 | 5.7 | 7.6 | 2200 |
| Example 5 | Compound B40 | 5.6 | 7.9 | 2050 |
| Example 6 | Compound B53 | 5.8 | 7.8 | 2250 |
| Comparative Example 1 | Comparative Compound C1 | 6.0 | 6.2 | 1500 |
| Comparative Example 2 | Comparative Compound C2 | 6.0 | 6.2 | 1450 |
| Comparative Example 3 | Comparative Compound C3 | 5.9 | 6.0 | 1500 |
| Comparative Example 4 | Comparative Compound C4 | 5.9 | 6.0 | 1400 |

Referring to the results of Table 2, it may be found that the examples of the organic electroluminescence devices using the condensed cyclic compounds of exemplary embodiments of the inventive step as hole transport materials showed low driving voltage, excellent device life characteristics and excellent device efficiency when compared to those of the comparative examples using the comparative compounds in a hole transport layer. The condensed cyclic compound of an embodiment according to the inventive concept is an amine compound having a pyrrolopyrole skeleton

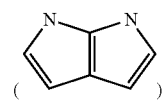

in a core part, and may show low driving voltage and light-emitting device characteristics of long life and high efficiency.

Particularly, the condensed cyclic compounds suggested in exemplary embodiments disclose an amine compound having indoloindole in a core part and thus, were found to show lower driving voltage, longer life and higher efficiency when compared with the comparative examples.

That is, in an embodiment using the condensed cyclic compound of an embodiment as a hole transport material, by introducing a condensed core part of an amine group having life improving effect and indole or the derivatives thereof, which have excellent heat and charge tolerance, or by introducing a core part having a pyrrolopyrole skeleton, device characteristics were improved further by the amine group and long life was achieved.

In the condensed cyclic compound of an embodiment, a nitrogen atom included in a core part having a pyrrolopyrrole skeleton improves hole transport capability of a whole compound to improve the recombination probability of holes and electrons in an emission layer of an organic electroluminescence device and improve emission efficiency of the device.

In Example 1, since Compound A8 had a folded structure of a condensed indoloindole ring toward a nitrogen atom, high device efficiency was shown. This was because, the degree of symmetry in a whole molecule was collapsed in the condensed cyclic compound of Compound A8 and thus, crystallization was restrained and hole transport properties were improved, thereby improving the recombination probability of holes and electrons in an emission layer.

In Examples 2 to 4 including Example Compounds A48, A57 and A59, respectively, the amine group of the example compounds was substituted for an aryl ring in which two nitrogen atoms having plentiful electrons were substituted, and in Example Compound B53, an amine group and a nitrogen atom were positioned in para-position, and Examples 2 to 4 and Example 6 showed markedly improved device life. This was because orbital in a HOMO state was sufficiently expanded and stability in a radical state was improved.

In addition, in Example 5 including an amine-substituted condensed cyclic compound such as Example Compound B40, device efficiency and device life kept balance and both were favorably improved.

The Comparative Compounds of Comparative Examples 1 to 3 were amine compounds having a condensed cyclic nitrogen-containing heterocycle in a core part, but the number of nitrogen atoms included in the heterocycle was different from that of the examples. Thus, low efficiency was shown when compared with the examples. This was thought that carrier balance was collapsed in the comparative compounds, and the nitrogen atoms included in the condensed heterocycle largely contributed to the improvement of hole transport properties.

Since Comparative Example 4 used an amine compound including an indoloindole skeleton but did not include a rigid condensed cyclic core, it was liable to arise decomposition under high temperature conditions and attained short device life when compared with the examples. In addition, since a phenyl group bonded to a nitrogen atom was orthogonal, distance between molecules increased, the propagation of holes decreased, and low device efficiency was shown when compared with the examples.

Referring to the results of Table 2, if the condensed cyclic compound of an embodiment of the inventive concept was included in a hole transport layer, longer life and higher efficiency were found when compared with a case where the comparative compound was included in the hole transport layer. That is, the condensed cyclic compound of an embodiment was an amine compound including a pyrrolopyrole skeleton in a core part which was a condensed ring part, and kept the properties of the amine compound which exhibited hole transport properties, improved the electron tolerance of a material due to the condensed ring part and layer quality and thermal stability, and achieved both high emission efficiency and long life.

In addition, the organic electroluminescence device of an embodiment included the condensed cyclic compound of an embodiment in at least one organic layer which was disposed between a first electrode and a second electrode, or particularly in a hole transport region, and might achieve improved device efficiency and long life.

The organic electroluminescence device of an embodiment may show improved device properties with a low driving voltage, long life and high efficiency.

The condensed cyclic compound of an embodiment may be applied in the hole transport region of an organic electroluminescence device and contribute to the long life and high efficiency of the organic electroluminescence device.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:
1. An organic electroluminescence device, comprising:
a first electrode;
a second electrode disposed on the first electrode; and
a plurality of organic layers disposed between the first electrode and the second electrode,
wherein the plurality of organic layers comprise an emission layer,
wherein the emission layer comprises at least one of anthracene derivatives, pyrene derivatives, fluoranthene derivatives, chrysene derivatives, dihydro benzanthracene derivatives, or triphenylene derivatives,
wherein at least one organic layer among the plurality of organic layers comprises a condensed cyclic compound represented by the following Formula 1:

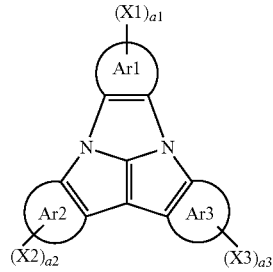

[Formula 1]

in Formula 1,
each of Ar1, Ar2, and Ar3 is independently a substituted or unsubstituted aryl group having 6 to 40 carbon atoms for forming a ring, or a substituted or unsubstituted heteroaryl group having 2 to 40 carbon atoms for forming a ring,
excluding a case where one or both of Ar2 or Ar3 is a substituted or unsubstituted carbazole group,
each of X1, X2, and X3 is independently *-L-NR$_1$R$_2$,
one of a1, a2, and a3 is 1 and the others are 0,
L is a direct linkage, a substituted or unsubstituted arylene group having 6 to 30 carbon atoms for forming a ring, or a substituted or unsubstituted heteroarylene group having 2 to 30 carbon atoms for forming a ring, and
each of R$_1$ and R$_2$ is independently a substituted or unsubstituted alkyl group having 1 to 20 carbon atoms, a substituted or unsubstituted aryl group having 6 to 40 carbon atoms for forming a ring, or a substituted or unsubstituted heteroaryl group having 2 to 40 carbon atoms for forming a ring, or combined with each other to form a ring.

2. The organic electroluminescence device of claim 1, wherein the plurality of organic layers further comprise:
   a hole transport region disposed between the first electrode and the emission layer,
   wherein the hole transport region comprises the condensed cyclic compound represented by Formula 1.

3. The organic electroluminescence device of claim 2, wherein the emission layer emits blue light.

4. The organic electroluminescence device of claim 1, wherein Formula 1 is represented by the following Formula 1-1 or Formula 1-2:

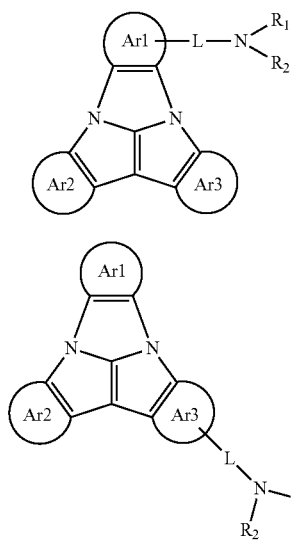

[Formula 1-1]

[Formula 1-2]

in Formula 1-1 and Formula 1-2, Ar1, Ar2, Ar3, L, $R_1$ and $R_2$ are the same as defined in Formula 1.

5. The organic electroluminescence device of claim 1, wherein Ar1 is a substituted or unsubstituted benzene ring, or a substituted or unsubstituted naphthalene ring.

6. The organic electroluminescence device of claim 1, wherein each of Ar2 and Ar3 is independently a substituted or unsubstituted benzene ring, a substituted or unsubstituted naphthalene ring, a substituted or unsubstituted phenanthrene ring, a substituted or unsubstituted benzofuran ring, a substituted or unsubstituted dibenzofuran ring, a substituted or unsubstituted benzothiophene ring, a substituted or unsubstituted dibenzothiophene ring, a substituted or unsubstituted pyridine ring, or a substituted or unsubstituted quinoline ring.

7. The organic electroluminescence device of claim 1, wherein Ar2 and Ar3 are the same.

8. The organic electroluminescence device of claim 1, wherein each of Ar2 and Ar3 is independently represented by any one of the following Ar-a to Ar-i:

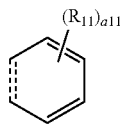
Ar-a

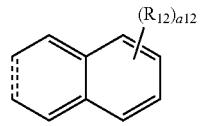
Ar-b

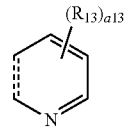
Ar-c

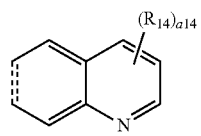
Ar-d

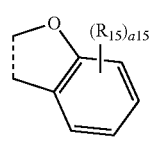
Ar-e

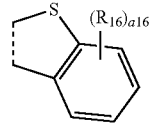
Ar-f

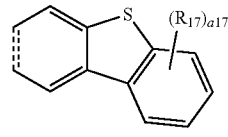
Ar-g

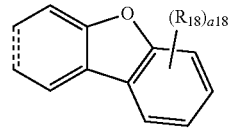
Ar-h

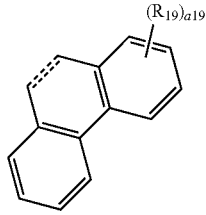
Ar-i in Ar-a to Ar-i,
each of $R_{11}$ to $R_{19}$ is independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring,
each of a11 to a19 is independently an integer of 0 to 4, and
dotted lines represent combined parts forming a condensed ring.

9. The organic electroluminescence device of claim 1, wherein Formula 1 is represented by the following Formula 2-1 or Formula 2-2:

[Formula 2-1]

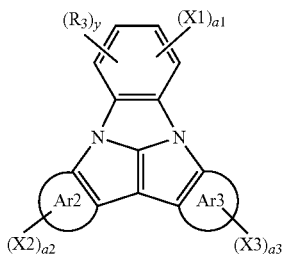

[Formula 2-2]

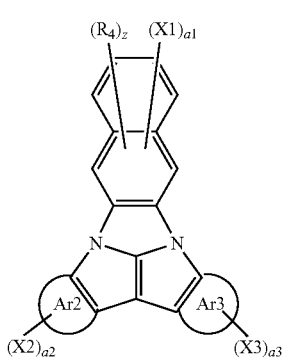

in Formula 2-1 and Formula 2-2, each of $R_3$ and $R_4$ is independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring, "y" and "z" are each independently an integer of 0 to 3, and X1 to X3, and a1 to a3 are the same as defined in Formula 1.

10. The organic electroluminescence device of claim 1, wherein at least one organic layer comprises at least one of compounds represented in the following Compound Group 1 and Compound Group 2:

[Compound Group 1]

A1

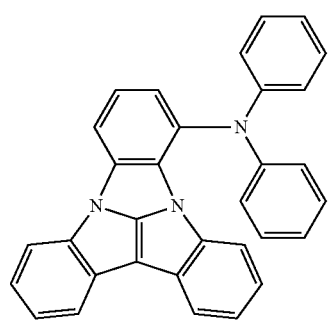

-continued

A2

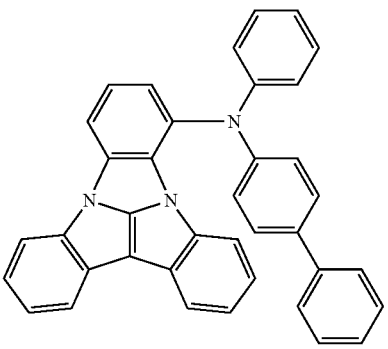

A3

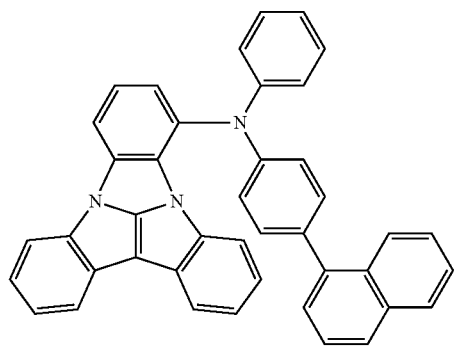

A4

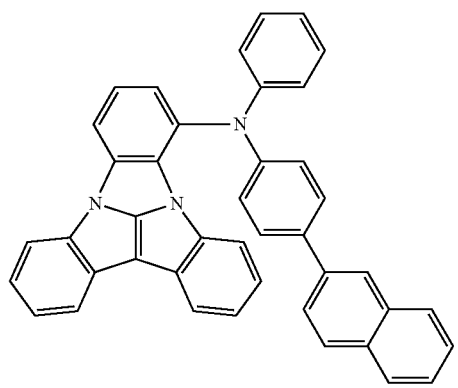

A5

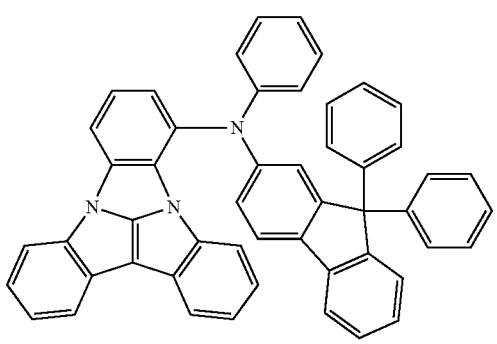

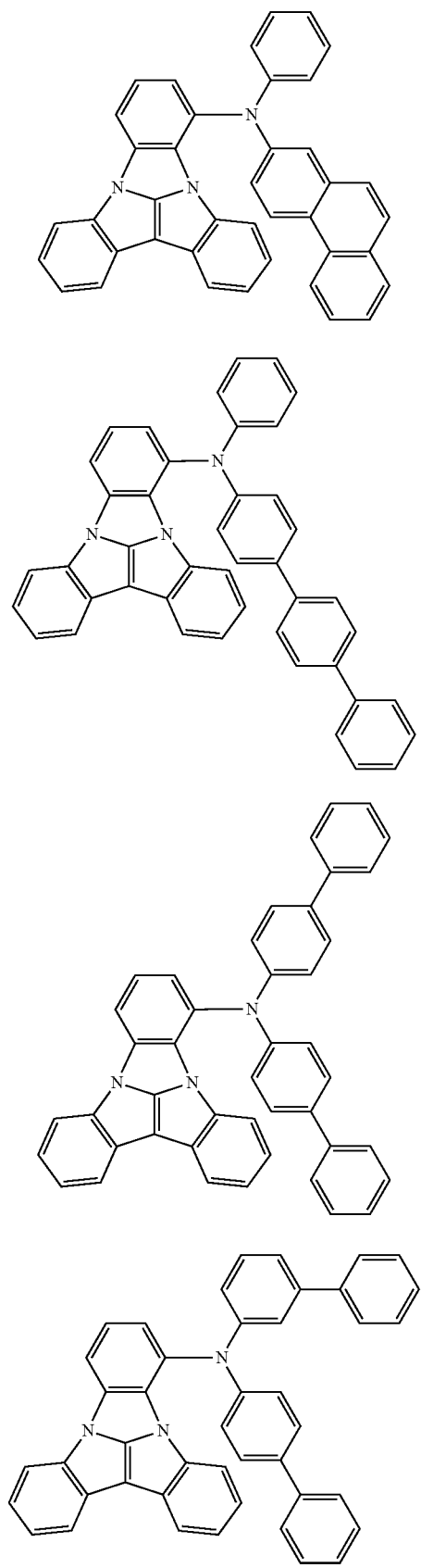
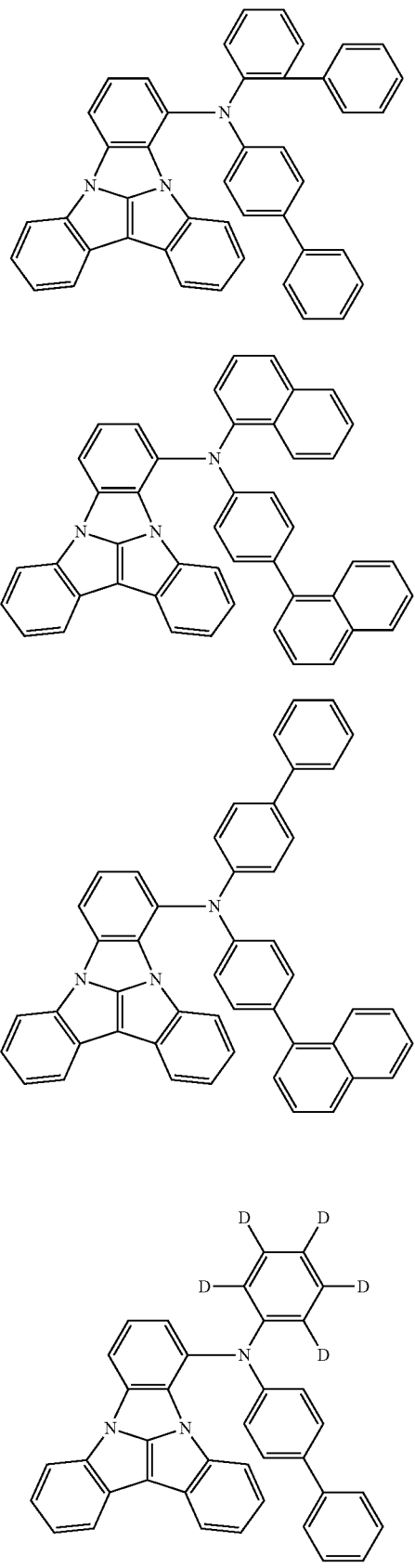

A14
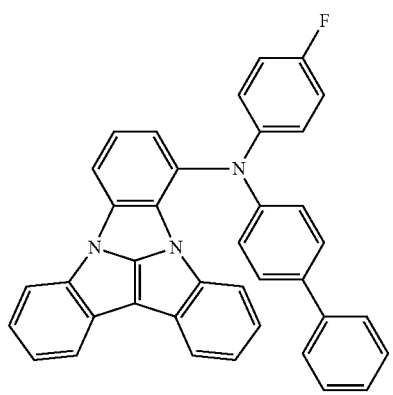
A17
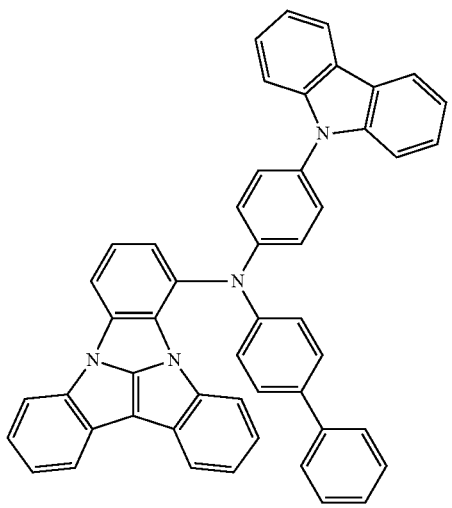
A15
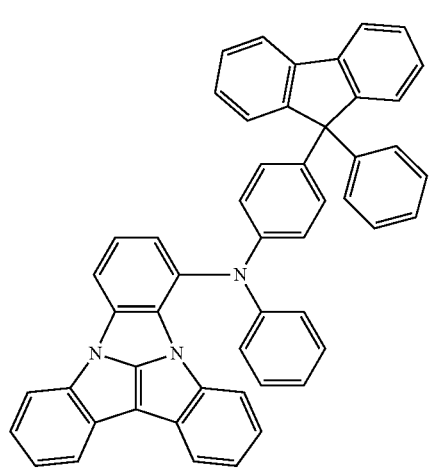
A18
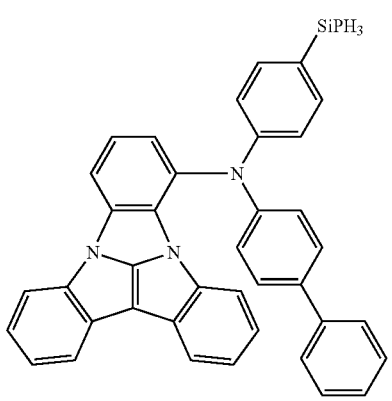
A16
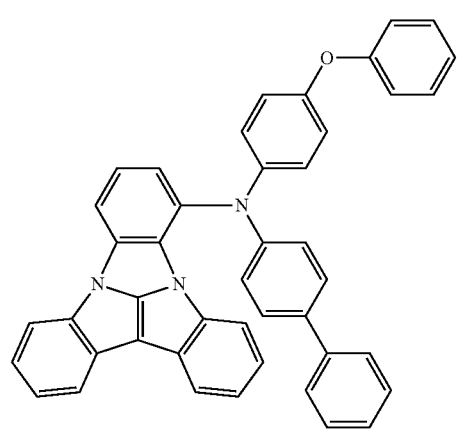
A19
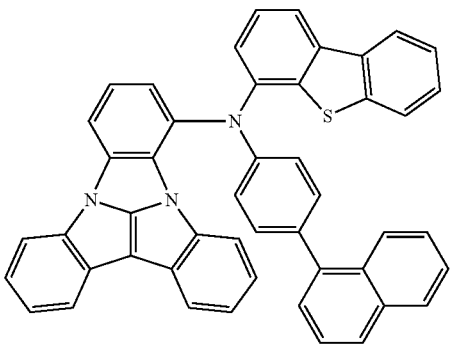

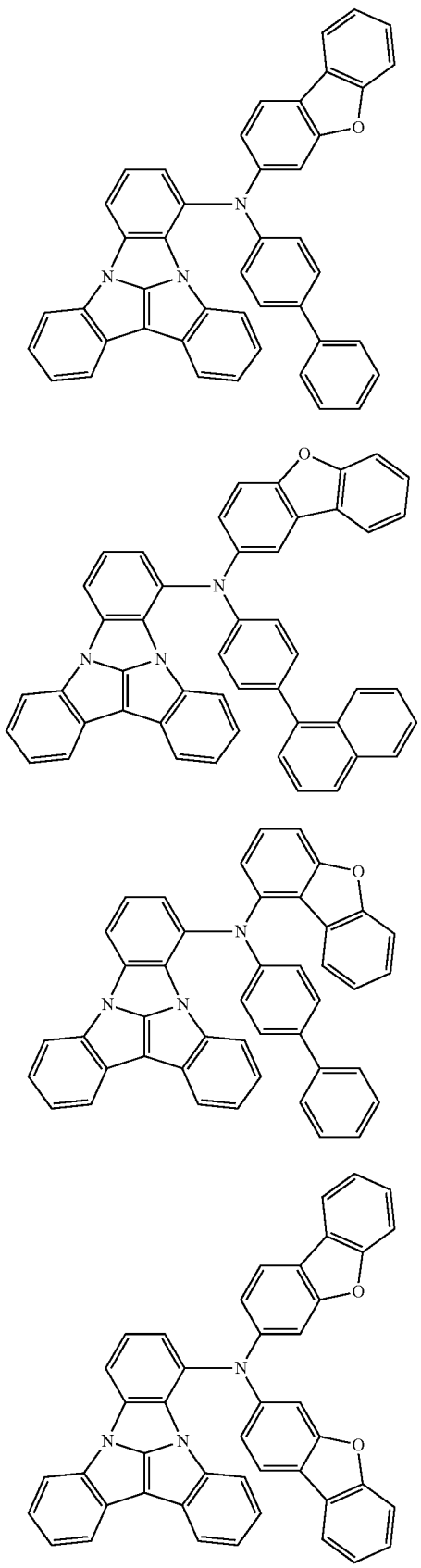
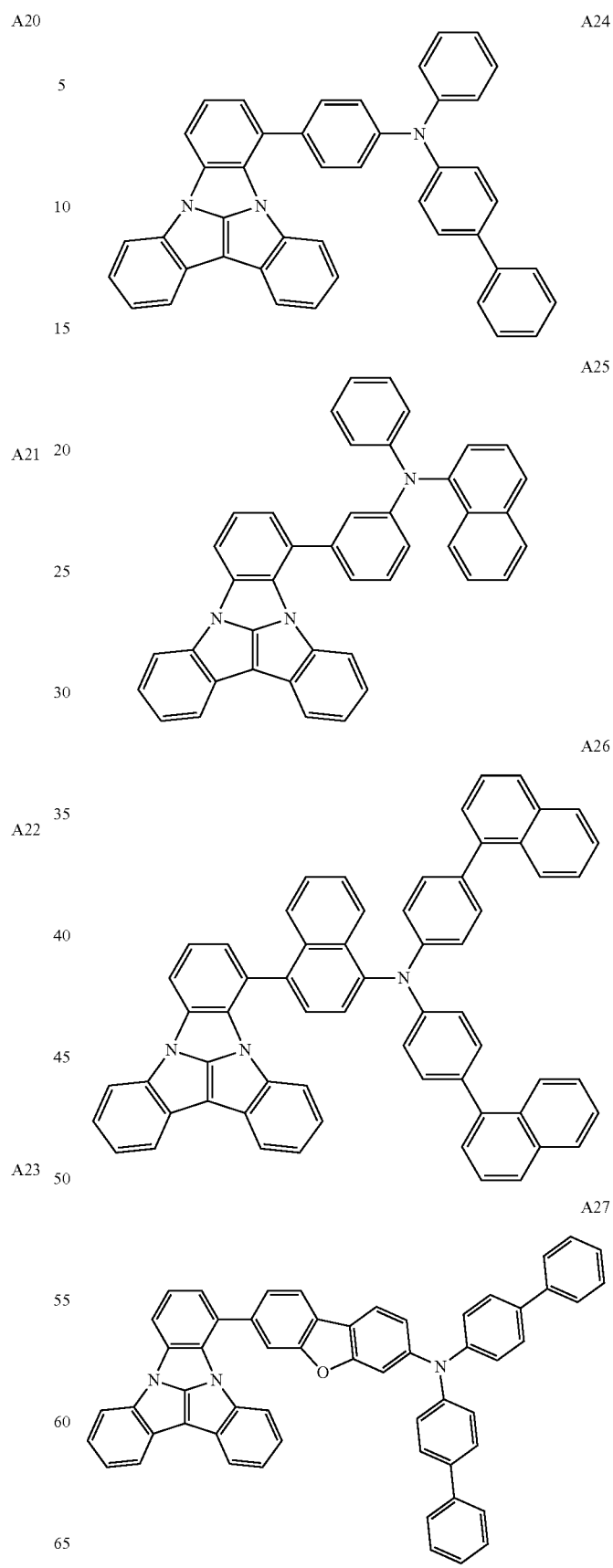

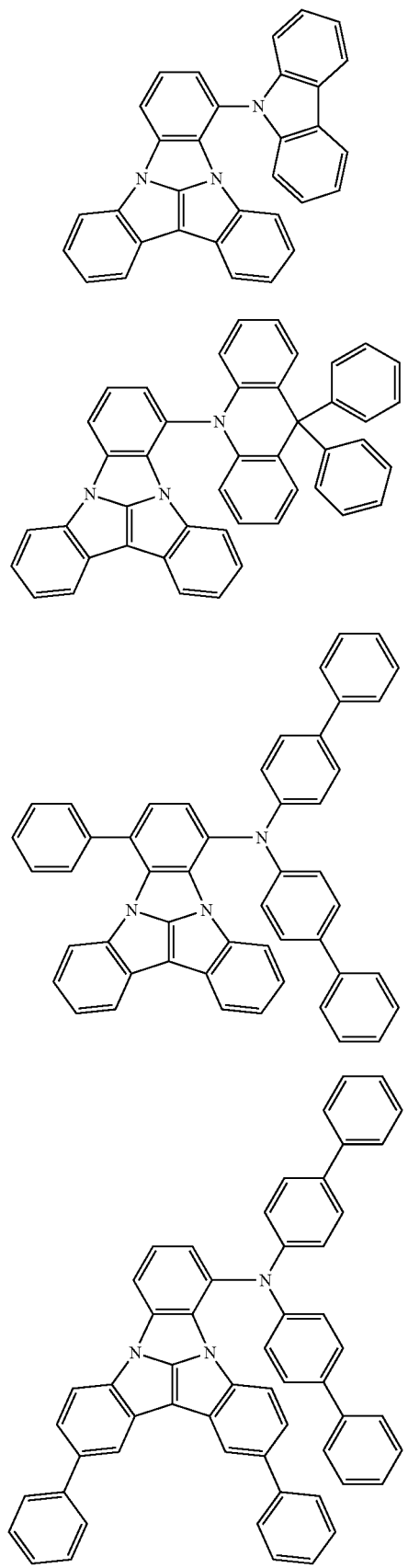
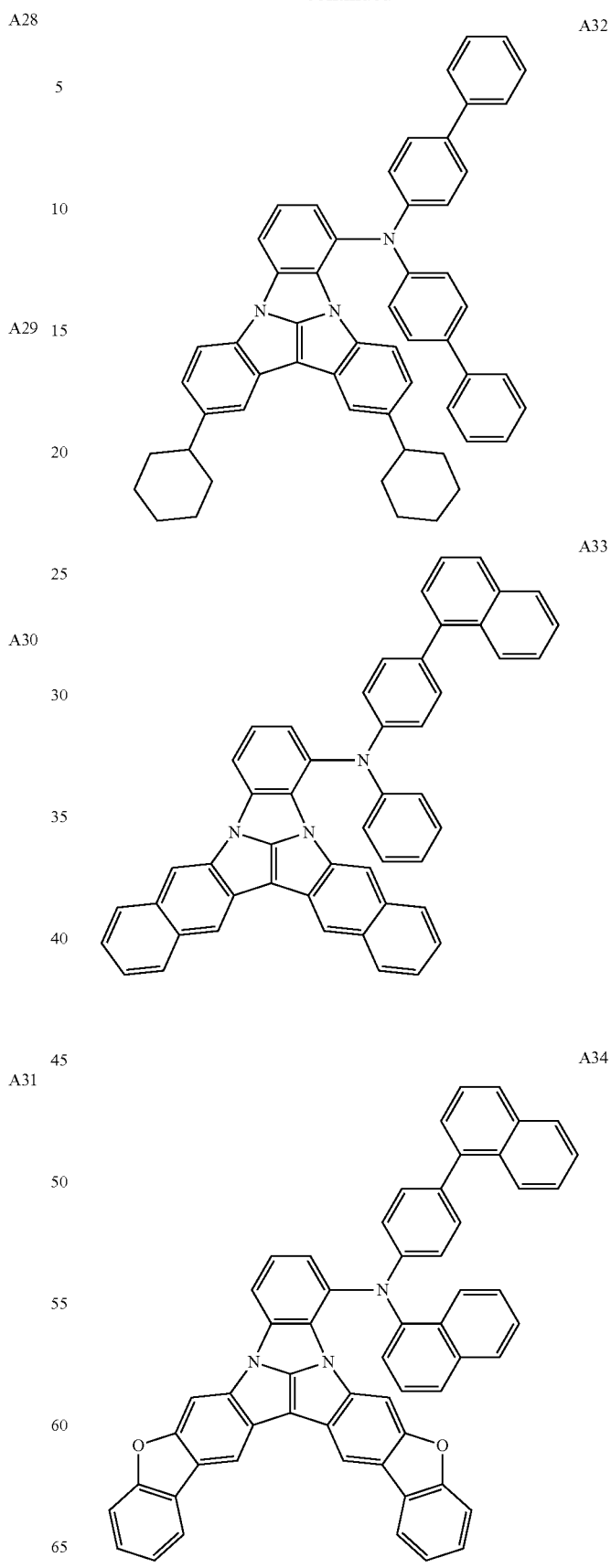

A35
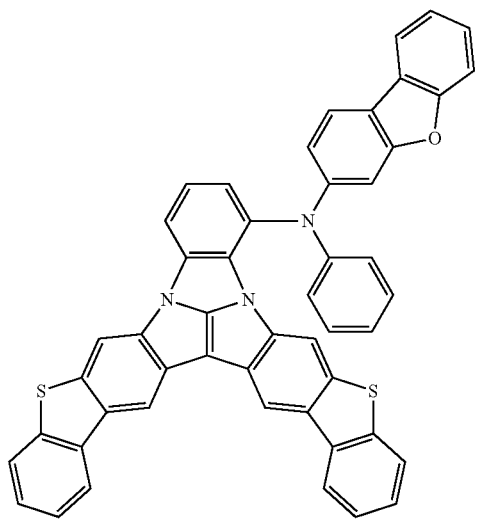
A36
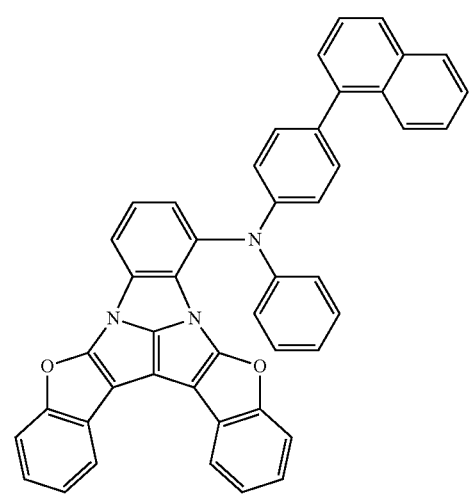
A37
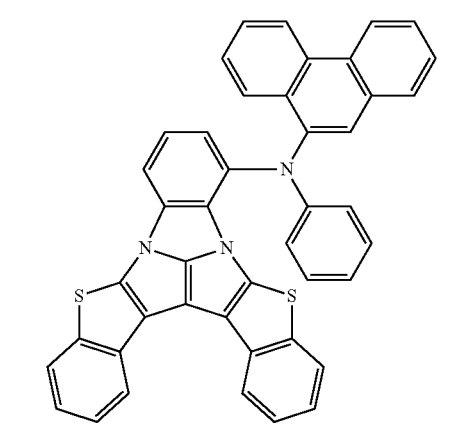
A38
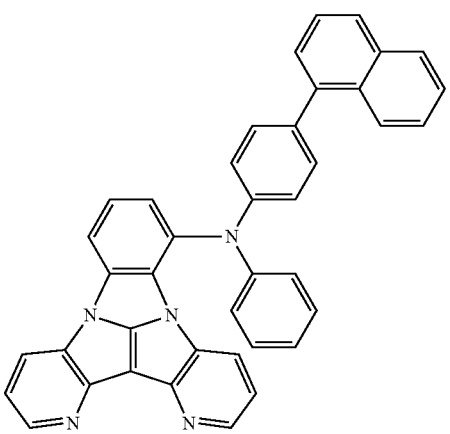
A39
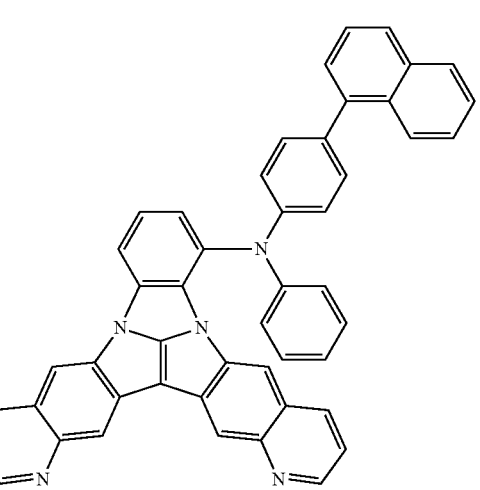
A40
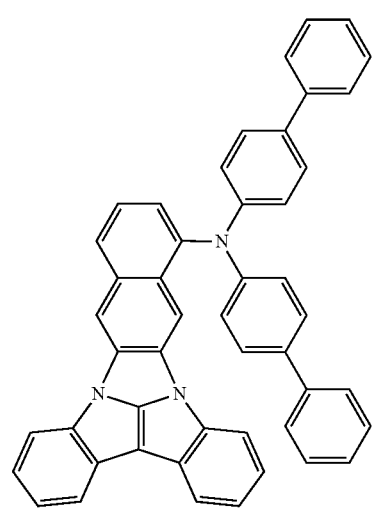

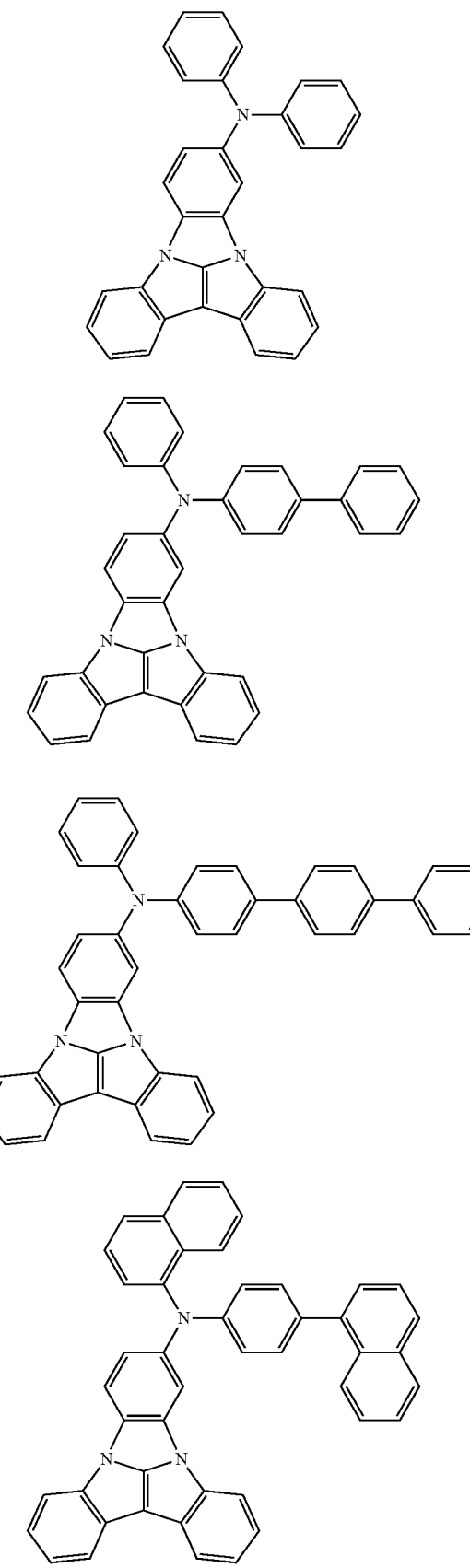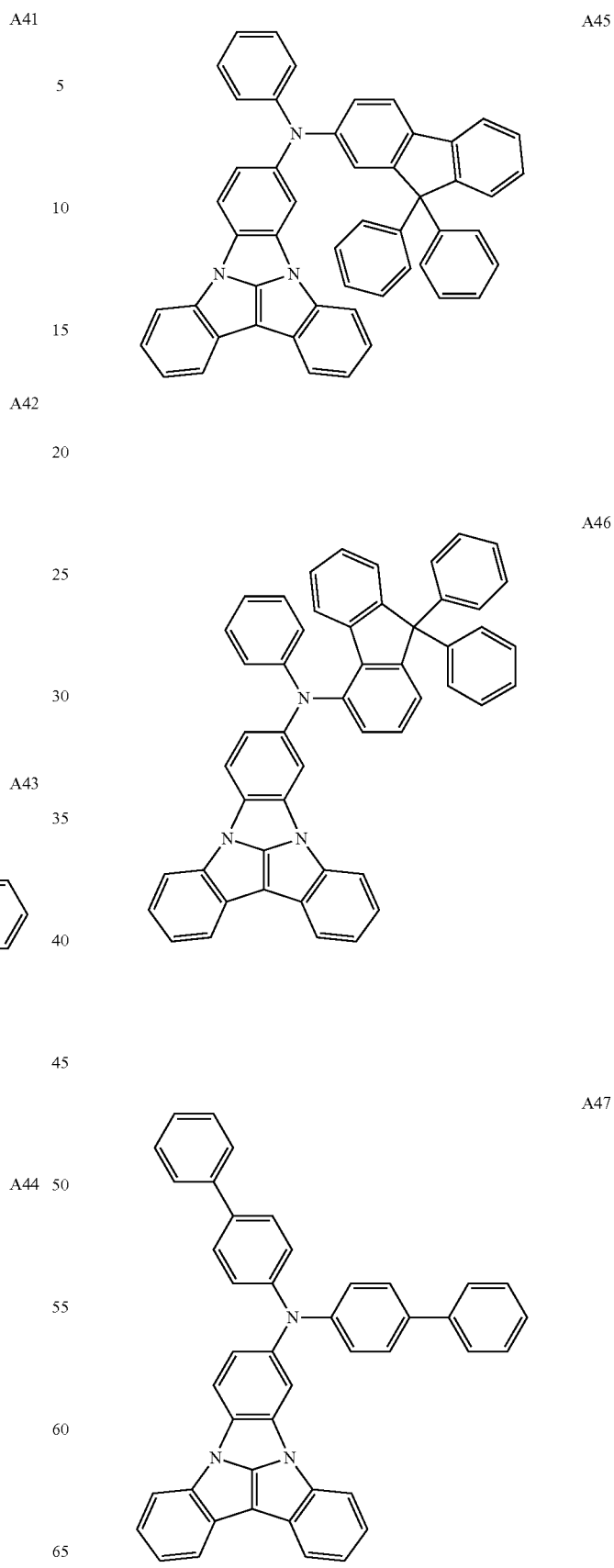

A48
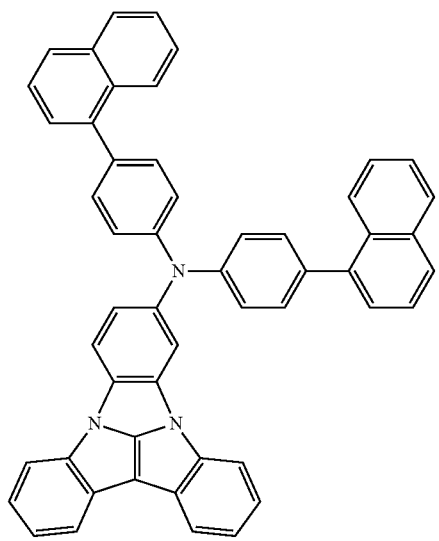
A49
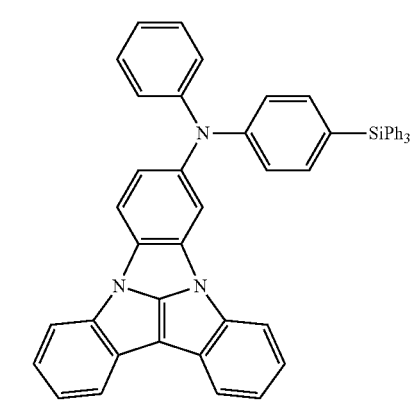
A50
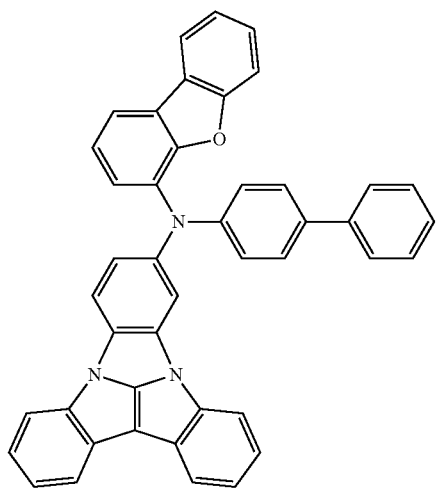
A51
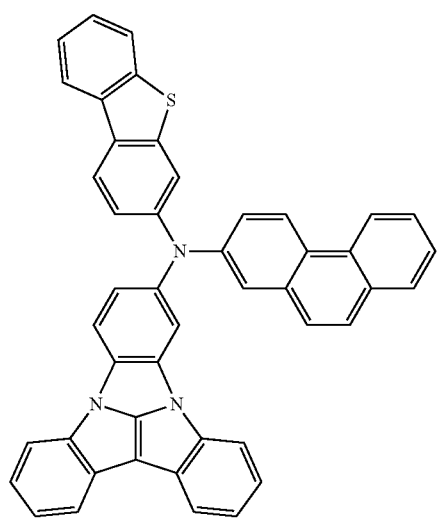
A52
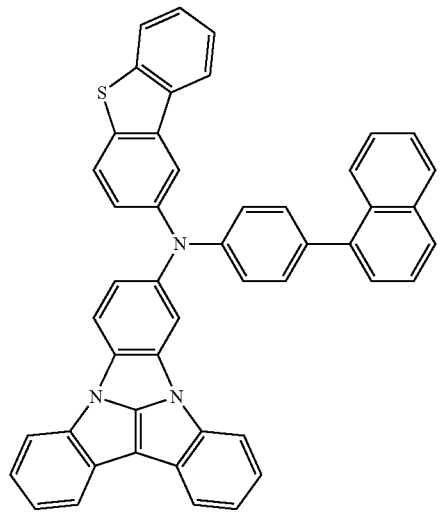
A53
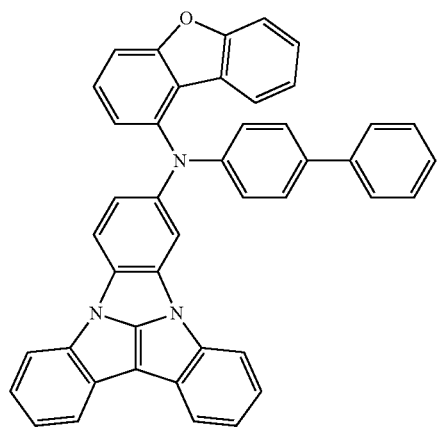

A54
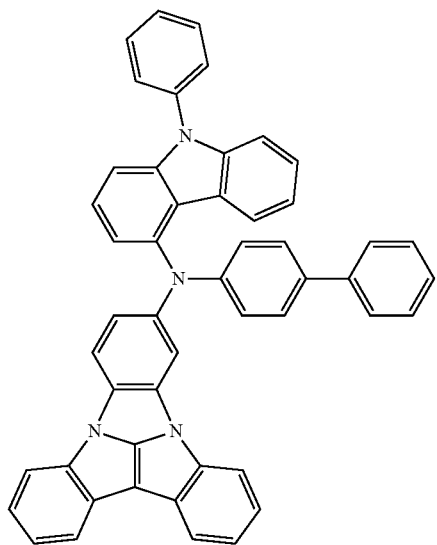
A55
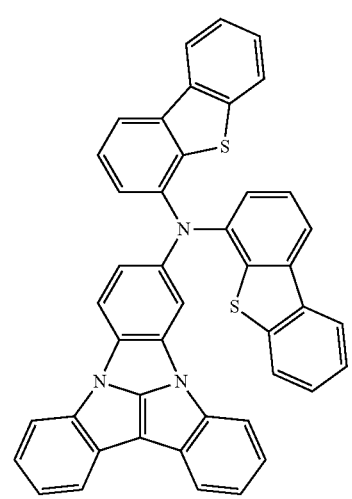
A56
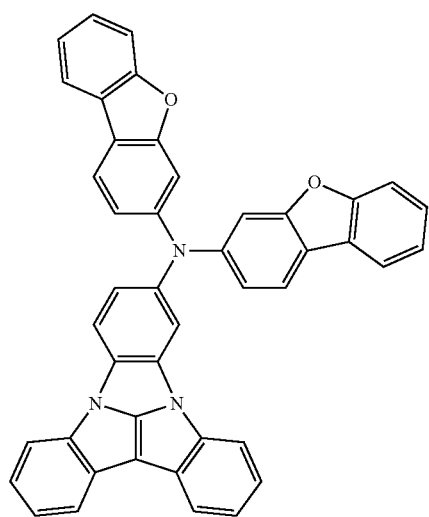
A57
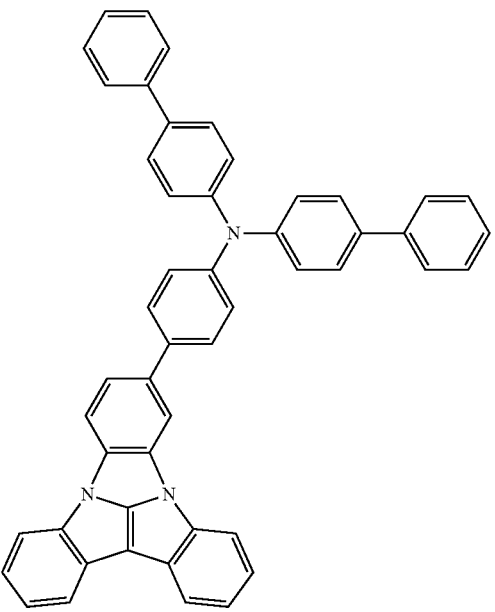
A58
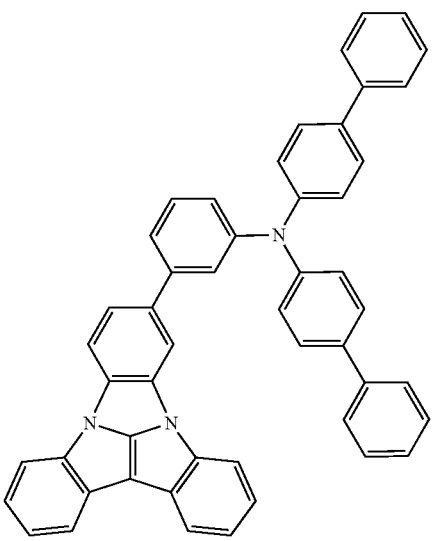

A59
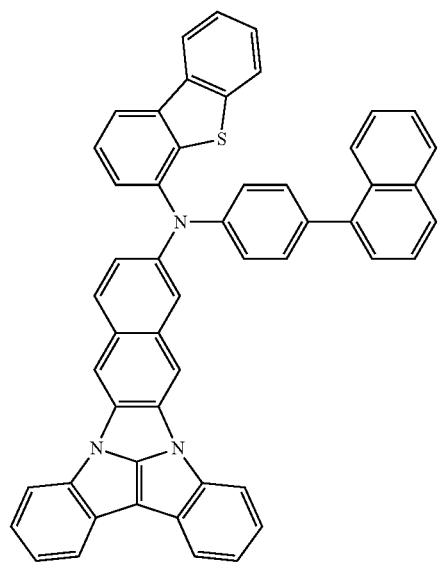
A60
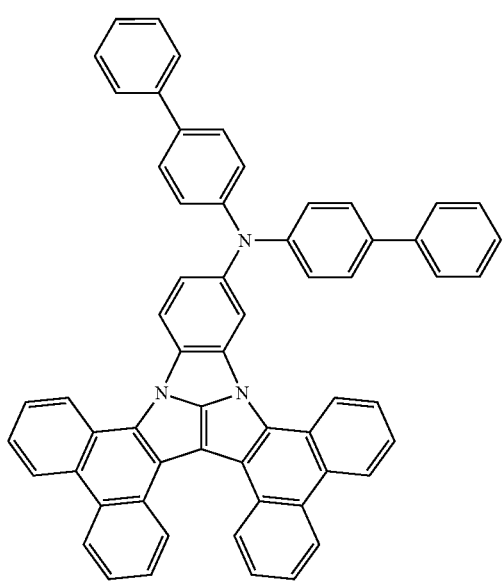
A61
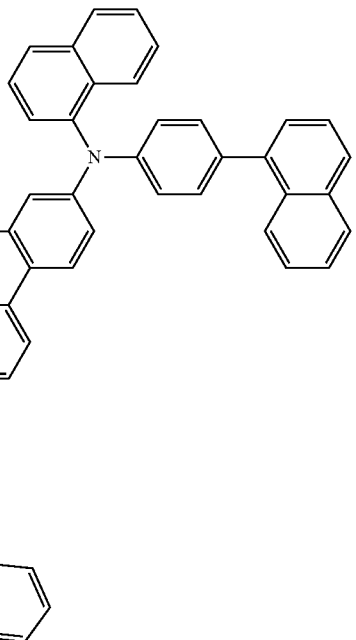
A62
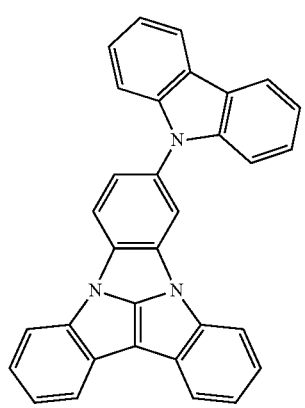
A63
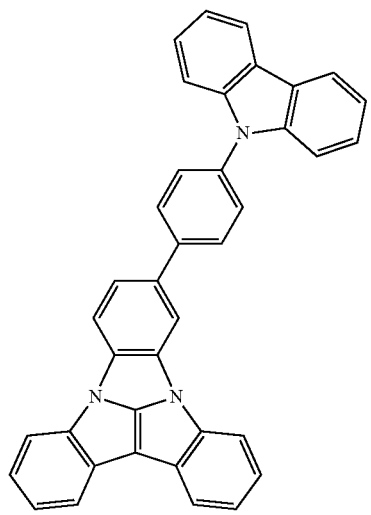

A64
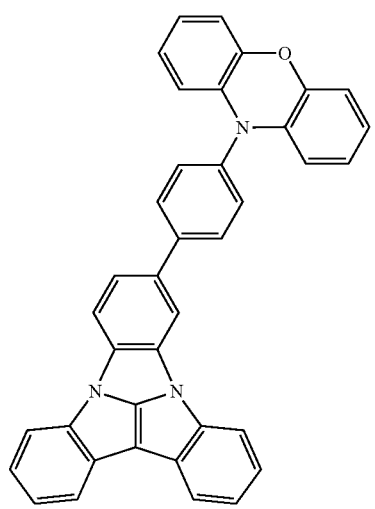
[Compound Group 2]
B1
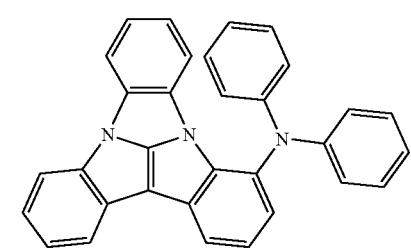
B2
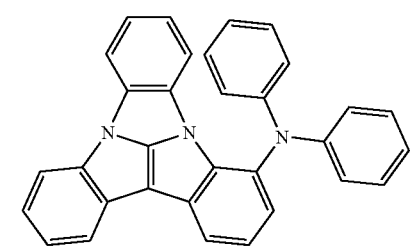
B3
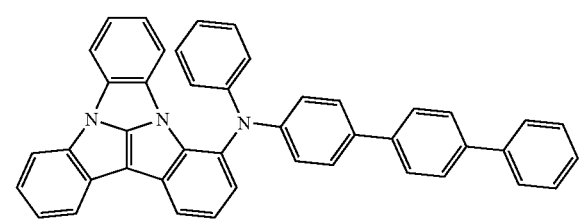
B4
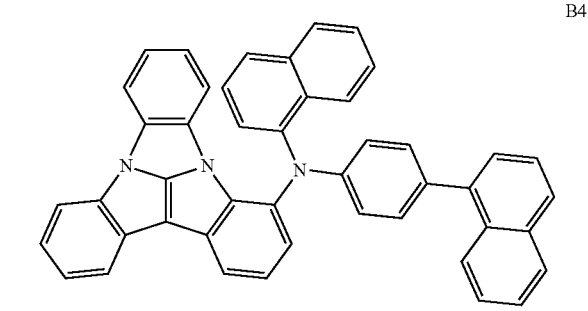
B5
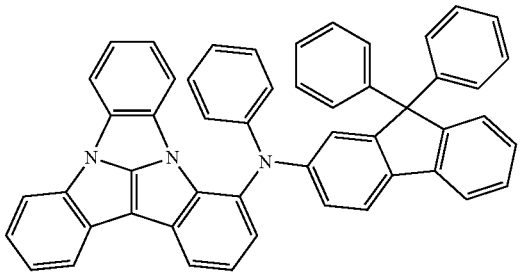
B6
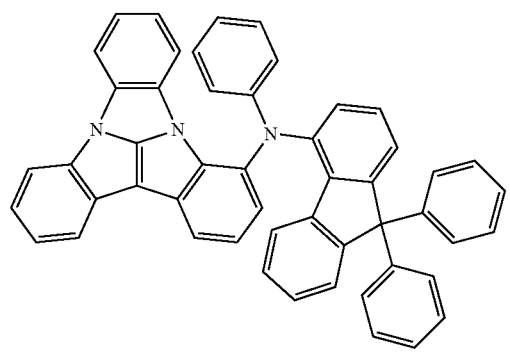
B7
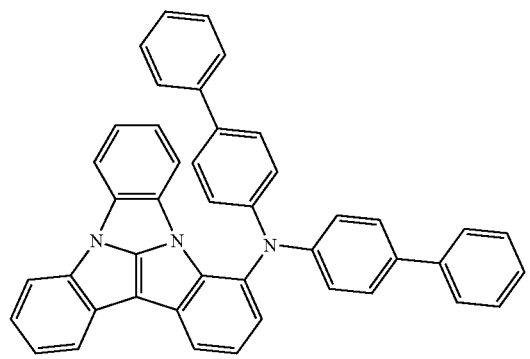
B8
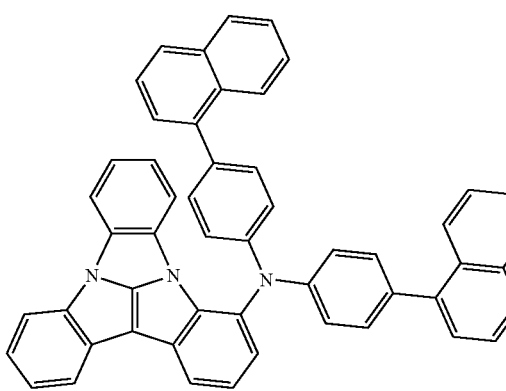

-continued
B9
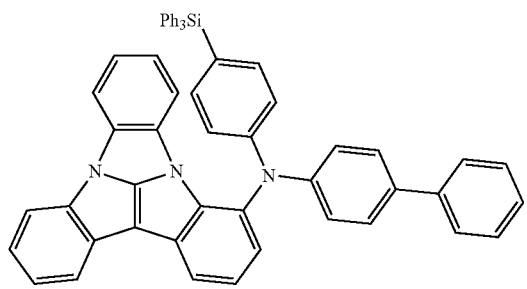
B10
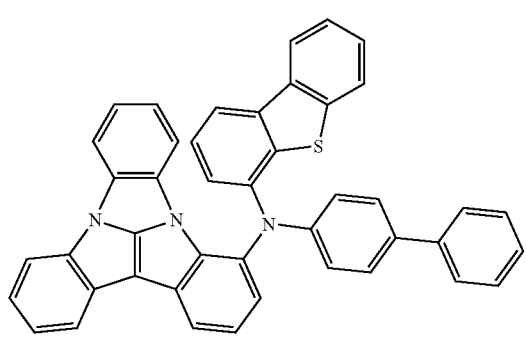
B11
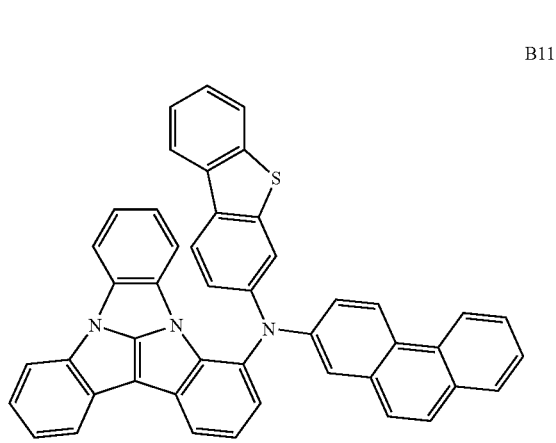
B12
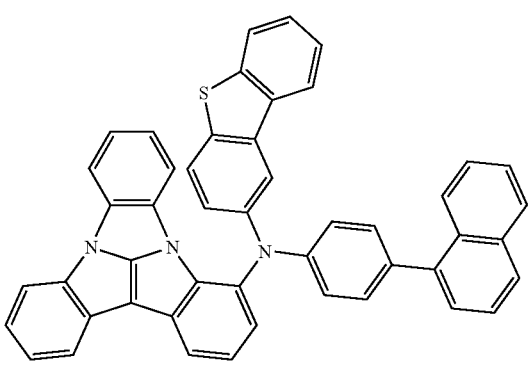
-continued
B13
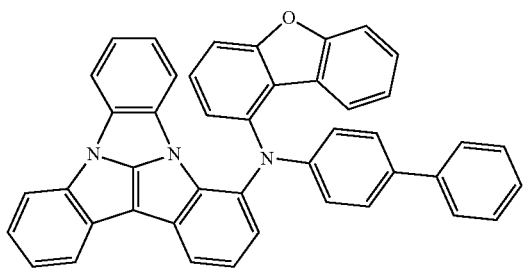
B14
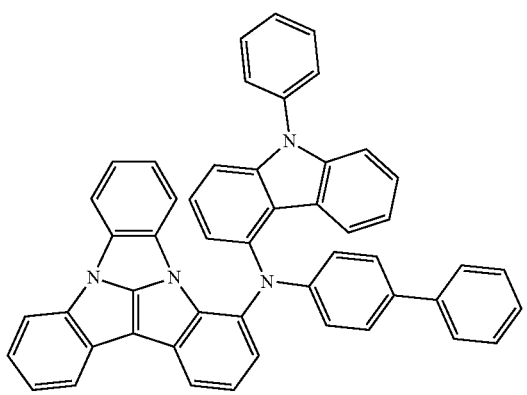
B15
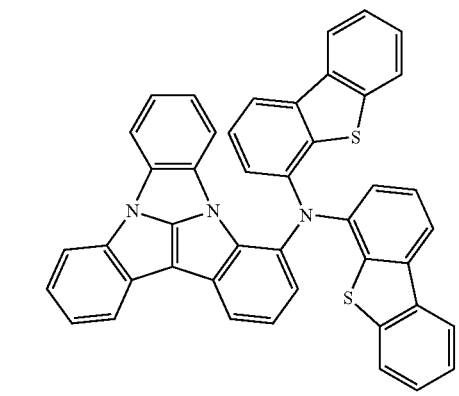
B16
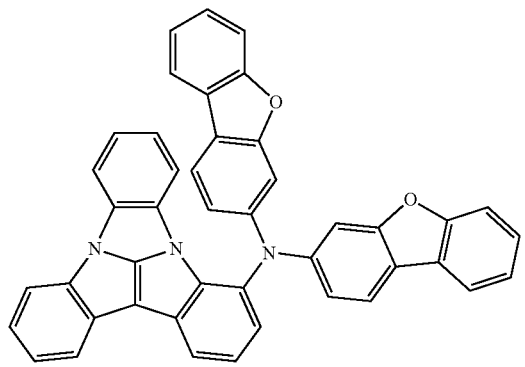

B17
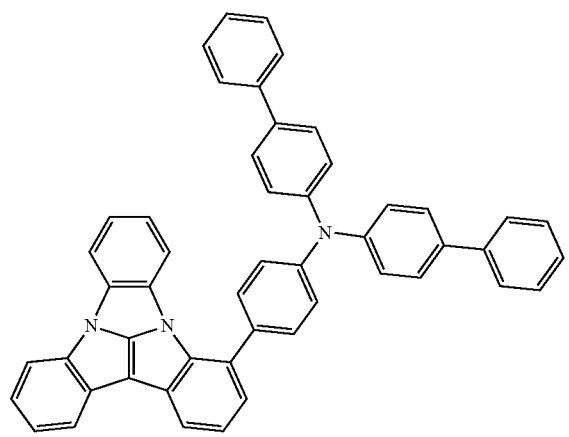
B18
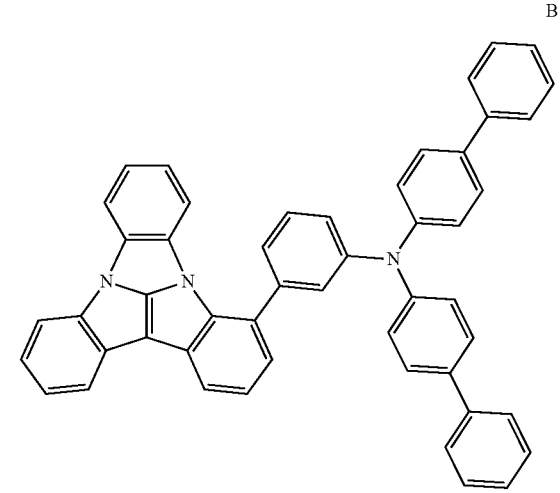
B19
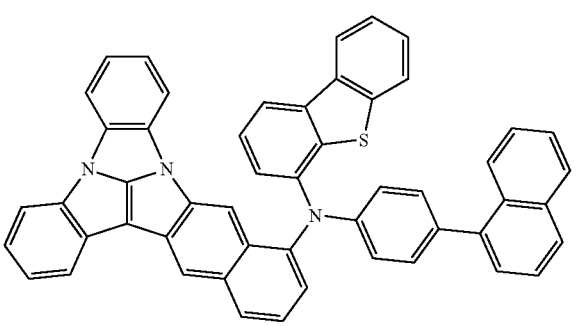
B20
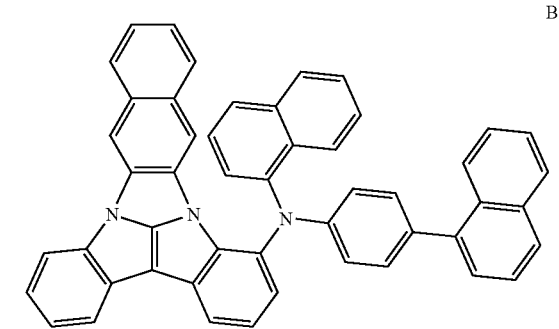
B21
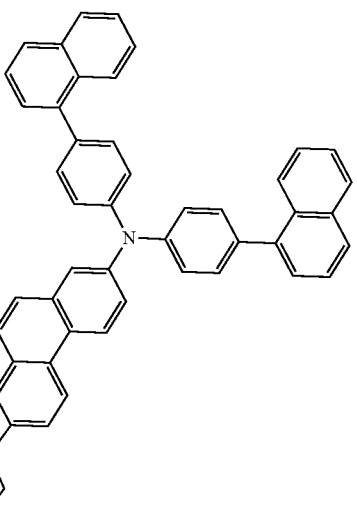
B22
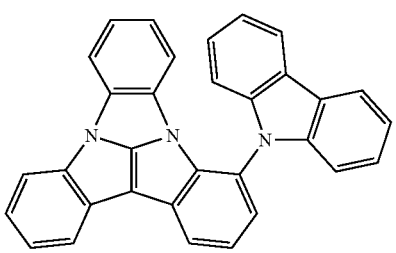
B23
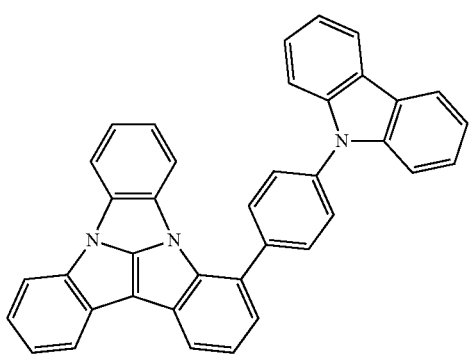
B24
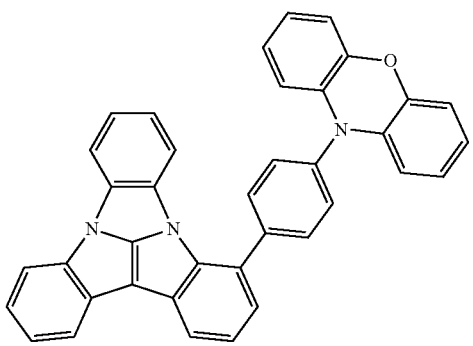

B25
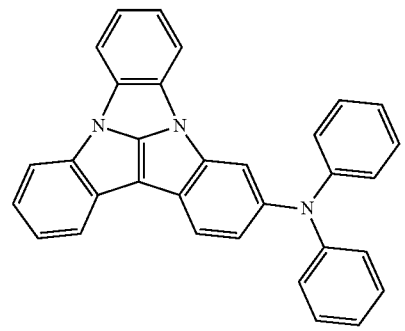
B26
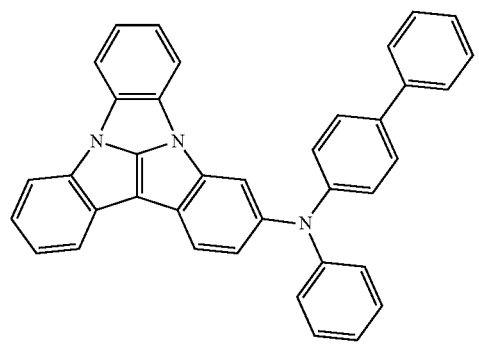
B27
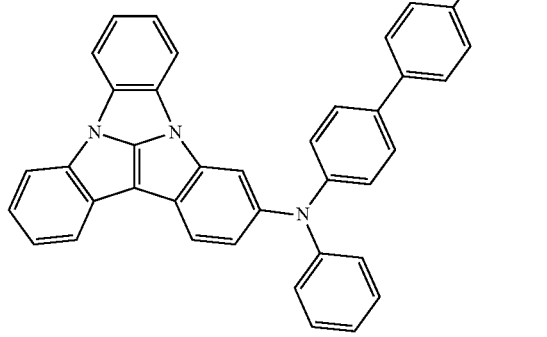
B28
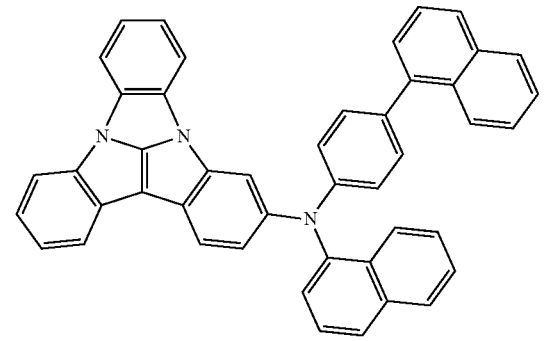
B29
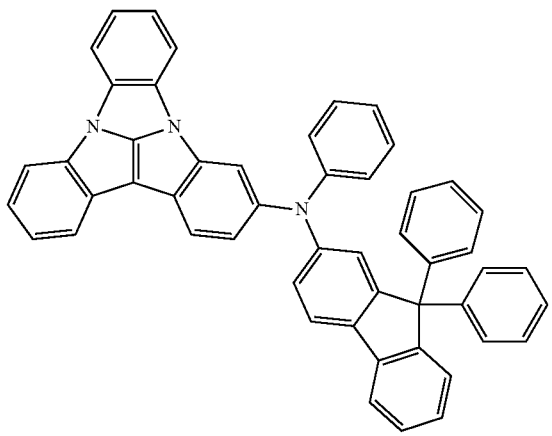
B30
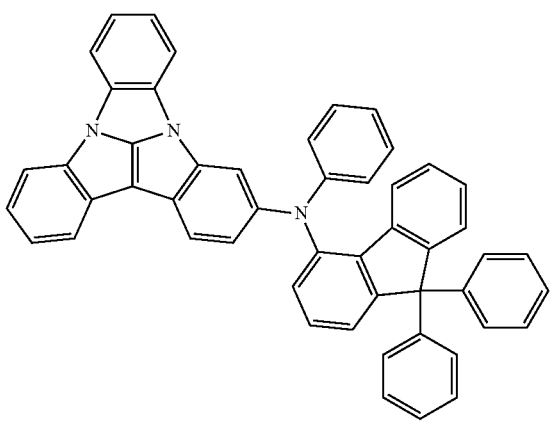
B31
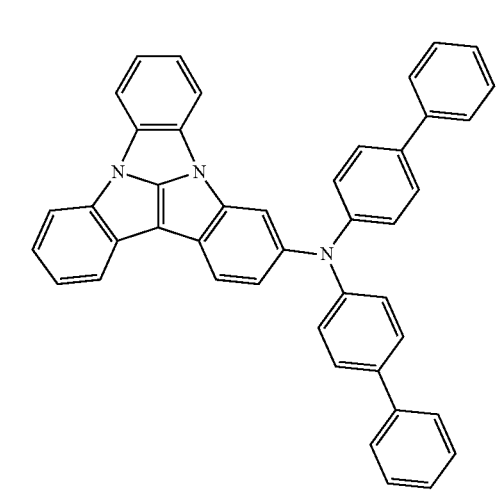

B32
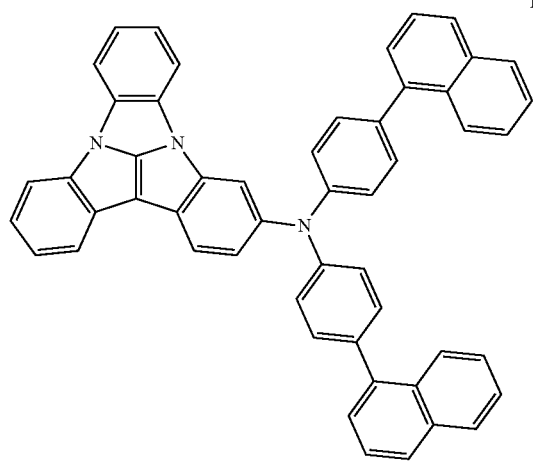
B36
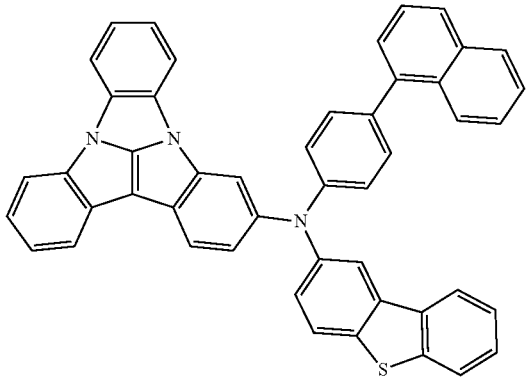
B33
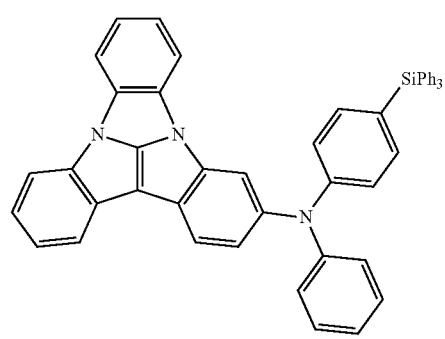
B37
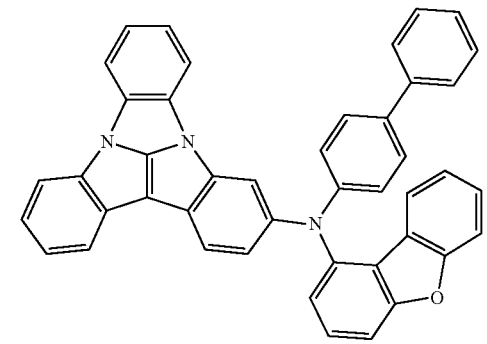
B34
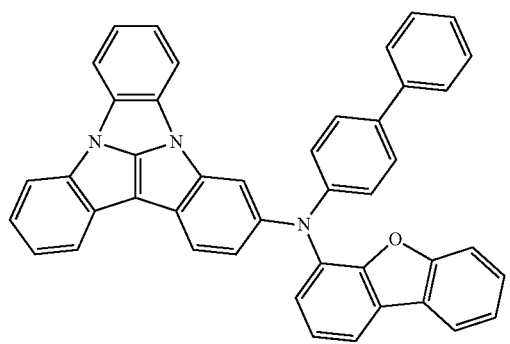
B38
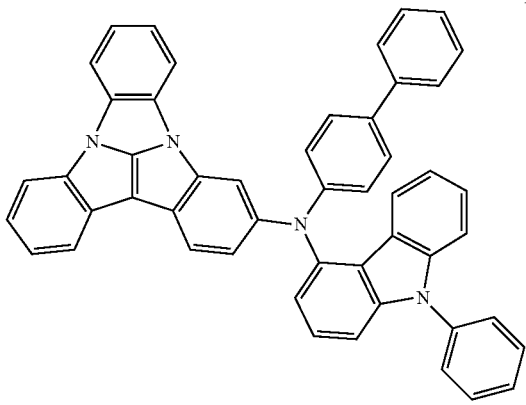
B35
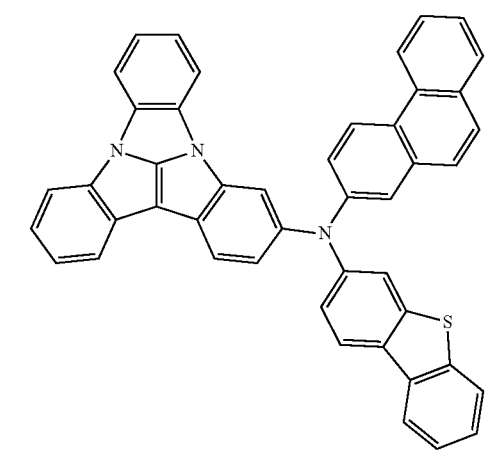
B39
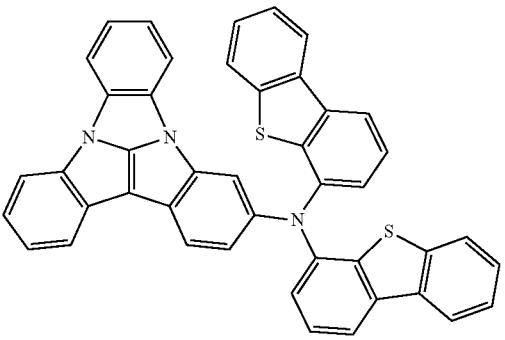

B40 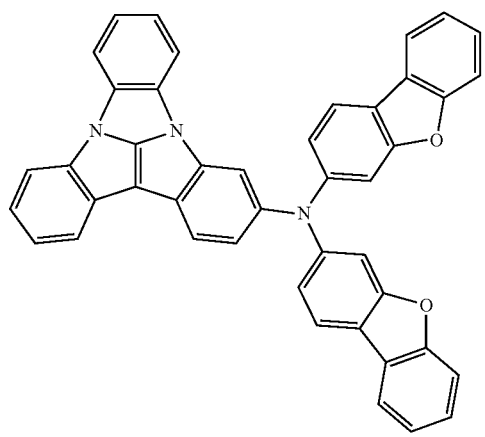
B41 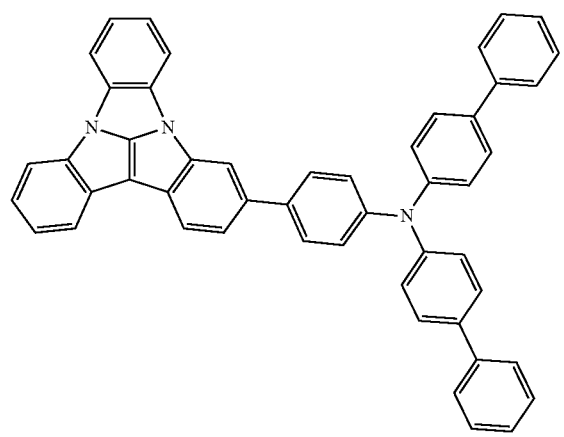
B42 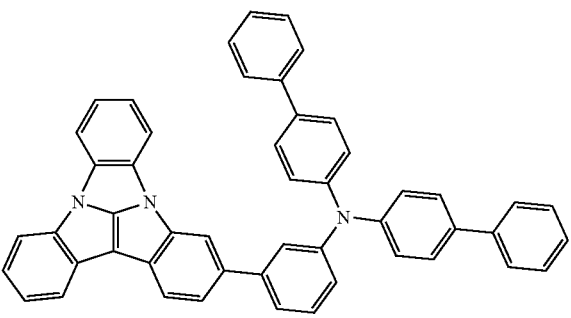
B43 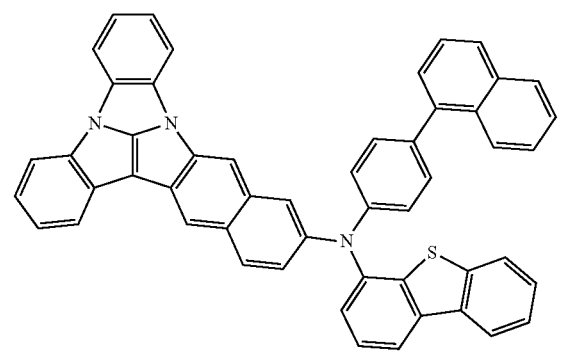
B44 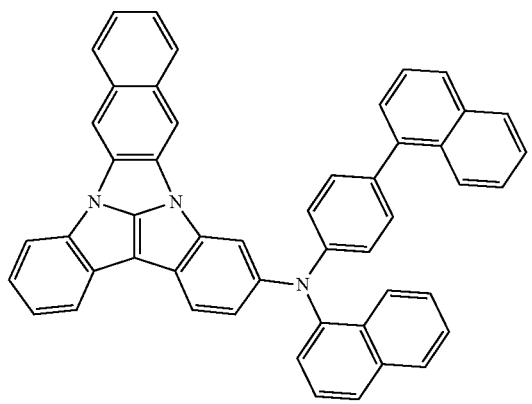
B45 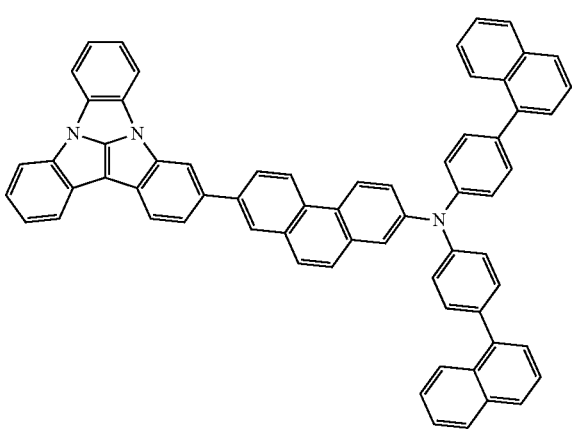
B46 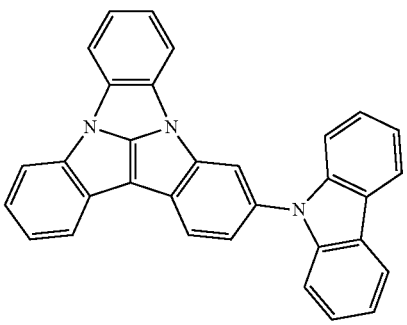
B47 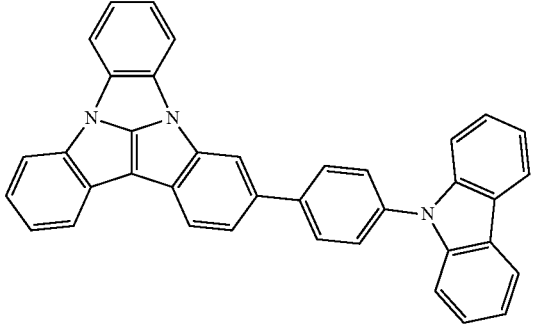

B48
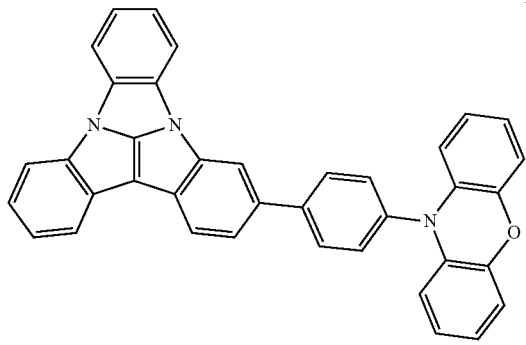
B49
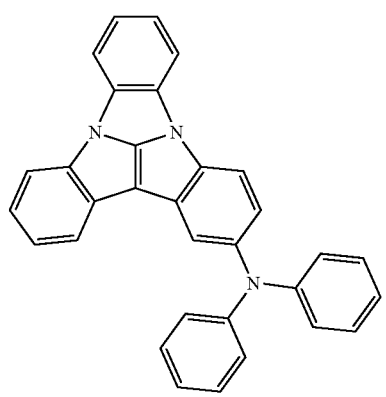
B50
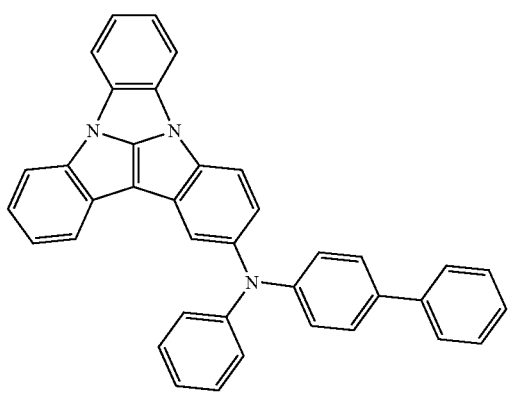
B51
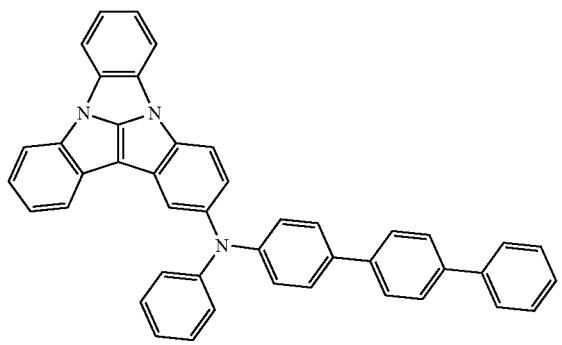
B52
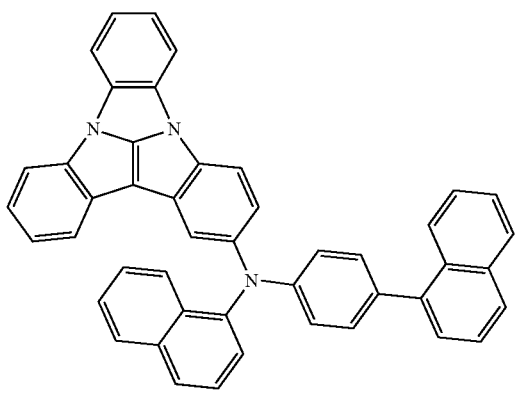
B53
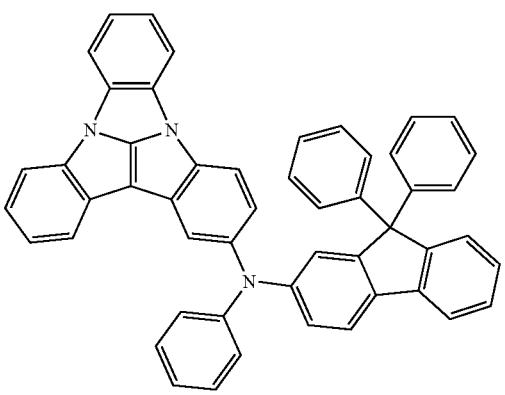
B54
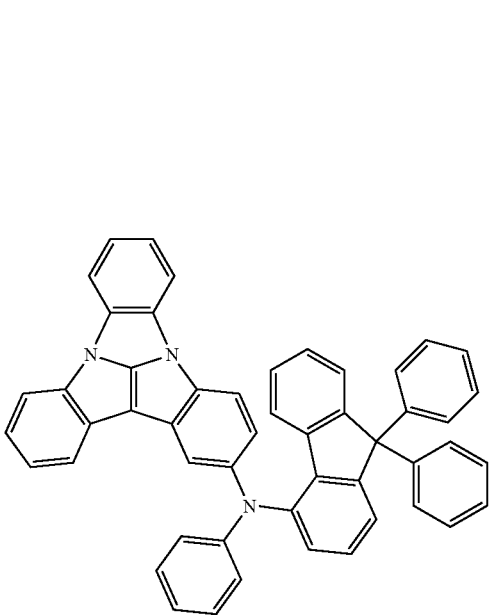

-continued
B55
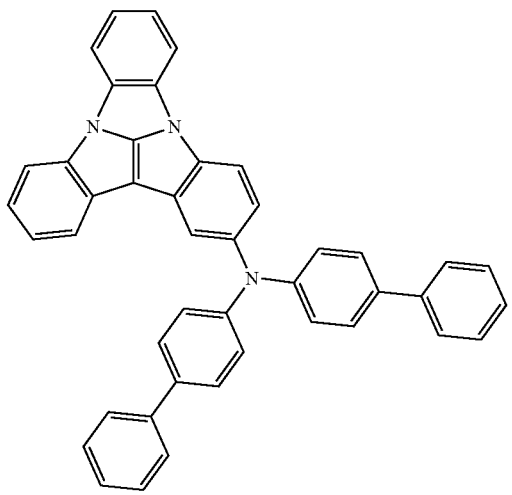
B56
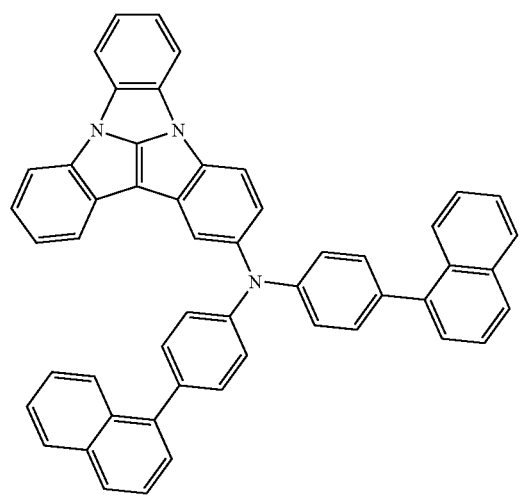
B57
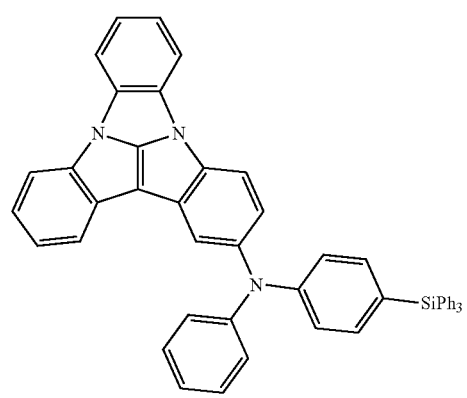
-continued
B58
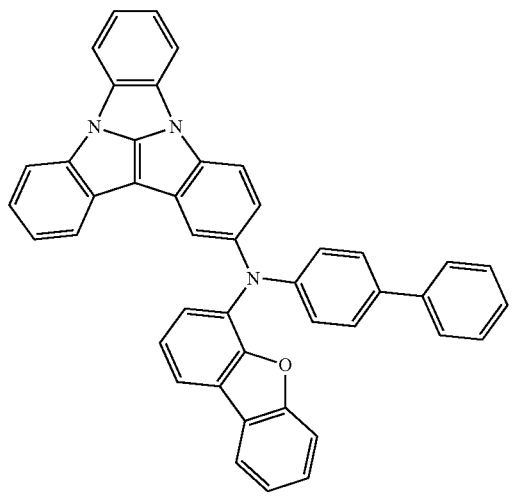
B59
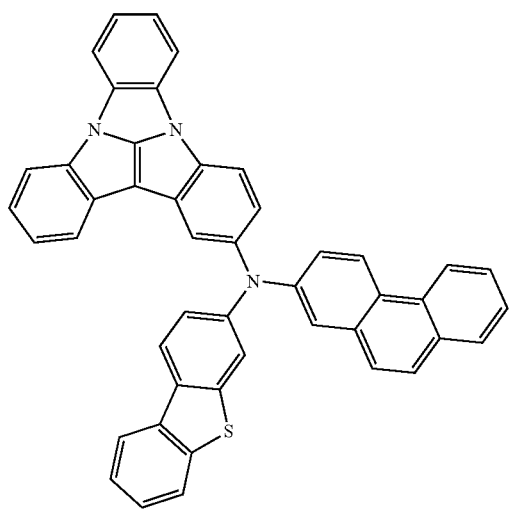
B60
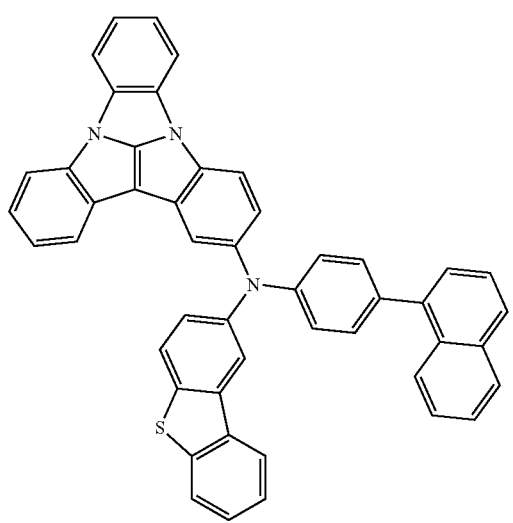

B61
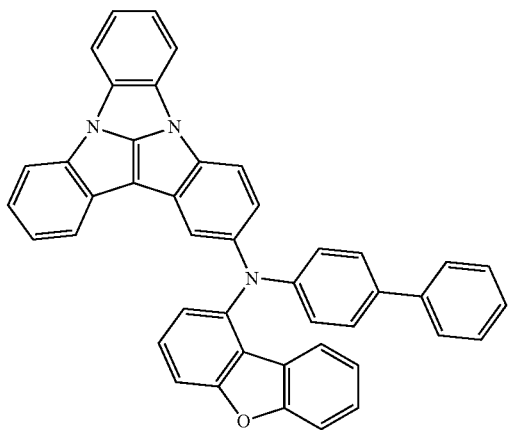
B62
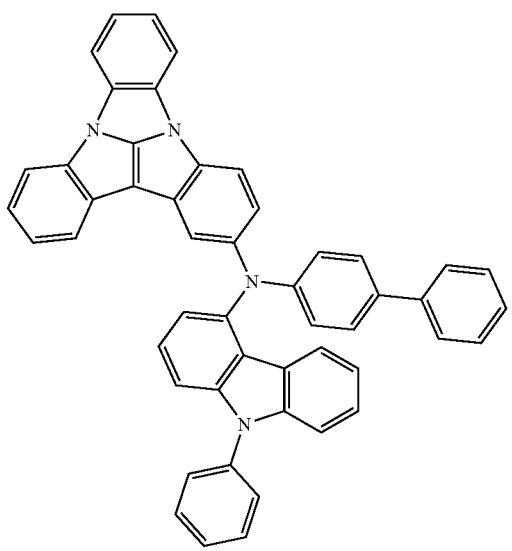
B63
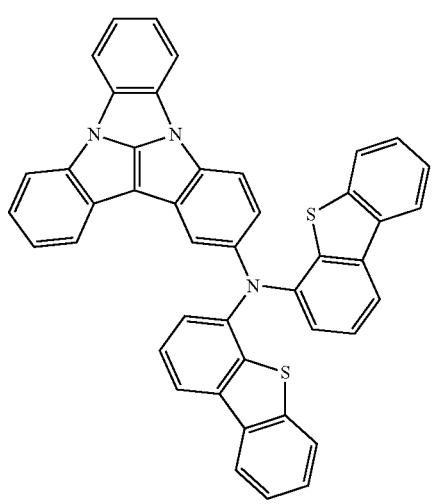
B64
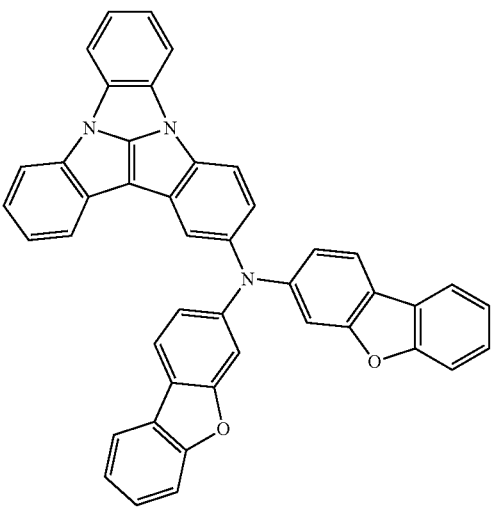
B65
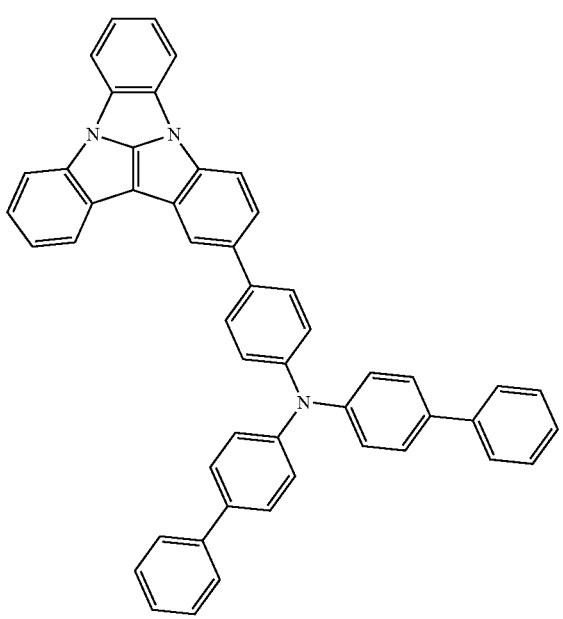

B66
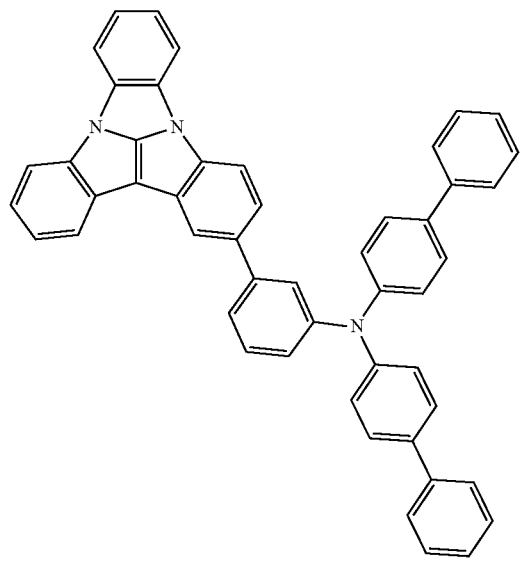
B67
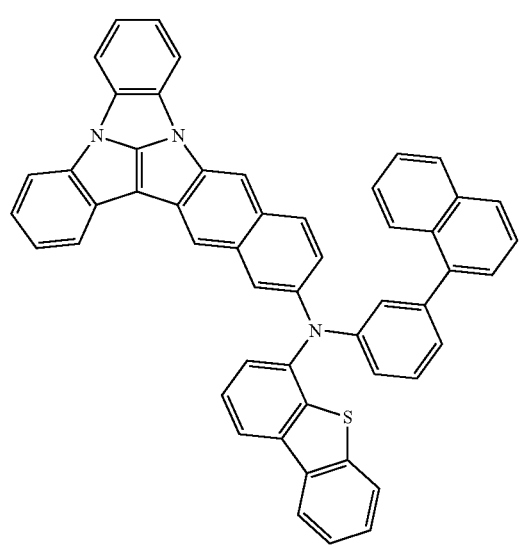
B68
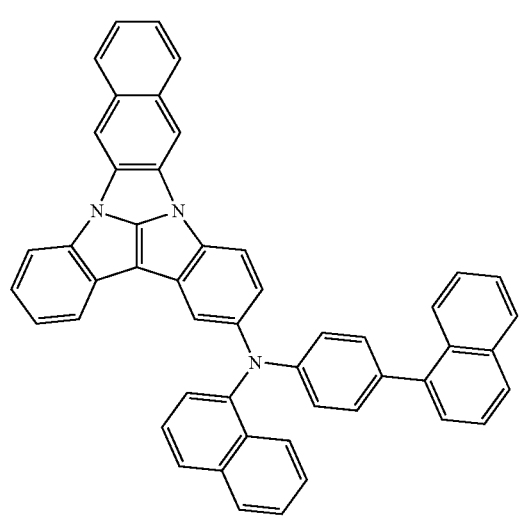
B69
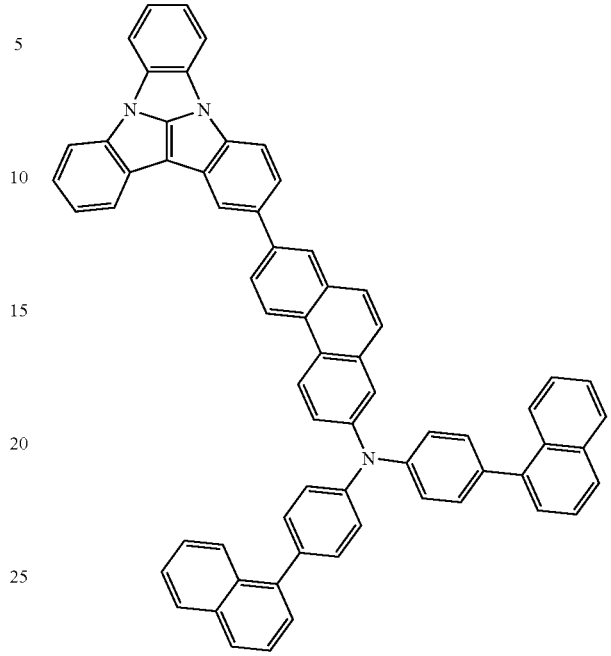
B70
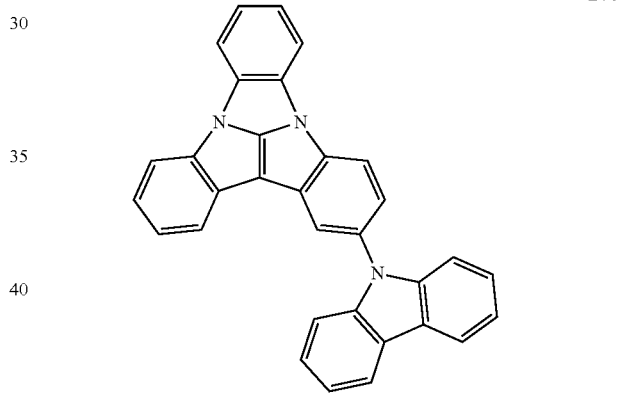
B71
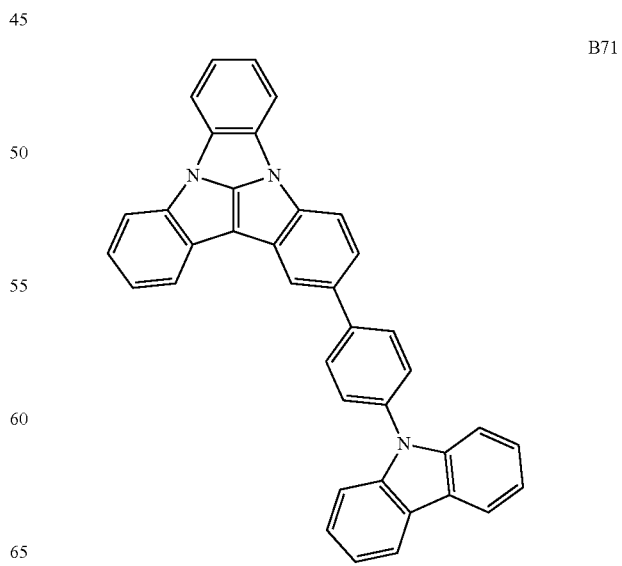

B72
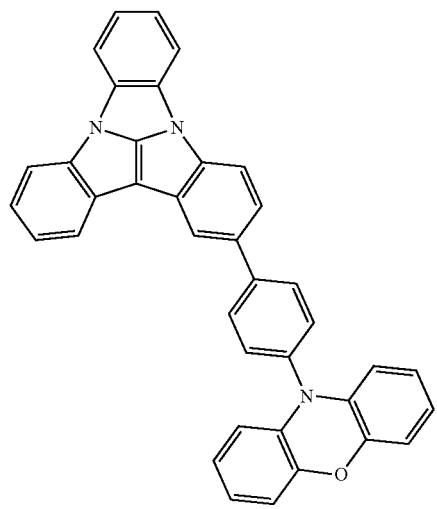
B75
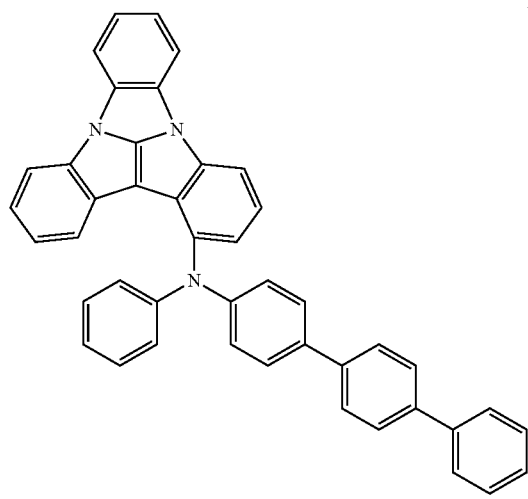
B73
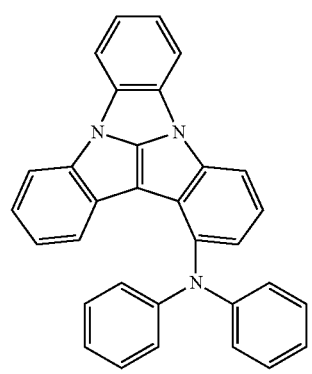
B76
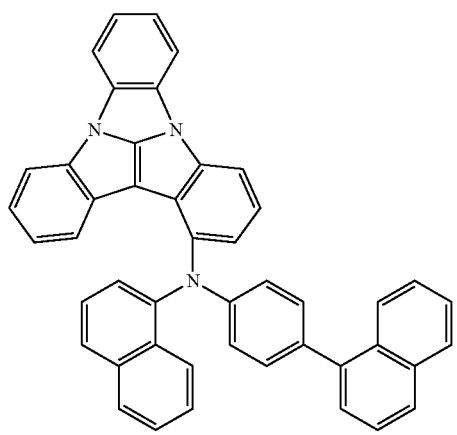
B74
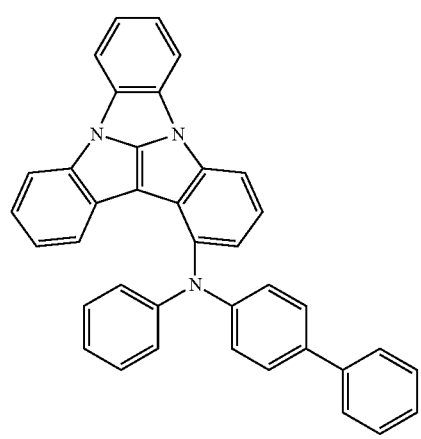
B77
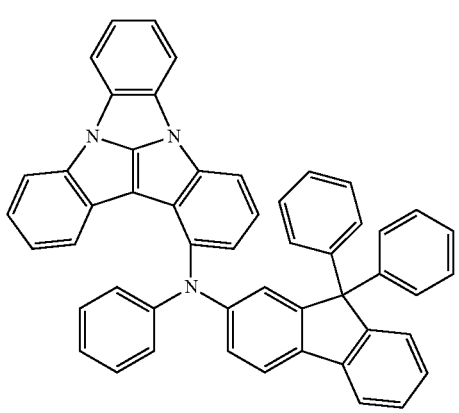

B78
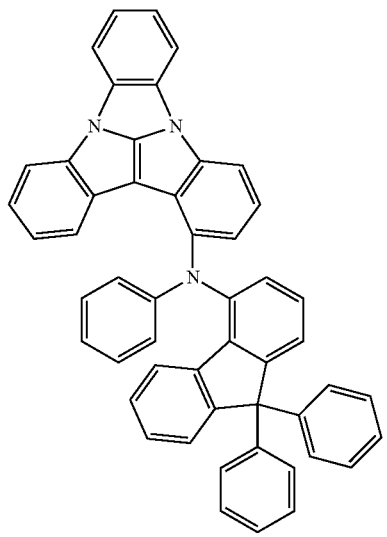
B79
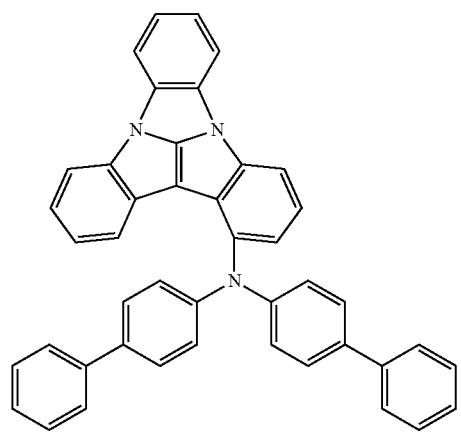
B80
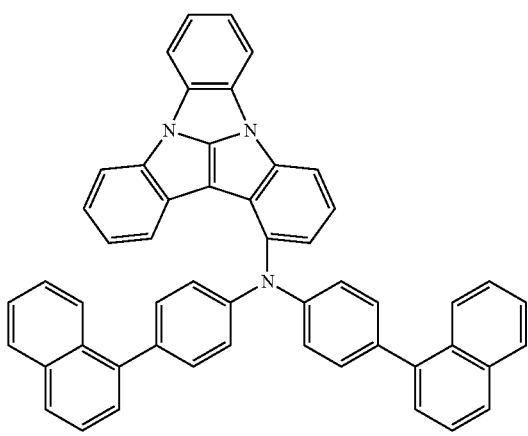
B81
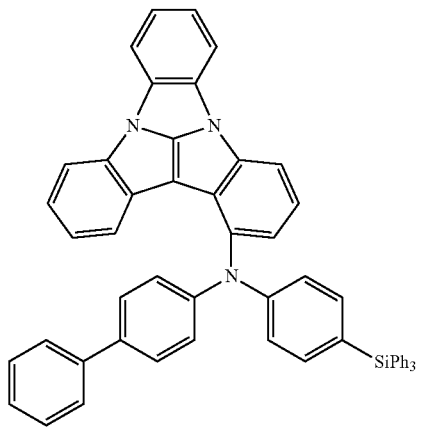
B82
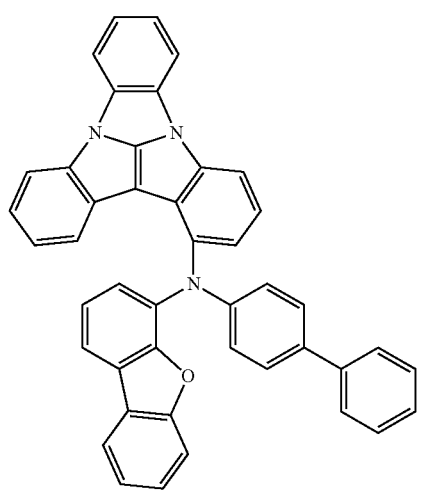
B83
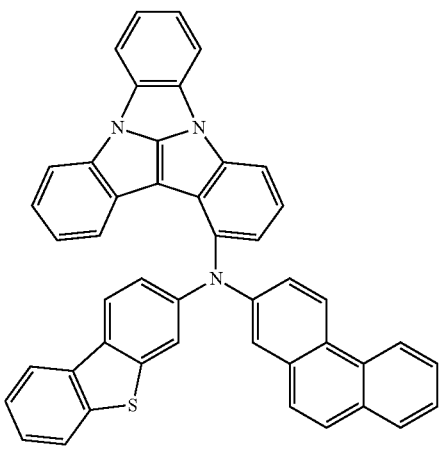

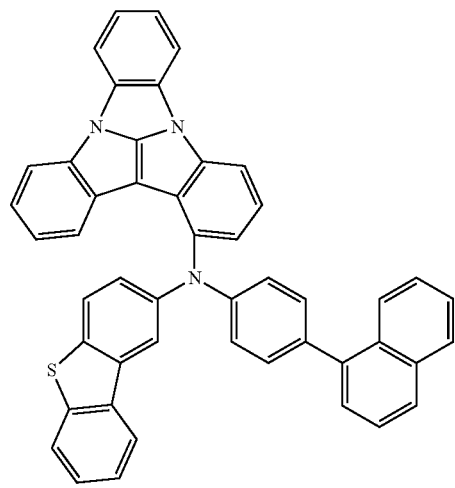
B84
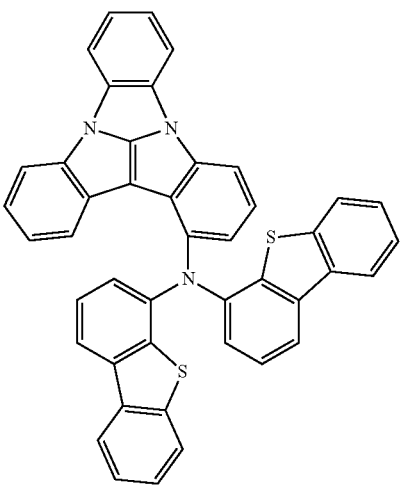
B87
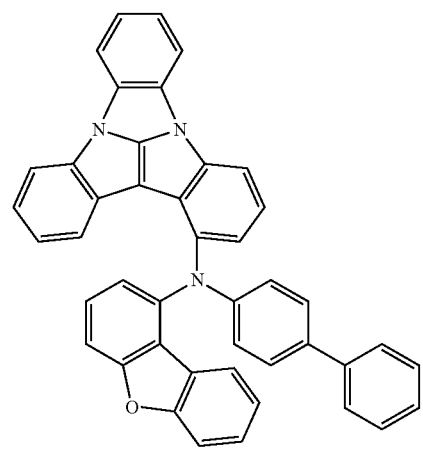
B85
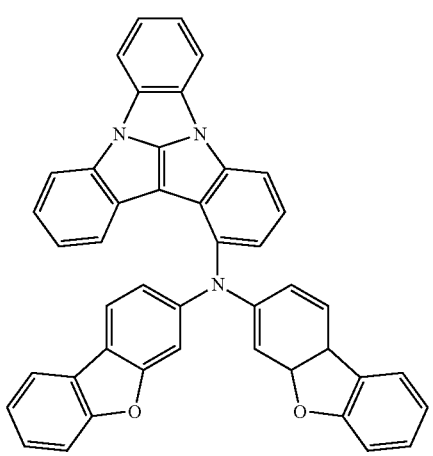
B88
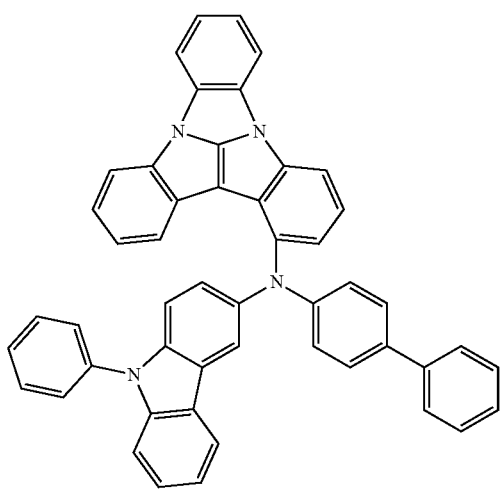
B86
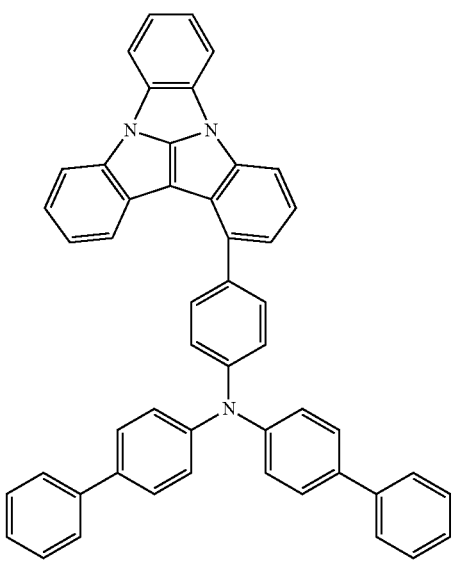
B89

-continued
B90
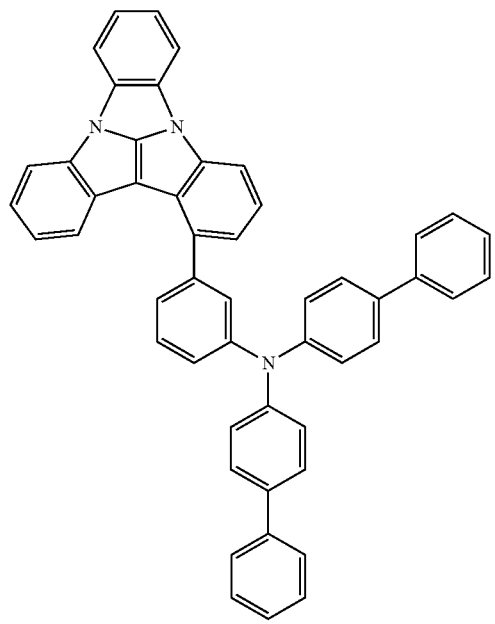
B91
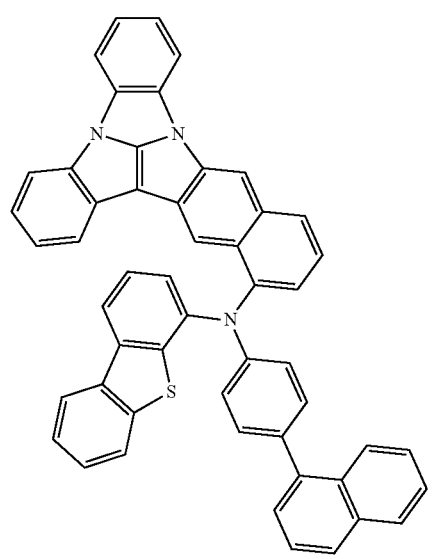
B92
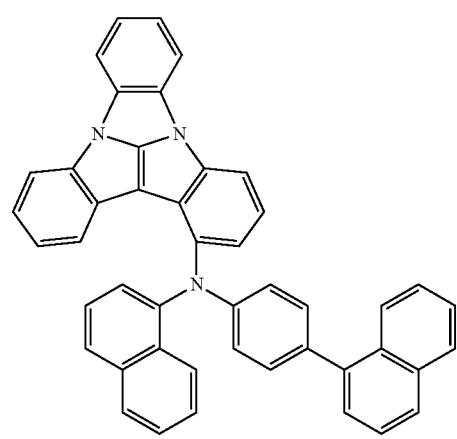
B93
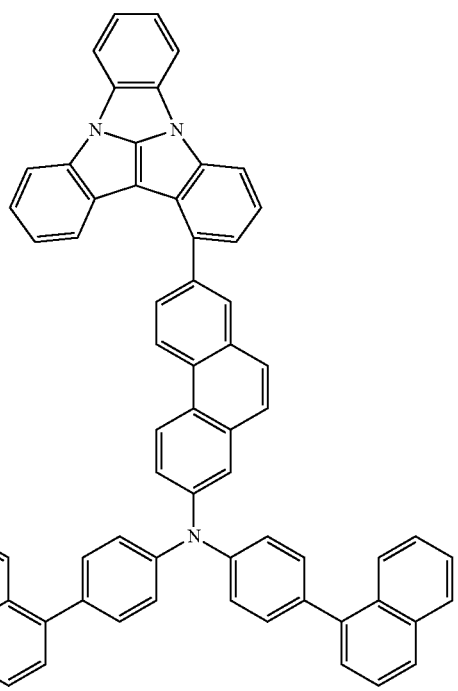
B94
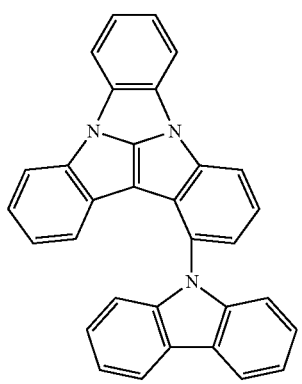
B95
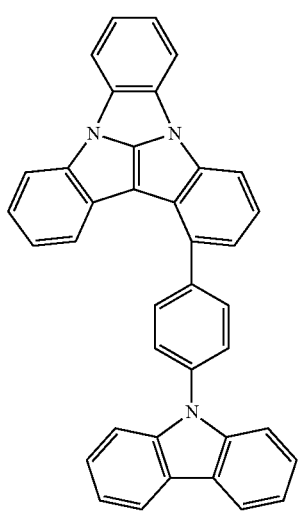

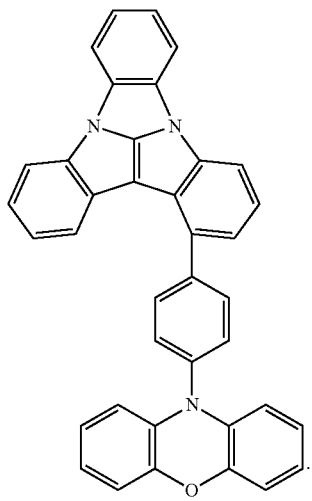

B96

11. A condensed cyclic compound represented by the following Formula 1:

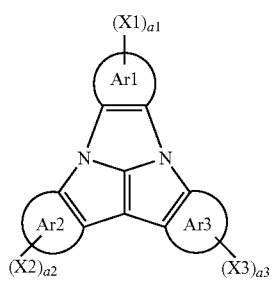

[Formula 1]

in Formula 1, each of Ar1, Ar2, and Ar3 is independently a substituted or unsubstituted aryl group having 6 to 40 carbon atoms for forming a ring, or a substituted or unsubstituted heteroaryl group having 2 to 40 carbon atoms for forming a ring, excluding a case where one or both of Ar2 and Ar3 is a substituted or unsubstituted carbazole group, each of X1, X2, and X3 is independently *-L-NR$_1$R$_2$, and is bonded to a carbon atom of a respective one of the Ar1, Ar2, and Ar3, any one of a1, a2, and a3 is 1, and the others are 0, L is a direct linkage, a substituted or unsubstituted arylene group having 6 to 30 carbon atoms for forming a ring, or a substituted or unsubstituted heteroarylene group having 2 to 30 carbon atoms for forming a ring, and Each of R$_1$ and R$_2$ is independently a substituted or unsubstituted alkyl group having 1 to 20 carbon atoms, a substituted or unsubstituted aryl group having 6 to 40 carbon atoms for forming a ring, or a substituted or unsubstituted heteroaryl group having 2 to 40 carbon atoms for forming a ring, or combined with each other to form a ring.

12. The condensed cyclic compound of claim 11, wherein Formula 1 is represented by the following Formula 1-1 or Formula 1-2:

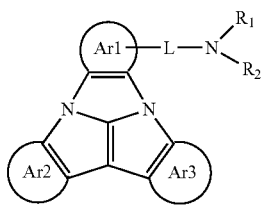

[Formula 1-1]

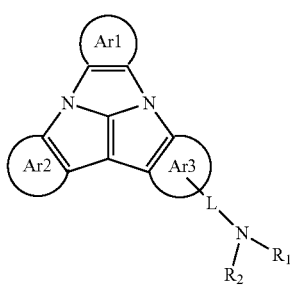

[Formula 1-2]

in Formula 1-1 and Formula 1-2, Ar1 to Ar3, L, R$_1$ and R$_2$ are the same as defined in Formula 1.

13. The condensed cyclic compound of claim 11, wherein Ar1 is a substituted or unsubstituted benzene ring, or a substituted or unsubstituted naphthalene ring.

14. The condensed cyclic compound of claim 11, wherein each of Ar2 and Ar3 is independently a substituted or unsubstituted benzene ring, a substituted or unsubstituted naphthalene ring, a substituted or unsubstituted phenanthrene ring, a substituted or unsubstituted benzofuran ring, a substituted or unsubstituted dibenzofuran ring, a substituted or unsubstituted benzothiophene ring, a substituted or unsubstituted dibenzothiophene ring, a substituted or unsubstituted pyridine ring, or a substituted or unsubstituted quinoline ring.

15. The condensed cyclic compound of claim 11, wherein Ar2 and Ar3 are the same.

16. The condensed cyclic compound of claim 11, wherein each of Ar2 and Ar3 is independently represented by any one of the following Ar-a to Ar-i:

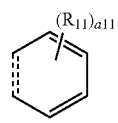

Ar-a

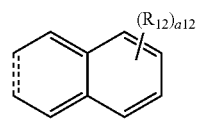

Ar-b

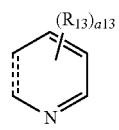

Ar-c

-continued

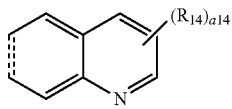 Ar-d

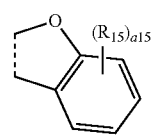 Ar-e

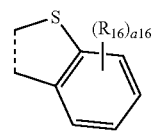 Ar-f

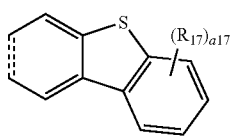 Ar-g

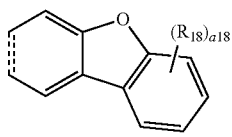 Ar-h

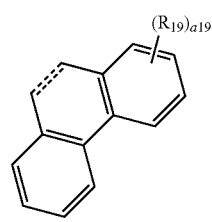 Ar-i in Ar-a to Ar-i, each of $R_{11}$ to $R_{19}$ is independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring, each of a11 to a19 is independently an integer of 0 to 4, and dotted lines represent combined parts forming a condensed ring.

17. The condensed cyclic compound of claim 11, wherein Formula 1 is represented by the following Formula 2-1 or Formula 2-2:

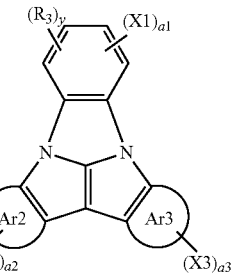 [Formula 2-1]

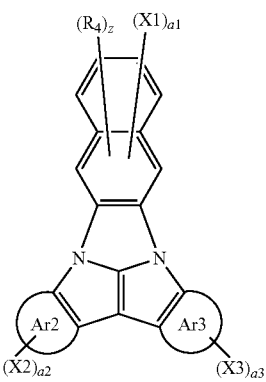 [Formula 2-2]

in Formula 2-1 and Formula 2-2, each of $R_3$ and $R_4$ is independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring, each of "y" and "z" is independently an integer of 0 to 3, and X1, X2, X3, a1, a2, and a3 are the same as defined in Formula 1.

18. The condensed cyclic compound of claim 11, wherein L is a direct linkage or represented by any one of the following L1, L2, L3, and L4:

 L1

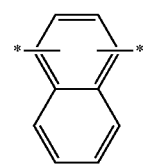 L2

-continued
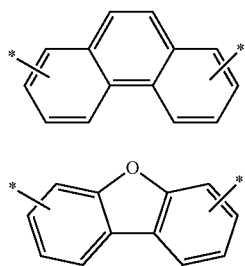
L3
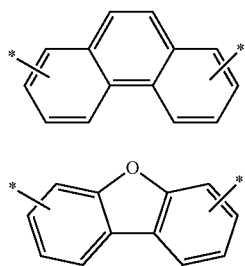
L4
19. A condensed cyclic compound represented by any of the compounds represented in the following Compound Group 1 and Compound Group 2:
[Compound Group 1]
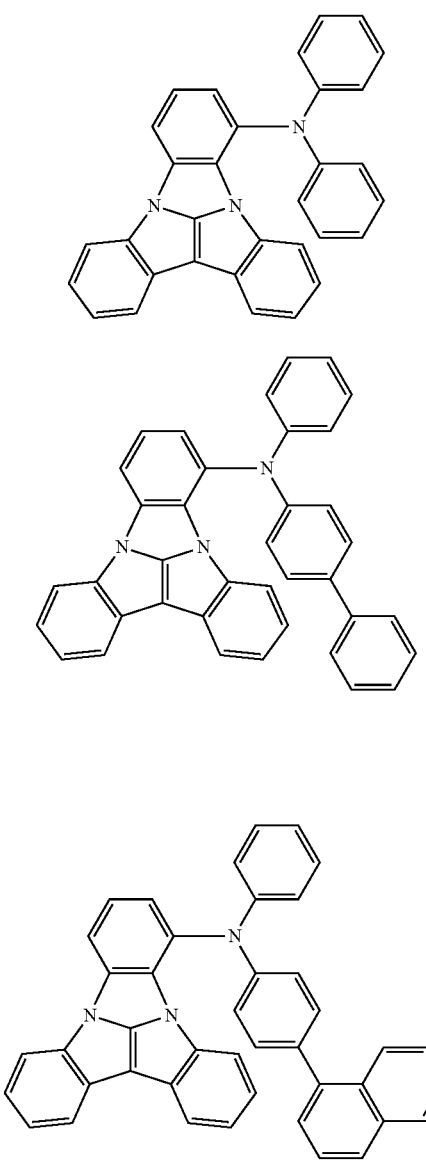
A1
A2
A3
-continued
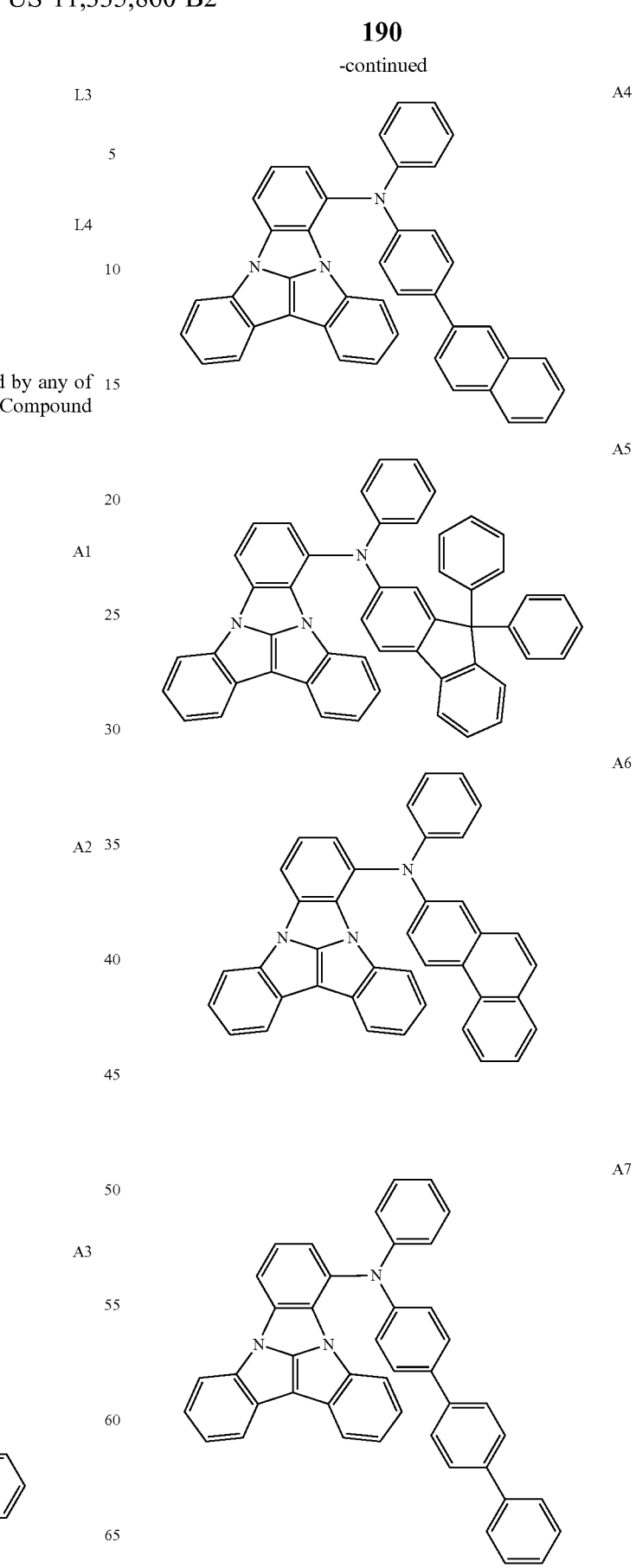
A4
A5
A6
A7

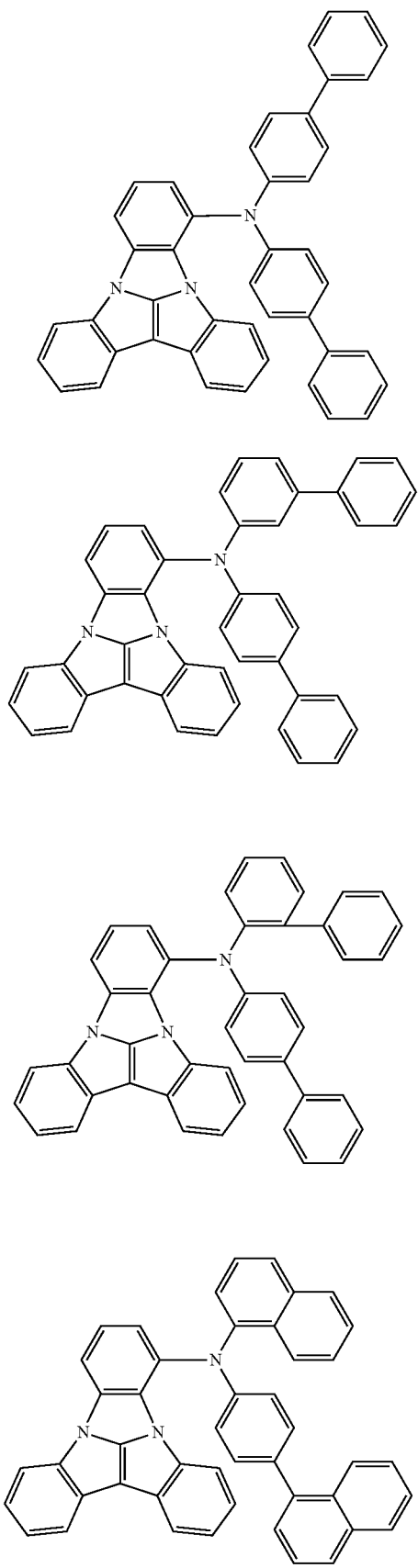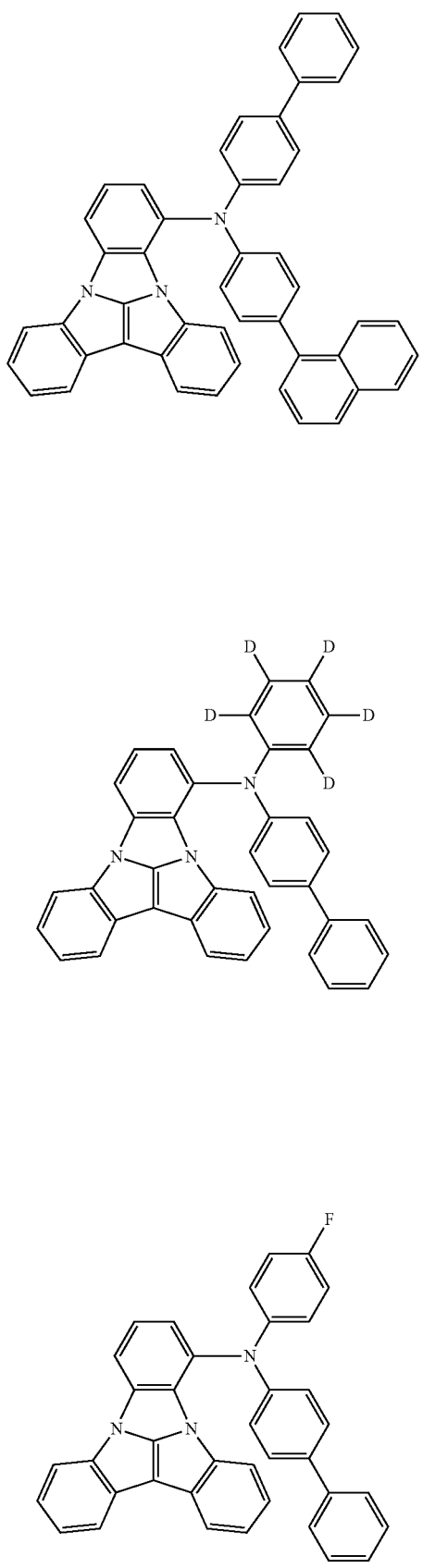

-continued
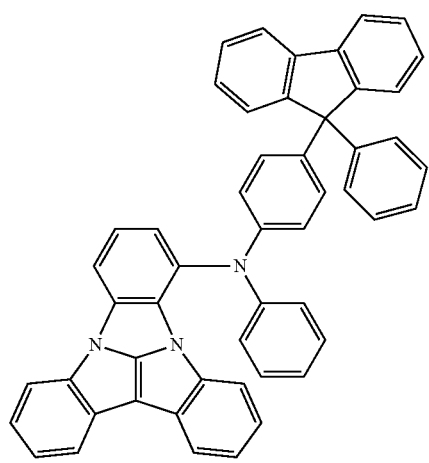 A15
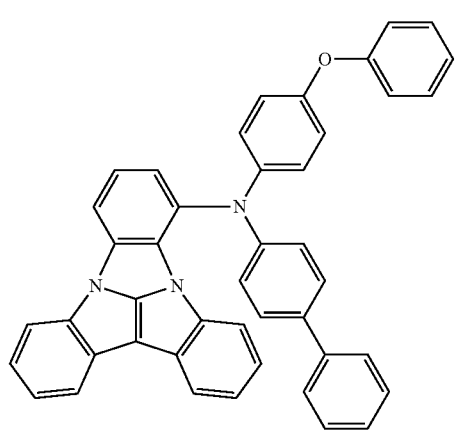 A16
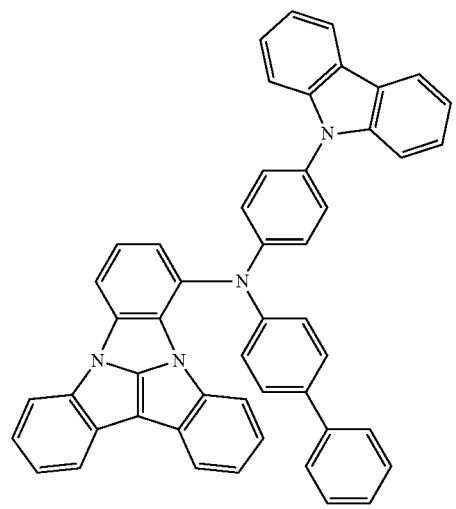 A17
-continued
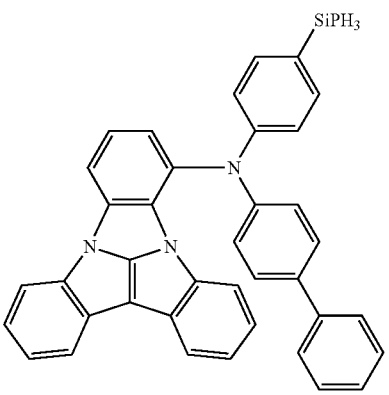 A18
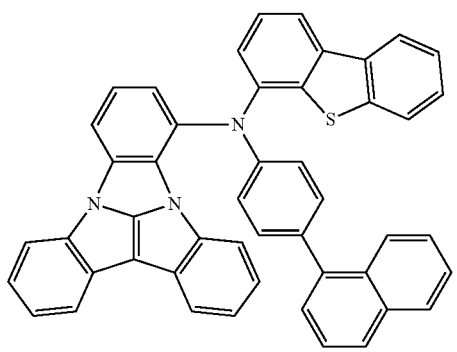 A19
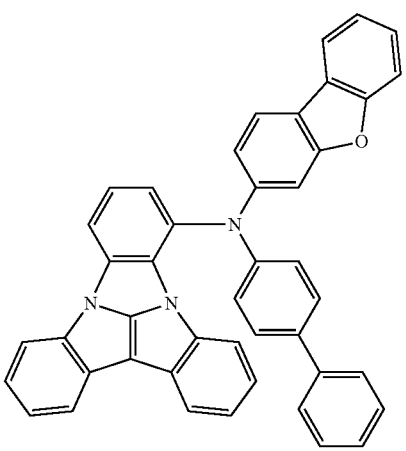 A20
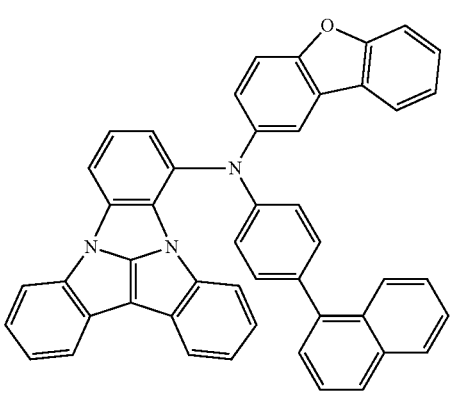 A21

A22
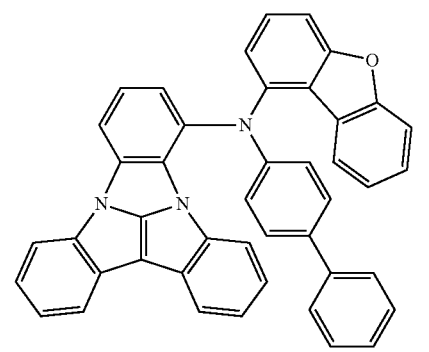
A23
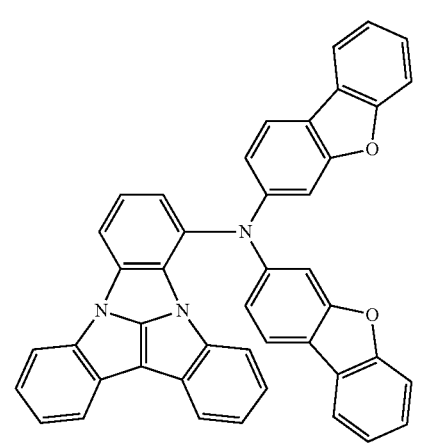
A24
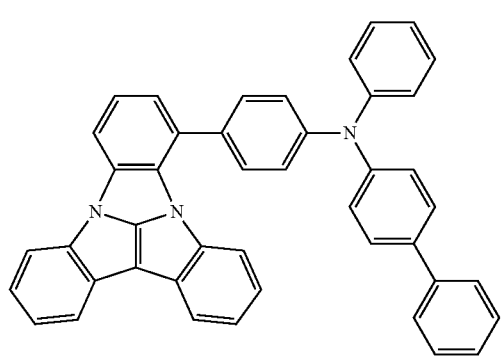
A25
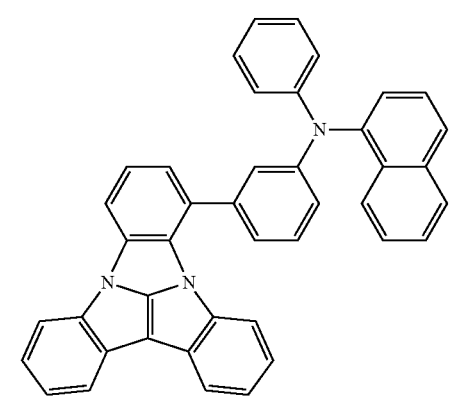
A26
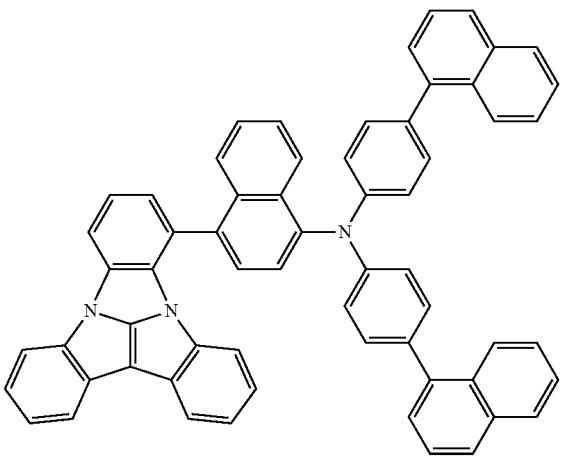
A27
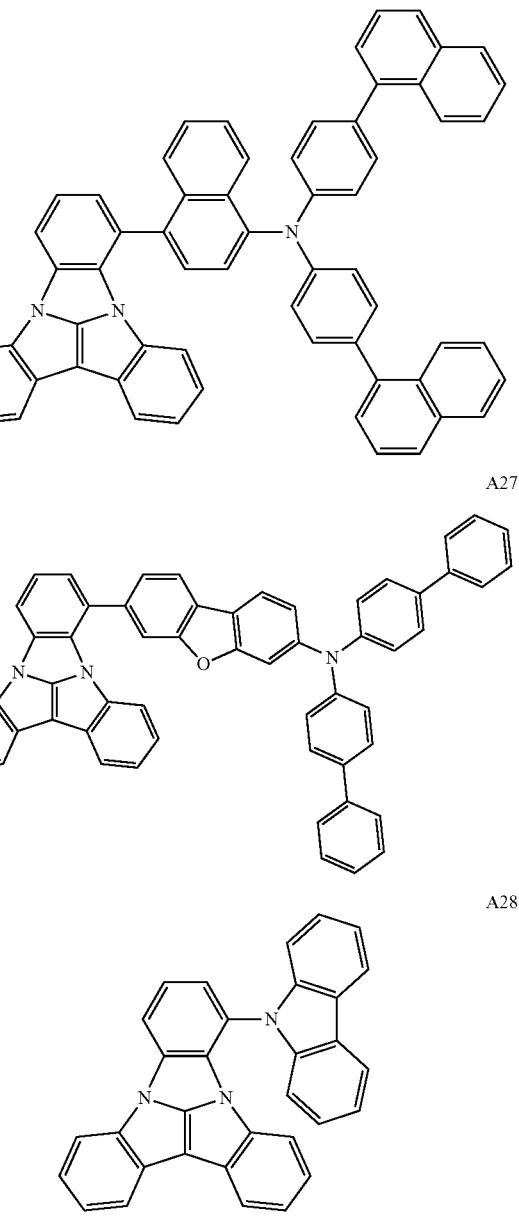
A28
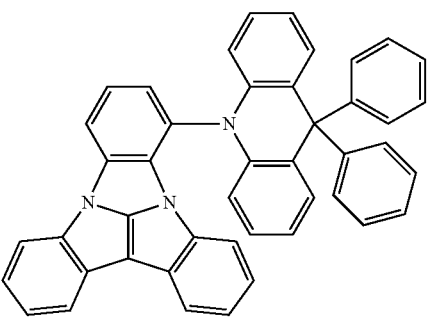
A29

A30
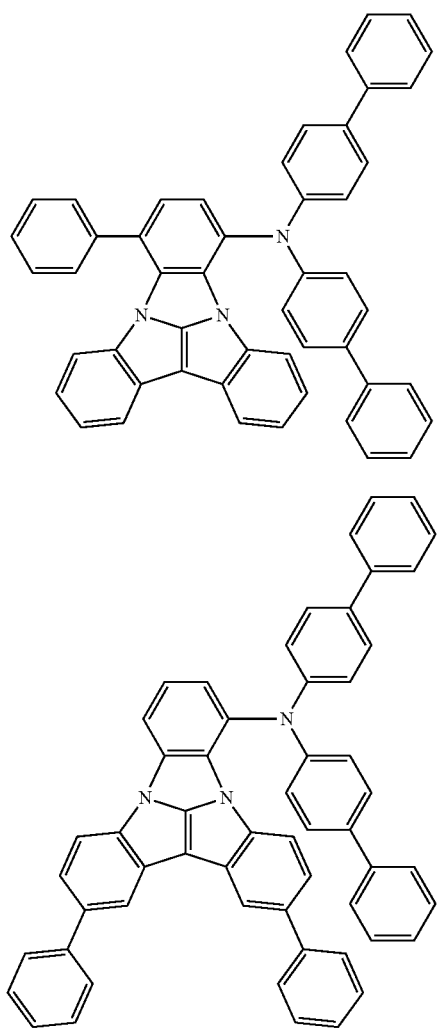
A31
A32
A33
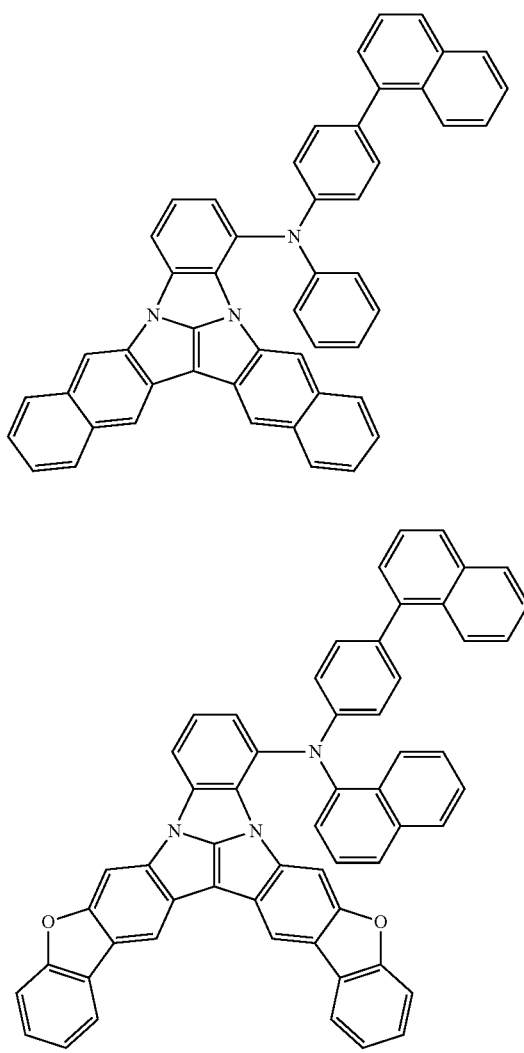
A34
A35
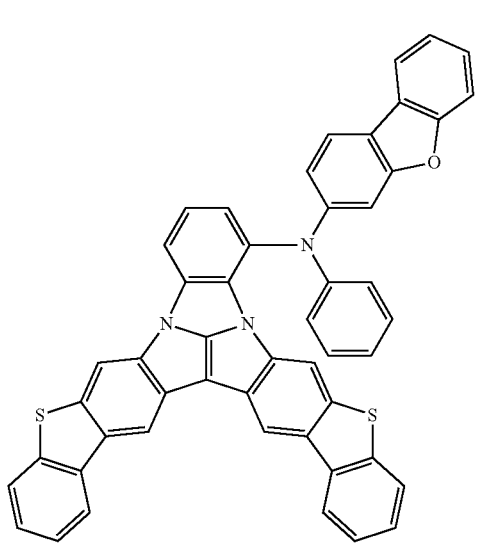

-continued
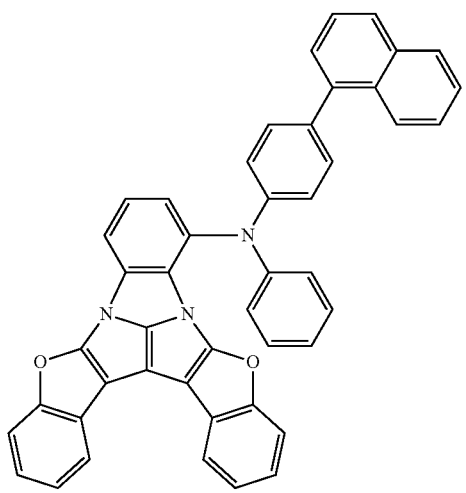
A36
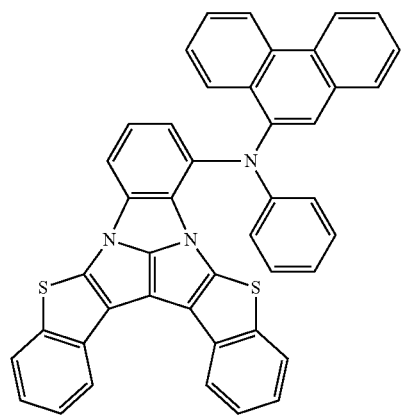
A37
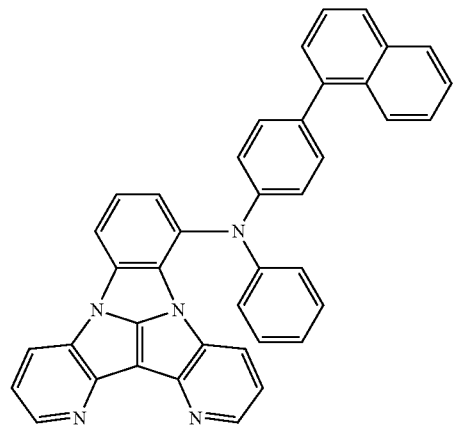
A38
-continued
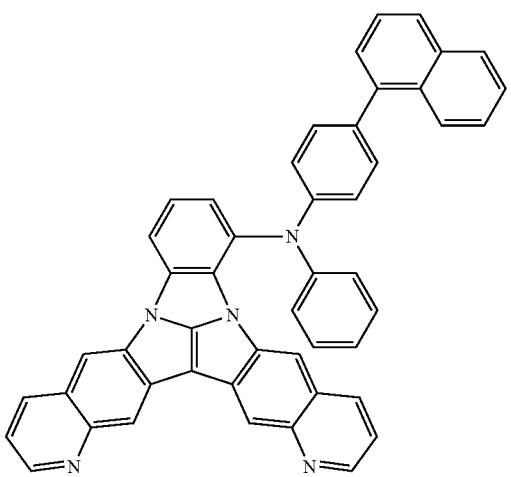
A39
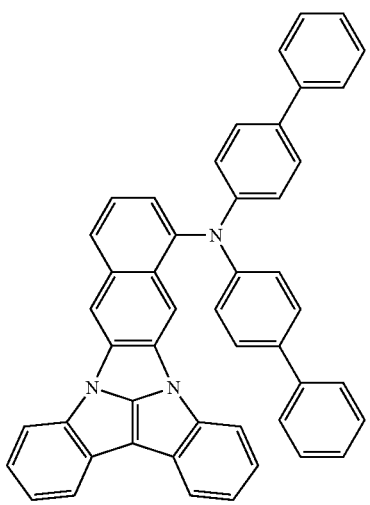
A40
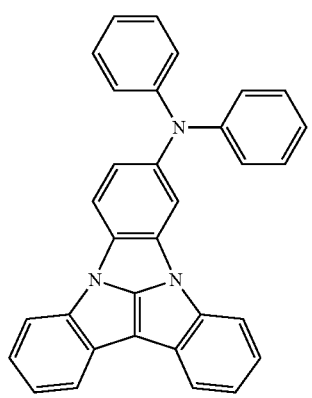
A41

201
-continued
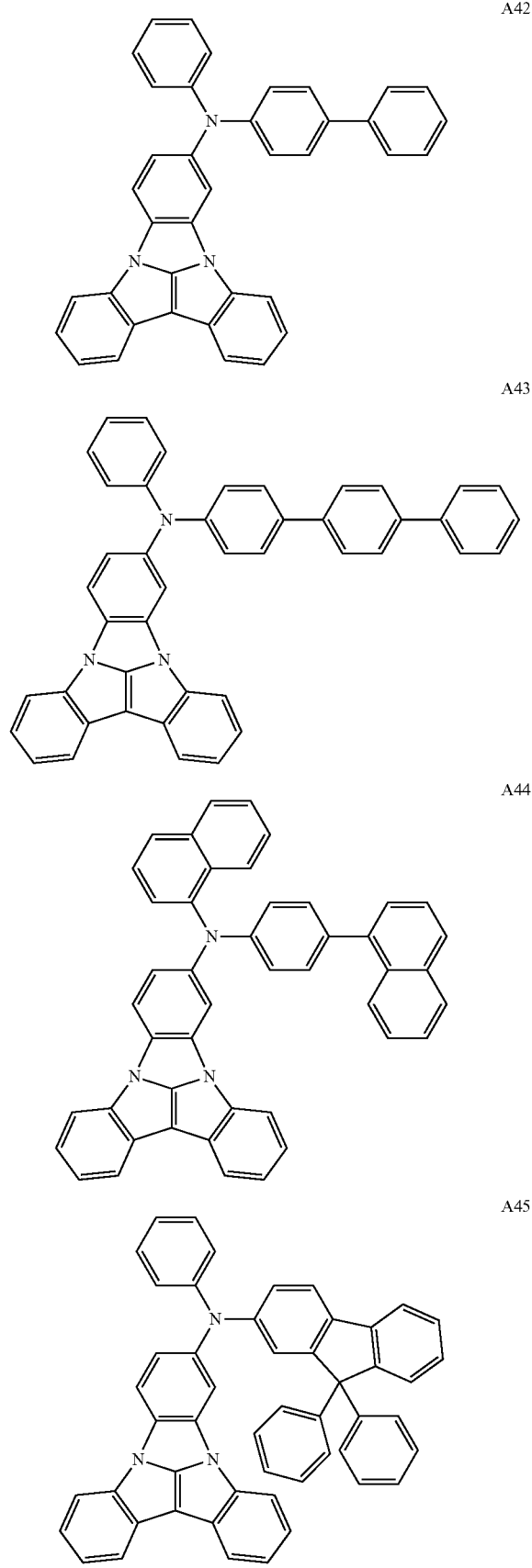
A42
A43
A44
A45
202
-continued
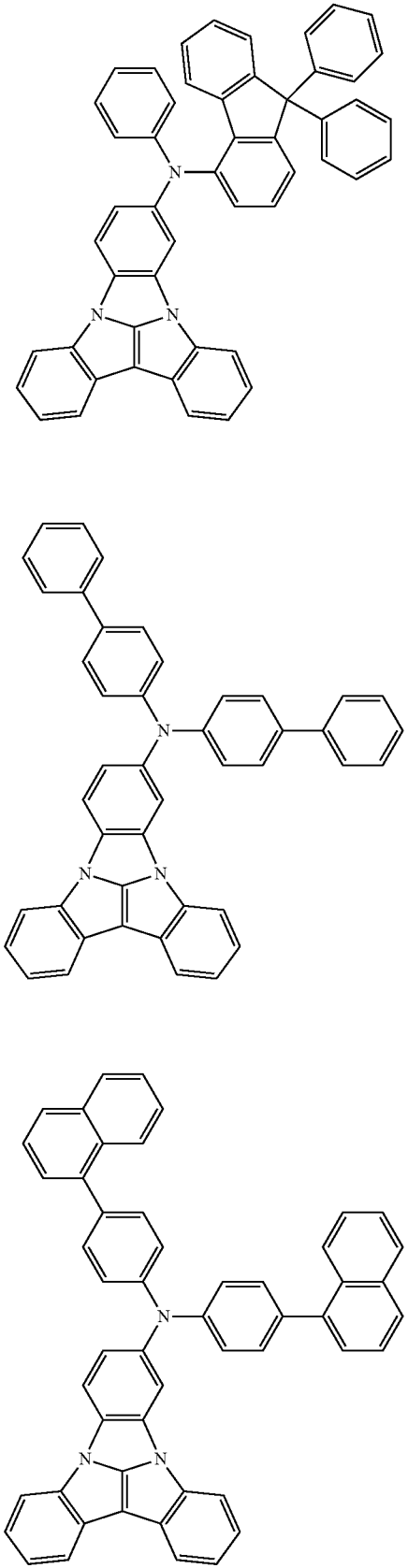
A46
A47
A48

A49
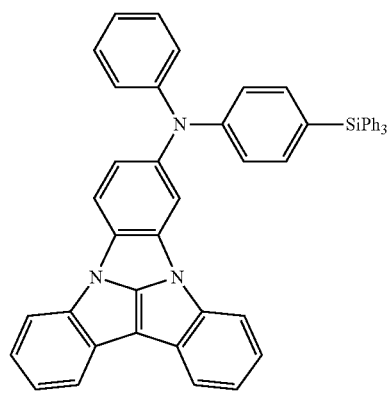
A50
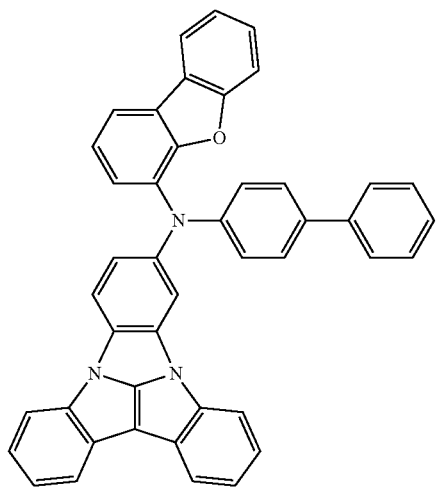
A51
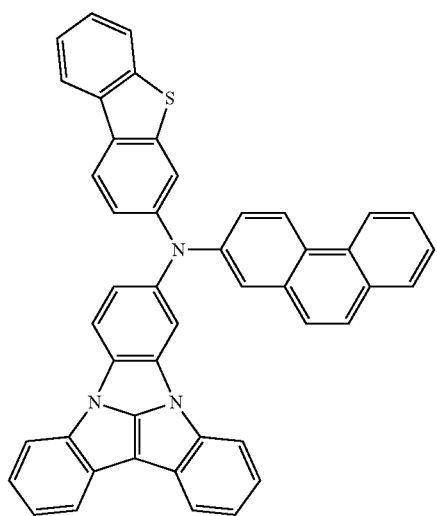
A52
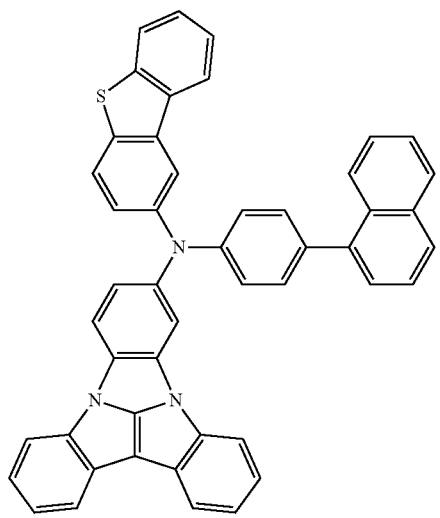
A53
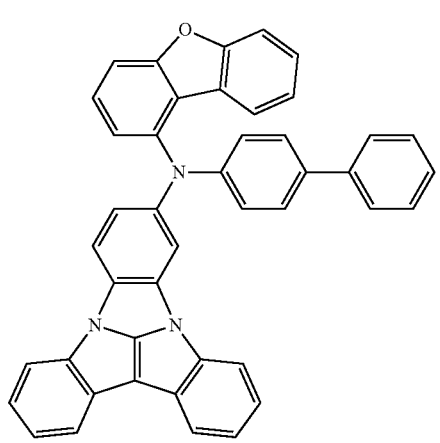
A54
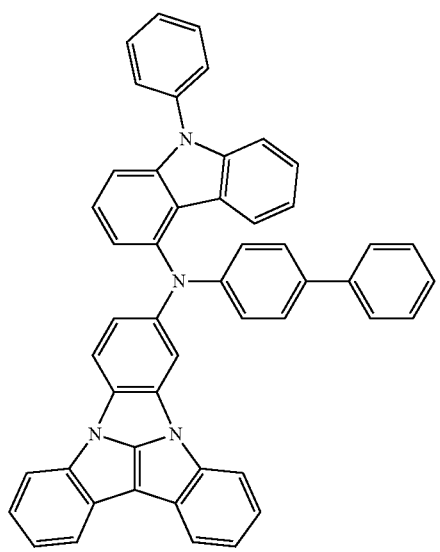

205
-continued
206
-continued
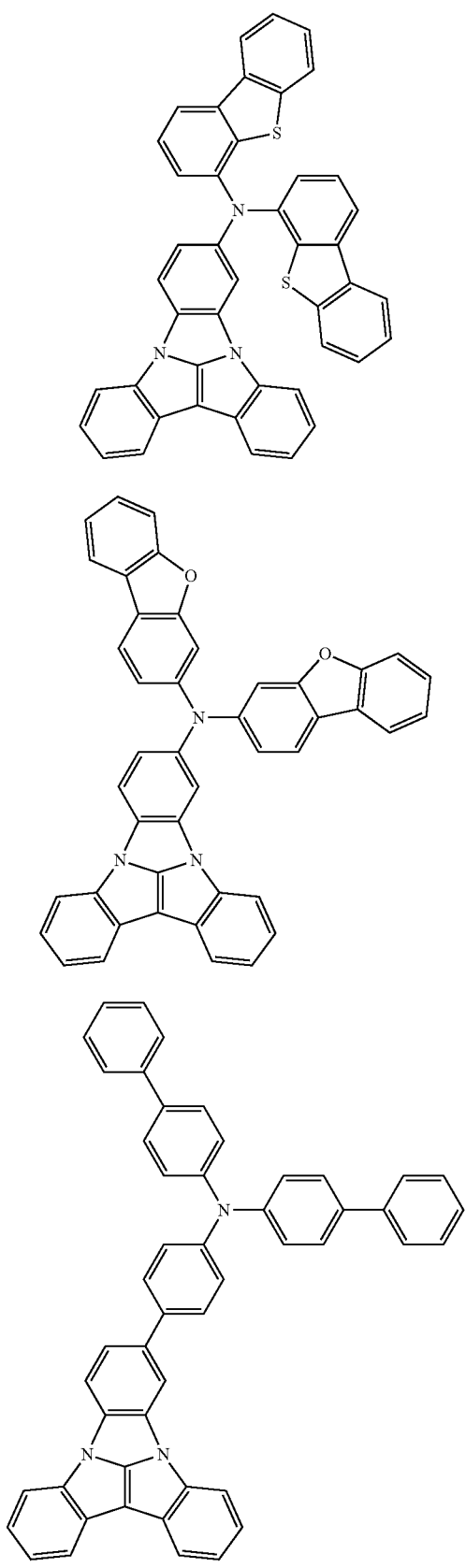
A55
A56
A57
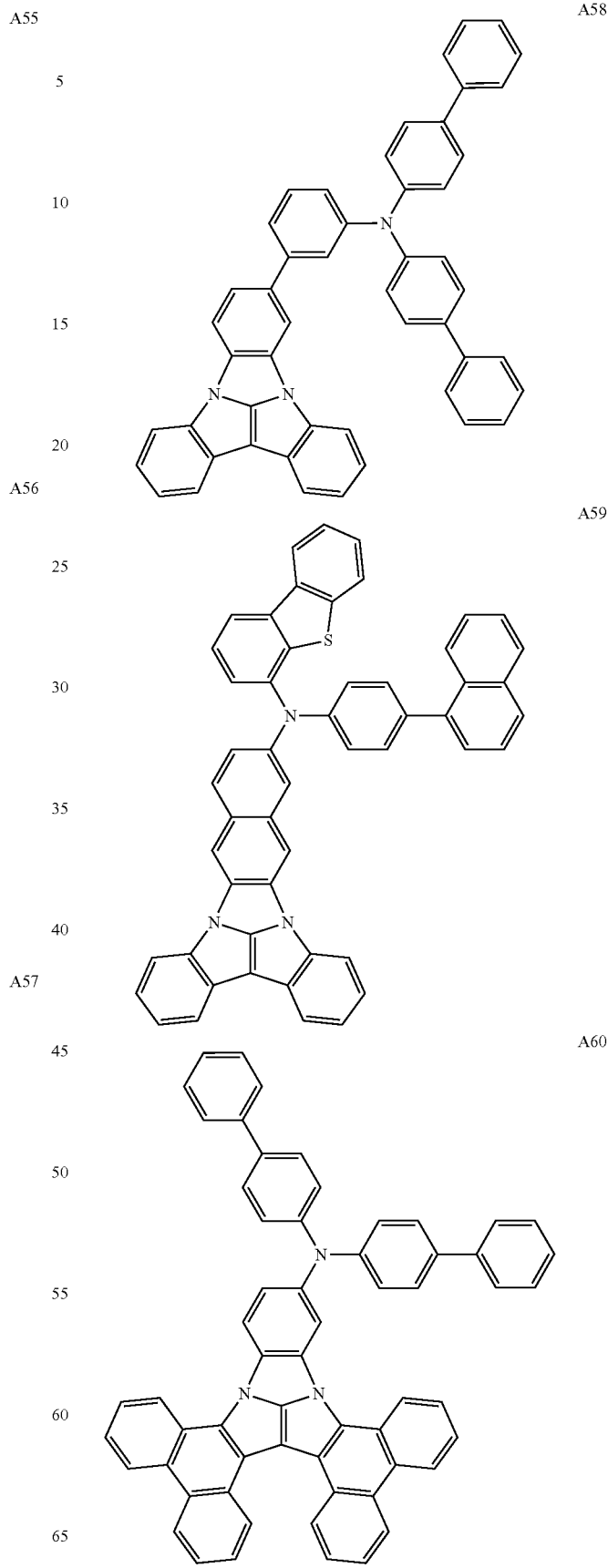
A58
A59
A60

A61
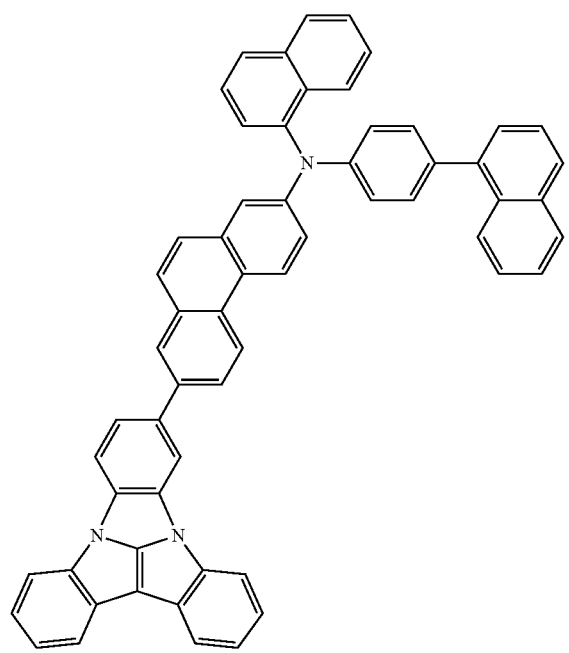
A62
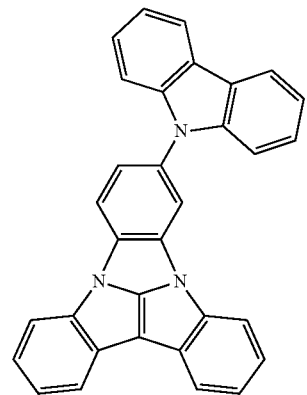
A63
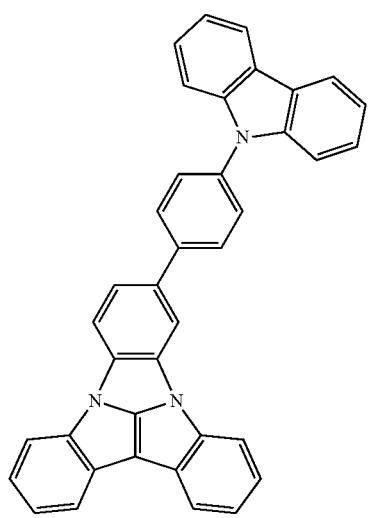
A64
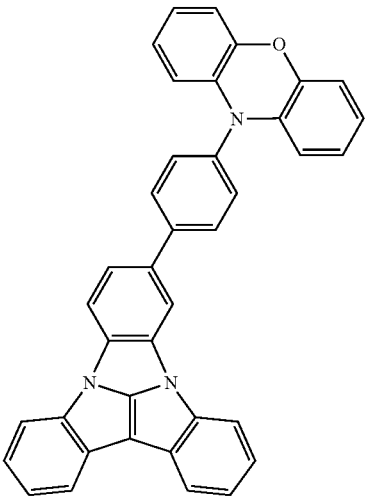
[Compound Group 2]
B1
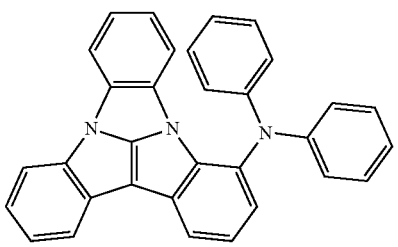
B2
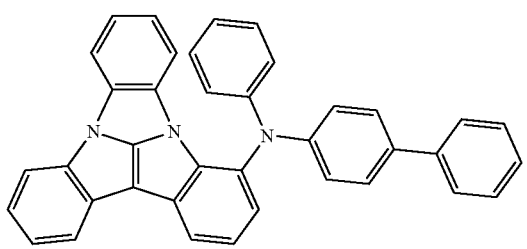
B3
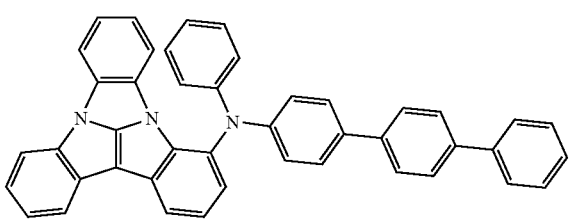
B4
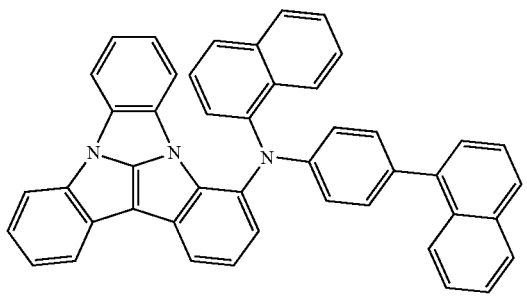

B5
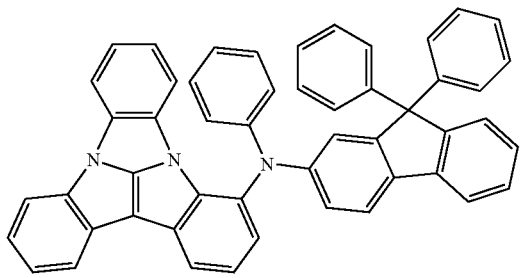
B6
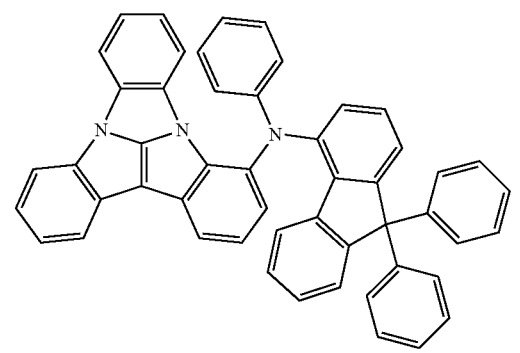
B7
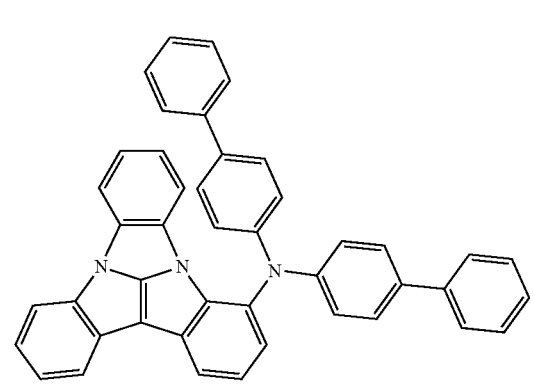
B8
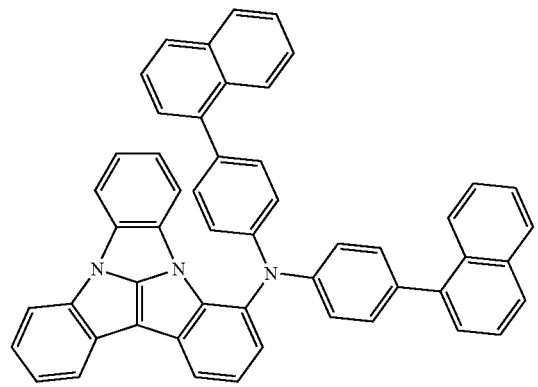
B9
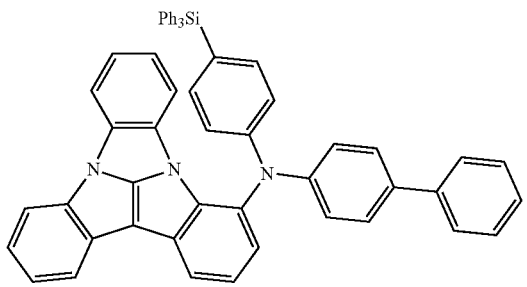
B10
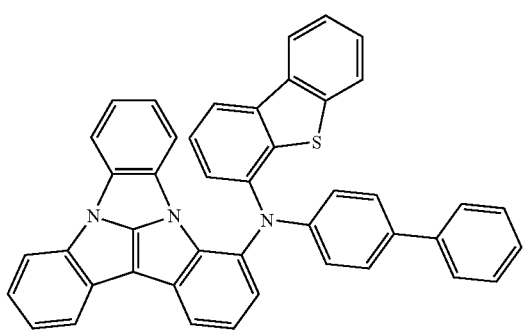
B11
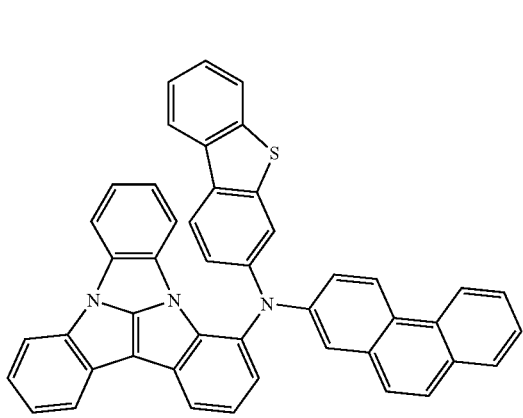
B12
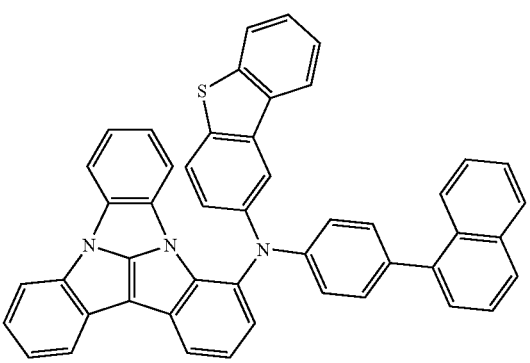

B13
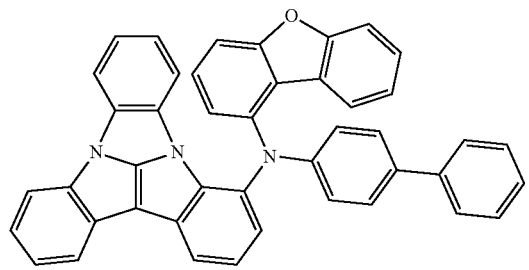
B14
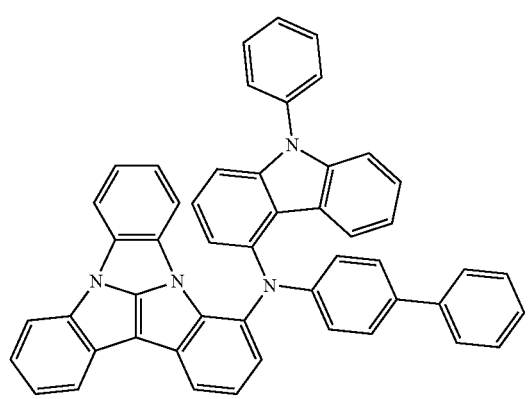
B15
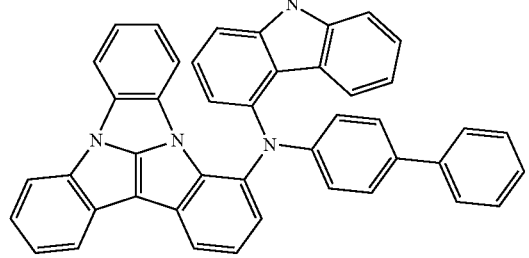
B16
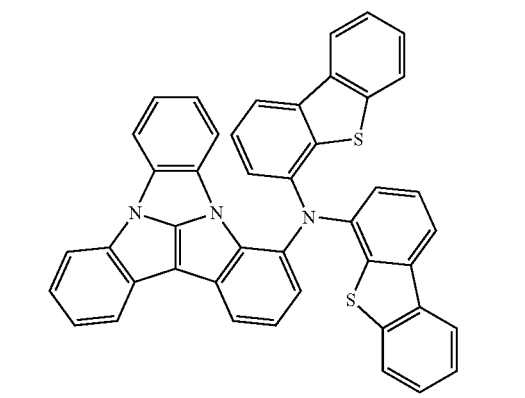
B17
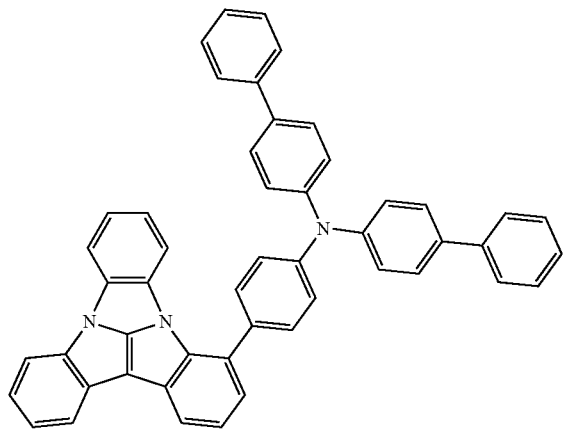
B18
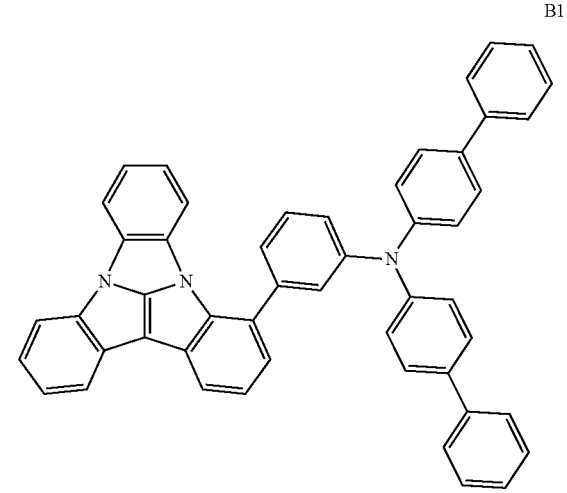
B19
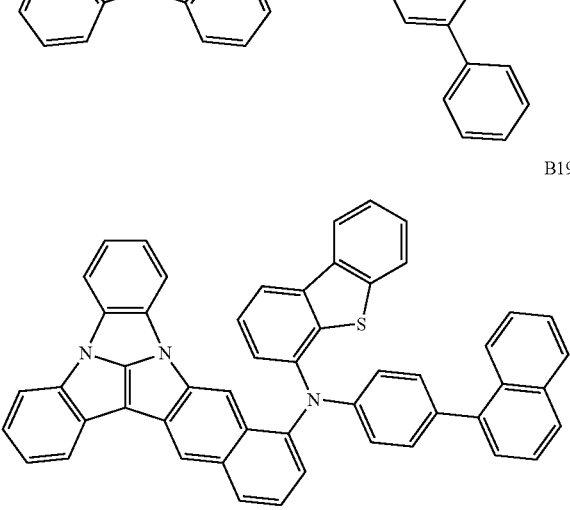
B20
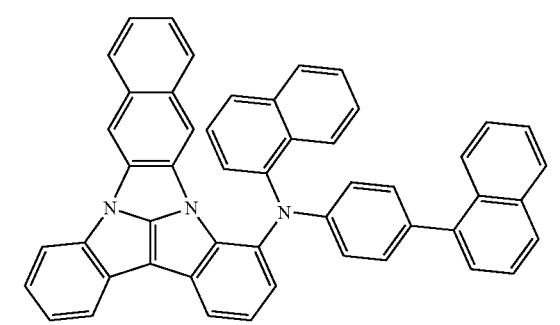

-continued
B21
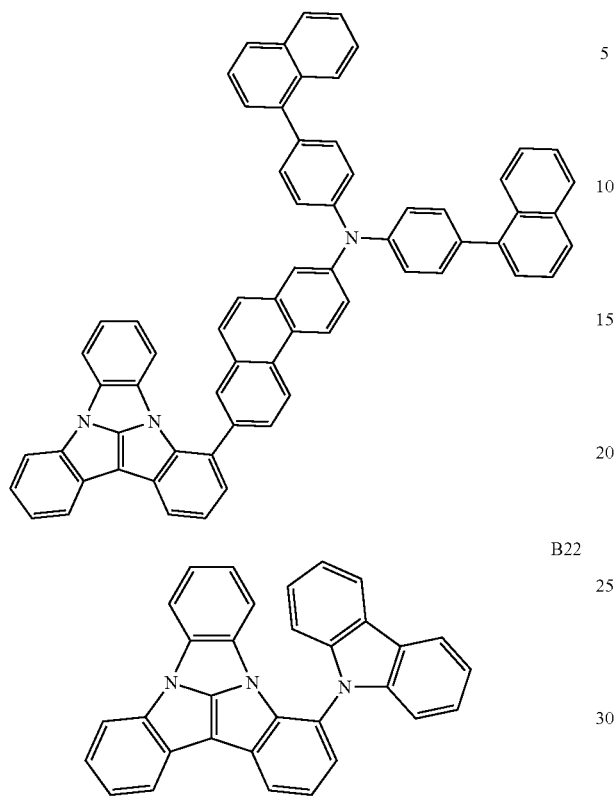
B22
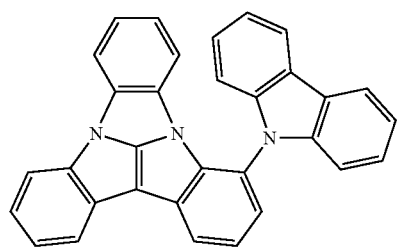
B23
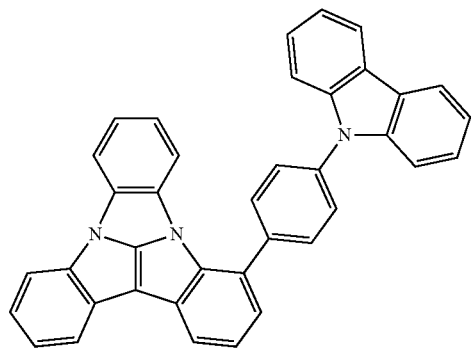
B24
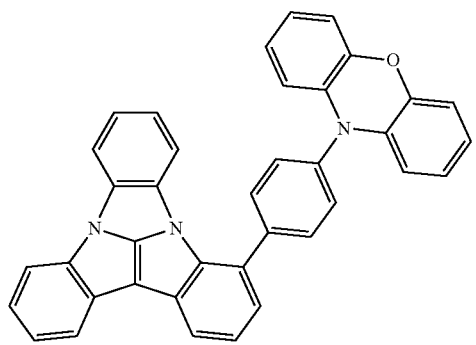
-continued
B25
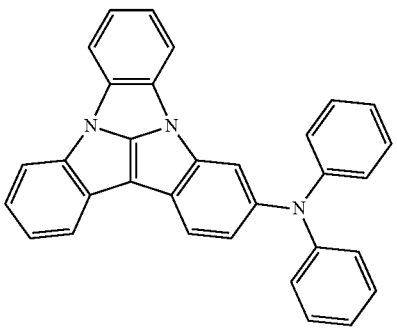
B26
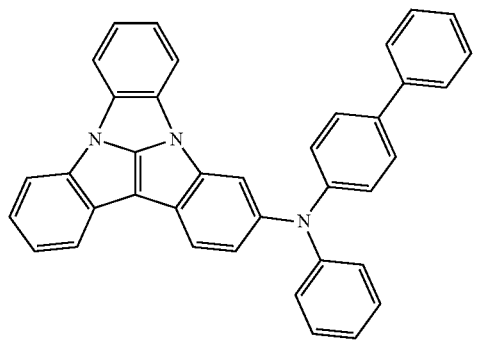
B27
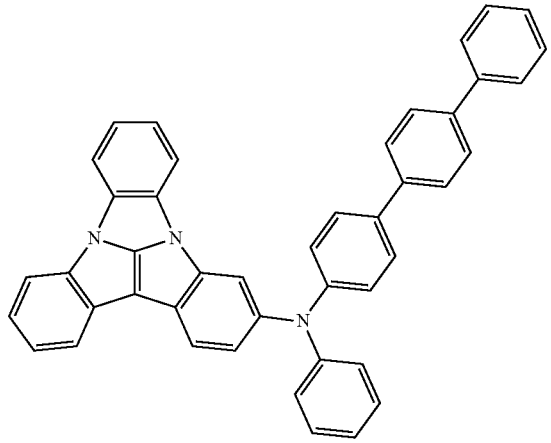
B28
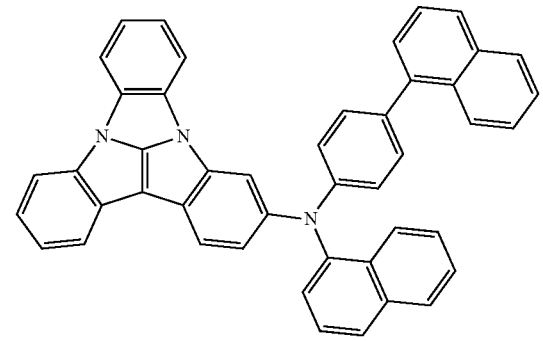

B29
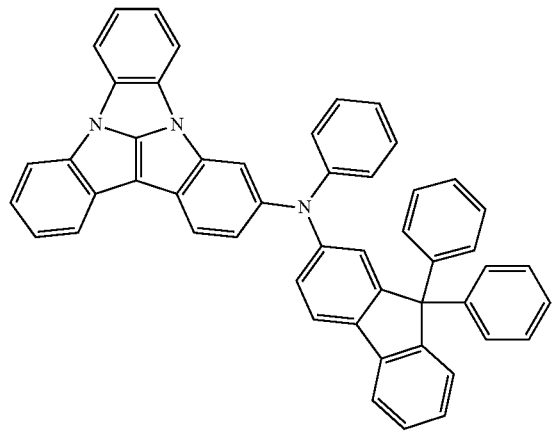
B30
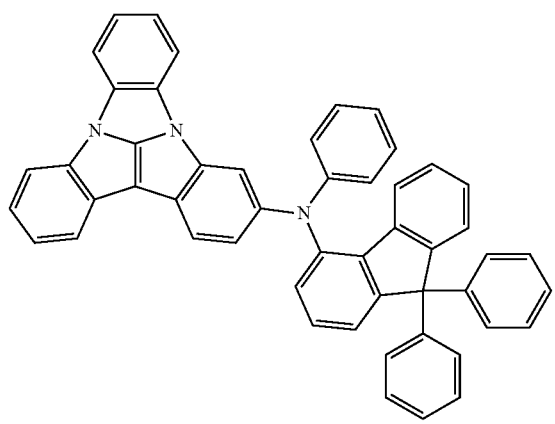
B31
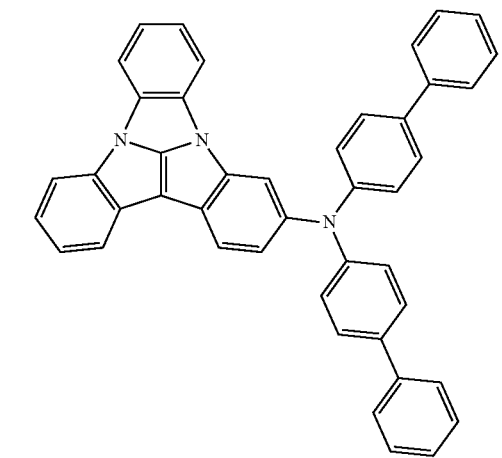
B32
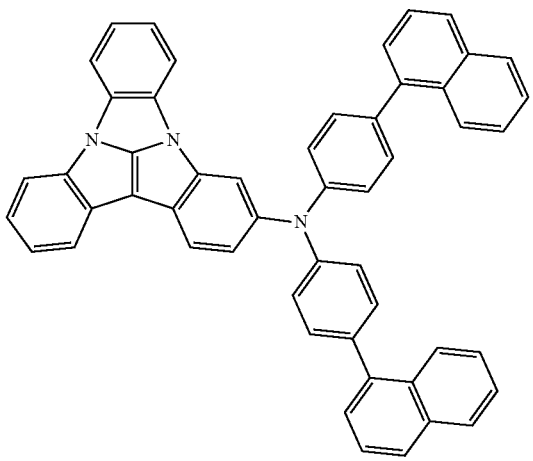
B33
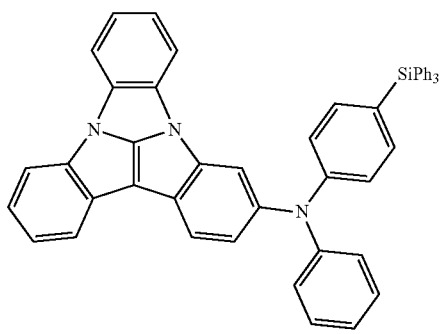
B34
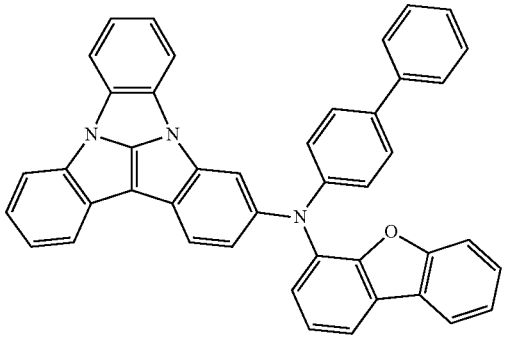
B35
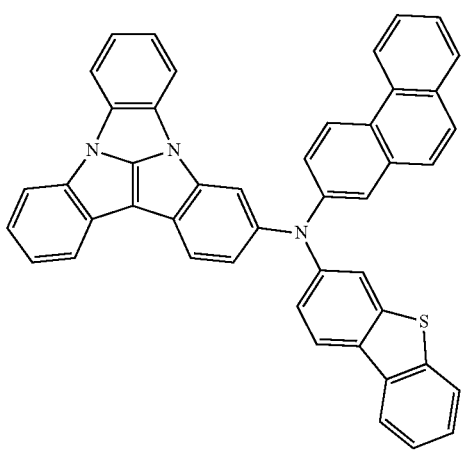

B36
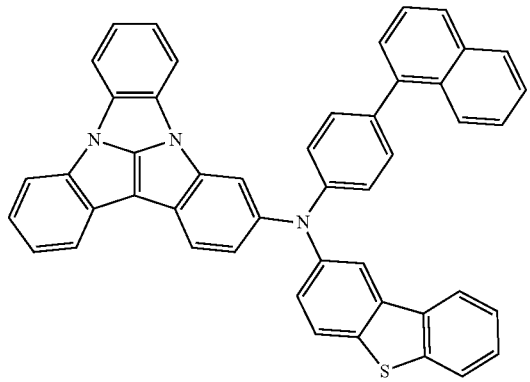
B37
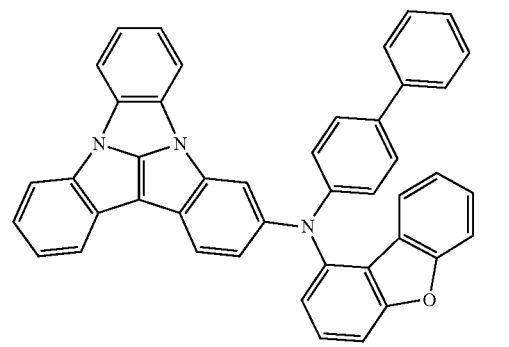
B38
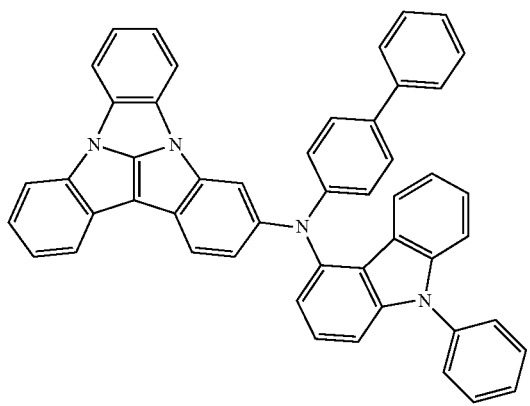
B39
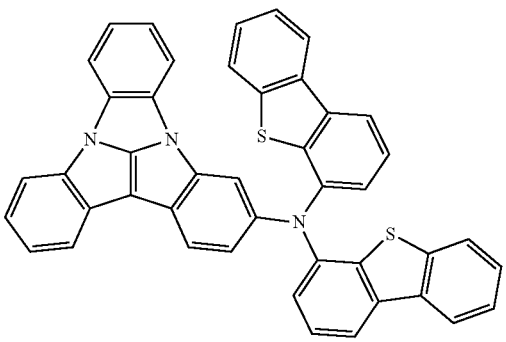
B40
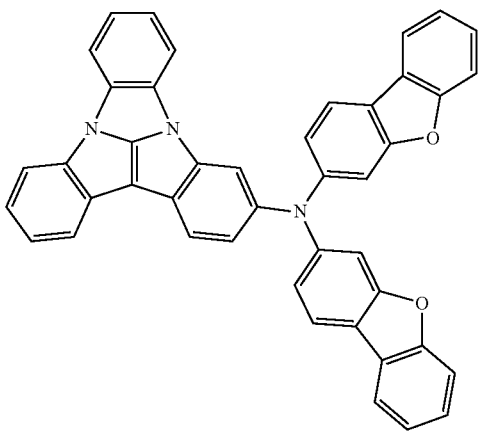
B41
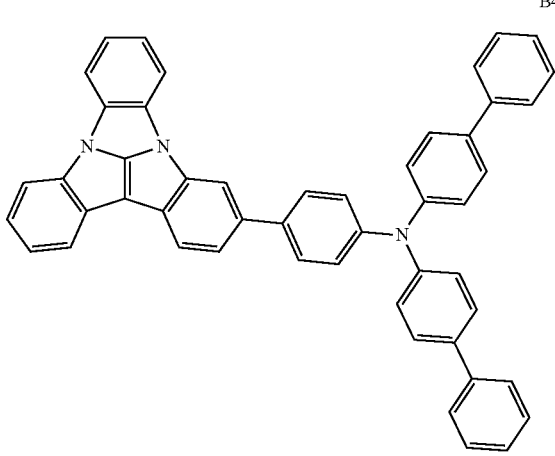
B42
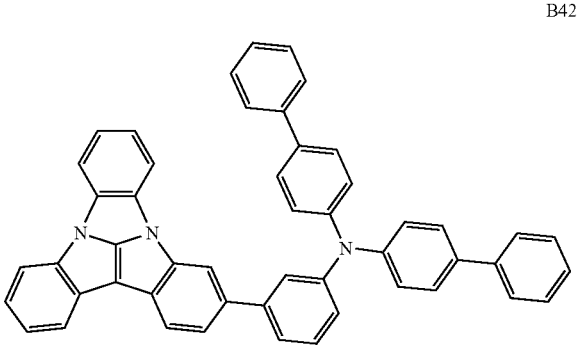
B43
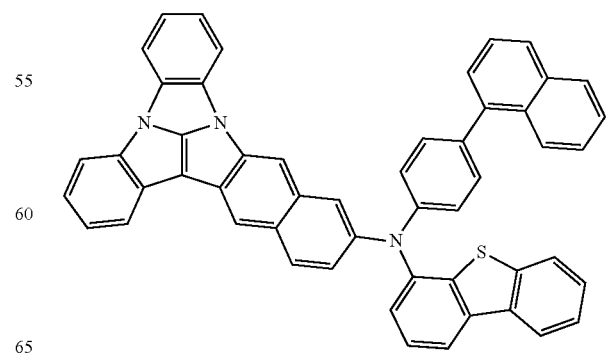

B44
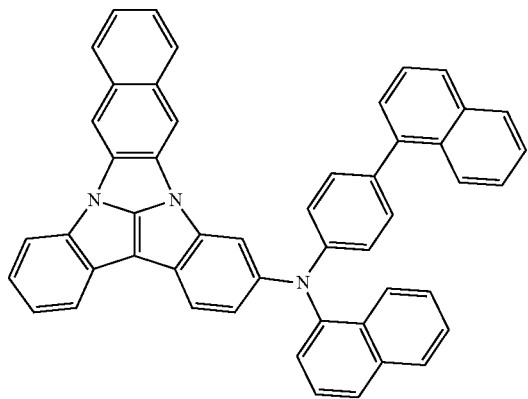
B45
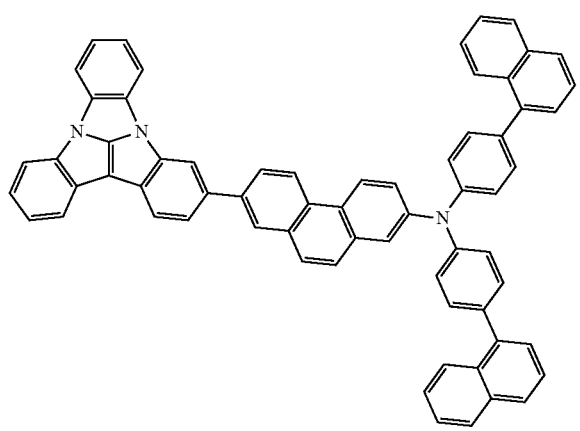
B46
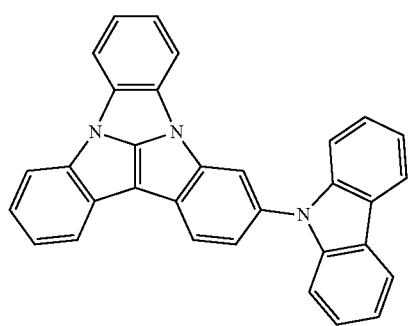
B47
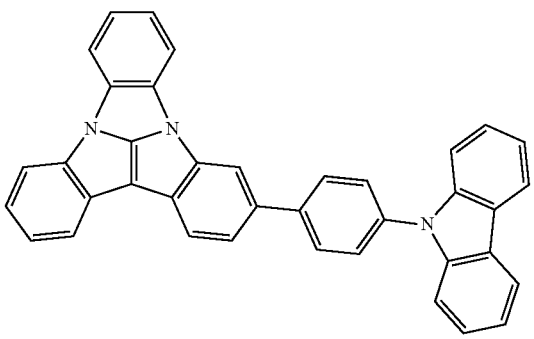
B48
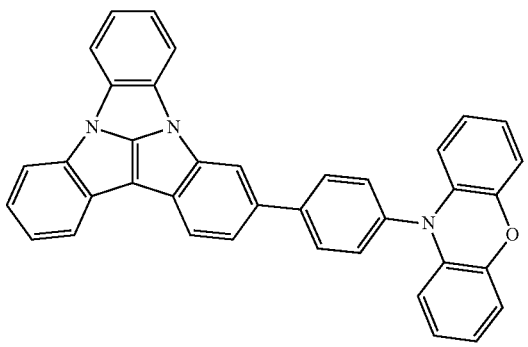
B49
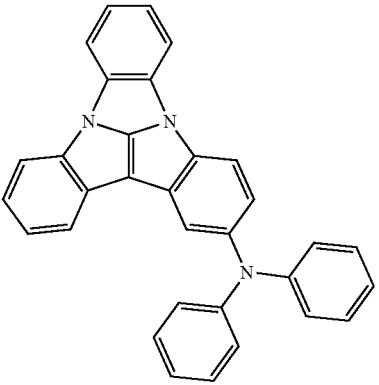
B50
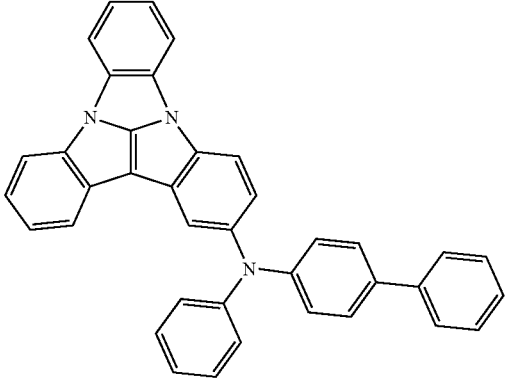
B51
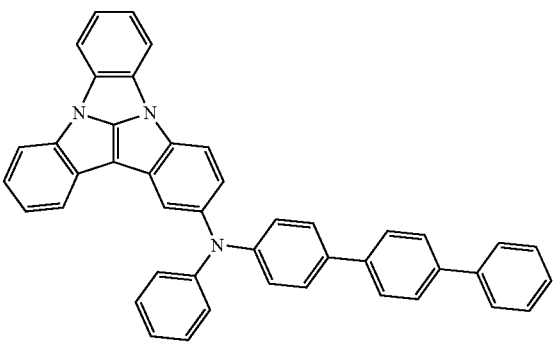

B52
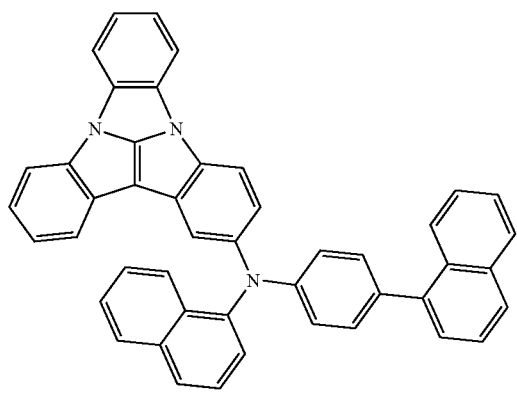
B55
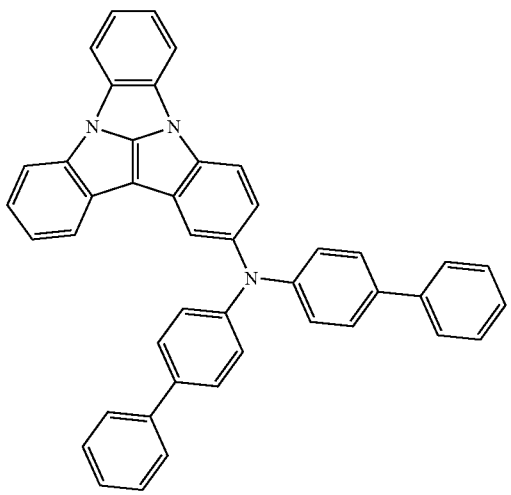
B53
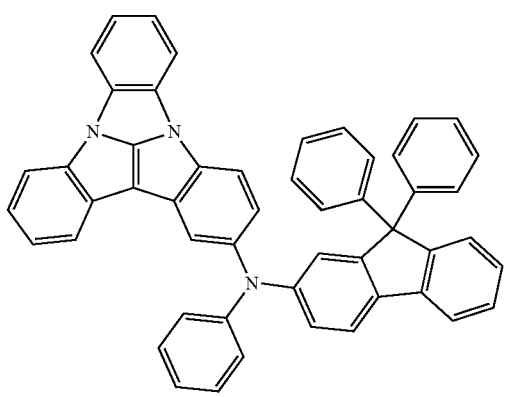
B56
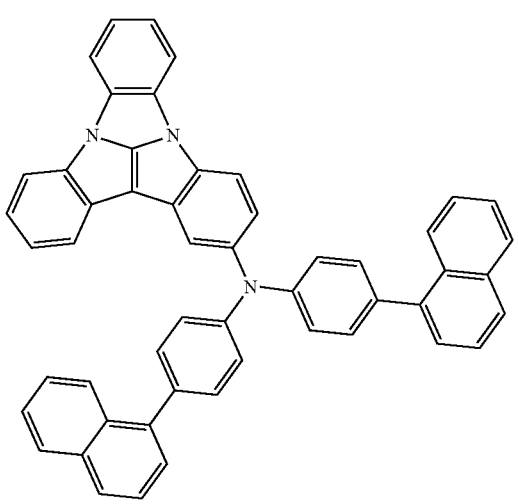
B54
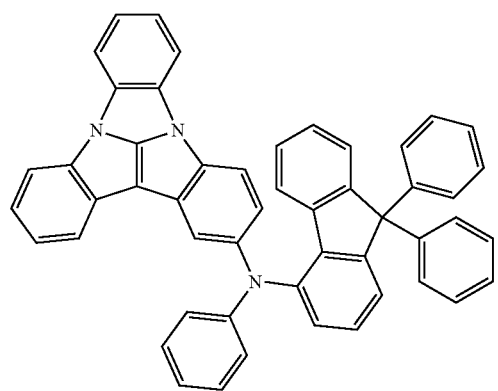
B57
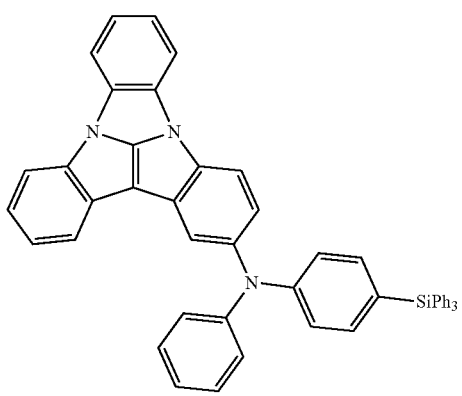

-continued
B58
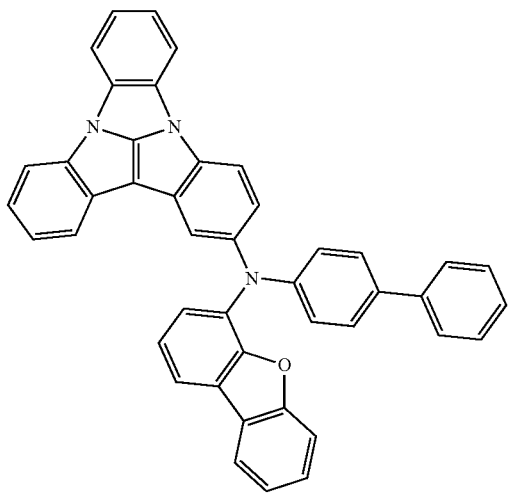
B59
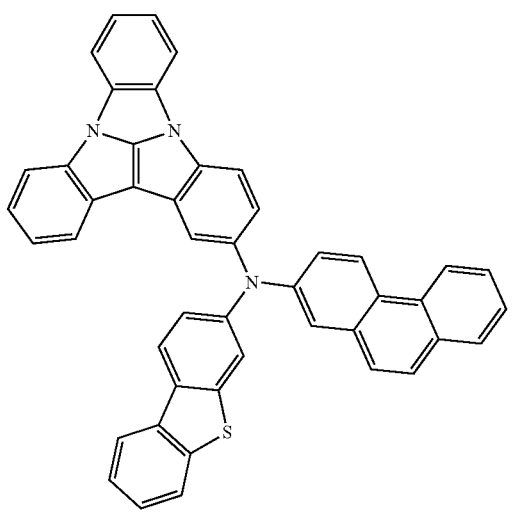
B60
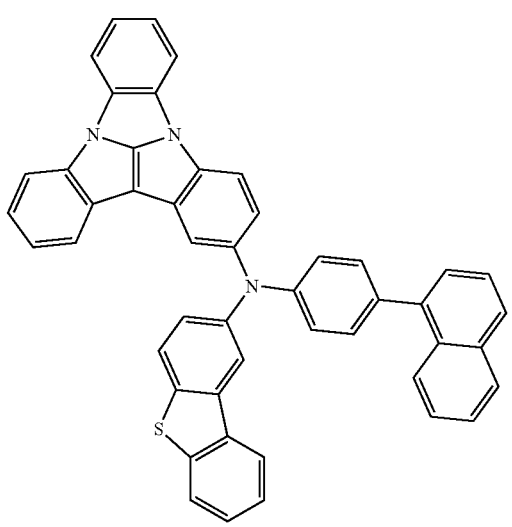
-continued
B61
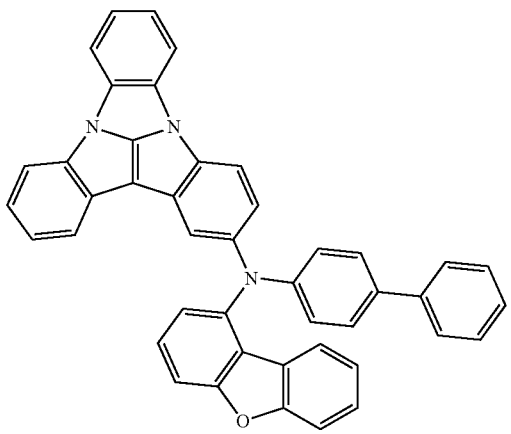
B62
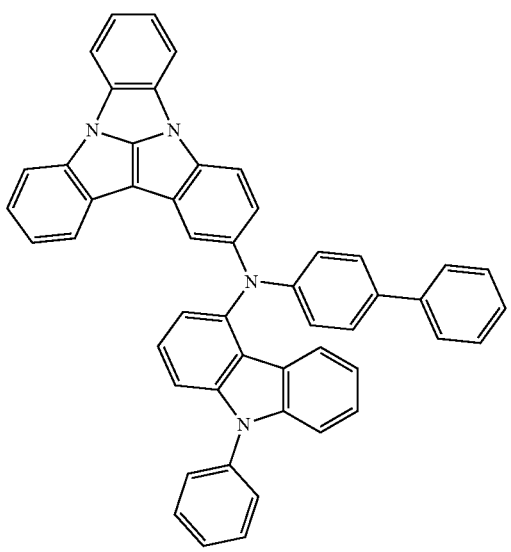
B63
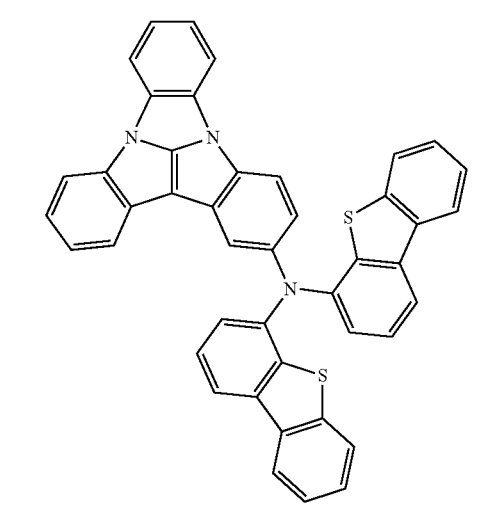

B64
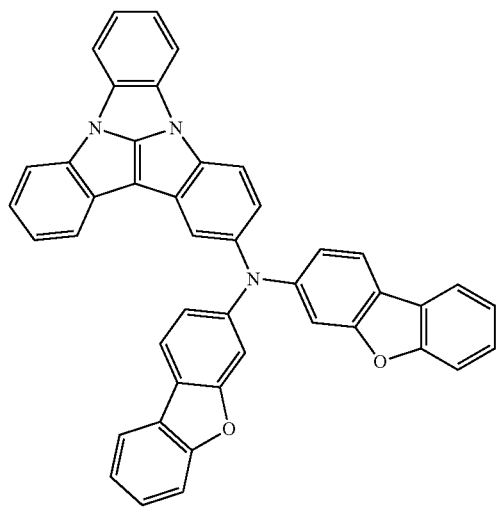
B66
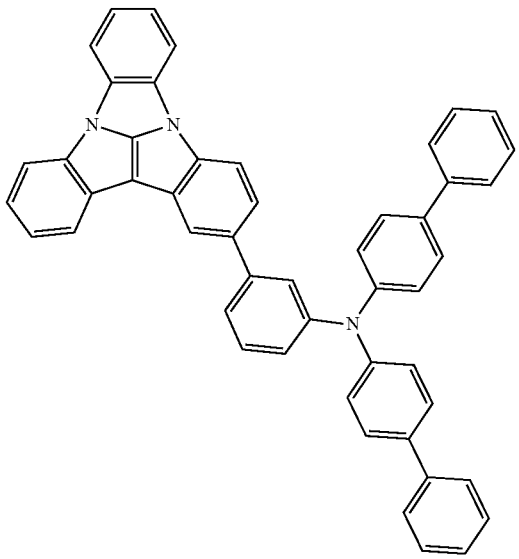
B67
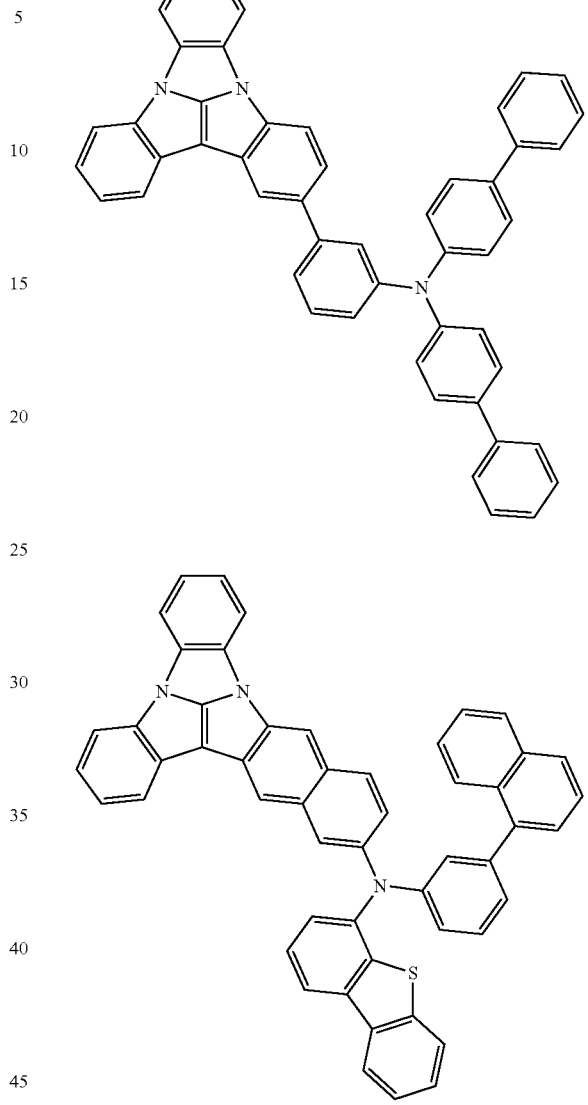
B65
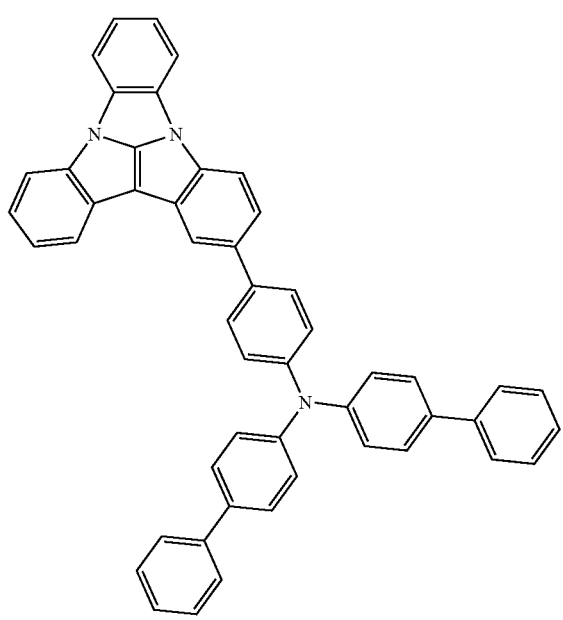
B68
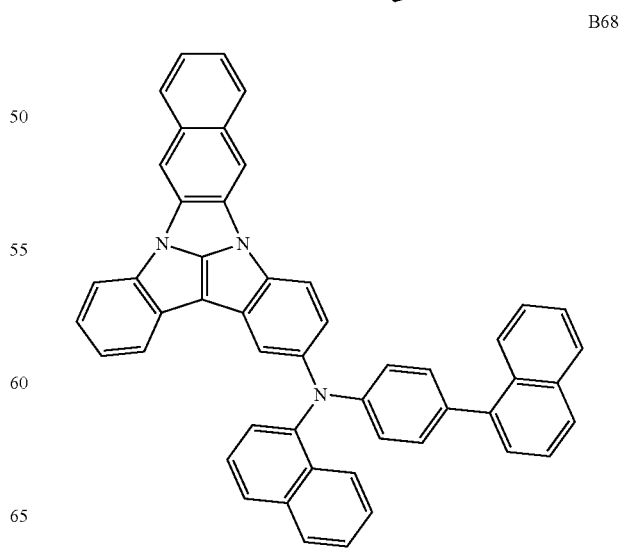

B69
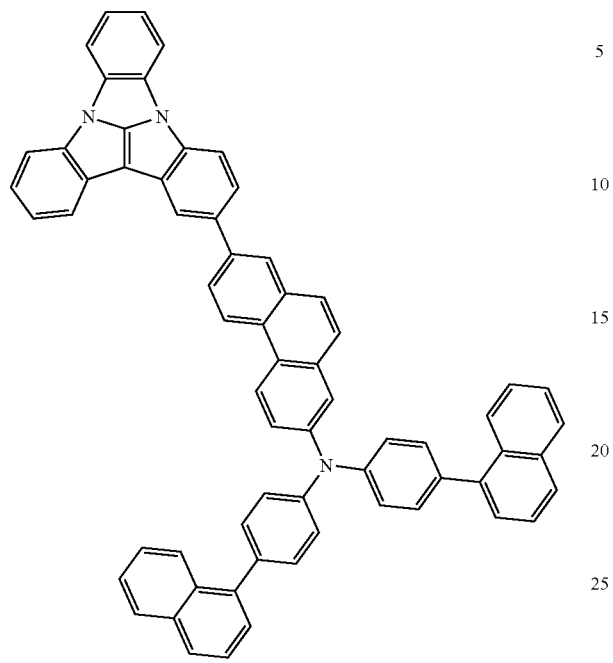
B72
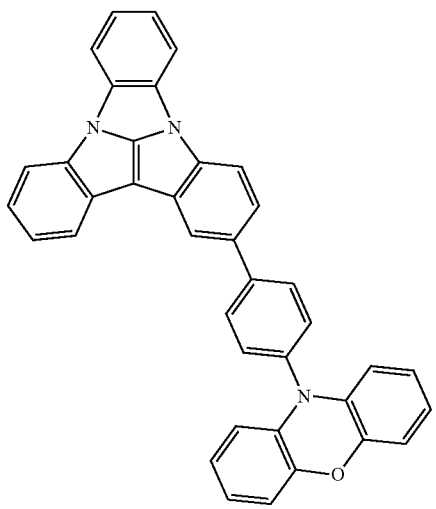
B70
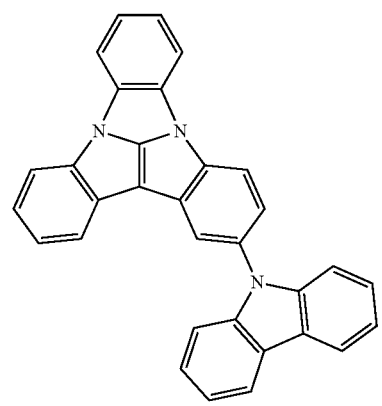
B73
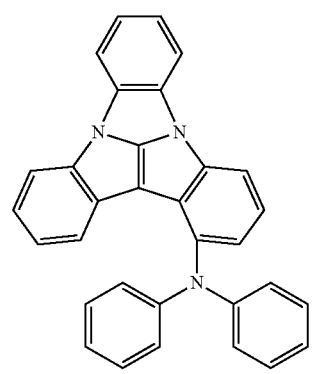
B71
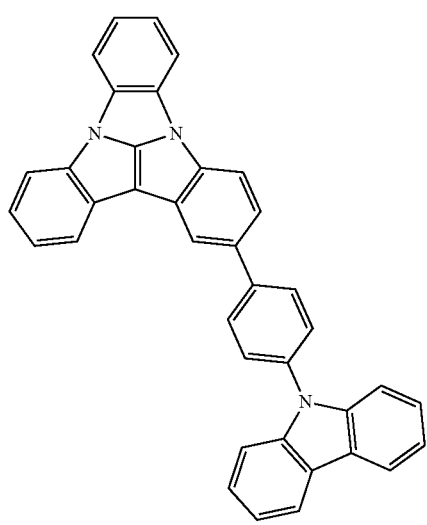
B74
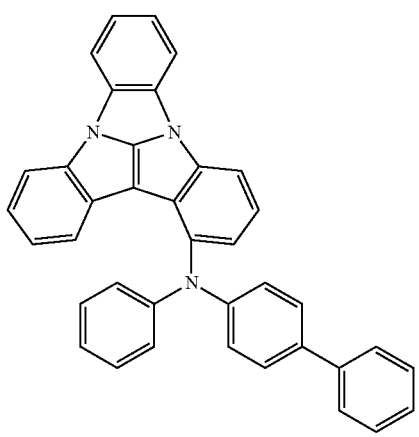

B75
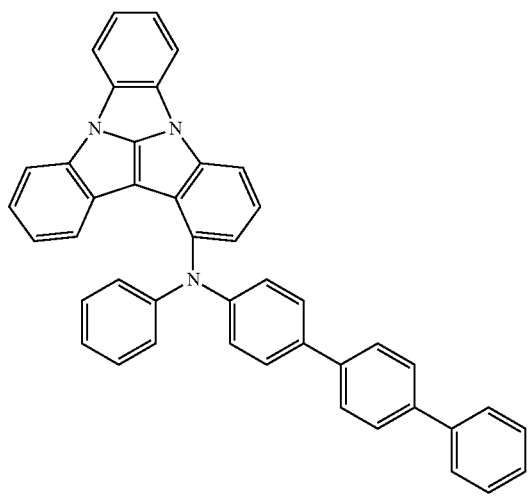
B76
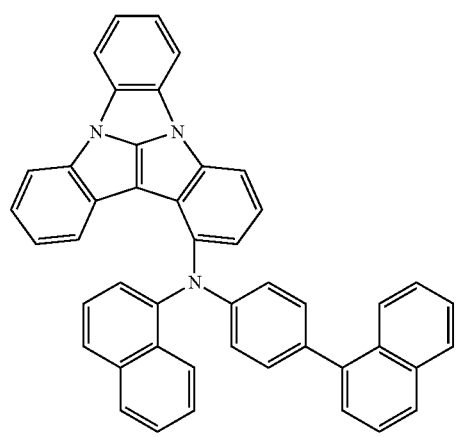
B77
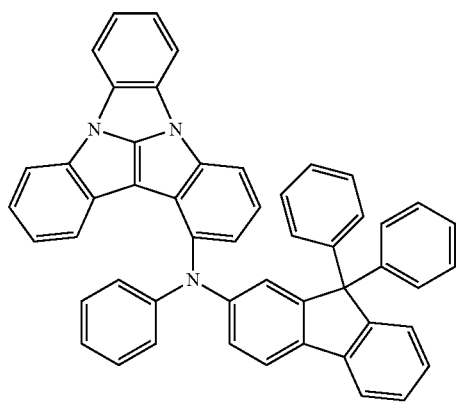
B78
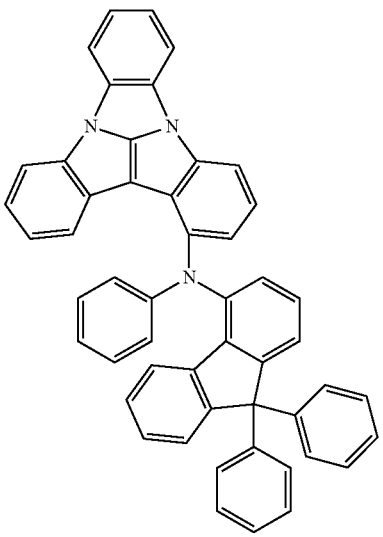
B79
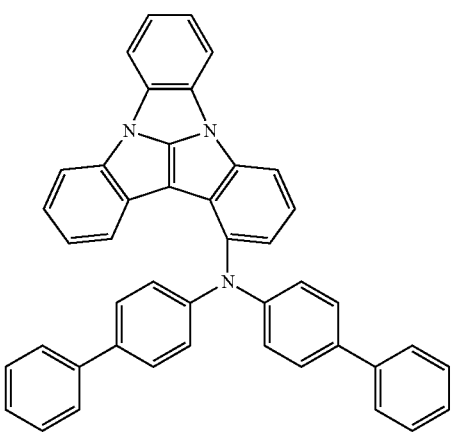
B80
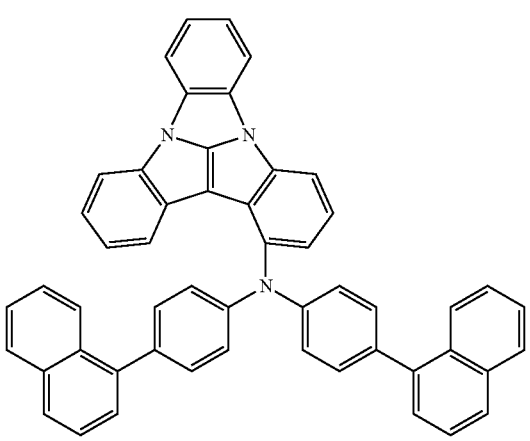

B81 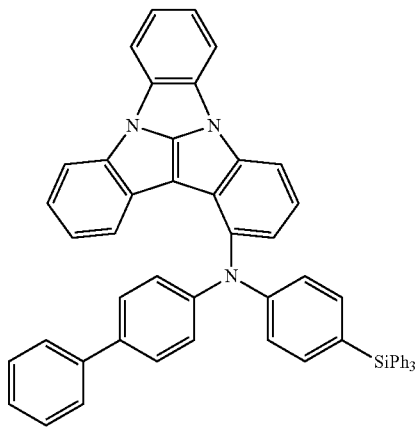
B82 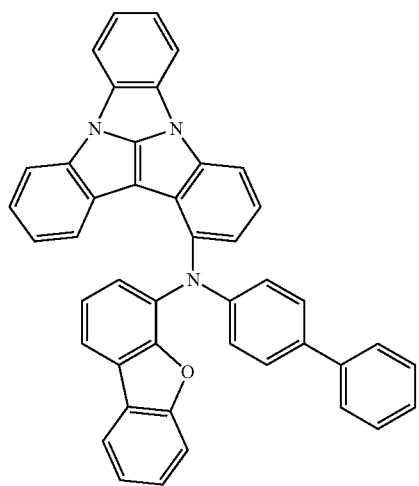
B83 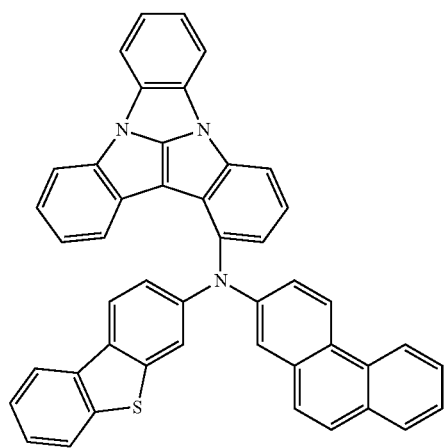
B84 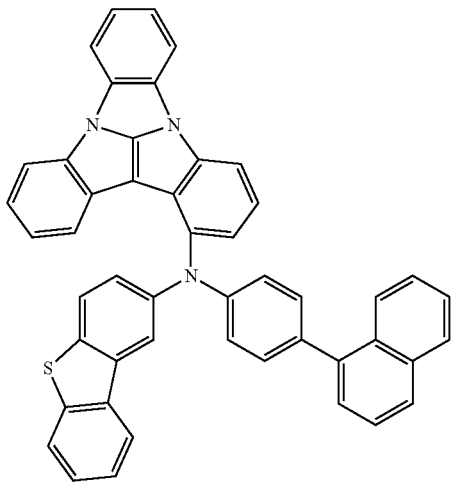
B85 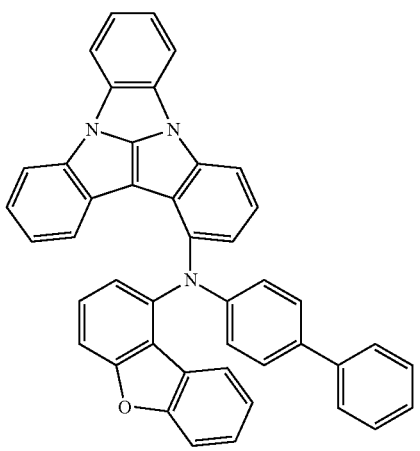
B86 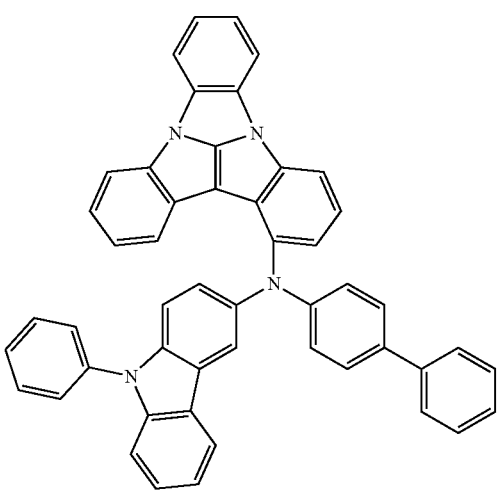

B87
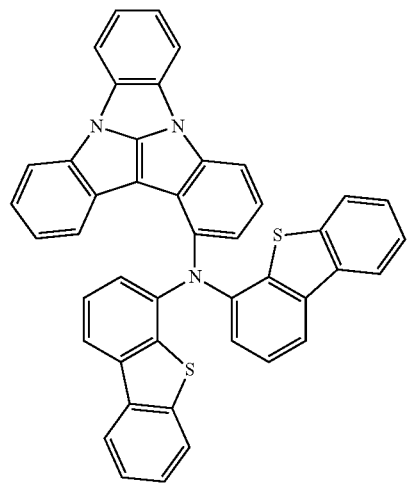
B88
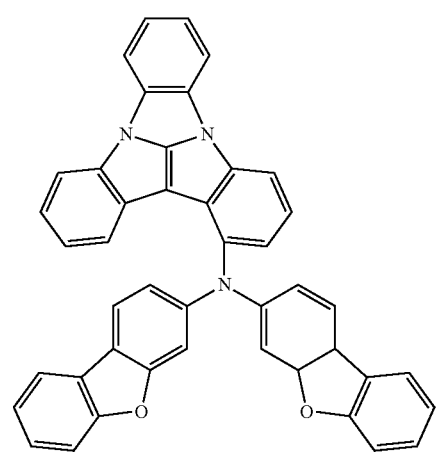
B89
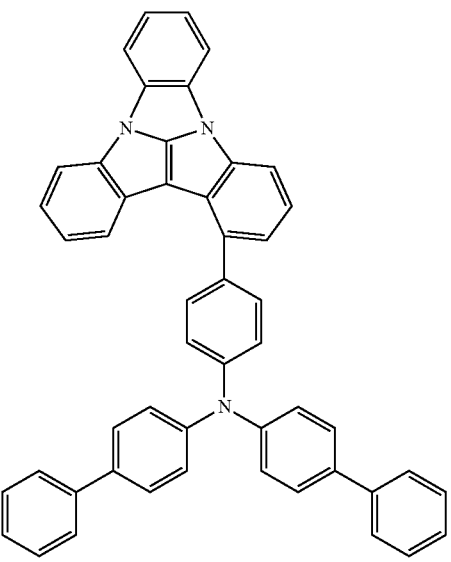
B90
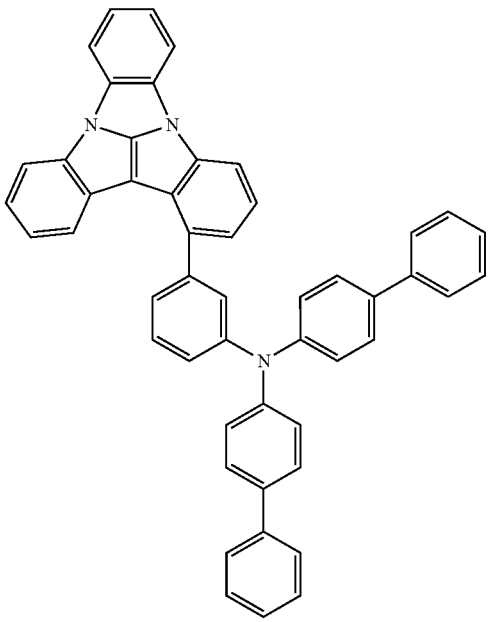
B91
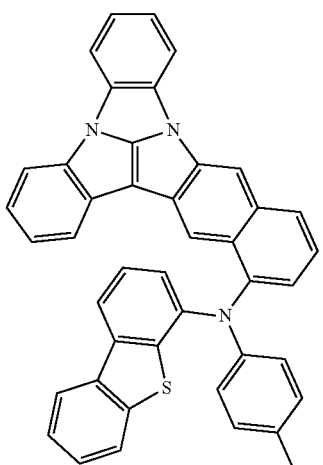
B92
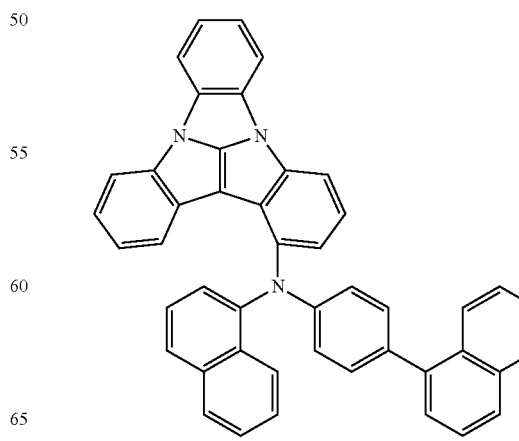

B93
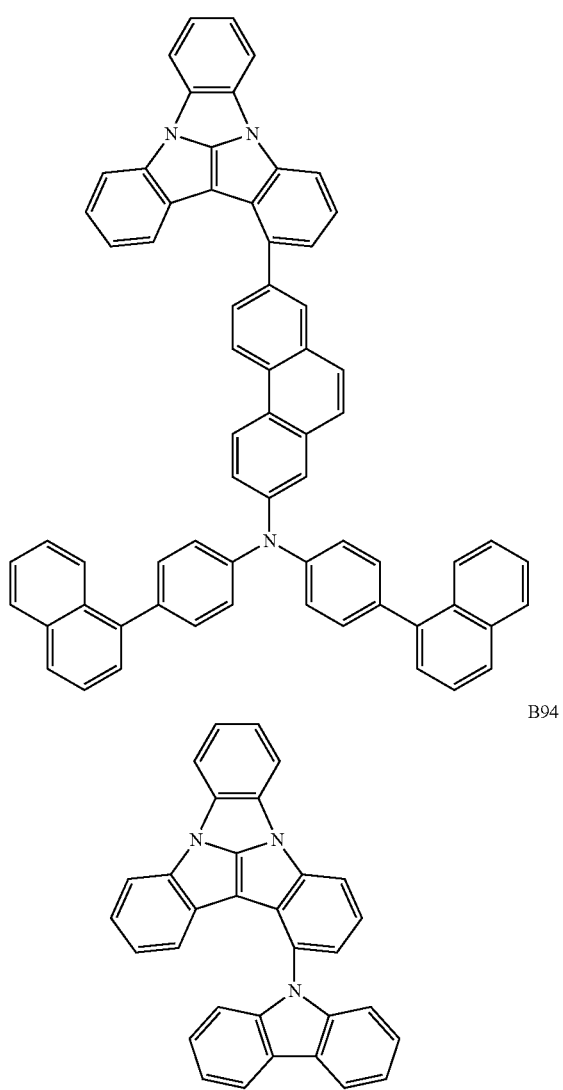
B94
B95
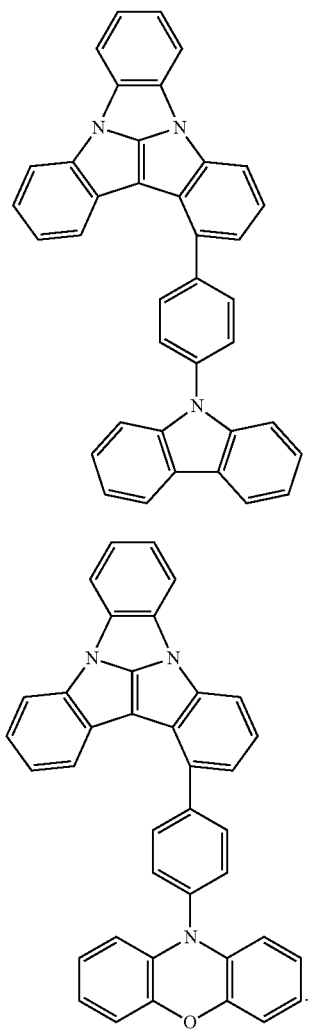
B96
* * * * *